(12) United States Patent
Jones et al.

(10) Patent No.: US 10,563,224 B2
(45) Date of Patent: Feb. 18, 2020

(54) REPLICATION DEFECTIVE ADENOVIRUS VECTOR IN VACCINATION

(71) Applicant: Etubics Corporation, Seattle, WA (US)

(72) Inventors: Frank R. Jones, Seattle, WA (US); Elizabeth Gabitzsch, Seattle, WA (US)

(73) Assignee: Etubics Corporation, Seattle, WA (US)

(*) Notice: Subject to any disclaimer, the term of this patent is extended or adjusted under 35 U.S.C. 154(b) by 0 days.

(21) Appl. No.: 15/433,934

(22) Filed: Feb. 15, 2017

(65) Prior Publication Data

US 2017/0165341 A1    Jun. 15, 2017

Related U.S. Application Data

(62) Division of application No. 14/422,504, filed as application No. PCT/US2013/032688 on Mar. 15, 2013, now Pat. No. 9,605,276.

(60) Provisional application No. 61/693,187, filed on Aug. 24, 2012, provisional application No. 61/694,013, filed on Aug. 28, 2012, provisional application No. 61/748,494, filed on Jan. 3, 2013, provisional application No. 61/756,870, filed on Jan. 25, 2013.

(51) Int. Cl.
| | | |
|---|---|---|
| C12N 15/86 | (2006.01) | |
| C07K 14/705 | (2006.01) | |
| A61K 39/00 | (2006.01) | |
| C12N 7/00 | (2006.01) | |
| C07K 14/47 | (2006.01) | |

(52) U.S. Cl.
CPC .......... *C12N 15/86* (2013.01); *A61K 39/0011* (2013.01); *C07K 14/4748* (2013.01); *C07K 14/70503* (2013.01); *C07K 14/70596* (2013.01); *C12N 7/00* (2013.01); *A61K 2039/5254* (2013.01); *A61K 2039/5256* (2013.01); *A61K 2039/53* (2013.01); *A61K 2039/545* (2013.01); *C12N 2710/10034* (2013.01); *C12N 2710/10043* (2013.01); *C12N 2710/10343* (2013.01); *C12N 2799/022* (2013.01)

(58) Field of Classification Search
CPC ....................................................... C12N 15/86
USPC ....................................................... 424/199.1
See application file for complete search history.

(56) References Cited

U.S. PATENT DOCUMENTS

| | | | |
|---|---|---|---|
| 4,436,727 A | 3/1984 | Ribi | |
| 4,603,112 A | 7/1986 | Paoletti et al. | |
| 4,683,202 A | 7/1987 | Mullis | |
| 4,769,330 A | 9/1988 | Paoletti et al. | |
| 4,777,127 A | 10/1988 | Suni et al. | |
| 4,866,034 A | 9/1989 | Ribi | |
| 4,877,611 A | 10/1989 | Cantrell | |
| 4,912,094 A | 3/1990 | Myers et al. | |
| 5,017,487 A | 5/1991 | Stunnenberg et al. | |
| 5,118,627 A | 6/1992 | Browne | |
| 5,145,684 A | 9/1992 | Liversidge et al. | |
| 5,168,062 A | 12/1992 | Stinski | |
| 5,466,468 A | 11/1995 | Schneider et al. | |
| 5,552,157 A | 9/1996 | Yagi et al. | |
| 5,565,213 A | 10/1996 | Nakamori et al. | |
| 5,567,434 A | 10/1996 | Szoka, Jr. | |
| 5,725,871 A | 3/1998 | Illum | |
| 5,738,868 A | 4/1998 | Shinkarenko | |
| 5,780,045 A | 7/1998 | McQuinn et al. | |
| 5,795,587 A | 8/1998 | Gao et al. | |
| 5,856,462 A | 1/1999 | Agrawal | |
| 6,015,567 A | 1/2000 | Hudziak et al. | |
| 6,038,750 A | 3/2000 | Pabst | |
| 6,045,802 A | 4/2000 | Schlom et al. | |
| 6,057,158 A | 5/2000 | Chamberlain et al. | |
| 6,063,622 A | 5/2000 | Chamberlain et al. | |
| 6,083,750 A | 7/2000 | Chamberlain et al. | |
| 6,348,450 B1 | 2/2002 | Tang et al. | |
| 6,451,596 B1 | 9/2002 | Chamberlain et al. | |
| 6,544,947 B2 | 4/2003 | Holaday et al. | |
| 6,706,693 B1 | 3/2004 | Tang et al. | |
| 6,716,823 B1 | 4/2004 | Tang et al. | |
| 6,756,038 B1* | 6/2004 | Schlom ............ | C07K 14/70503 424/185.1 |
| 7,009,042 B1 | 3/2006 | Skeiky et al. | |
| 7,022,482 B2 | 4/2006 | Zagury et al. | |
| 7,211,569 B2 | 5/2007 | Neeper et al. | |
| 7,410,758 B2 | 8/2008 | Sastry et al. | |
| 7,488,482 B2 | 2/2009 | Balloul et al. | |
| 7,547,681 B2 | 6/2009 | Scholler et al. | |
| 7,553,494 B2 | 6/2009 | Gaiger et al. | |
| 7,662,586 B2 | 2/2010 | Monaci et al. | |
| 7,723,096 B2 | 5/2010 | Schlom et al. | |

(Continued)

FOREIGN PATENT DOCUMENTS

| | | |
|---|---|---|
| EP | 0345242 A2 | 12/1989 |
| EP | 1017810 B1 | 5/2004 |

(Continued)

OTHER PUBLICATIONS

Gabitzsch et al (Cancer Immunol Immunother, 2010, 59: 1131-1135; IDS Jul. 24, 2018).*

(Continued)

*Primary Examiner* — Sean E Aeder

(74) *Attorney, Agent, or Firm* — Sheridan Ross P.C.

(57) ABSTRACT

Methods for generating immune responses using adenovirus vectors that allow multiple vaccinations with the same adenovirus vector and vaccinations in individuals with pre-existing immunity to adenovirus are provided.

18 Claims, 18 Drawing Sheets

Specification includes a Sequence Listing.

(56) References Cited

U.S. PATENT DOCUMENTS

| | | | |
|---|---|---|---|
| 7,771,715 | B2 | 8/2010 | Schlom et al. |
| 7,786,278 | B2 | 8/2010 | Parrington et al. |
| 7,829,678 | B2 | 11/2010 | Bristol et al. |
| 7,999,071 | B2 | 8/2011 | Schlom et al. |
| 8,012,468 | B2 | 9/2011 | Kim et al. |
| 8,017,590 | B1 | 9/2011 | Berinstein et al. |
| 8,188,244 | B2 | 5/2012 | La et al. |
| 8,207,314 | B2 | 6/2012 | Berinstein et al. |
| 8,298,549 | B2 | 10/2012 | Balint et al. |
| 8,609,395 | B2 | 12/2013 | Schlom et al. |
| 9,248,177 | B2 | 2/2016 | Tang et al. |
| 9,605,276 | B2 | 3/2017 | Jones et al. |
| 2004/0091995 | A1 | 5/2004 | Schlom et al. |
| 2004/0265274 | A1 | 12/2004 | Wei et al. |
| 2005/0037439 | A1 | 2/2005 | Bourner et al. |
| 2006/0104986 | A1 | 5/2006 | Duke et al. |
| 2006/0222665 | A1 | 10/2006 | Schreiber |
| 2007/0042002 | A1 | 2/2007 | Weeks-Levy et al. |
| 2007/0104685 | A1 | 5/2007 | La et al. |
| 2010/0055069 | A1 | 3/2010 | Rooke et al. |
| 2010/0209386 | A1 | 8/2010 | Schlom et al. |
| 2010/0285065 | A1* | 11/2010 | Parrington ......... A61K 39/0011 424/232.1 |
| 2011/0086061 | A1 | 4/2011 | Robertson et al. |
| 2013/0224144 | A1 | 8/2013 | Balint et al. |
| 2013/0251741 | A1 | 9/2013 | Pietersz et al. |
| 2013/0302409 | A1 | 11/2013 | Fuchs et al. |
| 2013/0315941 | A1 | 11/2013 | Franzusoff et al. |
| 2014/0220056 | A1 | 8/2014 | Shishido et al. |
| 2014/0377294 | A1 | 12/2014 | Fueyo-Margareto et al. |
| 2015/0132286 | A1 | 5/2015 | Domon et al. |
| 2015/0182621 | A1 | 7/2015 | Wu et al. |
| 2015/0232525 | A1 | 8/2015 | Durrant et al. |
| 2015/0352198 | A1 | 12/2015 | Berinstein et al. |
| 2015/0374790 | A1 | 12/2015 | Liu et al. |
| 2016/0076053 | A1 | 3/2016 | Jones et al. |
| 2017/0065693 | A1 | 3/2017 | Balint et al. |
| 2017/0065706 | A1 | 3/2017 | Balint et al. |

FOREIGN PATENT DOCUMENTS

| | | | |
|---|---|---|---|
| EP | 1447414 | B1 | 6/2007 |
| EP | 1227837 | B1 | 5/2008 |
| EP | 1015035 | B1 | 1/2009 |
| EP | 2465520 | A2 | 6/2012 |
| GB | 2200651 | A | 8/1988 |
| WO | WO-8901973 | A2 | 3/1989 |
| WO | WO-9102805 | A2 | 3/1991 |
| WO | WO-9113160 | A1 | 9/1991 |
| WO | WO-9118926 | A1 | 12/1991 |
| WO | WO-9602555 | A1 | 2/1996 |
| WO | WO-9614876 | A1 | 5/1996 |
| WO | WO-9858956 | A2 | 12/1998 |
| WO | WO-9858956 | A3 | 3/1999 |
| WO | WO-9933488 | A2 | 7/1999 |
| WO | WO-0034494 | A1 | 6/2000 |
| WO | WO-0208436 | A2 | 1/2002 |
| WO | WO-03008649 | A1 | 1/2003 |
| WO | WO 03/059379 | A2 * | 7/2003 |
| WO | WO-2004058157 | A2 | 7/2004 |
| WO | WO 2004/099247 | A2 * | 11/2004 |
| WO | WO-2005012527 | A1 | 2/2005 |
| WO | WO-2005051991 | A2 | 6/2005 |
| WO | WO-2005058937 | A2 | 6/2005 |
| WO | WO-2005058950 | A2 | 6/2005 |
| WO | WO-2006033672 | A2 | 3/2006 |
| WO | WO-2006044923 | A2 | 4/2006 |
| WO | WO-2006033672 | A3 | 6/2006 |
| WO | WO-2007008780 | A2 | 1/2007 |
| WO | WO-2007008780 | A3 | 3/2007 |
| WO | WO-2009006479 | A2 | 1/2009 |
| WO | WO-2009006479 | A3 | 3/2009 |
| WO | WO-2010121180 | A1 | 10/2010 |
| WO | WO-2011032119 | A1 | 3/2011 |
| WO | WO-2012019127 | A2 | 2/2012 |
| WO | WO-2012125998 | A1 | 9/2012 |
| WO | WO-2013025972 | A1 | 2/2013 |
| WO | WO-2014031178 | A1 | 2/2014 |
| WO | WO-2014043518 | A1 | 3/2014 |
| WO | WO-2015061416 | A2 | 4/2015 |
| WO | WO-2015103602 | A1 | 7/2015 |
| WO | WO-2015127027 | A1 | 8/2015 |
| WO | WO-2016007499 | A1 | 1/2016 |
| WO | WO-2016112195 | A1 | 7/2016 |
| WO | WO-2016172249 | A1 | 10/2016 |

OTHER PUBLICATIONS

Akiyama, et al. The transforming potential of the c-erbB-2 protein is regulated by its autophosphorylation at the carboxyl-terminal domain. Mol Cell Biol. Feb. 1991;11(2):833-42.

Altschul, et al. Basic local alignment search tool. J Mol Biol. Oct. 5, 1990;215(3):403-10.

Altschul, et al. Gapped BLAST and PSI-BLAST: a new generation of protein database search programs. Nucleic Acids Res. Sep. 1, 1997;25(17):3389-402.

Amalfitano, A. Use of multiply deleted adenovirus vectors to probe adenovirus vector performance and toxicities. Curr Opin Mol Ther. Aug. 2003;5(4):362-6.

Amalfitano, et al. (1996) Improved Adenovirus Packaging Cell Lines to Support the Growth of Replication-defective Gene-Delivery Vectors. Proc Natl Acad Sci U S A 93:3352-3356.

Amalfitano, et al. (1997) Isolation and Characterization of Packaging Cell Lines That Coexpress the Adenovirus E1, DNA Polymerase, and Preterminal Proteins: Implications for Gene Therapy. Gene Ther. 4:258-263.

Amalfitano, et al. (1998) Production and Characterization of Improved Adenovirus Vectors With the E1, E2b, and E3 Genes Deleted. J Virol 72:926-933.

Amalfitano, et al. Separating fact from fiction: assessing the potential of modified adenovirus vectors for use in human gene therapy. Curr Gene Ther 2:111-133 (2002).

Amalfitano, et al. Systemic correction of the muscle disorder glycogen storage disease type II after hepatic targeting of a modified adenovirus vector encoding human acid-alpha-glucosidase. Proc Natl Acad Sci U S A 96;8861-6 (1999).

Amara, et al. A new generation of HIV vaccines. Trends Mol Med 8;489-95 (2002).

Amara, et al. Different patterns of immune responses but similar control of a simian-human immunodeficiency virus 89.6P mucosal challenge by modified vaccinia virus Ankara (MVA) and DNA/MVA vaccines. J Virol 76;7625-31 (2002b).

Andre, et al. Increased immune response elicited by DNA vaccination with a synthetic gp120 sequence with optimized codon usage. J Virol. 72:1497-503 (1998).

Arthur, et al. 1997. A comparison of gene transfer methods in human dendritic cells. Cancer Gene Ther 4:17-25.

ASCO. Collaborating to Conquer Cancer. Annual 2012. Annual meeting program. ASCO.org. McCormick Place, Chicago, Illinois. Jun. 1-5, 2012. http://chicago2012.asco.org/LinkClick.aspx?fileticket=--U-OYLsze8%3d&tabid=3122.

Ashkar, et al. Local delivery of CpG oligodeoxynucleotides induces rapid changes in the genital mucosa and inhibits replication, but not entry, of herpes simplex virus type 2. J Virol 77;8948-56 (2003).

Ausubel, et al. Current Protocols in Molecular Biology. John Wiley & Sons, New York, 1989.

Badaro, et al. Successful use of a defined antigen/GM-CSF adjuvant vaccine to treat mucosal leishmaniasis refractory to antimony: a case report. Braz J Infect Dis 5, 223-232 (2001).

Badaro, et al. Immunotherapy for drug-refractory mucosal leishmaniasis. J Infect Dis 194:8 1151-59 (2006).

Balachandran, et al. Protection against lethal challenge of BALB/c mice by passive transfer of monoclonal antibodies to five glycoproteins of herpes simplex virus type 2. Infect Immun 37;1132-7. (1982).

Balint, et al. Extended evaluation of a phase 1/2 trial on dosing, safety, immunogenicity, and overall survival after immunizations

(56) References Cited

OTHER PUBLICATIONS with an advanced-generation Ad5 [E1-, E2b-]-CEA (6D) vaccine in late-stage colorectal cancer. Cancer Immunology, Immunotherapy 64.8 (2015): 977-987.
Bangari, et al. (2006) Development of nonhuman adenoviruses as vaccine vectors. Vaccine 24:849-862.
Bangari, et al. Current strategies and future directions for eluding adenoviral vector immunity. Curr Gene Ther. Apr. 2006; 6(2):215-226.
Barjot, et al. Gutted adenoviral vector growth using E1/E2b/E3-deleted helper viruses. J Gene Med 4;480-9 (2002).
Barouch, et al. Adenovirus vector-based vaccines for human immunodeficiency virus type 1. Hum Gene Ther. 16:149-156 (2005).
Barouch, et al. Augmentation of immune responses to HIV-1 and simian immunodeficiency virus DNA vaccines by IL-2/Ig plasmid administration in rhesus monkeys. PNAS, 2000. 97(8): p. 4192-7.
Barouch, et al. Control of viremia and prevention of clinical AIDS in rhesus monkeys by cytokine-augmented DNA vaccination. Science 290;486-92 (2000).
Barouch, et al. Eventual AIDS vaccine failure in a rhesus monkey by viral escape from cytotoxic T lymphocytes. Nature 415;335-9 (2002).
Barouch, et al. Plasmid chemokines and colony-stimulating factors enhance the immunogenicity of DNA priming-viral vector boosting human immunodeficiency virus type 1 vaccines. J Virol 77;8729-35 (2003).
Barouch, et al. Reduction of simian-human immunodeficiency virus 89.6P viremia in rhesus monkeys by recombinant modified vaccinia virus Ankara vaccination. J Virol 75;5151-8 (2001).
Barratt-Boyes, et al. Broad cellular immunity with robust memory responses to simian immunodeficiency virus following serial vaccination with adenovirus 5- and 35-based vectors. J Gen Virol 87:.Pt 1 139-149 (2006).
Belkaid, et al. CD8+ T cells are required for primary immunity in C57BL/6 mice following low-dose, intradermal challenge with Leishmania major. J Immunol 168(8):3992-4000 (2002).
Berinstein. (2002) Carcinoembryonic antigen as a target for therapeutic anticancer vaccines: a review. J Clin Oncol 20:2197-2107.
Berkner. Development of adenovirus vectors for the expression of heterologous genes. Biotechniques 6(7):616-629 (1988).
Betts, et al. HIV nonprogressors preferentially maintain highly functional HIV-specific CD8+ T-cells. Blood, 2006; 107(12):4781-4789.
Borges, et al. Potent Stimulation of the Innate Immune System by a Leishmania brasiliensis Recombinant Protein. Infect Immun 69, 5270-5277 (2001).
Borrow, et al. Virus-specific CD8+ cytotoxic T-lymphocyte activity associated with control of viremia in primary human immunodeficiency virus type 1 infection. J Virol 68;6103-10 (1994).
Boshart, et al. A cyclic AMP response element mediates repression of tyrosine aminotransferase gene transcription by the tissue-specific extinguisher locus Tse-1. Cell. Jun. 1, 1990;61(5):905-16.
Brave, et al. Vaccine delivery methods using viral vectors. Mol Pharm 4:.1 18-32 (2007).
Bregni, et al. 1998. Adenovirus vectors for gene transduction into mobilized blood CD34+ cells. Gene Ther 5:465-472.
Bremers, et al. (1995) The use of Epstein-Barr virus-transformed B lymphocyte cell lines in a peptide-reconstitution assay: identification of CEA-related HLA-A0301-restricted potential cytotoxic T-lymphocyte epitopes. J. Immunother. Emphasis Tumor Immunol. 18:77-85.
Brossart, et al. 1997. Virus-mediated delivery of antigenic epitopes into dendritic cells as a means to induce CTL. J Immunol 158:3270-3276.
Butterfield, et al. 1998. Generation of melanoma-specific cytotoxic T lymphocytes by dendritic cells transduced with a MART-1 adenovirus. J Immunol 161:5607-5613.
Campos, et al. (2007) Current advances and future challenges in adenoviral vector biology and targeting. Curr Gene Ther 7:189-204.

Campos-Neto, et al. Protection against cutaneous leishmaniasis induced by recombinant antigens in murine and nonhuman primate models of the human disease. Infect Immun 69, 4103-4108 (2001).
Campos-Neto, et al. Vaccination with plasmid DNA encoding TSA/LmSTI1 leishmanial fusion proteins confers protection against Leishmania major infection in susceptible BALB/c mice. Infect Immun 70:2828-36 (2002).
Cao, et al. (2001) Analysis of the frequencies of HLA-A, B, and C alleles and haplotypes in the five major ethnic groups of the United States reveals high levels of diversity in these loci and contrasting distribution patterns in these populations. Hum Immunol 62:1009-1030.
Caravokyri, et al. Constitutive episomal expression of polypeptide IX (pIX) in a 293-based cell line complements the deficiency of pIX mutant adenovirus type 5. J Virol. Nov. 1995;69(11):6627-33.
Casimiro, et al. 2003. Comparative immunogenicity in rhesus monkeys of DNA plasmid, recombinant vaccinia virus, and replication-defective adenovirus vectors expressing a human immunodeficiency virus type 1 gag gene. J Virol 77:6305-6313.
Chamberlain, et al. Deletion screening of the Duchenne muscular dystrophy locus via multiplex DNA amplification. Nucleic Acids Res 16;11141-56 (1988).
Chamberlain, et al. Packaging cell lines for generating replication-defective and gutted adenoviral vectors. Methods Mol Med 76;153-66 (2003).
Chan, et al. Two distinct upstream regulatory domains containing multicopy cellular transcription factor binding sites provide basal repression and inducible enhancer characteristics to the immediate-early IES (US3) promoter from human cytomegalovirus. J Virol. Aug. 1996;70(8):5312-28.
Chandran, et al. Recent trends in drug delivery systems: liposomal drug delivery system—preparation and characterisation. Indian J Exp Biol. Aug. 1997;35(8):801-9.
Chartier, et al. Efficient generation of recombinant adenovirus vectors by homologous recombination in *Escherichia coli*. J Virol 70;4805-10 (1996).
Cheever, et al. (2009) The prioritization of cancer antigens: A National Cancer Institute pilot project for the acceleration of translational research. Clin Cancer Res 15:5323-5337.
Chen et al, Dissecting the multifactorial causes of immunodominance in class I-restricted T cell responses to viruses. Immunity, 2000. 12(1): p. 83-93.
Chirmule, et al. 1999. Immune responses to adenovirus and adeno-associated virus in humans. Gene Ther 6:1574-1583.
Chun, et al. Distribution fate and mechanism of immune modulation following mucosal delivery of plasmid DNA encoding IL-10. J Immunol 163;2393-402 (1999).
Chung, et al. A 5' element of the chicken beta-globin domain serves as an insulator in human erythroid cells and protects against position effect in *Drosophila*. Cell. Aug. 13, 1993;74(3):505-14.
Cohen. Prevention cocktails: combining tools to prevents HIV's spread. Science. 309:1002-1005 (2005).
Coler, et al. Immunization with a polyprotein vaccine consisting of the T-Cell antigens thiol-specific antioxidant, Leishmania major stress-inducible protein 1, and Leishmania elongation initiation factor protects against leishmaniasis. Infect Immun 70:4215-25 (2002).
Coler, et al. Second-generation vaccines against leishmaniasis. Trends Parasitol 21:244-9 (2005).
Conry, et al. 2000. Human autoantibodies to carcinoembryonic antigen (CEA) induced by a vaccinia-CEA vaccine. Clin Cancer Res 6:34-41.
Corey, et al. (2004) TRPA1 is a candidate for the mechanosensitive transduction channel of vertebrate hair cells. Nature 432:723-730.
Corey, et al. Recombinant glycoprotein vaccine for the prevention of genital HSV-2 infection: two randomized controlled trials. Chiron HSV Vaccine Study Group. JAMA 282;331-40. (1999).
Cory, et al. (1991) Use of an aqueous soluble tetrazolium/formazan assay for cell growth assays in culture. Cancer Comm 3:207-212.
Couvreur, P. Polyalkylcyanoacrylates as colloidal drug carriers. Crit Rev Ther Drug Carrier Syst. 1988;5(1):1-20.

(56) References Cited

OTHER PUBLICATIONS

Cox, et al. 1993. Induction of cytotoxic T lymphocytes by recombinant canarypox (ALVAC) and attenuated vaccinia (NYVAC) viruses expressing the HIV-1 envelope glycoprotein. Virology 195:845-850.
CTEP Cancer Therapy Evaluation Program. CTCAE and CTC Website (2010) http://ctep.cancer.gov/protocolDevelopment/electronic_applications/ctc.htm. Accessed Feb. 10, 2012.
Cunningham, et al. Randomised trial of irinotecan plus supportive care versus supportive care alone after fluorouracil failure for patients with metastatic colorectal cancer. The Lancet 352.9138 (1998): 1413-1418.
Current Protocols in Immunology, Edited by: John E. Coligan, Ada M. Kruisbeek, David H. Margulies, Ethan M. Shevach, Warren Strober (2001 John Wiley & Sons, NY, NY).
Dayhoff, M.O. (1978) A model of evolutionary change in proteins—Matrices for detecting distant relationships. In Dayhoff, M.O. (ed.) Atlas of Protein Sequence and Structure, National Biomedical Research Foundation, Washington DC vol. 5, Suppl. 3, pp. 345-358.
Dellorusso, et al. Functional correction of adult mdx mouse muscle using gutted adenoviral vectors expressing full-length dystrophin. Proc Natl Acad Sci U S A. Oct. 1, 2002;99(20):12979-84. Epub Sep. 23, 2002.
Diao, et al. 1999. Human PBMC-derived dendritic cells transduced with an adenovirus vectorinduce cytotoxic T-lymphocyte responses against a vector-encoded antigen in vitro. Gene Ther 6:845-853.
Dietz, et al. 1998. High efficiency adenovirus-mediated gene transfer to human dendritic cells. Blood 91:392-398.
Ding, et al. (2002) Efficacy of Gene Therapy for a Prototypical Lysosomal Storage Disease (GSD-II) Is Critically Dependent on Vector Dose, Transgene Promoter, and the Tissues Targeted for Vector Transduction. Molecular Ther. 5:436-446.
Ding, et al. Long-term efficacy after [E1-, polymerase-] adenovirus-mediated transfer of human acid-alpha-glucosidase gene into glycogen storage disease type II knockout mice. Hum Gene Ther 12;955-65 (2001).
Dix, et al. Use of monoclonal antibody directed against herpes simplex virus glycoproteins to protect mice against acute virus-induced neurological disease. Infect Immun 34;192-9. (1981).
Doerfler. In Adenovirus DNA. The Viral Genome and its Expression. Martinus Nijhoff Publishing Boston, 1986.
Donahue, et al. The integrin alpha v gene: identification and characterization of the promoter region. Biochim Biophys Acta. Sep. 13, 1994;1219(1):228-32.
Dunaway, et al. The activity of the scs and scs' insulator elements is not dependent on chromosomal context. Mol Cell Biol. Jan. 1997;17(1):182-9.
Eder, et al. (2000) A phase I trial of a recombinant vaccinia virus expressing prostate-specific antigen in advanced prostate cancer. Clin Cancer Res 6:1632-1638.
Ehrenfeld, et al. Anatomy of the poliovirus internal ribosome entry site. Curr Top Microbiol Immunol. 1995;203:65-83.
Eisenhauer, et al. (2009) New response evaluation criteria in solid tumors: revised RECIST guideline (version 1.1). Eur J Cancer 45:228-247.
Eo, et al. Prime-boost immunization with DNA vaccine: mucosal route of administration changes the rules. J Immunol 166;5473-9 (2001).
Epstein, et al. Protection against multiple influenza A subtypes by vaccination with highly conserved nucleoprotein. Vaccine, 2005. 23(46-47): p. 5404-10.
Ertl, et al. Novel vaccine approaches. J Immunol. 156:3579-3582 (1996).
Etubics press release. Etubics and Duke Cancer Institute report positive phase I/II results for colorectal cancer immunotherapy. Etubics corporation. Seattle (May 16, 2012) http://www.etubics.com/news/Press%20Release-%20ASCO%202012.pdf.
European Application No. 16153921.8-1412 Extended Search report dated Jun. 22, 2016.
European search report dated Mar. 28, 2013 for EP Application No. 08781241.8.
Evans, et al. Development of stable liquid formulations for adenovirus-based vaccines. J Pharm Sci. Oct. 2004;93(10):2458-75.
Everett, et al. Liver toxicities typically induced by first-generation adenoviral vectors can be reduced by use of E1, E2b-deleted adenoviral vectors. Hum Gene Ther, 2003. 14(18): p. 1715-26.
Everett, et al. Strain-specific rate of shutdown of CMV enhancer activity in murine liver confirmed by use of persistent [E1(-), E2b(-)] adenoviral vectors. Virology. Jul. 20, 2004; 325(1):96-105.
Feldmann, et al. Molecular biology and evolution of filoviruses. Arch Virol Suppl. 1993;7:81-100.
Fisher-Hoch, et al. Protection of rhesus monkeys from fatal Lassa fever by vaccination with a recombinant vaccinia virus containing the Lassa virus glycoprotein gene. Proc Natl Acad Sci U S A. Jan. 1989;86(1):317-21.
Fleming, et al. Herpes simplex virus type 2 in the United States, 1976 to 1994. N Engl J Med 337;1105-11. (1997).
Flexner, et al. Attenuation and immunogenicity in primates of vaccinia virus recombinants expressing human interleukin-2. Vaccine. Feb. 1990;8(1):17-21.
Foon, et al. 1997. Clinical and immune responses in advanced colorectal cancer patients treated with anti-idiotype monoclonal antibody vaccine that mimics the carcinoembryonic antigen. Clin Cancer Res 3:1267-1276.
Foon, et al. 1999. Clinical and immune responses in resected colon cancer patients treated with anti-idiotype monoclonal antibody vaccine that mimics the carcinoembryonic antigen. J Clin Oncol 17:2889-2895.
Gabaglia, et al. A single intramuscular injection with an adenovirus-expressing IL-12 protects BALB/c mice against Leishmania major infection, while treatment with an IL-4-expressing vector increases disease susceptibility in B10.D2 mice.J Immunol 162:.2 753-760 (1999).
Gabitzch; et al., "Gabitzch et al. Induction and comparison of SIV immunity in Ad5 naïve and Ad5 immune non-human primates using an Ad5 [E1-, E2b-] based vaccine. Vaccine. Oct. 19, 2011; 29(45):8101-7."
Gabitzsch, et al. (2009) Novel adenovirus type 5 vaccine platform induces cellular immunity aginst HIV-Gag, Pol, Nef despite the presence of Ad5 immunity. Vaccine 27:6394-6398.
Gabitzsch, et al. (2010) Anti-tumor immunity despite immunity to adenovirus using a novel adenoviral vector Ad5 [E1-, E2b-]-CEA. Cancer Immunol Immunother 59:1131-1135.
Gabitzsch, et al. (2011) an Ad5 [E1-, E2b-]-HER2/neu vector induces immune responses and inhibits HER2/neu expressing tumor progression in Ad5 immune mice. Cancer Gene Ther 18:326-335.
Gabitzsch, et al. (2011) Induction and Comparison of SIV immunity in Ad5 Naïve and Ad5 Immune Non-human Primates using an Ad5 [E1-, E2b-] based vaccine. Vaccine 29:8101-8107.
Gabitzsch, et al. (2011) New Recombinant Ad5 Vector Overcomes Ad5 Immunity Allowing for Multiple Safe, Homologous Immunizations. J Clin Cell Immunol. S4:001. doi:10.4172/2155-9899.S4-001.
Gabitzsch, et al. A preliminary and comparative evaluation of a novel Ad5 [E1-, E2b-] recombinant-based vaccine used to induce cell mediated immune responses. Immunol Lett. Jan. 29, 2009;122(1):44-51. doi: 10.1016/j.imlet.2008.11.003. Epub Dec. 13, 2008.
Gabitzsch, et al. An Ad5 [E1-, E2b-]-HER2/neu vector induces immune responses and inhibits HER2/neu expressing tumor progression in Ad5 immune mice. Cancer Gene Ther. May 2011; 18(5):326-335.
Gabitzsch et al. Anti-tumor immunotherapy despite immunity to adenovirus using a novel adenoviral vector Ad5 [E1-, E2b-]-CEA. Cancer Immunol Immunother. Jul. 2010; 59(7):1131-5.
Gabitzsch, et al. Control of SIV infection and subsequent induction of pandemic H1N1 immunity in rhesus macaques using an Ad5 [E1-, E2b-] vector platform. Vaccine Nov. 26, 2012; 30(50):7265-7270.
Gabitzsch, et al. New Recombinant Ad5 Vector Overcomes Ad5 Immunity Allowing for Multiple Safe, Homologous Immunizations. J Clin Cell Immunol. 2011; S4-001.

(56) References Cited

OTHER PUBLICATIONS

Gabitzsch, et al. Novel adenovirus type 5 vaccine platform induces cellular immunity against HIV-Gag, Pol, Nef despite the presence of Ad5 immunity. Vaccine. Oct. 30, 2009; 27(46):6394-9398.
Gallichan, et al. Long-lived cytotoxic T lymphocyte memory in mucosal tissues after mucosal but not systemic immunization. J Exp Med 184;1879-90 (1996).
Gallichan, et al. Long-term immunity and protection against herpes simplex virus type 2 in the murine female genital tract after mucosal but not systemic immunization. J Infect Dis 177;1155-61 (1998).
Gallichan, et al. Mucosal immunity and protection after intranasal immunization with recombinant adenovirus expressing herpes simplex virus glycoprotein B. J Infect Dis 168;622-9. (1993).
Gallichan, et al. Mucosal immunization with a recombinant adenovirus vector induces local and systemic immunity and protection from herpes simplex virus. Adv Exp Med Biol, 1995. 371B: p. 1581-5.
Gao et al. Protection of mice and poultry from lethal H5N1 avian influenza virus through adenovirus-based immunization. J Virol, 2006. 80(4): p. 1959-64.
Garnett, et al. TRICOM vector based cancer vaccines. Curr Pharm Des. 2006;12(3):351-61.
Gaynor, et al. Cis-acting induction of adenovirus transcription. Cell. Jul. 1983;33(3):683-93.
Gdula, et al. Genetic and molecular analysis of the gypsy chromatin insulator of *Drosophila*. Proc Natl Acad Sci U S A. Sep. 3, 1996;93(18):9378-83.
Gennaro. Remington's Pharmaceutical Sciences. 17th Edition, 1985.
Gomez-Roman, et al. Adenoviruses as vectors for HIV vaccines. AIDS Rev 5;178-85 (2003).
Goping, et al. A gene-type-specific enhancer regulates the carbamyl phosphate synthetase I promoter by cooperating with the proximal GAG activating element. Nucleic Acids Res. May 25, 1995;23(10):1717-21.
Gorzigilia, et al. Elimination of both E1 and E2 from adenovirus vectors further improves prospects for in vivo human gene therapy. J Virol. Jun. 1996;70(6):4173-8.
Greene, et al. Envelope glycoprotein mutations mediate equine amplification and virulence of epizootic venezuelan equine encephalitis virus. J Virol 79:9128-33. (2005).
Gulley, et al. (2002) Phase I study of a vaccine using recombinant vaccinia virus expressing PSA (rV-PSA) in patients with metastatic androgen-independent prostate cancer. Prostate 53:109-117.
Gulley, et al. (2010) Immunologic and prognostic factors associated with overall survival employing a poxviral-based PSA vaccine in metastatic castrate-resistant prostate cancer. Cancer Immunol Immunother 59:663-674.
Gulley, et al. (2011) Impact of tumor volume on the potential efficacy of therapeutic vaccines. Curr Oncol 8:150-157.
Guzman, et al. Efficient and selective adenovirus-mediated gene transfer into vascular neointima. Circulation. Dec. 1993;88(6):2838-48.
Guzman, et al. Efficient gene transfer into myocardium by direct injection of adenovirus vectors. Circ Res. Dec. 1993;73(6):1202-7.
Haecker, et al. Repression of the ovalbumin gene involves multiple negative elements including a ubiquitous transcriptional silencer. Mol Endocrinol. Sep. 1995;9(9):1113-26.
Haglund, et al. Robust recall and long-term memory T-cell responses induced by prime-boost regimens with heterologous live viral vectors expressing human immunodeficiency virus type 1 Gag and Env proteins. J Virol 76;7506-17 (2002).
Hammarstrom, S. (1999) The carcinoembryonic antigen (CEA) family: structures, suggested functions and expression in normal and malignant tissues. Semin Cancer Biol 9: 67-81.
Hampton, R. Serological Methods, a Laboratory Manual. APS Press, St. Paul, Minnesota, (1990).
Handman. Leishmaniasis: current status of vaccine development. Clin Microbiol Rev 14:.2 229-243 (2001).
Hanke, et al. Effective induction of simian immunodeficiency virus-specific cytotoxic T lymphocytes in macaques by using a multiepitope gene and DNA prime—modified vaccinia virus Ankara boost vaccination regimen. J Virol 73;7524-32. (1999). 0.
Harandi, et al. A protective role of locally administered immunostimulatory CpG oligodeoxynucleotide in a mouse model of genital herpes infection. J Virol 77;953-62 (2003).
Harindranath, et al. Structure of the VH and VL segments of polyreactive and monoreactive human natural antibodies to HIV-1 and *Escherichia coli* ?-galactosidase. International Immunology. Dec. 1993; 5(12): 1523-1533. Abstract only.
Harlow and Lane, Antibodies: A Laboratory Manual, Cold Spring Harbor Laboratory, 1988.
Harris, et al. (2002) Acute Regression of Advanced and Retardation of Early Aortic Atheroma in Immunocompetent Apolipoprotein-E (Apoe) Deficient Mice by Administration of a Second Generation [E1 (−), E3(−), Polymerase(−)] Adenovirus Vector Expressing Human Apoe. Human Molecular Genetics 11:43-58.
Hartigan-O'Connor, et al. Developments in gene therapy for muscular dystrophy. Microsc Res Tech 48;223-38 (2000).
Hartigan-O'Connor, et al. Efficient rescue of gutted adenovirus genomes allows rapid production of concentrated stocks without negative selection. Hum Gene Ther. Mar. 1, 2002;13(4):519-31.
Hartigan-O'Connor, et al. Generation and growth of gutted adenoviral vectors. Methods Enzymol 346;224-46 (2002).
Hartigan-O'Connor, et al. Immune evasion by muscle-specific gene expression in dystrophic muscle. Mol Ther. Dec. 2001;4(6):525-33.
Hartigan-O'Connor, et al. Improved production of gutted adenovirus in cells expressing adenovirus preterminal protein and DNA polymerase. J Virol 73;7835-7841 (1999a).
Hartman, et al. Adenoviral infection induces a multi-faceted innate cellular immune response that is mediated by the toll-like receptor pathway in A549 cells. Virology. Feb. 20, 2007;358(2):357-72. Epub Oct. 5, 2006.
Hartman, et al. Adenovirus infection triggers a rapid, MyD88-regulated transcriptome response critical to acute-phase and adaptive immune responses in vivo. J Virol. Feb. 2007;81(4):1796-812. Epub Nov. 22, 2006.
Harui, et al. 2004. Vaccination with helper-dependent adenovirus enhances the generation of transgene-specific CTL. Gene Ther 11:1617-1626.
Hauser, et al. Analysis of muscle creatine kinase regulatory elements in recombinant adenoviral vectors. Mol Ther 2;16-25 (2000).
Hauser, et al. Improved adenoviral vectors for gene therapy of Duchenne muscular dystrophy. Neuromuscul Disord 7;277-83 (1997).
Hein, J. Unified approach to alignment and phylogenies. Methods Enzymol. 1990;183:626-45.
Henikoff, et al. Amino acid substitution matrices from protein blocks. Proc Natl Acad Sci U S A. Nov. 15, 1992;89(22):10915-9.
Higano, et al. (2009) Integrated data from 2 randomized, double-blind, placebo-controlled, phase 3 trials of active cellular immunotherapy with sipuleucel-T in advanced prostate cancer. Cancer 115:3670-3679.
Higgins, et al. Fast and sensitive multiple sequence alignments on a microcomputer. Comput Appl Biosci. Apr. 1989;5(2):151-3.
Hirschowitz, et al. 2000. Murine dendritic cells infected with adenovirus vectors show signs of activation. Gene Ther 7:1112-1120.
Hodge, et al. 1997. Diversified prime and boost protocols using recombinant vaccinia virus and recombinant non-replicating avian pox virus to enhance T-cell immunity and antitumor responses. Vaccine 15:759-768.
Hodges, et al. (2000) Multiply deleted [E1, polymerase-, and pTP-] adenovirus vector persists despite deletion of the preterminal protein. J Gene Med 2:250-259.
Hodges, et al. (2001) Adenovirus Vectors With the 100K Gene Deleted and Their Potential for Multiple Gene Therapy Applications. J Virol. 75:5913-5920.
Hodges, et al. Adenovirus vectors with the 100K gene deleted and their potential for multiple gene therapy applications. J Virol. Jul. 2001;75(13):5913-20.
Hoelscher, et al. Development of adenoviral-vector-based pandemic influenza vaccine against antigenically distinct human H5N1 strains in mice. Lancet, 2006. 367(9509): p. 475-81.

(56) References Cited

OTHER PUBLICATIONS

Horig, et al. 2000. Phase I clinical trial of a recombinant canarypoxvirus (ALVAC) vaccine expressing human carcinoembryonic antigen and the B7.1 co-stimulatory molecule. Cancer Immunol Immunother 49:504-514.

Hu, et al. Functional analyses of albumin expression in a series of hepatocyte cell lines and in primary hepatocytes. Cell Growth Differ. Sep. 1992;3(9):577-88.

Hu, et al. Persistence of an [E1-, polymerase-] adenovirus vector despite transduction of a neoantigen into immune-competent mice. Hum Gene Ther 10;355-64 (1999).

Huang Chun-Ming et al. A differential proteome in tumors suppressed by an adenovirus-based skin patch vaccine encoding human carcinoembryonic antigen. Proteomics, 5(4); 1013-1023 (Mar. 2005).

Huang, et al. Human immunodeficiency virus type 1-specific immunity after genetic immunization is enhanced by modification of Gag and Pol expression. J Virol. 75:4947-51 (2001).

Imler. Adenovirus vectors as recombinant viral vaccines. Vaccine. 13:1143-1151 (1995).

International search report and written opinion dated Jan. 7, 2014 for PCT Application No. US2013/032688.

International search report and written opinion dated Dec. 29, 2008 for PCT/US2008/068924.

Ishida, et al. 1999. Dendritic cells transduced with wild-type p53 gene elicit potent anti-tumour immune responses. Clin Exp Immunol 117:244-251.

Jin, et al. Dramatic rise in plasma viremia after CD8(+) T cell depletion in simian immunodeficiency virus-infected macaques. J Exp Med 189;991-8 (1999).

Jones. Advancement of a Novel Cancer Immunotherapeutic into Clinical Trials Through SBIR Granting Mechanisms. 13th Annual NIH SBIR/STTR Conference Poster Abstracts. 2011. http://grants.nih.gov/grants/funding/SBIRConf2011/docs/Abstracts_for_printing.pdf.

Jones, et al. (2011) Prevention of influenza virus shedding and protection from lethal H1N1 challenge using a consensus 2009 H1N1 HA and NA adenovirus vector vaccine. Vaccine 29:7020-7026.

Jonker, et al. (2007) Cetuximab for the treatment of colorectal cancer. N Engl J Med 357:2040-2048.

Jonuleit, et al. 2000. Efficient transduction of mature CD83+ dendritic cells using recombinant adenovirus suppressed T cell stimulatory capacity. Gene Ther 7:249-254.

Jooss, et al. Transduction of dendritic cells by DNA viral vectors directs the immune response to transgene products in muscle fibers. J Virol 72;4212-23 (1998).

Joshi, et al. (2009) Adenovirus DNA polymerase is recognized by human CD8+ T cells. J Gen Virol 90:84-94.

Kafri, et al. Cellular immune response to adenoviral vector infected cells does not require de novo viral gene expression: implications for gene therapy. Proc Natl Acad Sci U S A 95;11377-82 (1998).

Kalos, et al. Position-independent transgene expression mediated by boundary elements from the apolipoprotein B chromatin domain. Mol Cell Biol. Jan. 1995;15(1):198-207.

Kantoff, et al. (2010) Overall survival analysis of a phase II randomized controlled trial of a Poxviral-based PSA-targeted immunotherapy in metastatic castration-resistant prostate cancer. J Clin Oncol 28:1099-1105.

Kantoff, et al. (2010) Sipuleucel-T immunotherapy for castration-resistant prostate cancer. N Engl J Med 363:411-422.

Karapetis, et al. (2008) K-ras mutations and benefit from Cetuximab in advanced colorectal cancer. New Engl J Med 359:1757-1765.

Karem, et al. Protective immunity against herpes simplex virus (HSV) type 1 following oral administration of recombinant *Salmonella typhimurium* vaccine strains expressing HSV antigens. J Gen Virol 78 ( Pt 2);427-34 (1997).

Kass, et al. 1999. Induction of protective host immunity to carcinoembryonic antigen (CEA), a self-antigen in CEA transgenic mice, by immunizing with a recombinant vaccinia-CEA virus. Cancer Res 59:676-683.

Kass, et al. 2001. Granulocyte/macrophage-colony stimulating factor produced by recombinant avian poxviruses enriches the regional lymph nodes with antigen-presenting cells and acts as an immunoadjuvant. Cancer Res 61:206-214.

Kass-Eisler, et al. Quantitative determination of adenovirus-mediated gene delivery to rat cardiac myocytes in vitro and in vivo. Proc Natl Acad Sci U S A. Dec. 15, 1993;90(24):11498-502.

Kaufman, et al. (2004) Phase II randomized study of vaccine treatment of advanced prostate cancer (E7897): A trial of the Eastern Cooperative Oncology Group. J Clin Oncol 22:2122-2132.

Kawashima, et al. (1998) The multi-epitope approach for immunotherapy for cancer: identification of several CTL epitopes from various tumor-associated antigens expressed on solid epithelial tumors. Hum Immunol. 59:1-14.

Kawashima, et al. (1999) Identification of HLA-A3-restricted cytotoxic T lymphocyte epitopes from carcinoembryonic antigen and HER-2/neu by primary in vitro immunization with peptide-pulsed dendritic cells. Cancer Res. 59:431-435.

Kemp, et al. Dichotomy of the human T cell response to Leishmania antigens. I. Th1-like response to Leishmania major promastigote antigens in individuals recovered from cutaneous leishmaniasis. Clin Exp Immunol 96:.3 410-15 (1994).

Khanam, et al. An adenovirus prime/plasmid boost strategy for induction of equipotent immune responses to two dengue virus serotypes. BMC Biotechnol 7:.1-11 (2007).

Kiang et al. Fully deleted Ad persistently expressing GAA accomplishes long-term skeletal muscle glycogen correction in tolerant and nontolerant GSD-II mice. Mol Ther, 2006. 13(1):127.

Kiang, et al. Multiple innate inflammatory responses induced after systemic adenovirus vector delivery depend on a functional complement system. Mol Ther. Oct. 2006;14(4):588-98. Epub Jun. 2, 2006.

Kim, et al. (1998) In vitro induction of HLA-A2402-restricted and carcinoembryonic-antigen-specific cytotoxic T lymphocytes on fixed autologous peripheral blood cells. Cancer Immunol. Immunother. 47:90-96.

Kinney, et al. Nucleotide sequences of the 26S mRNAs of the viruses defining the Venezuelan equine encephalitis antigenic complex. Am J Trop Med Hyg 59:952-64. (1998).

Kirk, et al. Gene-modified dendritic cells for use in tumor vaccines. Hum Gene Ther 11;797-806 (2000).

Kirk, et al. T cell-dependent antitumor immunity mediated by secondary lymphoid tissue chemokine: augmentation of dendritic cell-based immunotherapy. Cancer Res 61;2062-70 (2001b).

Kirk, et al. The dynamics of the T-cell antitumor response: chemokine-secreting dendritic cells can prime tumor-reactive T cells extranodally. Cancer Res 61;8794-802 (2001a).

Kolls, et al. Prolonged and effective blockade of tumor necrosis factor activity through adenovirus-mediated gene transfer. Proc Natl Acad Sci U S A. Jan. 4, 1994;91(1):215-9.

Kong, et al. Immunogenicity of multiple gene and clade human immunodeficiency virus type 1 DNA vaccines. J Virol. 77:12764-72 (2003).

Koup, et al. Temporal association of cellular immune responses with the initial control of viremia in primary human immunodeficiency virus type 1 syndrome. J Virol 68;4650-5 (1994).

Krougliak, et al. Development of cell lines capable of complementing E1, E4, and protein IX defective adenovirus type 5 mutants. Hum Gene Ther. Dec. 1995;6(12):1575-86.

Kuklin, et al. Role of mucosal immunity in herpes simplex virus infection. J Immunol 160;5998-6003 (1998).

Kumar-Singh, et al. Encapsidated adenovirus minichromosomes allow delivery and expression of a 14 kb dystrophin cDNA to muscle cells. Hum Mol Genet 5;913-21 (1996).

Lasic, DD. Novel applications of liposomes. Trends Biotechnol. Jul. 1998;16(7):307-21.

Lauer, et al. Natural variation among human adenoviruses: genome sequence and annotation of human adenovirus serotype 1. J Gen Virol. Sep. 2004;85(Pt 9):2615-25.

Lemaigre, et al. Identification of regulatory sequences and protein-binding sites in the liver-type promoter of a gene encoding 6-phosphofructo-2-kinase/fructose-2,6-bisphosphatase. Mol Cell Biol. Feb. 1991;11(2):1099-106.

(56) References Cited

OTHER PUBLICATIONS

Lemiale, et al. Enhanced mucosal immunoglobulin a response of intranasal adenoviral vector human immunodeficiency virus vaccine and localization in the central nervous system. J Virol 77;10078-87 (2003).
Letvin, et al. Heterologous envelope immunogens contribute to AIDS vaccine protection in rhesus monkeys. J Virol. 78;7490-7 (2004).
Leza, et al. Cellular transcription factor binds to adenovirus early region promoters and to a cyclic AMP response element. J Virol. Aug. 1988;62(8):3003-13.
Logan, et al. Adenovirus tripartite leader sequence enhances translation of mRNAs late after infection. Proc Natl Acad Sci U S A. Jun. 1984;81(12):3655-9.
Loser, et al. 1998. Reactivation of the previously silenced cytomegalovirus major immediate-early promoter in the mouse liver: involvement of NFkappaB. J Virol 72:180-190.
Lowery, et al. CRF-1 antagonist and CRF-2 agonist decrease binge-like ethanol drinking in C57BL/6J mice independent of the HPA axis. Neuropsychopharmacology 35.6 (2010): 1241-1252.
Lozier, et al. Toxicity of a first-generation adenoviral vector in rhesus macaques. Hum Gene Ther 13;113-24 (2002).
Lu, et al. 1999. Adenoviral delivery of CTLA4lg into myeloid dendritic cells promotes their in vitro tolerogenicity and survival in allogeneic recipients. Gene Ther 6:554-563.
Lubaroff, et al. Clinical protocol: phase I study of an adenovirus/prostate-specific antigen vaccine in men with metastatic prostate cancer. Hum Gene Ther. 17:220-229 (2006).
Luebke, et al. (2001) A Modified Adenovirus Can Transfect Cochlear Hair Cells in Vivo Without Compromising Cochlear Function. Gene Ther. 8:789-794.
Maddox, et al. Elevated serum levels in human pregnancy of a molecule immunochemically similar to eosinophil granule major basic protein. J Exp Med. Oct. 1, 1983;158(4):1211-26.
Maione, et al. An improved helper-dependent adenoviral vector allows persistent gene expression after intramuscular delivery and overcomes preexisting immunity to adenovirus. Proc Natl Acad Sci U S A. May 22, 2001;98(11):5986-91. Epub May 15, 2001.
Maione, et al. Prolonged expression and effective readministration of erythropoietin delivered with a fully deleted adenoviral vector. Hum Gene Ther. Apr. 10, 2000;11(6):859-68.
Maniatis, et al. Molecular Cloning. Cold Spring Harbor Laboratory, 1982.
Manickan, et al. Vaccination with recombinant vaccinia viruses expressing ICP27 induces protective immunity against herpes simplex virus through CD4+ Th1+ T cells. J Virol 69;4711-6 (1995a).
Margalit, R. Liposome-mediated drug targeting in topical and regional therapies. Crit Rev Ther Drug Carrier Syst. 1995;12(2-3):233-61.
Marshall, et al. 1999. Phase I study in cancer patients of a replication-defective avipox recombinant vaccine that expresses human carcinoembryonic antigen. J Clin Oncol 17:332-337.
Marshall, et al. 2000. Phase I study in advanced cancer patients of a diversified prime- and-boost vaccination protocol using recombinant vaccinia virus and recombinant nonreplicating avipox virus to elicit anti-carcinoembryonic antigen immune responses. J Clin Oncol 18:3964-3973.
Marshall, et al. Phase I study of sequential vaccinations with fowlpox-CEA(6D)-TRICOM alone and sequentially with vaccinia-CEA(6D)-TRICOM, with and without granulocyte-macrophage colony-stimulating factor, in patients with carcinoembryonic antigen-expressing carcinomas. J Clin Oncol. Feb. 1, 2005;23(4):720-31. Epub Dec. 21, 2004.
Marshall, John L. et al. Phase I study in advanced cancer patients of a diversified prime- and-boost vaccination protocol using recombinant vaccinia virus and recombinant nonreplicating avipox virus to elicit anti-carcinoembryonic antigen immune responses, Journal of Clinical Oncology, American Society of Clinical Oncology, US 18(23);3964-3973 (Dec. 1, 2000).

Martin-Padura, et al. Expression of VE (vascular endothelial)-cadherin and other endothelial-specific markers in haemangiomas. J Pathol. Jan. 1995;175(1):51-7.
Mata, et al. The MHC class I-restricted immune response to HIV-Gag in BALB/c mice selects a single epitope that does not have a predictable MHC-binding motif and binds to Kd through interactions between a glutamine at P3 and pocket D. J Immunol 161;2985-93 (1998).
Mccoy, et al. Effect of preexisting immunity to adenovirus human serotype 5 antigens on the immune responses of nonhuman primates to vaccine regimens based on human- or chimpanzee-derived adenovirus vectors. J Virol. Jun. 2007;81(12):6594-604. Epub Apr. 11, 2007.
Mcdermott, et al. Cytotoxic T-Lymphocyte Escape Does Not Always Explain the Transient Control of Simian Immunodeficiency Virus SIVmac239 Viremia in Adenovirus-Boosted and DNA-Primed Mamu-A01-Positive Rhesus Macaques. J Virol. 79:15556-66 (2005).
Mcdermott, et al. Immunity in the female genital tract after intravaginal vaccination of mice with an attenuated strain of herpes simplex virus type 2. J Virol 51;747-53 (1984).
Mcdermott, et al. Protection of mice against lethal challenge with herpes simplex virus by vaccination with an adenovirus vector expressing HSV glycoprotein B. Virology 169;244-7. (1989b).
Mcmichael, et al. The quest for an AIDS vaccine: is the CD8+ T-cell approach feasible? Nat Rev Immunol. Apr. 2002;2(4):283-91.
Miller, et al. 2000. Intratumoral administration of adenoviral interleukin 7 gene-modified dendritic cells augments specific antitumor immunity and achieves tumor eradication. Hum Gene Ther 11:53-65.
Milligan, et al. T lymphocytes are required for protection of the vaginal mucosae and sensory ganglia of immune mice against reinfection with herpes simplex virus type 2. J Immunol 160;6093-100 (1998).
Miralles, et al. The adenovirus inverted terminal repeat functions as an enhancer in a cell-free system. J Biol Chem. Jun. 25, 1989;264(18):10763-72.
Mitani, et al. Rescue, propagation, and partial purification of a helper virus-dependent adenovirus vector. Proc Natl Acad Sci U S A. Apr. 25, 1995;92(9):3854-8.
Mizuno, et al. A silencer-like cis element for the testis-specific phosphoglycerate-kinase-2-encoding gene. Gene. Oct. 1, 1992;119(2):293-7.
Mohebtash, et al. A pilot study of MUC-1/CEA/TRICOM poxviral-based vaccine in patients with metastatic breast and ovarian cancer. Clin Cancer Res. Nov. 15, 2011;17(22):7164-73. doi: 10.1158/1078-0432.CCR-11-0649. Epub Nov. 8, 2011.
Mole, et al. The impact of active herpes simplex virus infection on human immunodeficiency virus load. J Infect Dis 176;766-70 (1997).
Moog, et al. Autologous and heterologous neutralizing antibody responses following initial seroconversion in human immunodeficiency virus type 1-infected individuals. J Virol 71;3734-41 (1997).
Moore, et al. Effects of antigen and genetic adjuvants on immune responses to human immunodeficiency virus DNA vaccines in mice. J Virol 76;243-50 (2002).
Moorhead, et al. A replication-incompetent adenovirus vector with the preterminal protein gene deleted efficiently transduces mouse ears. J Virol. Feb. 1999;73(2):1046-53.
Morelli, et al. 2000. Recombinant adenovirus induces maturation of dendritic cells via an NF-kappaB-dependent pathway. J Virol 74:9617-9628.
Morral, et al. 1998. High doses of a helper-dependent adenoviral vector yield supraphysiological levels of alpha1-antitrypsin with negligible toxicity. Hum Gene Ther 9:2709-2716.
Morse, et al. (2005) Phase I study of immunization with dendritic cells modified with recombinant fowlpox encoding carcinoembryonic antigen and the triad of costimulatory molecules CD54, CD58, and CD80 in patients with advanced malignancies. Clin Cancer Res 11:3017-3024.
Morse, et al. (2008) Depletion of human regulatory T cells specifically enhances antigen-specific immune responses to cancer vaccines. Blood 112:610-618.

(56) References Cited

OTHER PUBLICATIONS

Morse, et al. (2010) An alphavirus vector overcomes the presence of neutralizing antibodies and elevated numbers of Tregs to induce immune responses in humans with advanced cancer. J Clin Invest 120:3234-3241.
Morse, et al. (2013) Novel Adenoviral Vector Induces T Cell Responses Despite Anti-Adenoviral Neutralizing Antibodies in Colorectal Cancer Patients. Cancer Immunol Immunother. 62:1293-1301.
Morse, et al. Effect of the vaccine Ad5 [E1-, E2b-]-CEA(6D) on CEA-directed CMI responses in patients with advanced CEA-expressing malignancies in a phase I/II clinical trial. Etubics Corporation, Seattle, WA. Poster. 2012. http://www.etubics.com/pdf/ASCO%202012.pdf.
Morse, et al. Synergism from combined immunologic and pharmacologic inhibition of HER2 in vivo. Int J Cancer. Jun. 15, 2010;126(12):2893-903.
Morsy, et al. An adenoviral vector deleted for all viral coding sequences results in enhanced safety and extended expression of a leptin transgene. Proc Natl Acad Sci U S A 95;7866-71 (1998).
Moss, et al. Vaccinia virus expression vectors. Ann N Y Acad Sci. 1989;569:86-103.
Mossman, et al. TH1 and TH2 cells: different patterns of lymphokine secretion lead to different functional properties. Annu Rev Immunol. 1989;7:145-73.
Muller, et al. Efficient transfection and expression of heterologous genes in PC12 cells. DNA Cell Biol. Apr. 1990;9(3):221-9.
Myers, et al. Optimal alignments in linear space. Comput Appl Biosci. Mar. 1988;4(1):11-7.
Najera, et al. Pol gene quasispecies of human immunodeficiency virus: mutations associated with drug resistance in virus from patients undergoing no drug therapy. J Virol 69;23-31 (1995).
Nazir, et al. Innate immune response to adenovirus. J Investig Med. Sep. 2005;53(6):292-304.
Needleman, et al. A general method applicable to the search for similarities in the amino acid sequence of two proteins. J Mol Biol. Mar. 1970;48(3):443-53.
Nemunaitis, et al. Pilot trial of intravenous infusion of a replication-selective adenovirus (ONYX-015) in combination with chemotherapy or IL-2 treatment in refractory cancer patients. Cancer Gene Ther. 10:341-352 (2003).
Nevins, Jr. Mechanism of activation of early viral transcription by the adenovirus E1A gene product. Cell. Oct. 1981;26(2 Pt 2):213-20.
Notice of allowance dated Nov. 15, 2016 for U.S. Appl. No. 14/422,504.
Notice of Allowance in U.S. Appl. No. 14/163,331 dated May 13, 2016.
Nukaya, et al. (1999) Identification of HLA-A24 epitope peptides of carcinoembryonic antigen which induce tumor-reactive cytotoxic T lymphocyte. Int. J. Cancer 80:92-97.
Nwanegbo, et al. (2004) Prevalence of neutralizing antibodies to adenoviral serotypes 5 and 35 in the adult populations of The Gambia, South Africa, and the United States. Clin Diagn Lab Immunol 11:351-357.
Office action dated Apr. 3, 2017 for U.S. Appl. No. 13/622,263.
Office action dated Apr. 19, 2012 for U.S. Appl. No. 12/651,836.
Office action dated May 9, 2017 for U.S. Appl. No. 15/265,723.
Office action dated Sep. 26, 2011 for U.S. Appl. No. 12/651,836.
"Ojima, T. et al. Successful cancer vacine therapy for carcinoembryonic antigen (CEA)—expressing colon cancer using genetically modified dendritic cells that express CEA and T helper-type 1 cytokine in CEA transgenic mice, International Journal of Cancer 120, 585-593 (2006)."
Openshaw, et al. Immune responses and disease enhancement during respiratory syncytial virus infection. Clin Microbiol Rev, 2005. 18(3): p. 541-55.
Ortega, et al. Single-step purification on DEAE-sephacel of recombinant polypeptides produced in *Escherichia coli*. Biotechnology (N Y). Jul. 1992;10(7):795-798.
Osada, et al. (2009) Optimization of vaccine responses with an E1, E2b and E3-deleted Ad5 vector circumvents pre-existing anti-vector immunity. Cancer Gene Ther 16:673-682.
Osada, et al. Optimization of vaccine responses with an E1, E2b and E3-deleted Ad5 vector circumvents pre-existing anti-vector immunity. Cancer Gene Ther.vol. 16, Issue No. 9, pp. 673-82 (Sep. 2009).
Palena, et al. (2010) Vaccines against human carcinomas: Strategies to improve antitumor immune responses. J Biomed Biotechnol 2010:380697=.
Palucka, et al. (2011) Dendritic cells and immunity against cancer. J Inter Med 269:64-73.
Paoletti, E. 1996. Applications of pox virus vectors to vaccination: an update. Proc Natl Acad Sci U S A 93:11349-11353.
Parker, et al. Scheme for ranking potential HLA-A2 binding peptides based on independent binding of individual peptide side-chains. J Immunol. Jan. 1, 1994;152(1):163-75.
Parks, et al. A helper-dependent adenovirus vector system: removal of helper virus by Cre-mediated excision of the viral packaging signal. Proc Natl Acad Sci U S A. Nov. 26, 1996;93(24):13565-70.
Parr, et al. Immunoglobulin G is the main protective antibody in mouse vaginal secretions after vaginal immunization with attenuated herpes simplex virus type 2. J Virol 71;8109-15. (1997).
Parr, et al. Mucosal immunity to herpes simplex virus type 2 infection in the mouse vagina is impaired by in vivo depletion of T lymphocytes. J Virol 72;2677-85 (1998).
Paul. Fundamental Immunology. 3rd Edition, pp. 243-247, Raven Press, 1993.
Pearson, et al. Improved tools for biological sequence comparison. Proc Natl Acad Sci U S A. Apr. 1988;85(8):2444-8.
Perkins, et al. Boosting with an adenovirus-based vaccine improves protective efficacy against Venezuelan equine encephalitis virus following DNA vaccination. Vaccine. 2006; 24:3440-5.
Phillpotts, et al. Intranasal immunization with defective adenovirus serotype 5 expressing the Venezuelan equine encephalitis virus E2 glycoprotein protects against airborne challenge with virulent virus. Vaccine 23:1615-1623. (2005).
Posavad, et al. Severe genital herpes infections in HIV-infected individuals with impaired herpes simplex virus-specific CD8+ cytotoxic T lymphocyte responses. Proc Natl Acad Sci U S A 94;10289-94 (1997).
Posavad, et al. T cell immunity to herpes simplex viruses in seronegative subjects: silent infection or acquired immunity? J Immunol 170;4380-8 (2003).
Pronk, et al. Adenovirus DNA replication: the function of the covalently bound terminal protein. Chromosoma. 1992;102(1 Suppl):S39-45.
Pyles, et al. Use of immunostimulatory sequence-containing oligonucleotides as topical therapy for genital herpes simplex virus type 2 infection. J Virol 76;11387-96 (2002).
Qiu, et al. Evaluation of novel human immunodeficiency virus type 1 Gag DNA vaccines for protein expression in mammalian cells and induction of immune responses. J Virol. 73:9145-52 (1999).
Qualikene, et al. Protease-deleted adenovirus vectors and complementing cell lines: potential applications of single-round replication mutants for vaccination and gene therapy. um Gene Ther. Jun. 10, 2000;11(9):1341-53.
Quintanar-Guerrero, et al. Preparation techniques and mechanisms of formation of biodegradable nanoparticles from preformed polymers. Drug Dev Ind Pharm. Dec. 1998;24(12):1113-28.
Ras, et al. (1997) Identification of potential HLA-A 0201 restricted CTL epitopes derived from the epithelial cell adhesion molecule (Ep-CAM) and the carcinoembryonic antigen (CEA). Hum. Immunol. 53:81-89.
Rea, et al. 1999. Adenoviruses activate human dendritic cells without polarization toward a T-helper type 1-inducing subset. J Virol 73:10245-10253.
Reddy, et al. Sustained human factor VIII expression in hemophilia a mice following systemic delivery of a gutless adenoviral vector. Mol Ther. Jan. 2002;5(1):63-73.
Rees, et al. Bicistronic vector for the creation of stable mammalian cell lines that predisposes all antibiotic-resistant cells to express recombinant protein. Biotechniques. Jan. 1996;20(1):102-4, 106, 108-10.

(56) References Cited

OTHER PUBLICATIONS

Renneisen, et al. Inhibition of expression of human immunodeficiency virus-1 in vitro by antibody-targeted liposomes containing antisense RNA to the env region. J Biol Chem. Sep. 25, 1990;265(27):16337-42.
Renzi, et al. Herpes simplex virus type 2 infection as a risk factor for human immunodeficiency virus acquisition in men who have sex with men. J Infect Dis 187;19-25. (2003).
Rettig, et al. Identification of endosialin, a cell surface glycoprotein of vascular endothelial cells in human cancer. Proc Natl Acad Sci U S A. Nov. 15, 1992;89(22):10832-6.
Ribas, et al. 1997. Genetic immunization for the melanoma antigen MART-1/Melan—A using recombinant adenovirus-transduced murine dendritic cells. Cancer Res 57:2865-2869.
Roberts, et al. Hexon-chimaeric adenovirus serotype 5 vectors circumvent pre-existing anti-vector immunity. Nature, 2006. 441(7090):239-43.
Robinson. Comparison of Labeled Trees with Valency Three. Journal of Combinatorial Theory 11:105-119 (1971).
Rodriques, et al. Importance of CD8 T cell-mediated immune response during intracellular parasitic infections and its implications for the development of effective vaccines. An Acad Bras Cienc 75:.4 443-468 (2003).
Rosenfeld, et al. Adenovirus-mediated transfer of a recombinant alpha 1-antitrypsin gene to the lung epithelium in vivo. Science. Apr. 19, 1991;252(5004):431-4.
Saitou, et al. The neighbor-joining method: a new method for reconstructing phylogenetic trees. Mol Biol Evol. Jul. 1987;4(4):406-25.
Samanci, et al. 1998. Pharmacological administration of granulocyte/macrophage-colony-stimulating factor is of significant importance for the induction of a strong humoral and cellular response in patients immunized with recombinant carcinoembryonic antigen. Cancer Immunol Immunother 47:131-142.
Sambrook, et al. (1989 Molecular Cloning, Second Ed., Cold Spring Harbor Laboratory, Plainview, NY).
Sanda, et al. (1999) Recombinant vaccinia-PSA (PROSTVAC) can induce a prostate specific immune response in androgen-modulated human prostate cancer. Urology 53:260-266.
Sandig, et al. Optimization of the helper-dependent adenovirus system for production and potency in vivo. Proc Natl Acad Sci U S A. Feb. 1, 2000;97(3):1002-7.
Santosuosso, et al. Mucosal luminal manipulation of T cell geography switches on protective efficacy by otherwise ineffective parenteral genetic immunization. J Immunol 178:.4 2387-395 (2007).
Sato, et al. Immunostimulatory DNA sequences necessary for effective intradermal gene immunization. Science. Jul. 19, 1996;273(5273):352-4.
Savanger, et al. Two silencers regulate the tissue-specific expression of the collagen II gene. J Biol Chem. Apr. 25, 1990;265(12):6669-74.
Schaack, et al. E1A and E1B proteins inhibit inflammation induced by adenovirus. Proc Natl Acad Sci U S A. Mar. 2, 2004;101(9):3124-9. Epub Feb. 19, 2004.
Schaack. Induction and inhibition of innate inflammatory responses by adenovirus early region proteins. Viral Immunol. 2005;18(1):79-88.
Schacker, et al. Frequent recovery of HIV-1 from genital herpes simplex virus lesions in HIV-1-infected men. Jama 280;61-6 (1998).
Scharf, et al. Heat stress promoters and transcription factors. Results Probl Cell Differ. 1994;20:125-62.
Schiedner, et al. Genomic DNA transfer with a high-capacity adenovirus vector results in improved in vivo gene expression and decreased toxicity [published erratum appears in Nat Genet Mar. 1998;18(3):298]. Nature Genetics 18;180-3 (1998).
Schirle, et al. (2000) Identification of tumor-associated MHC class I ligands by a novel T cell-independent approach. Eur. J. Immunol. 30:2216-2225.
Schmitz, et al. Control of viremia in simian immunodeficiency virus infection by CD8+ lymphocytes. Science 283;857-60 (1999).
Schneider, et al. Inactivation of the human immunodeficiency virus type 1 inhibitory elements allows Rev-independent expression of Gag and Gag/protease and particle formation. J Virol. 71:4892-903 (1997).
Scott, et al. Effects of the su(Hw) insulator protein on the expression of the divergently transcribed *Drosophila* yolk protein genes. EMBO J. Dec. 15, 1995;14(24):6258-67.
Scott, et al. Gutted adenoviral vectors for gene transfer to muscle. Methods Mol Biol 219;19-28 (2003).
Scott, et al. Viral vectors for gene transfer of micro-, mini-, or full-length dystrophin. Neuromuscul Disord 12 Suppl 1;523-9 (2002).
Seregin, et al. (2009) Overcoming pre-existing Adenovirus immunity by genetic engineering of Adenovirus-based vectors. Expert Opin Biol Ther 9:1-11.
Shiver, et al. Recent advances in the development of HIV-1 vaccines using replication-incompetent adenovirus vectors. Annu Rev Med. 55;355-72 (2004).
Shiver, et al. 2002. Replication-incompetent adenoviral vaccine vector elicits effective anti-immunodeficiency-virus immunity. Nature 415:331-335.
Sjolander, et al. Induction of a Th1 immune response and simultaneous lack of activation of a Th2 response are required for generation of immunity to leishmaniasis. J Immunol 160:.83949-957. (1998).
Skeiky, et al. LeIF: a recombinant Leishmania protein that induces an IL-12-medicated Th 1 cytokine profile. J Immunol 161, 6171-6179 (1998).
Skeiky, et al. A recombinant Leishmania antigen that stimulates human peripheral blood mononuclear cells to express a Th1-type cytokine profile and to produce interleukin 12. J Exp Med 181, 1527-1537 (1995).
Skeiky, et al. Cloning, expression, and immunological evaluation of two putative secreted serine protease antigens of Mycobacterium tuberculosis. Infect Immun. Aug. 1999;67(8):3998-4007.
Slack, et al. 2001. Association between CEA-specific T cell responses following treatment wiht vaccinia CEA and survival in patients with CEA bearing cancers (abstr 1086). In Proc Am Soc Clin Oncol 272a.
Small, et al. (2006) Placebo-controlled phase III trial of immunologic therapy with sipuleucel-T (APC8015) in patients with metastatic, asymptomatic hormone refractory prostate cancer. J Clin Oncol 24:3089-3094.
Smith, et al. Comparison of Biosequences. Advances in Applied Mathematics 2, 482-489, 1981.
Smith, et al., Transient immunosuppression permits successful repetitive intravenous administration of an adenovirus vector. Gene Ther, 1996. 3(6): p. 496-502.
Sneath, P.H.A. and Sokal, R.R., Numerical Taxonomy—the Principles and Practice of Numerical Taxonomy, Freeman Press, San Francisco, CA (1973).
Stanberry, et al. Glycoprotein-D-adjuvant vaccine to prevent genital herpes. N Engl J Med 347;1652-61. (2002).
Sugimoto, et al. Efficient expression of drug-selectable genes in retroviral vectors under control of an internal ribosome entry site. Biotechnology (N Y). Jul. 1994;12(7):694-8.
Sullivan, et al. Development of a preventive vaccine for Ebola virus infection in primates. Nature 408;605-9 (2000).
Sumida, et al. Neutralizing antibodies and CD8+ T lymphocytes both contribute to immunity to adenovirus serotype 5 vaccine vectors. J Virol. Mar. 2004;78(6):2666-73.
Takakura, et al. [Drug delivery systems in gene therapy]. Nihon Rinsho. Mar. 1998;56(3):691-5.
Takenaga, et al. Microparticle resins as a potential nasal drug delivery system for insulin. Control Release. Mar. 2, 1998;52(1-2):81-7.
Talmadge, et al. Murine models to evaluate novel and conventional therapeutic strategies for cancer. The American journal of pathology 170.3 (2007): 793-804.
Tan, et al. A re-evaluation of the frequency of CD8+ T cells specific for EBV in healthy virus carriers. J Immunol, 1999. 162(3): p. 1827-35.

(56) References Cited

OTHER PUBLICATIONS

Tangri, et al. Structural features of peptide analogs of human histocompatibility leukocyte antigen class I epitopes that are more potent and immunogenic than wild-type peptide. J Exp Med. Sep. 17, 2001; 194(6):833-846.

Tatsis, et al. (2004) Adenoviruses as vaccine vectors. Molecular Ther 10:616-629.

Tatsis, et al. A CD46-binding Chimpanzee Adenovirus Vector as a Vaccine Carrier. Mol Ther (2007).

Taylor, et al. 1991. Efficacy studies on a canarypox-rabies recombinant virus. Vaccine 9:190-193.

Thomas, et al. DNA replication and the early to late transition in adenovirus infection. Cell. Nov. 1980;22(2 Pt 2):523-33. 0.

Thomas, et al. Peripheral infection with adenovirus causes unexpected long-term brain inflammation in animals injected intracranially with first-generation, but not with high-capacity, adenovirus vectors: toward realistic long-term neurological gene therapy for chronic diseases. Proc Natl Acad Sci U S A 97;7482-7 (2000).

Thorner, et al. Immunogenicity of heterologous recombinant adenovirus prime-boost vaccine regimens is enhanced by circumventing vector cross-reactivity. J Virol. Dec. 2006;80(24):12009-16. Epub Oct. 11, 2006.

Tillman, et al. 2000. Adenoviral vectors targeted to CD40 enhance the efficacy of dendritic cell-based vaccination against human papillomavirus 16-induced tumor cells in a murine model. Cancer Res 60:5456-5463.

Treanor, et al. Safety and immunogenicity of an inactivated subviron influenza A (H5N1) N Engl J Med. 354:1343-1351 (2006).

Tsang, et al. (1995) Generation of human cytotoxic T cells specific for human carcinoembryonic antigen epitopes from patients immunized with recombinant vaccinia-CEA vaccine. J. Natl. Cancer Inst. 87:982-990.

Tsang, et al. Phenotypic stability of a cytotoxic T-cell line directed against an immunodominant epitope of human carcinoembryonic antigen. Clin Cancer Res. Dec. 1997;3(12 Pt 1):2439-49.

Unaids. Epidemiology. http://www.unaids.org/en/resources/epidemiology.asp. Accessed Sep. 1, 2003.

U.S. Appl. No. 13/622,263 Non-final Office Action dated Jun. 3, 2016.

U.S. Appl. No. 14/422,504 Non-Final Office Action dated Apr. 20, 2016.

Uyttendaele, et al. Notch4/int-3, a mammary proto-oncogene, is an endothelial cell-specific mammalian Notch gene. Development. Jul. 1996;122(7):2251-9.

Van Cutsem, et al. (2007) Open-label Phase III trial of panitumumab plus best supportive care compared with best supportive care alone in patients with chemotherapy-refractory metastatic colorectal cancer. J Clin Oncol 25:1658-1664.

Van Kampen, et al. Safety and immunogenicity of adenovirus-vectored nasal and epicutaneous influenza vaccines in humans. Vaccine, 2005. 23(8): p. 1029-36.

Varnavski, et al. Evaluation of toxicity from high-dose systemic administration of recombinant adenovirus vector in vector-naive and pre-immunized mice. Gene Ther 12:.5 427-436.(2005).

Vaxgen I. VaxGen Announces Initial Results of its Phase III Aids Vaccine Trial. http://www.corporate-ir.net/ireye/ir_site.zhtml?ticker=VXGN&script=410&layout=-6&item_id=385014. Accessed Jul. 14, 2003.

Vergati, et al. (2010) Strategies for cancer vaccine development. J Biomed Biotechnol 2010. pii: 596432.

Villa-Garcia, et al. Isolation and characterization of a TATA-less promoter for the human beta 3 integrin gene. Blood. Feb. 1, 1994;83(3):668-76.

Von Mehren, et al. 2000. Phase I study of vaccine therapy with ALVAC-CEA B7.1 and GM-CSF in patients with advanced CEA-expressing cancers (abstr 1883). In Proc Am Soc Clin Oncol 480a.

Von Mehren, et al. 2000. Pilot study of a dual gene recombinant avipox vaccine containing both carcinoembryonic antigen (CEA) and B7.1 transgenes in patients with recurrent CEA-expressing adenocarcinomas. Clin Cancer Res 6:2219-2228.

Von Mehren, et al. 2001. The influence of granulocyte macrophage colony-stimulating factor and prior chemotherapy on the immunological response to a vaccine (ALVAC-CEA B7.1) in patients with metastatic carcinoma. Clin Cancer Res 7:1181-1191.

Wald, et al. Polymerase Chain Reaction for Detection of Herpes Simplex Virus (HSV) DNA on Mucosal Surfaces: Comparison with HSV Isolation in Cell Culture. J Infect Dis 188;1345-51 (2003).

Wald, et al.. Risk of human immunodeficiency virus infection in herpes simplex virus type 2-seropositive persons: a meta-analysis. J Infect Dis 185;45-52. (2002).

Wallace, et al. The cytotoxic T-cell response to herpes simplex virus type 1 infection of C57BL/6 mice is almost entirely directed against a single immunodominant determinant. J Virol 73;7619-26 (1999).

Walpole, et al. The weight of nations: an estimation of adult human biomass. BMC public health 12:439; (2012).

Wan, et al. 1997. Dendritic cells transduced with an adenoviral vector encoding a model tumor-associated antigen for tumor vaccination. Hum Gene Ther 8:1355-1363.

Wan, et al. 1999. Murine dendritic cells transduced with an adenoviral vector expressing a defined tumor antigen can overcome anti-adenovirus neutralizing immunity and induce effective tumor regression. Int J Oncol 14:771-776.

Wang, et al. A monoclonal antibody detects heterogeneity in vascular endothelium of tumours and normal tissues. Int J Cancer. May 28, 1993;54(3):363-70.

Wang, et al. A packaging cell line for propagation of recombinant adenovirus vectors containing two lethal gene-region deletions. Gene Ther. Dec. 1995;2(10):775-83.

Wang, et al. Episomal segregation of the adenovirus enhancer sequence by conditional genome rearrangement abrogates late viral gene expression. J Virol. 2000; 74:11296-303.

Wang, et al. Structure and function of the hepatitis C virus internal ribosome entry site. Curr Top Microbiol Immunol. 1995;203:99-115.

Weaver, et al. Comparison of replication-competent, first generation, and helper-dependent adenoviral vaccines. PLoS One. 2009;4(3):e5059. doi: 10.1371/journal.pone.0005059. Epub Mar. 31, 2009.

Webb, et al. Human and murine immune responses to a novel Leishmania major recombinant protein encoded by members of a multicopy gene family. Infect Immun 66, 3279-3289 (1998).

Wilbur, et al. Rapid similarity searches of nucleic acid and protein data banks. Proc Natl Acad Sci U S A. Feb. 1983;80(3):726-30.

Wille-Reece, et al. Toll-like receptor agonists influence the magnitude and quality of memory T cell responses after prime-boost immunization in nonhuman primates. J Exp Med 203:.51249-258 (2006).

Wit, et al. Outcome and predictors of failure of highly active antiretroviral therapy: one-year follow-up of a cohort of human immunodeficiency virus type 1-infected persons. J Infect Dis 179;790-8 (1999).

Wong, et al. Rapid development of T cell memory. J Immunol 172:.12 7239-245 (2004).

Yang, et al. Overcoming immunity to a viral vaccine by DNA priming before vector boosting. J Virol 77;799-803 (2003).

Yang, et al. Role of viral antigens in destructive cellular immune responses to adenovirus vector-transduced cells in mouse lungs. J Virol. Oct. 1996;70(10):7209-12.

Yeh, et al. Efficient dual transcomplementation of adenovirus E1 and E4 regions from a 293-derived cell line expressing a minimal E4 functional unit. J Virol. Jan. 1996;70(1):559-65.

Zambaux, et al. Influence of experimental parameters on the characteristics of poly(lactic acid) nanoparticles prepared by a double emulsion method. J Control Release. Jan. 2, 1998;50(1- 3):31-40.

Zaremba, et al. Identification of an enhancer agonist cytotoxic T lymphocyte peptide from human carcinoembryonic antigen. Cancer Res. Oct. 15, 1997;57(20):4570-7.

Zhao, et al. Enhanced cellular immunity to SIV Gag following co-administration of adenoviruses encoding wild-type or mutant HIV Tat and SIV Gag. Virology 342:.1 1-12 (2005).

Zhu, et al. (2000) Specific cytolytic T-cell responses to human CEA from patients immunized with recombinant avipox-CEA vaccine. Clin. Cancer Res. 6:24-33.

(56) References Cited

OTHER PUBLICATIONS

Zur Muhlen, et al. Solid lipid nanoparticles (SLN) for controlled drug delivery—drug release and release mechanism. Eur J Pharm Biopharm. Mar. 1998;45(2):149-55.
Appledorn, et al. (2008) Adenovirus vector-induced innate inflammatory mediators, MAPK signaling, as well as adaptive immune responses are dependent upon both TLR2 and TLR9 in vivo. J Immunol. 181:2134-2144.
Appledorn, et al. (2008) Wild-type adenoviruses from groups A-F evoke unique innate immune responses, of which HAd3 and SAd23 are partially complement dependent. Gene Ther. 15:885-901.
Barouch, et al. (2011) International seroepidemiology of adenovirus serotypes 5, 26, 35, and 48 in pediatric and adult populations. Vaccine 29:5203-5209.
Berinstein, Neil L. Carcinoembryonic antigen as a target for therapeutic anticancer vaccines: a review. Journal of Clinical Oncology, J Clin Oncol. Apr. 15, 2002;20(8):2197-207.
Bewig, et al. (2000) Accelerated titering of adenoviruses. BioTechniques 28:871-873.
Co-pending U.S. Appl. No. 15/542,005, filed Jul. 6, 2017.
Co-pending U.S. Appl. No. 15/564,413, filed Oct. 4, 2017.
Fernando, et al. (2010) The T-box transcription factor Brachyury promotes epithelial-mesenchymal transition in human tumor cells. J Clin Invest. 120:533-544.
Gabaglia CR, Sercarz EE, Diaz-De-Durana Y, Hitt M, Graham FL, Gauldie J, and Braciak TA. Life-long systemic protection in mice vaccinated with L. major and adenovirus IL-12 vector requires active infection, macrophages and intact lymph nodes.Vaccine 23:.2 247-257 (2004).
Gabitzsch, et al. The generation and analyses of a novel combination of recombinant adenovirus vaccines targeting three tumor antigens as an immunotherapeutic. Oncotarget. Oct. 13, 2015; 6(31): 31344-31359.
Gulley, et al. (2008) Pilot study of vaccination with recombinant CEA-MUC-1-TRICOM poxviral-based vaccines in patients with metastatic carcinoma. Clin Cancer Res. 14:3060-3069.
Hamilton, et al. (2012) Cancer vaccines targeting the epithelial mesenchymal transition: Tissue distribution of Brachyury and other drivers of the mesenchymal-like phenotype of carcinomas. Sem Oncol. 39:358-366.
Hartman, et al. (2008) Adenovirus vector induced innate immune responses: impact upon efficacy and toxicity in gene therapy and vaccine applications. Virus Res 132:1-14.
Heery, et al. (2014) NCI experience using yeast-Brachyury vaccine (GI-6301) in patients with advanced chordoma. J Clin Oncol. 32:abstract 3081.
Heery, et al. Phase I trial of a yeast-based therapeutic cancer vaccine (GI-6301) targeting the transcription factor brachyury. Cancer Immunol Res. Nov. 2015; 3(11): 1248-1256.
Hollingsworth, et al. (2004) Mucins in cancer: protection and control of the cell surface. Nat Rev Cancer 4:45-60.
International Application No. PCT/US2016/012496 International Search Report and Written Opinion dated Apr. 12, 2016.
International preliminary report on patentability dated Oct. 24, 2017 for PCT Application No. PCT/US2016/028496.
International search report and written opinion dated Oct. 3, 2016 for PCT Application No. PCT/US16/28496.
Jochems, et al. (2013) Identification and characterization of agonist epitopes of the MUC1-C oncoprotein. Cancer Immunol Immunother. 63:161-174.
Kawano, et al. (2007) MUC1 oncoprotein regulates Bcr-Abl stability and pathogenesis in chronic myelogenous leukemia cells. Cancer Res. 67:11576-11584.
Kilic, et al. (2011) Brachyury expression predicts poor prognosis at early stages of colorectal cancer. Eur J Cancer 47:1080-1085.
Kufe, DW. (2009) Functional targeting of the MUC1 oncogene in human cancers. Cancer Biol Ther. 8:1197-1203.
Limacher, et al. (2012) TG4010: A therapeutic vaccine against MUC1 expressing tumors. OncoImmunology 1:791-792.
Moore, et al. Progress in DNA-based heterologous prime-boost immunization strategies for malaria. Immunol Rev. 199:126-143 (2004).
Morral, et al. Lethal toxicity, severe endothelial injury, and a threshold effect with high doses of an adenoviral vector in baboons. Hum Gene Ther 13;143-54 (2002).
Morse, et al. (2013) a randomized Phase II study of immunization with dendritic cells modified with poxvectors encoding CEA and MUC1 compared with the same poxvectors plus GM-CSF for resected metastatic colorectal cancer. Ann Surg. 258:879-886.
Oh, et al. Dendritic cells transduced with recombinant adenoviruses induce more efficient anti-tumor immunity than dendritic cells pulsed with peptide. Vaccine, 24; 2860-2868 (2006).
Palena, et al. (2007) The human T-box mesodermal transcription factor brachyury is a candidate target for T-cell mediated cancer immunotherapy. Clin Cancer Res. 13:2471-2478.
Etubics press release. Etubics and Duke Cancer Institute report positive phase I/II results for colorectal cancer immunotherapy. Etubics corporation. Seattle (May 16, 2012). URL:< http://etubics.com/etubics-and-duke-cancer-institute-report-positive-phase-iii-results-for-colorectal-cancer-immunotherapy/>.
Ramlau, et al. (2008) A phase II study of Tg4010 (Mva-Muc1-II2) in association with chemotherapy in patients with stage III/IV Non-small cell lung cancer. J Thorac Oncol. 3:735-744.
Rice, et al. An HPV-E6/E7 immunotherapy plus PD-1 checkpoint inhibition results in tumor regression and reduction in PD-L1 expression. Cancer Gene Therapy 22, 454-462 (Sep. 2015).
Sarkar, et al. (2012) Brachyury confers cancer stem cell characteristics on colorectal cancer cells. Int J Cancer 130:328-337.
Morse, et al. Synergism from combined immunologic and pharmacologic inhibition of HER2 in vivo. Int J Cancer 126(12):2893-2903 (2010). First published online Oct. 23, 2009. URL: <https://doi.org/10.1002/ijc.24995>.
Rice, et al. An HPV-E6/E7 immunotherapy plus PD-1 checkpoint inhibition results in tumor regression and reduction in PD-L1 expression (Poster Presentation). Journal for ImmunoTherapy of Cancer 3(Suppl 2):P449 (2015).
Steel, et al. Interleukin-15 and its Receptor Augment Dendritic Cell Vaccination Against the neu Oncogene Through the Induction of Antibodies Partially Independent of CD4-help. Cancer Res. Feb. 1, 2010; 70(3): 1072.
Tsang, et al. (2004) A human cytotoxic T-lymphocyte epitope and its agonist epitope from the nonvariable number of tandem repeat sequence of MUC-1. Clin Cancer Res. 10:2139-2149.
Tucker, et al. (2014) Identification and characterization of a cytotoxic T-lymphocyte agonist epitope of brachyury, a transcription factor involved in epithelial to mesenchymal transition and metastasis. Cancer Immunol Immunother. 63:1307-1317.
Ward, et al. *E. coli* expression and purification of human and cynomolgus IL-15. Protein Expr Purif. Nov. 2009;68(1):42-8. doi: 10.1016/j.pep.2009.05.004. Epub May 10, 2009.
Wieking, et al. (2012) A non-oncogenic HPV 16 E6/E7 vaccine enhances treatment of HPV expressing tumors. Cancer Gene Ther. 2012; 19:667-674.
Yin, et al. (2010) Survival of human multiple myeloma cells is dependent on MUC1 C-terminal transmembrane subunit oncoprotein function. Mol Pharmacol. 78:166-174.
Yin, et al. (2011) MUC1-C Oncoprotein Blocks Terminal Differentiation of Chronic Myelogenous Leukemia Cells by a ROS-Mediated Mechanism. Genes Cancer 2:56-64.
Zhi, et al. Efficacy of severe acute respiratory syndrome vaccine based on a nonhuman primate adenovirus in the presence of immunity against human adenovirus. Hum Gene Ther 17:.5 500-06 (2006).
Bergamaschi, et al. Intracellular interaction of interleukin-15 with its receptor alpha during production leads to mutual stabilization and increased bioactivity. J Biol Chem. Feb. 15, 2008;283(7):4189-99.
Chevinsky, A.H. CEA in tumors of other than colorectal origin. Semin Surg Oncol. May-Jun. 1991;7(3):162-6.

(56) References Cited

OTHER PUBLICATIONS

Dubois, et al. Preassociation of IL-15 with IL-15R alpha-IgG1-Fc enhances its activity on proliferation of NK and CD8+/CD44high T cells and its antitumor action. J Immunol. Feb. 15, 2008;180(4):2099-2106.

Epardaud, et al. Interleukin-15/interleukin-15R alpha complexes promote destruction of established tumors by reviving tumor-resident CD8+ T cells. Cancer Res. Apr. 15, 2008;68(8):2972-83.

Gendler, et al. (1990) Molecular cloning and expression of human tumor-associated polymorphic epithelial mucin. J Biol Chem. 265:15286-15293.

Mittereder, et al. (1996) Evaluation of the concentration and bioactivity of adenovirus vectors for gene therapy. J Virol. 70:7498-7509.

Mortier, et al. Soluble interleukin-15 receptor alpha (IL-15R alpha)—sushi as a selective and potent agonist of IL-15 action through IL-15R beta/gamma. Hyperagonist IL-15 × IL-15R alpha fusion proteins.J Biol Chem. Jan. 20, 2006;281(3):1612-9. Epub Nov. 11, 2005.

Oualikene, et al. Protease-deleted adenovirus vectors and complementing cell lines: potential applications of single-round replication mutants for vaccination and gene therapy. Hum Gene Ther. Jun. 10, 2000;11(9):1341-53.

Robbins, et al. 1991 Transduction and expression of the human carcinoembryonic antigen gene in a murine colon carcinoma cell line. Cancer Research 51:3657-3662.

Rubinstein, et al. Converting IL-15 to a superagonist by binding to soluble IL-15Ra. Proc Natl Acad Sci U SA. Jun. 13, 2006; 103(24): 9166-9171.

Shayakhmetov, "Efficacy, Toxicity, and Immunogenicity of Adenoviral Vectors," Gene Therapy of Cancer, Ed. Hunt et al., Humana Press Inc., 2007, pp. 23-38.

Stoklasek, et al. Combined IL-15/IL-15Ra Immunotherapy Maximizes IL-15 Activity In Vivo. J Immunol. Nov. 1, 2006; 177(9): 6072-6080.

Tanaka, et al. Adenovirus-mediated prodrug gene therapy for carcinoembryonic antigen-producing human gastric carcinoma cells in vitro. Cancer research 56.6 (1996): 1341-1345.

EP08781241.8 Summons to attend oral proceedings dated Mar. 6, 2015.

EP16153921.8 Summons to attend oral proceedings dated Jan. 15, 2018.

Notice of Intention to Grant for European Patent Application No. 16153921.8 dated Oct. 15, 2018, 7 pages.

Official Action for U.S. Appl. No. 13/622,263 dated May, 31, 2018, 15 pages.

Official Action for U.S. Appl. No. 13/622,263 dated Jan. 28, 2019, 27 pages.

Official Action for U.S. Appl. No. 15/265,709 dated Jun. 7, 2017, 15 pages.

Official Action for U.S. Appl. No. 15/265,709 dated Jan. 16, 2018, 16 pages.

Official Action for U.S. Appl. No. 15/265,709 dated Aug. 16, 2018, 43 pages.

Official Action for U.S. Appl. No. 15/265,709 dated Jan. 7, 2019, 37 pages.

Official Action for U.S. Appl. No. 15/265,723 dated Dec. 26, 2017, 13 pages.

Official Action for U.S. Appl. No. 15/265,723 dated Aug. 23, 2018, 43 pages.

Official Action for U.S. Appl. No. 15/265,723 dated Jan. 23, 2019, 26 pages.

Official Action for U.S. Appl. No. 15/265,709 dated Jun. 25, 2019, 41 pages.

Official Action for U.S. Appl. No. 15/265,723 dated Jun. 14, 2019, 29 pages.

\* cited by examiner

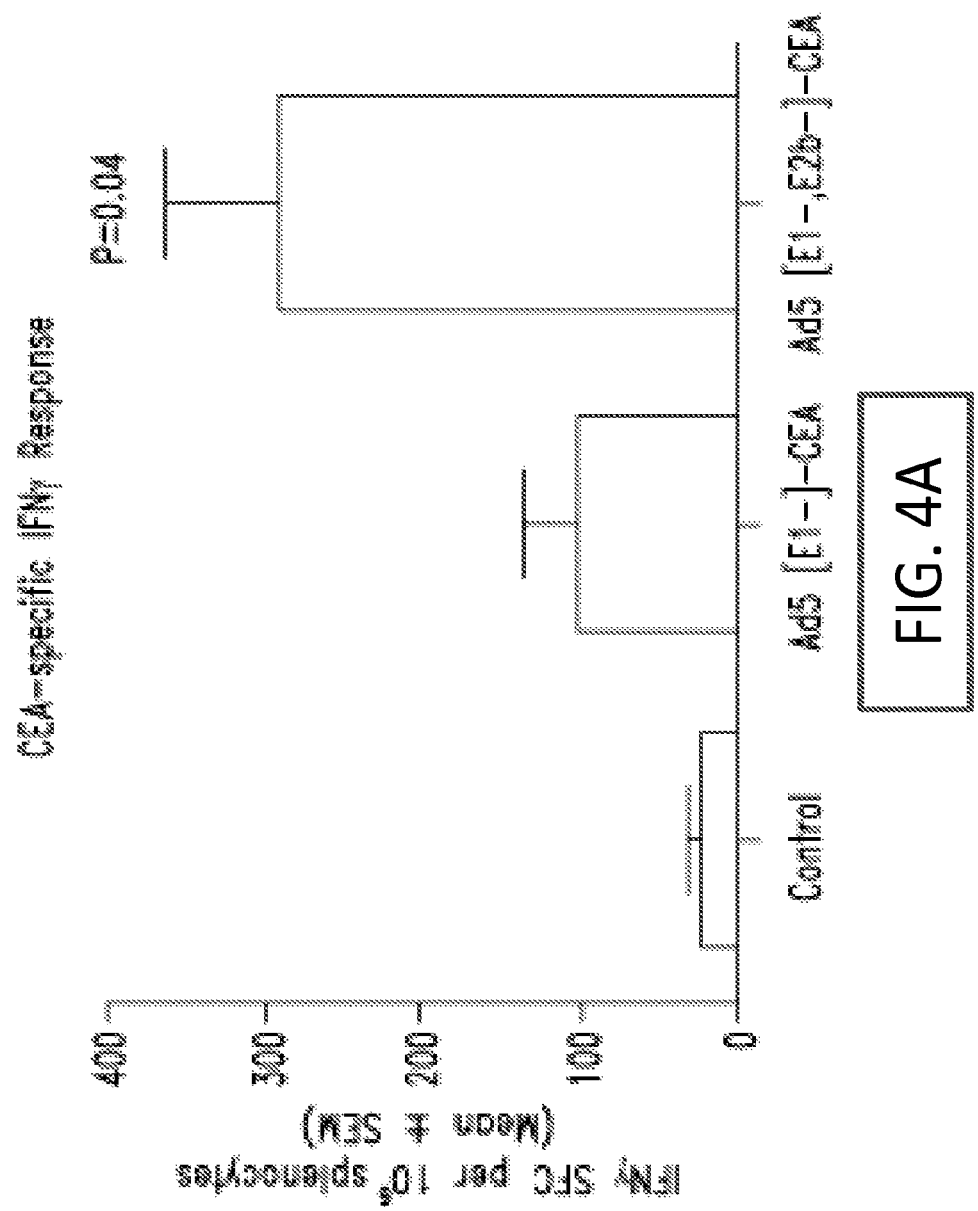

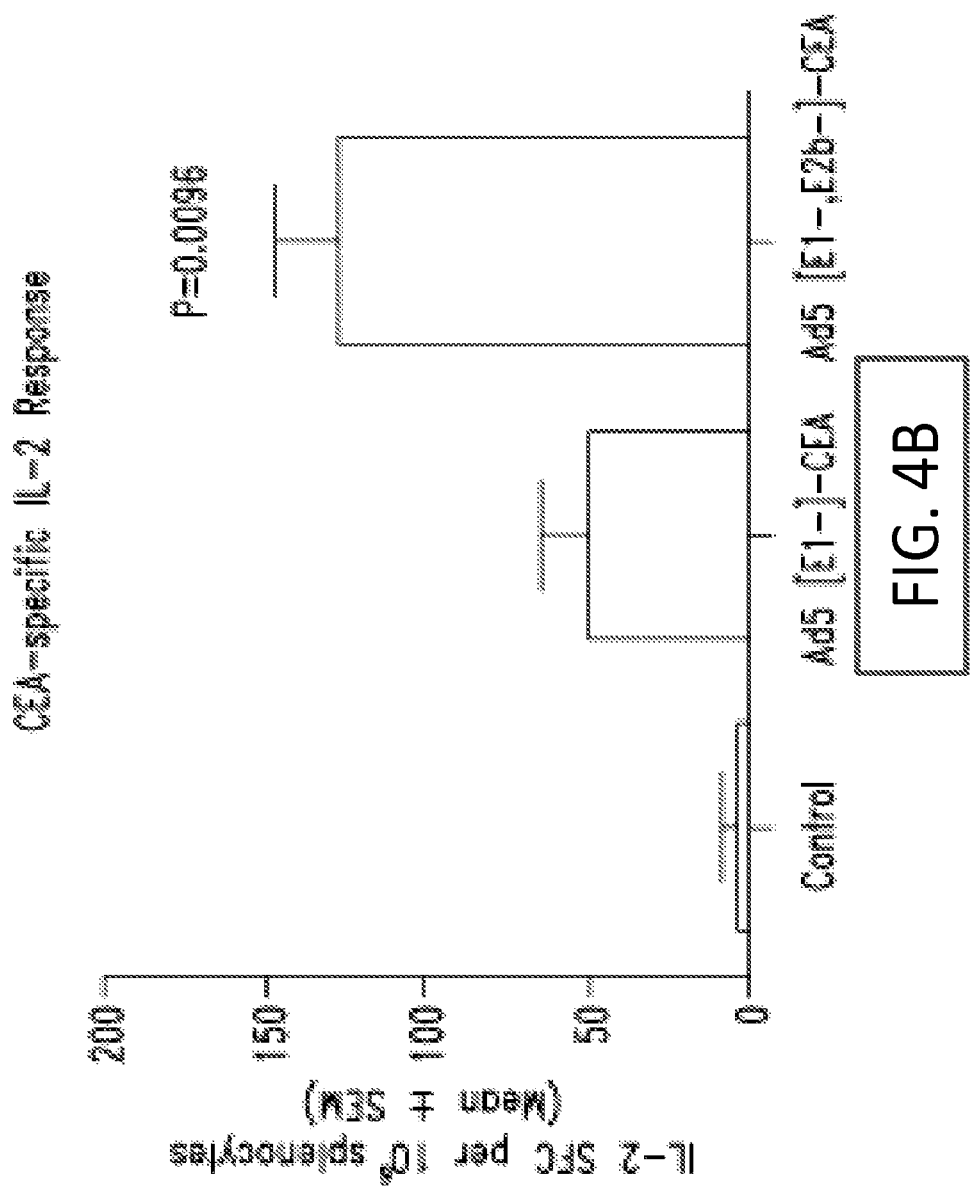

REPLICATION DEFECTIVE ADENOVIRUS VECTOR IN VACCINATION

CROSS-REFERENCE

This application is a Divisional Application of U.S. National Stage application Ser. No. 14/422,504, filed Feb. 19, 2015, which is a National Stage of International Application No. PCT/US2013/032688, filed Mar. 15, 2013, which claims priority to U.S. Provisional Application Nos. 61/693,187, filed Aug. 24, 2012, 61/694,013, filed Aug. 28, 2012, 61/748,494, filed Jan. 3, 2013, and 61/756,870, filed Jan. 25, 2013, each of which applications are hereby incorporated by reference in their entirety.

STATEMENT AS TO FEDERALLY SPONSORED RESEARCH

This invention was made with government support under Contract No. HHSN 261200900059C, awarded by the National Cancer Institute; and Contract No. HHSN 261201100097C, awarded by the National Cancer Institute; Grant No. 1R43CA134063, awarded by the National Cancer Institute; Grant No. 2R44CA134063 awarded by the National Cancer Institute; and Contract No. HHSN 261200900059C, awarded by the National Cancer Institute; and Contract No. HHSN 261201100097C, awarded by the National Cancer Institute. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 29, 2015 is named 38981-710-831 SL.txt and is 48 Kilobytes in size.

BACKGROUND

Cancer immunotherapy achieved by delivering tumor-associated antigens (TAA) has recently demonstrated survival benefits; however limitations to these strategies exist and more immunologically potent vaccines are needed. To address the low immunogenicity of self-tumor antigens, a variety of advanced, multi-component vaccination strategies including co-administration of adjuvants and immune stimulating cytokines have been employed. Alternatives include the use of recombinant viral vectors that inherently provide innate pro-inflammatory signals, while simultaneously engineered to express the antigen of interest. Of particular interest are adenovirus serotype-5 (Ad5)-based immunotherapeutics that have been repeatedly used in humans to induce robust T cell-mediated immune (CMI) responses, all while maintaining an extensive safety profile. In addition, Ad5 vectors can be reliably manufactured in large quantities and are stable for storage and delivery for outpatient administration. Nonetheless, a major obstacle to the use of first generation (E1-deleted) Ad5-based vectors is the high frequency of pre-existing anti-adenovirus type 5 neutralizing antibodies. These antibodies can be present in a potential vaccinee due to either prior wild type adenovirus infection and/or induction of adenovirus neutralizing antibodies by repeated injections with Ad5-based vaccines, each resulting in inadequate immune stimulation against the target TAA.

A major problem with adenovirus vectors has been their inability to sustain long-term transgene expression due largely to the host immune response that eliminates the adenovirus vector and virally transduced cells in immune-competent subjects. Thus, the use of First Generation adenovirus vector vaccines is severely limited by preexisting or induced immunity of vaccines to adenovirus (Ad) (Yang, et al. J Virol 77/799-803 (2003); Casimiro, et al. J Virol 77/6305-6313 (2003)). One group reported that a preponderance of humans have antibody against adenovirus type 5 (Ad5), the most widely used serotype for gene transfer vectors, and that two-thirds of humans studied have lymphoproliferative responses against Ad (Chirmule, et al. Gene Ther 6/1574-1583 (1999)). In another study, an adenovirus vector vaccine carrying an HIV-1 envelope gene was incapable of reimmunizing a primed immune response using non-adjuvanted DNA (Barouch, et al. J. Virol 77/8729-8735 (2003)). Another group reported that non-human primates having pre-existing immunity against Ad5 due to a single immunization with Ad5 were unable to generate transgene-specific antibodies to HIV proteins, as well as altering the overall T cell responses (McCoy, et al. J. Virol 81/6594-6604 (2007)).

There are numerous mechanisms by which preexisting immunity interferes with adenovirus vector vaccines but one major concern is the presence of neutralizing antibody followed by cell mediated immune elimination of Ad infected antigen harboring cells. Both of these responses can be directed to several Ad proteins. One approach is to increase the vector vaccine dose. Although there is evidence that increasing vaccine doses can increase induction of desired cell mediated immune (CMI) responses in Ad-immune animals (Barouch, et al. J. Virol 77/8729-8735 (2003)), it often results in unacceptable adverse effects in animals and humans. When using First Generation Ad5 vector vaccines, one option can be to use the approach of a heterologous prime-boost regimen, using naked (non-vectored) DNA as the priming vaccination, followed by an Ad5 vector immunization. This protocol may result in a subsequent immune response against Ad5 such that one cannot administer a further re-immunization (boost) with the same (or a different) adenovirus vector vaccine that utilizes the same viral backbone. Therefore, with the current First Generation of Ad5 vectors, using this approach can also abrogate any further use of Ad5 vector immunization in the Ad5 immunized vaccinee.

First Generation (E1 deleted) adenovirus vector vaccines express Ad late genes, albeit at a decreased level and over a longer time period than wild-type Ad virus (Nevins, et al. Cell 26/213-220 (1981); Gaynor, et al. Cell 33/683-693 (1983); Yang, et al. J Virol 70/7209-7212 (1996)). When using First Generation adenovirus vectors for immunization, vaccine antigens are presented to the immune system simultaneously with highly immunogenic Ad capsid proteins. The major problem with these adenovirus vectors is that the immune responses generated are less likely to be directed to the desired vaccine epitopes (McMichael, et al. Nat Rev Immunol 2/283-291 (2002)) and more likely to be directed to the adenovirus-derived antigens, i.e., antigenic competition. There is controversy about the mechanism by which First Generation adenovirus vectors are potent immunogens. It has been hypothesized that the composition of the Ad capsid or a toxic effect of viral genes creates generalized inflammation resulting in a nonspecific immune stimulatory effect. The E1 proteins of Ad act to inhibit inflammation following infection (Schaack, et al. PNAS 101/3124-3129 (2004)). Removal of the gene segments for these proteins, which is the case for First Generation adenovirus vectors, results in increased levels of inflammation (Schaack, et al. PNAS 101/3124-3129 (2004); Schaack, et al. Viral Immunol 18/79-88 (2005)).

Thus, it is apparent that there remains a need for a more effective cancer vaccine vector candidate. In particular, there remains a need in the art for cancer targeting Ad vaccine vectors that allow multiple vaccinations and vaccinations in individuals with preexisting immunity to Ad. The present invention provides this and other advantages.

BRIEF SUMMARY

In a first aspect, the invention relates to a composition comprising a recombinant nucleic acid vector comprising a sequence with a first identity value of at least 80% to SEQ ID NO: 3. In some embodiments, the recombinant nucleic acid vector further comprises a region with a second identity value of at least 80% to a region in SEQ ID NO: 3, wherein the region is selected from 26048-26177, 26063-26141, 1-103, 54-103, 32214-32315, and 32214-32262. In some embodiments, the recombinant nucleic acid vector further comprises a region encoding a peptide with a third identity value of at least 80% to a peptide encoded by a region in SEQ ID NO: 3 between positions 1057 and 3165. In some embodiments, the first identity value is at least 90%. In some embodiments, the first identity value is at least 95%. In some embodiments, the first identity value is at least 99%. In some embodiments, the first identity value is 100%. In some embodiments, the second identity value is at least 90%. In some embodiments, the second identity value is at least 95%. In some embodiments, the second identity value is at least 99%. In some embodiments, the second identity value is 100%. In some embodiments, the third identity value is at least 90%. In some embodiments, the third identity value is at least 95%. In some embodiments, the third identity value is at least 99%. In some embodiments, the third identity value is 100%.

In a second aspect, the invention relates to a composition comprising a recombinant nucleic acid vector comprising a sequence encoding a modified CEA; wherein the modified CEA comprises a sequence with a first identity value of at least 80% to SEQ ID NO: 2; and wherein the recombinant nucleic acid vector comprises a replication defective adenovirus vector. In some embodiments, the replication defective adenovirus vector comprises a replication defective adenovirus 5 vector. In some embodiments, the replication defective adenovirus vector comprises a deletion in the E2b region. In some embodiments, the replication defective adenovirus vector further comprises a deletion in the E1 region. In some embodiments, the first identity value is at least 90%. In some embodiments, the first identity value is at least 95%. In some embodiments, the first identity value is at least 99%. In some embodiments, the first identity value is 100%. In some embodiments, the first identity value is at least 90%. In some embodiments, the first identity value is at least 95%. In some embodiments, the first identity value is at least 99%. In some embodiments, the first identity value is 100%. In some embodiments, the first identity value is at least 90%. In some embodiments, the first identity value is at least 95%. In some embodiments, the first identity value is at least 99%. In some embodiments, the first identity value is 100%.

In a third aspect, the invention relates to a composition comprising a recombinant nucleic acid vector comprising a sequence encoding a modified CEA; wherein the modified CEA comprises a modification in up to 25 amino acids; and wherein the recombinant nucleic acid vector comprises a replication defective adenovirus 5 vector having a deletion in the E2b region. In some embodiments, the modified CEA comprises a modification in up to 20 amino acids. In some embodiments, the modified CEA comprises a modification in up to 15 amino acids. In some embodiments, the modified CEA comprises a modification in up to 10 amino acids. In some embodiments, the modified CEA comprises a modification in up to 5 amino acids. In some embodiments, the recombinant nucleic acid vector is capable of effecting overexpression of the modified CEA in transfected cells. In some embodiments, the recombinant nucleic acid vector is capable of inducing a specific immune response against cells expressing CEA in a human that is at least 25 fold over basal. In some embodiments, the human has an inverse Ad5 neutralizing antibody titer of greater than 200. In some embodiments, the human has an inverse Ad5 neutralizing antibody titer of greater than 4767. In some embodiments, the immune response is measured as CEA antigen specific cell-mediated immunity (CMI). In some embodiments, the immune response is measured as CEA antigen specific IFN-γ secretion. In some embodiments, the immune response is measured as CEA antigen specific IL-2 secretion. In some embodiments, the immune response against CEA is measured by ELISspot assay. In some embodiments, the CEA antigen specific CMI is greater than 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic CEA expressing cells from a tumor cell line or from an autologous tumor. In some embodiments, the composition further comprises an immunogenic component. In some embodiments, the immunogenic component comprises a cytokine selected from the group of. IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7. In some embodiments, the modified CEA comprises a modification in 1 amino acid compared to wild type. In some embodiments, the modification comprises a substitution into aspartate in a position corresponding to position 610 in SEQ. ID. NO. 3.

In a fourth aspect, the invention relates to a composition comprising a recombinant nucleic acid vector, wherein the recombinant nucleic acid vector comprises a replication defective adenovirus vector, and wherein upon administration to a human, the composition is capable of inducing an immune response directed towards cells expressing CEA antigen in said human; wherein the immune response comprises cell mediated immunity. In some embodiments, the replication defective adenovirus vector comprises a replication defective adenovirus 5 vector. In some embodiments, the immune response is measured as CEA antigen specific cell-mediated immunity (CMI). In some embodiments, the immune response is measured as CEA antigen specific IFN-γ secretion. In some embodiments, the immune response is measured as CEA antigen specific 1L-2 secretion. In some embodiments, the immune response against CEA is measured by ELISspot assay. In some embodiments, the CEA antigen specific CMI is greater than 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic CEA expressing cells from a tumor cell line or from an autologous tumor.

In a fifth aspect, the invention relates to a vial comprising a composition consisting of a therapeutic solution of a volume in the range of 0.8-1.2 ml, the therapeutic solution comprising $4.5$-$5.5 \times 10^{11}$ virus particles; wherein the virus particle is a replication defective adenovirus comprising a recombinant nucleic acid vector. In some embodiments, the recombinant nucleic acid vector is capable of effecting overexpression of the modified CEA in transfected cells. In some embodiments, the replication defective adenovirus comprises a nucleic acid sequence encoding a protein that is capable of inducing a specific immune response against CEA expressing cells in a human. In some embodiments, the replication defective adenovirus vector comprises a replication defective adenovirus 5 vector. In some embodiments, the immune response is measured as CEA antigen specific cell-mediated immunity (CMI). In some embodiments, the immune response is measured as CEA antigen specific IFN-γ secretion. In some embodiments, the immune response is measured as CEA antigen specific IL-2 secretion. In some embodiments, the immune response against CEA is measured by ELISspot assay. In some embodiments, the CEA antigen specific CMI is greater than 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic CEA expressing cells from a tumor cell line or from an autologous tumor. In some embodiments, the therapeutic solution comprises $4.8$-$5.2 \times 10^{11}$ virus particles. In some embodiments, the therapeutic solution comprises $4.9$-$5.1 \times 10^{11}$ virus particles. In some embodiments, the therapeutic solution comprises $4.95$-$5.05 \times 10^{11}$ virus particles. In some embodiments, the therapeutic solution comprises $4.99$-$5.01 \times 10^{11}$ virus particles. In some embodiments, the replication defective adenovirus comprises a replication defective adenovirus 5. In some embodiments, the vial further comprises an immunogenic component. In some embodiments, the immunogenic component comprises a cytokine selected from the group of: IFN-γ, TNFα IL-2, IL-8, IL-12, IL-18, IL-7, IL-3, IL-4, IL-5, IL-6, IL-9, IL-10, and IL-13. In some embodiments, the immunogenic component is selected from the group consisting of IL-7, a nucleic acid encoding IL-7, a protein with substantial identity to IL-7, and a nucleic acid encoding a protein with substantial identity to IL-7.

In various aspects, the invention relates to methods of treatment with the compositions described herein, wherein the treatment comprises raising an immune response against CEA. In one aspect, the invention relates to a method of treatment comprising: (a) selecting a first phase and a second phase of treatment; (b) during the first phase, administering to a human a total of 3 times, in about 3 week intervals, a first replication defective adenovirus encoding an antigen that is capable of inducing an immune response directed towards cells expressing CEA antigen in a human; and (c) during the second phase, administering to said human a total of 3 times, in about 3 month intervals, a second replication defective adenovirus encoding an antigen that is capable of inducing an immune response directed towards cells expressing CEA antigen in a human; wherein the second phase starts about 3 months after the end of the first phase. In some embodiments, the first replication defective adenovirus encoding an antigen that is capable of inducing an immune response directed towards cells expressing CEA antigen in a human and the second replication defective adenovirus encoding an antigen that is capable of inducing an immune response directed towards cells expressing CEA antigen in a human are the same. In some embodiments, the first replication defective adenovirus comprises a replication defective adenovirus 5. In some embodiments, the second replication defective adenovirus comprises a replication defective adenovirus 5. In some embodiments, the first phase is at least five weeks. In some embodiments, the second phase is at least 5 months. In some embodiments, the immune response is measured as CEA antigen specific cell-mediated immunity (CMI). In some embodiments, the immune response is measured as CEA antigen specific IFN-γ secretion. In some embodiments, the immune response is measured as CEA antigen specific IL-2 secretion. In some embodiments, the immune response against CEA is measured by ELISspot assay. In some embodiments, the CEA antigen specific CMI is greater than 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic CEA expressing cells from a tumor cell line or from an autologous tumor. In some embodiments, the first or second replication defective adenovirus infects dendritic cells in the human and wherein the infected dendritic cells present CEA antigen, thereby inducing the immune response. In some embodiments, the administering steps comprise subcutaneous administration. In some embodiments, the administering step in b or c comprises delivering $4.8$-$5.2 \times 10^{11}$ replication defective adenovirus particles. In some embodiments, the administering step in b or c comprises delivering $4.9$-$5.1 \times 10^{11}$ replication defective adenovirus particles. In some embodiments, the administering step in b or c comprises delivering $4.95$-$5.05 \times 10^{11}$ replication defective adenovirus particles. In some embodiments, the administering step in b or c comprises delivering $4.99$-$5.01 \times 10^{11}$ replication defective adenovirus particles. In some embodiments, the human carries an inverse Ad5 neutralizing antibody titer that is of greater than 200 prior to the administering step. In some embodiments, the human has an inverse Ad5 neutralizing antibody titer of greater than 4767. In some embodiments, the human is not concurrently being treated by any one of steroids, corticosteroids, immunosuppressive agents, and immunotherapy. In some embodiments, the human has not been treated by any one of steroids, corticosteroids, immunosuppressive agents, and immunotherapy prior to the administering step. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human is not undergoing cytotoxic chemotherapy concurrently. In some embodiments, the human is not undergoing radiation therapy concurrently. In some embodiments, the human has autoimmune related thyroid disease or vitiligo. In some embodiments, the human has colorectal adenocarcinoma, metastatic colorectal cancer, advanced CEA expressing colorectal cancer, breast cancer, lung cancer, bladder cancer, or pancreas cancer. In some embodiments, the human has three sites of metastatic disease. In some embodiments, the human has received chemotherapy prior to the administering step. In some embodiments, prior to the first phase, the human has received at least one medication of the group consisting of fluoropyrimidine, irinotecan, oxaliplatin, bevacizunab, Capecitabine, Mitomycin, Regorafenib, cetuxinab, and panitumumab. In some embodiments, the human concurrently receives chemotherapy or radiation therapy treatment. In some embodiments, the human concurrently receives a therapy comprising the administration of at least one medication of the group consisting of fluoropyrimidine, irinotecan, oxaliplatin, bevacizunab, Capecitabine, Mitomycin, Regorafenib, cetuxinab, panitumumab, and acetinophen. In some embodiments, the human comprises cells overexpressing CEA. In some embodiments, the cells overexpressing CEA overexpress CEA by at least 10 times over the baseline CEA expression in a non-cancer cell. In some embodiments, cells overexpressing CEA comprise cancer cells. In some embodiments, cells overexpressing CEA are not gastrointestinal epithelium cells. In some embodiments, cells overexpressing CEA overexpress CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, or PSG11. In some embodiments, the human expresses a human leukocyte antigen of serotype HLA-A2, HLA-A3, or HLA-A24. In some embodiments, the first or second replication defective adenovirus comprises a recombinant nucleic acid vector comprising a sequence encoding a modified CEA; wherein the modified CEA comprises a modification in up to 5 amino acids; and wherein the recombinant nucleic acid vector comprises a replication defective adenovirus 5 vector having a deletion in the E2b region. In some embodiments, the first or second replication defective adenovirus comprises a recombinant nucleic acid vector comprising a sequence with a first identity value of at least 80% to SEQ ID NO: 3. In some embodiments, the recombinant nucleic acid vector further comprises a region with a second identity value of at least 80% to a region in SEQ ID NO: 3, wherein the region is selected from 26048-26177, 26063-26141, 1-103, 54-103, 32214-32315, and 32214-32262. In some embodiments, the recombinant nucleic acid vector further comprises a region encoding a peptide with a third identity value of at least 80% to a peptide encoded by a region in SEQ ID NO: 3 between positions 1057 and 3165. In some embodiments, the first or second replication defective adenovirus comprises a recombinant nucleic acid vector comprising a sequence encoding a modified CEA; wherein the modified CEA comprises a sequence with a first identity value of at least 80% to SEQ ID NO: 2; and wherein the recombinant nucleic acid vector comprises a replication defective adenovirus vector.

In a further aspect, the invention relates to a method of treatment comprising: (a) selecting a first phase and a second phase of treatment; (b) during the first phase, administering to a human, a total of n times, a first replication defective adenovirus encoding an antigen that is capable of inducing an immune response directed towards cells expressing CEA antigen in a human; and (c) during the second phase, administering said human, a total of m times, a second replication defective adenovirus encoding an antigen that is capable of inducing an immune response directed towards cells expressing CEA antigen in a human. In some embodiments, the first replication defective adenovirus encoding an antigen that is capable of inducing an immune response directed towards cells expressing CEA antigen in a human and the second replication defective adenovirus encoding an antigen that is capable of inducing an immune response directed towards cells expressing CEA antigen in a human are the same. In some embodiments, the first replication defective adenovirus comprises a replication defective adenovirus 5. In some embodiments, the second replication defective adenovirus comprises a replication defective adenovirus 5. In some embodiments, n is greater than 1. In some embodiments, n is 3. In some embodiments, m is greater than 1. In some embodiments, m is 3. In some embodiments, the first phase is about six weeks. In some embodiments, the first phase is at least five weeks. In some embodiments, the second phase is at least 5 months. In some embodiments, the second phase starts 3 weeks-16 weeks after first phase ends. In some embodiments, in the first phase two administrations of the replication defective adenovirus are at least 18 days apart. In some embodiments, in the first phase two administrations of the replication defective adenovirus are about 21 days apart. In some embodiments, in the first phase two administrations of the replication defective adenovirus are at most 24 days apart. In some embodiments, in the second phase two administrations of the replication defective adenovirus are at least 10 weeks apart. In some embodiments, in the second phase two administrations of the replication defective adenovirus are about 13 weeks apart. In some embodiments, in the second phase two administrations of the replication defective adenovirus are at most 16 weeks apart. In some embodiments, the immune response is measured as CEA antigen specific cell-mediated immunity (CMI). In some embodiments, the immune response is measured as CEA antigen specific IFN-γ secretion. In some embodiments, the immune response is measured as CEA antigen specific IL-2 secretion. In some embodiments, the immune response against CEA is measured by ELISspot assay. In some embodiments, the CEA antigen specific CMI is greater than 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic CEA expressing cells from a tumor cell line or from an autologous tumor. In some embodiments, the first or second replication defective adenovirus infects dendritic cells in the human and wherein the infected dendritic cells present CEA antigen, thereby inducing the immune response. In some embodiments, the administering steps comprise subcutaneous administration. In some embodiments, the administering step in b or c comprises delivering $4.8\text{-}5.2\times10^{11}$ replication defective adenovirus particles. In some embodiments, the administering step in b or c comprises delivering $4.9\text{-}5.1\times10^{11}$ replication defective adenovirus particles. In some embodiments, the administering step in b or c comprises delivering $4.95\text{-}5.05\times10^{11}$ replication defective adenovirus particles. In some embodiments, the administering step in b or c comprises delivering $4.99\text{-}5.01\times10^{11}$ replication defective adenovirus particles. In some embodiments, the human carries an inverse Ad5 neutralizing antibody titer that is of greater than 200 prior to the administering step. In some embodiments, the human has an inverse Ad5 neutralizing antibody titer of greater than 4767. In some embodiments, the human is not concurrently being treated by any one of steroids, corticosteroids, immunosuppressive agents, and immunotherapy. In some embodiments, the human has not been treated by any one of steroids, corticosteroids, immunosuppressive agents, and immunotherapy prior to the administering step. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human is not undergoing cytotoxic chemotherapy concurrently. In some embodiments, the human is not undergoing radiation therapy concurrently. In some embodiments, the human has autoimmune related thyroid disease or vitiligo. In some embodiments, the human has colorectal adenocarcinoma, metastatic colorectal cancer, advanced CEA expressing colorectal cancer breast cancer, lung cancer, bladder cancer or pancreas cancer. In some embodiments, the human has three sites of metastatic disease. In some embodiments, the human has received chemotherapy prior to the administering step. In some embodiments, prior to the first phase, the human has received at least one medication of the group consisting of fluoropyrimidine, irinotecan, oxaliplatin, bevacizunab, Capecitabine, Mitomycin, Regorafenib, cetuxinab, and panitumumab. In some embodiments, the human concurrently receives chemotherapy or radiation therapy treatment. In some embodiments, the human concurrently receives a therapy comprising the administration of at least one medication of the group consisting of fluoropyrimidine, irinotecan, oxaliplatin, bevacizunab, Capecitabine, Mitomycin, Regorafenib, cetuxinab, panitumumab, and acetinophen. In some embodiments, the human comprises cells overexpressing CEA. In some embodiments, the cells overexpressing CEA overexpress CEA more than 20 times over the baseline CEA expression in a non-cancer cell. In some embodiments, cells overexpressing CEA comprise cancer cells. In some embodiments, cells overexpressing CEA are not gastrointestinal epithelium cells. In some embodiments, cells overexpressing CEA overexpress CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, or PSG11. In some embodiments, the human expresses a human leukocyte antigen of serotype HLA-A2, HLA-A3, or HLA-A24. In some embodiments, the first or second replication defective adenovirus comprises a recombinant nucleic acid vector comprising a sequence encoding a modified CEA; wherein the modified CEA comprises a modification in up to 5 amino acids; and wherein the recombinant nucleic acid vector comprises a replication defective adenovirus 5 vector having a deletion in the E2b region. In some embodiments, the first or second replication defective adenovirus comprises a recombinant nucleic acid vector comprising a sequence with a first identity value of at least 80% to SEQ ID NO: 3. In some embodiments, the recombinant nucleic acid vector further comprises a region with a second identity value of at least 80% to a region in SEQ ID NO: 3, wherein the region is selected from 26048-26177, 26063-26141, 1-103, 54-103, 32214-32315, and 32214-32262. In some embodiments, the recombinant nucleic acid vector further comprises a region encoding a peptide with a third identity value of at least 80% to a peptide encoded by a region in SEQ ID NO: 3 between positions 1057 and 3165. In some embodiments, the first or second replication defective adenovirus comprises a recombinant nucleic acid vector comprising a sequence encoding a modified CEA; wherein the modified CEA comprises a sequence with a first identity value of at least 80% to SEQ ID NO: 2; and wherein the recombinant nucleic acid vector comprises a replication defective adenovirus vector.

In another aspect, the invention relates to a method of generating an immune response against CEA in a human, the method comprising: (a) administering to the human the composition as in any of the previous aspects described herein, thereby increasing the immune response to CEA by at least 25 fold. In some embodiments, the immune response is measured as CEA antigen specific cell-mediated immunity (CMI). In some embodiments, the immune response is measured as CEA antigen specific IFN-γ secretion. In some embodiments, the immune response is measured as CEA antigen specific IL-2 secretion. In some embodiments, the immune response against CEA is measured by ELISspot assay. In some embodiments, the CEA antigen specific CMI is greater than 300 IFN-γ spot forming cells (SFC) per $10^6$ peripheral blood mononuclear cells (PBMC). In some embodiments, the immune response is measured by T cell lysis of CAP-1 pulsed antigen-presenting cells, allogeneic CEA expressing cells from a tumor cell line or from an autologous tumor. In some embodiments, the recombinant nucleic acid vector infects dendritic cells in the human and wherein the infected dendritic cells present CEA antigen, thereby inducing the immune response. In some embodiments, the administering step comprises subcutaneous administration. In some embodiments, the administering step is repeated at least once. In some embodiments, the administering step is repeated after about 3 weeks following a previous administering step. In some embodiments, the administering step is repeated after about 3 months following a previous administering step. In some embodiments, the administering step is repeated twice. In some embodiments, the composition comprises $4.8-5.2 \times 10^{11}$ virus particles comprising the recombinant nucleic acid vector. In some embodiments, the composition comprises $4.9-5.1 \times 10^{11}$ virus particles comprising the recombinant nucleic acid vector. In some embodiments, the composition comprises $4.95-5.05 \times 10^{11}$ virus particles comprising the recombinant nucleic acid vector. In some embodiments, the composition comprises $4.99-5.01 \times 10^{11}$ virus particles comprising the recombinant nucleic acid vector. In some embodiments, the human carries an Ad5 neutralizing antibody titer that is of greater than 200 prior to the administering step. In some embodiments, the human has an inverse Ad5 neutralizing antibody titer of greater than 4767. In some embodiments, the human is not concurrently being treated by any one of steroids, corticosteroids, immunosuppressive agents, and immunotherapy. In some embodiments, the human has not been treated by any one of steroids, corticosteroids, immunosuppressive agents, and immunotherapy prior to the administering step. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human is not undergoing cytotoxic chemotherapy concurrently. In some embodiments, the human is not undergoing radiation therapy concurrently. In some embodiments, the human has autoimmune related thyroid disease or vitiligo. In some embodiments, the human has colorectal adenocarcinoma, metastatic colorectal cancer, advanced CEA expressing colorectal cancer breast cancer, lung cancer, bladder cancer, or pancreas cancer. In some embodiments, the human has three sites of metastatic disease. In some embodiments, the human has received chemotherapy prior to the administering step. In some embodiments, prior to the administering step, the human has received at least one medication of the group consisting of fluoropyrimidine, irinotecan, oxaliplatin, bevacizunab, Capecitabine, Mitomycin, Regorafenib, cetuxinab, and panitumumab. In some embodiments, the human concurrently receives chemotherapy or radiation therapy treatment. In some embodiments, the human concurrently receives a therapy comprising the administration of at least one medication of the group consisting of fluoropyrimidine, irinotecan, oxaliplatin, bevacizunab, Capecitabine, Mitomycin, Regorafenib, cetuxinab, panitumumab, and acetinophen. In some embodiments, the human comprises cells overexpressing CEA. In some embodiments, the cells overexpressing CEA overexpress CEA more than 10 times over the baseline CEA expression in a non-cancer cell. In some embodiments, cells overexpressing CEA comprise cancer cells. In some embodiments, cells overexpressing CEA are not gastrointestinal epithelium cells. In some embodiments, cells overexpressing CEA overexpress CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, or PSG11. In some embodiments, the human expresses a human leukocyte antigen of serotype HLA-A2, HLA-A3, or HLA-A24.

In yet another aspect, the invention relates to a method of selecting a human for administration of the composition as in any of the previous aspects described herein, comprising; (a) determining a HLA subtype of the human; and (b) administering the composition to the human, if the HLA subtype is determined to be one of a preselected subgroup of HLA subtypes. In some embodiments, the preselected subgroup of HLA subtypes comprises one or more of HLA-A2, HLA-A3, or HLA-A24. In some embodiments, the method induces a CEA-specific immune response that is measured as CEA antigen specific cell-mediated immunity (CMI). In some embodiments, the method induces a CEA-specific immune response that is measured as CEA antigen specific IFN-γ secretion. In some embodiments, the method induces a CEA-specific immune response that is measured as CEA antigen specific IL-2 secretion. In some embodiments, the method induces a CEA-specific immune response against CEA that is measured by ELISspot assay. In some embodiments, the CEA antigen specific CMI is greater than 300 IFN-γ spot forming cells (SFC) per $10^6$ peripheral blood mononuclear cells (PBMC). In some embodiments, the method induces a CEA-specific immune response that is measured by T cell lysis of CAP-1 pulsed antigen-presenting cells, allogeneic CEA expressing cells from a tumor cell line or from an autologous tumor. In some embodiments, the recombinant nucleic acid vector infects dendritic cells in the human and wherein the infected dendritic cells present CEA antigen, thereby inducing an immune response. In some embodiments, the administering step comprises subcutaneous administration. In some embodiments, the administering step is repeated at least once. In some embodiments, the administering step is repeated after about 3 weeks following a previous administering step. In some embodiments, the administering step is repeated after about 3 months following a previous administering step. In some embodiments, the administering step is repeated twice. In some embodiments, the composition comprises $4.8$-$5.2 \times 10^{11}$ virus particles comprising the recombinant nucleic acid vector. In some embodiments, the composition comprises $4.9$-$5.1 \times 10^{11}$ virus particles comprising the recombinant nucleic acid vector. In some embodiments, the composition comprises $4.95$-$5.05 \times 10^{11}$ virus particles comprising the recombinant nucleic acid vector. In some embodiments, the composition comprises $4.99$-$5.01 \times 10^{11}$ virus particles comprising the recombinant nucleic acid vector. In some embodiments, the human carries an inverse Ad5 neutralizing antibody titer that is of greater than 200 prior to the administering step. In some embodiments, the human has an inverse Ad5 neutralizing antibody titer of greater than 4767. In some embodiments, the human is not concurrently being treated by any one of steroids, corticosteroids, immunosuppressive agents, and immunotherapy. In some embodiments, the human has not been treated by any one of steroids, corticosteroids, immunosuppressive agents, and immunotherapy prior to the administering step. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human is not undergoing cytotoxic chemotherapy concurrently. In some embodiments, the human is not undergoing radiation therapy concurrently. In some embodiments, the human has autoimmune related thyroid disease or vitiligo. In some embodiments, the human has colorectal adenocarcinoma, metastatic colorectal cancer, advanced CEA expressing colorectal cancer breast cancer, lung cancer, bladder cancer, or pancreas cancer. In some embodiments, the human has three sites of metastatic disease. In some embodiments, the human has received chemotherapy prior to the administering step. In some embodiments, prior to the administering step, the human has received at least one medication of the group consisting of fluoropyrimidine, irinotecan, oxaliplatin, bevacizunab, Capecitabine, Mitomycin, Regorafenib, cetuxinab, and panitumumab. In some embodiments, the human concurrently receives chemotherapy or radiation therapy treatment. In some embodiments, the human concurrently receives a therapy comprising the administration of at least one medication of the group consisting of fluoropyrimidine, irinotecan, oxaliplatin, bevacizunab, Capecitabine, Mitomycin, Regorafenib, cetuxinab, panitumumab, and acetinophen. In some embodiments, the human comprises cells overexpressing CEA. In some embodiments, the cells overexpressing CEA overexpress CEA more than 10 times over the baseline CEA expression in a non-cancer cell. In some embodiments, cells overexpressing CEA comprise cancer cells. In some embodiments, cells overexpressing CEA are not gastrointestinal epithelium cells. In some embodiments, cells overexpressing CEA overexpress CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, or PSG11.

BRIEF DESCRIPTION OF THE SEVERAL VIEWS OF THE DRAWINGS

FIG. 4A is a bar graph showing INF-γ. secreting splenocytes from Ad5 immune mice immunized with Ad5 [E1-]-CEA or Ad5 [E1-, E2b-]-CEA. Note the significantly elevated response in splenocytes from the Ad5 [E1-, E2b]-CEA immunized group. Values represent mean±SEM.

FIG. 4B is a bar graph showing IL-2 secreting splenocytes from Ad5 immune mice immunized with Ad5 [E1-]-CEA or Ad5 [E1-, E2b-]-CEA. Note the significantly elevated response in splenocytes from the Ad5 [E1-, E2b]-CEA immunized group. Values represent mean±SEM.

DETAILED DESCRIPTION

Figure 1:
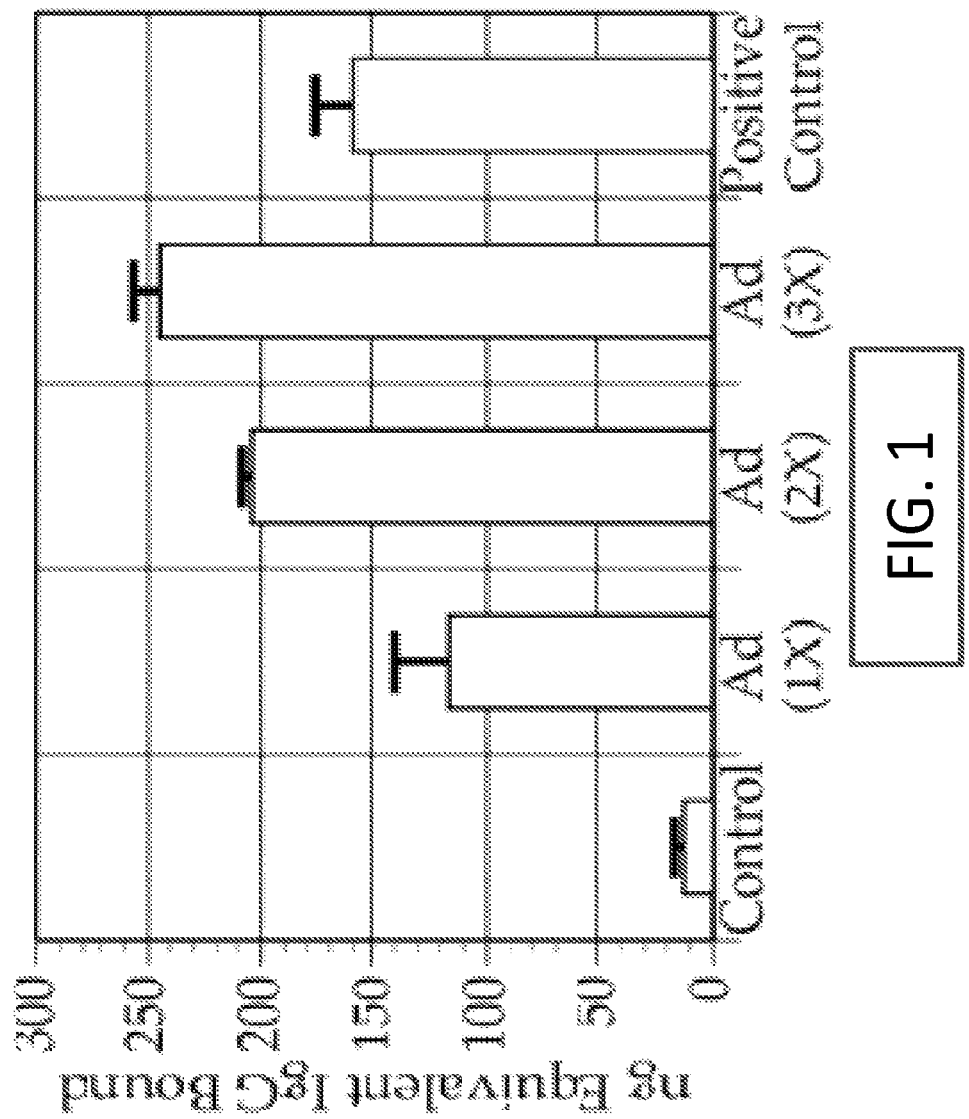
FIG. 1 is a bar graph showing antibody levels from mice immunized with Ad5Null. Mice were immunized three times with Ad5Null viral particles at 14 day intervals. Note the presence of increasing anti-Ad antibody levels after each immunization.

The present invention relates to methods and adenovirus vectors for generating immune responses against target antigens, in particular, those related to cancer cells. In various aspects of the invention, compositions and methods described herein relate to generating an immune response against cells expressing and/or presenting a target antigen, such as colorectal embryonic antigen (CEA). In some embodiments, a modified form of CEA is used in a vaccine directed to raising an immune response against CEA or cells expressing and/or presenting CEA. In particular, the present invention provides an improved adenovirus (Ad)-based vaccine such that multiple vaccinations against one or more antigenic target entity can be achieved. In some embodiments, the improved adenovirus (Ad)-based vaccine comprises a replication defective adenovirus carrying a target antigen, a fragment, a variant or a variant fragment thereof, such as Ad5 [E1-,E2b-]-CEA(6D). Variants and/or fragments of target antigens, for example CEA, can be selected based on a variety of factors, including immunogenic potential. Accordingly, a mutant CEA, CEA(6D) is utilized in various embodiments of the invention for its increased capability to raise an immune response relative to the wild type form. Importantly, vaccination can be performed in the presence of preexisting immunity to the Ad and/or administered to subjects previously immunized multiple times with the adenovirus vector of the present invention or other adenovirus vectors. The adenovirus vectors of the invention can be administered to subjects multiple times to induce an immune response against an antigen of interest, for example CEA, including but not limited to, the production of antibodies and cell-mediated immune responses against one or more target antigens.

The following passages describe different aspects of the invention in greater detail. Each aspect of the invention may be combined with any other aspect or aspects of the invention unless clearly indicated to the contrary. In particular, any feature indicated as being preferred or advantageous may be combined with any other feature of features indicated as being preferred or advantageous.

To facilitate an understanding of the present invention, a number of terms and phrases are defined below.

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, the term "or" can be conjunctive or disjunctive.

As used herein, unless otherwise indicated, any embodiment can be combined with any other embodiment.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

The term "adenovirus" or "Ad" refers to a group of non-enveloped DNA viruses from the family Adenoviridae. In addition to human hosts, these viruses can be found in, but are not limited to, avian, bovine, porcine and canine species. The present invention contemplates the use of any adenovirus from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutation, deletion or transposition of homologous or heterologous DNA sequences.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

The term "Adenovirus5 null (Ad5null)", as used herein, refers to a non-replicating Ad that does not contain any heterologous nucleic acid sequences for expression.

The term "First Generation adenovirus", as used herein, refers to an Ad that has the early region 1 (E1) deleted. In additional cases, the nonessential early region 3 (E3) may also be deleted.

The term "gutted" or "gutless", as used herein, refers to an adenovirus vector that has been deleted of all viral coding regions.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

The term "reporter gene" indicates a nucleotide sequence that encodes a reporter molecule (including an enzyme). A "reporter molecule" is detectable in any of a variety of detection systems, including, but not limited to enzyme-based detection assays (e.g., ELISA, as well as enzyme-based histochemical assays), fluorescent, radioactive, and luminescent systems. In one embodiment, the present invention contemplates the E. coli β-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene; other reporter genes are known to the art and may be employed.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The term "heterologous nucleic acid sequence", as used herein, refers to a nucleotide sequence that is ligated to, or is manipulated to become ligated to, a nucleic acid sequence to which it is not ligated in nature, or to which it is ligated at a different location in nature. Heterologous nucleic acid may include a nucleotide sequence that is naturally found in the cell into which it is introduced or the heterologous nucleic acid may contain some modification relative to the naturally occurring sequence.

The term "transgene" refers to any gene coding region, either natural or heterologous nucleic acid sequences or fused homologous or heterologous nucleic acid sequences, introduced into the cells or genome of a test subject. In the current invention, transgenes are carried on any viral vector that is used to introduce the transgenes to the cells of the subject.

The term "Second Generation Adenovirus", as used herein, refers to an Ad that has all or parts of the E1, E2, E3, and, in certain embodiments, E4 DNA gene sequences deleted (removed) from the virus.

The term "subject", as used herein, refers to any animal, e.g., a mammal or marsupial. Subjects of the present invention include but are not limited to humans, non-human primates (e.g., rhesus or other types of macaques), mice, pigs, horses, donkeys, cows, sheep, rats and fowl of any kind.

In particular embodiments, the present invention relates to a replication defective adenovirus vector of serotype 5 comprising a sequence encoding an immunogenic polypeptide. The immunogenic polypeptide may be a mutant CEA or a fragment thereof. In some embodiments, the immunogenic polypeptide comprises a mutant CEA with an Asn→Asp substitution at position 610. In some embodiments, the replication defective adenovirus vector comprises a sequence encoding a polypeptide with at least 75%, 80%, 85%, 90%, 95%, 98%, 99%, 99.5%, 99.9% identity to the immunogenic polypeptide. In some embodiments, the sequence encoding the immunogenic polypeptide comprises the following sequence identified by SEQ. ID. NO: 1:

```
                                              (SEQ. ID. NO.: 1).
ATGGAGTCTCCCTCGGCCCCTCCCCACAGATGGTGCATCCCCTGGCAGAG

GCTCCTGCTCACAGCCTCACTTCTAACCTTCTGGAACCCGCCCACCACTG

CCAAGCTCACTATTGAATCCACGCCGTTCAATGTCGCAGAGGGGAAGGAG

GTGCTTCTACTTGTCCACAATCTGCCCCAGCATCTTTTTGGCTACAGCTG

GTACAAAGGTGAAAGAGTGGATGGCAACCGTCAAATTATAGGATATGTAA

TAGGAACTCAACAAGCTACCCCAGGGCCCGCATACAGTGGTCGAGAGATA

ATATACCCCAATGCATCCCTGCTGATCCAGAACATCATCCAGAATGACAC

AGGATTCTACACCCTACACGTCATAAAGTCAGATCTTGTGAATGAAGAAG

CAACTGGCCAGTTCCGGGTATACCCGGAGCTGCCCAAGCCCTCCATCTCC

AGCAACAACTCCAAACCCGTGGAGGACAAGGATGCTGTGGCCTTCACCTG

TGAACCTGAGACTCAGGACGCAACCTACCTGTGGTGGGTAAACAATCAGA

GCCTCCCGGTCAGTCCCAGGCTGCAGCTGTCCAATGGCAACAGGACCCTC

ACTCTATTCAATGTCACAAGAAATGACACAGCAAGCTACAAATGTGAAAC

CCAGAACCCAGTGAGTGCCAGGCGCAGTGATTCAGTCATCCTGAATGTCC

TCTATGGCCCGGATGCCCCCACCATTTCCCCTCTAAACACATCTTACAGA
```

-continued

```
TCAGGGGAAAATCTGAACCTCTCCTGCCACGCAGCCTCTAACCCACCTGC

ACAGTACTCTTGGTTTGTCAATGGGACTTTCCAGCAATCCACCCAAGAGC

TCTTTATCCCCAACATCACTGTGAATAATAGTGGATCCTATACGTGCCAA

GCCCATAACTCAGACACTGGCCTCAATAGGACCACAGTCACGACGATCAC

AGTCTATGCAGAGCCACCCAAACCCTTCATCACCAGCAACAACTCCAACC

CCGTGGAGGATGAGGATGCTGTAGCCTTAACCTGTGAACCTGAGATTCAG

AACACAACCTACCTGTGGTGGGTAAATAATCAGAGCCTCCCGGTCAGTCC

CAGGCTGCAGCTGTCCAATGACAACAGGACCCTCACTCTACTCAGTGTCA

CAAGGAATGATGTAGGACCCTATGAGTGTGGAATCCAGAACGAATTAAGT

GTTGACCACAGCGACCCAGTCATCCTGAATGTCCTCTATGGCCCAGACGA

CCCCACCATTTCCCCCTCATACACCTATTACCGTCCAGGGGTGAACCTCA

GCCTCTCCTGCCATGCAGCCTCTAACCCACCTGCACAGTATTCTTGGCTG

ATTGATGGGAACATCCAGCAACACACACAAGAGCTCTTTATCTCCAACAT

CACTGAGAAGAACAGCGGACTCTATACCTGCCAGGCCAATAACTCAGCCA

GTGGCCACAGCAGGACTACAGTCAAGACAATCACAGTCTCTGCGGAGCTG

CCCAAGCCCTCCATCTCCAGCAACAACTCCAAACCCGTGGAGGACAAGGA

TGCTGTGGCCTTCACCTGTGAACCTGAGGCTCAGAACACAACCTACCTGT

GGTGGGTAAATGGTCAGAGCCTCCCAGTCAGTCCCAGGCTGCAGCTGTCC

AATGGCAACAGGACCCTCACTCTATTCAATGTCACAAGAAATGACGCAAG

AGCCTATGTATGTGGAATCCAGAACTCAGTGAGTGCAAACCGCAGTGACC

CAGTCACCCTGGATGTCCTCTATGGGCCGGACACCCCCATCATTTCCCCC

CCAGACTCGTCTTACCTTTCGGGAGCGAACCTCAACCTCTCCTGCCACTC

GGCCTCTAACCCATCCCCGCAGTATTCTTGGCGTATCAATGGGATACCGC

AGCAACACACACAAGTTCTCTTTATCGCCAAAATCACGCCAAATAATAAC

GGGACCTATGCCTGTTTTGTCTCTAACTTGGCTACTGGCCGCAATAATTC

CATAGTCAAGAGCATCACAGTCTCTGCATCTGGAACTTCTCCTGGTCTCT

CAGCTGGGGCCACTGTCGGCATCATGATTGGAGTGCTGGTTGGGGTTGCT

CTGATATAG,
```

In some embodiments, the sequence encoding the immunogenic polypeptide comprises a sequence with at least 75%, 80%, 85%, 90%, 95%, 98%, 99%, 99.5%, 99.9% identity to SEQ. ID. NO: 1 or a sequence generated from SEQ. ID. NO: 1 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human CEA sequence.

In some embodiments, the immunogenic polypeptide comprises a sequence from SEQ. ID. NO.:2 or a modified version, e.g. comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, of SEQ. ID. NO.:2:

SEQ. ID. NO.: 2.

-continued

```
ATGGAGTCTCCCTCGGCCCCTCCCCACAGATGGTGCATCCCTGGCAGAG
GCTCCTGCTCACAGCCTCACTTCTAACCTTCTGGAACCCGCCCACCACTG
CCAAGCTCACTATTGAATCCACGCCGTTCAATGTCGCAGAGGGGAAGGAG
GTGCTTCTACTTGTCCACAATCTGCCCCAGCATCTTTTTGGCTACAGCTG
GTACAAAGGTGAAAGAGTGGATGGCAACCGTCAAATTATAGGATATGTAA
TAGGAACTCAACAAGCTACCCCAGGGCCCGCATACAGTGGTCGAGAGATA
ATATACCCCAATGCATCCCTGCTGATCCAGAACATCATCCAGAATGACAC
AGGATTCTACACCCTACACGTCATAAAGTCAGATCTTGTGAATGAAGAAG
CAACTGGCCAGTTCCGGGTATACCCGGAGCTGCCCAAGCCCTCCATCTCC
AGCAACAACTCCAAACCCGTGGAGGACAAGGATGCTGTGGCCTTCACCTG
TGAACCTGAGACTCAGGACGCAACCTACCTGTGGTGGGTAAACAATCAGA
GCCTCCCGGTCAGTCCCAGGCTGCAGCTGTCCAATGGCAACAGGACCCTC
ACTCTATTCAATGTCACAAGAAATGACACAGCAAGCTACAAATGTGAAAC
CCAGAACCCAGTGAGTGCCAGGCGCAGTGATTCAGTCATCCTGAATGTCC
TCTATGGCCCGGATGCCCCCACCATTTCCCCTCTAAACACATCTTACAGA
TCAGGGGAAAATCTGAACCTCTCCTGCCACGCAGCCTCTAACCCACCTGC
ACAGTACTCTTGGTTTGTCAATGGGACTTTCCAGCAATCCACCCAAGAGC
TCTTTATCCCCAACATCACTGTGAATAATAGTGGATCCTATACGTGCCAA
GCCCATAACTCAGACACTGGCCTCAATAGGACCACAGTCACGACGATCAC
AGTCTATGCAGAGCCACCCAAACCCTTCATCACCAGCAACAACTCCAACC
CCGTGGAGGATGAGGATGCTGTAGCCTTAACCTGTGAACCTGAGATTCAG
AACACAACCTACCTGTGGTGGGTAAATAATCAGAGCCTCCCGGTCAGTCC
CAGGCTGCAGCTGTCCAATGACAACAGGACCCTCACTCTACTCAGTGTCA
CAAGGAATGATGTAGGACCCTATGAGTGTGGAATCCAGAACGAATTAAGT
GTTGACCACAGCGACCCAGTCATCCTGAATGTCCTCTATGGCCCAGACGA
CCCCACCATTTCCCCCTCATACACCTATTACCGTCCAGGGGTGAACCTCA
GCCTCTCCTGCCATGCAGCCTCTAACCCACCTGCACAGTATTCTTGGCTG
ATTGATGGGAACATCCAGCAACACACAAGAGCTCTTTATCTCCAACAT
CACTGAGAAGAACAGCGGACTCTATACCTGCCAGGCCAATAACTCAGCCA
GTGGCCACAGCAGGACTACAGTCAAGACAATCACAGTCTCTGCGGAGCTG
CCCAAGCCCTCCATCTCCAGCAACAACTCCAAACCCGTGGAGGACAAGGA
TGCTGTGGCCTTCACCTGTGAACCTGAGGCTCAGAACACAACCTACCTGT
GGTGGGTAAATGGTCAGAGCCTCCCAGTCAGTCCCAGGCTGCAGCTGTCC
AATGGCAACAGGACCCTCACTCTATTCAATGTCACAAGAAATGACGCAAG
AGCCTATGTATGTGGAATCCAGAACTCAGTGAGTGCAAACCGCAGTGACC
CAGTCACCCTGGATGTCCTCTATGGGCCGGACACCCCCATCATTTCCCCC
CCAGACTCGTCTTACCTTTCGGGAGCGAACCTCAACCTCTCCTGCCACTC
GGCCTCTAACCCATCCCGCAGTATTCTTGGCGTATCAATGGGATACCGC
AGCAACACACACAAGTTCTCTTTATCGCCAAAATCACGCCAAATAATAAC
GGGACCTATGCCTGTTTTGTCTCTAACTTGGCTACTGGCCGCAATAATTC
CATAGTCAAGAGCATCACAGTCTCTGCATCTGGAACTTCTCCTGGTCTCT
```

-continued

```
CAGCTGGGGCCACTGTCGGCATCATGATTGGAGTGCTGGTTGGGGTTGCT
CTGATATAG,
```

The compositions and methods of the invention, in some embodiments, relate to an adenovirus-derived vector comprising the following sequence identified by SEQ. ID. NO: 3:

(SEQ. ID. NO: 3).
```
CATCATCAATAATATACCTTATTTTGGATTGAAGCCAATATGATAATGAG
GGGGTGGAGTTTGTGACGTGGCGCGGGGCGTGGGAACGGGGCGGGTGACG
TAGTAGTGTGGCGGAAGTGTGATGTTGCAAGTGTGGCGGAACACATGTAA
GCGACGGATGTGGCAAAAGTGACGTTTTTGGTGTGCGCCGGTGTACACAG
GAAGTGACAATTTTCGCGCGGTTTTAGGCGGATGTTGTAGTAAATTTGGG
CGTAACCGAGTAAGATTTGGCCATTTTCGCGGGAAAACTGAATAAGAGGA
AGTGAAATCTGAATAATTTTGTGTTACTCATAGCGCGTAATACTGTAATA
GTAATCAATTACGGGGTCATTAGTTCATAGCCCATATATGGAGTTCCGCG
TTACATAACTTACGGTAAATGGCCCGCCTGGCTGACCGCCCAACGACCCC
CGCCCATTGACGTCAATAATGACGTATGTTCCCATAGTAACGCCAATAGG
GACTTTCCATTGACGTCAATGGGTGGAGTATTTACGGTAAACTGCCCACT
TGGCAGTACATCAAGTGTATCATATGCCAAGTACGCCCCCTATTGACGTC
AATGACGGTAAATGGCCCGCCTGGCATTATGCCCAGTACATGACCTTATG
GGACTTTCCTACTTGGCAGTACATCTACGTATTAGTCATCGCTATTACCA
TGGTGATGCGGTTTTGGCAGTACATCAATGGGCGTGGATAGCGGTTTGAC
TCACGGGGATTTCCAAGTCTCCACCCCATTGACGTCAATGGGAGTTTGTT
TTGGCACCAAAATCAACGGGACTTTCCAAAATGTCGTAACAACTCCGCCC
CATTGACGCAAATGGGCGGTAGGCGTGTACGGTGGGAGGTCTATATAAGC
AGAGCTGGTTTAGTGAACCGTCAGATCCGCTAGAGATCTGGTACCGTCGA
CGCGGCCGCTCGAGCCTAAGCTTGGTACCGAGCTCGGATCCACTAGTAAC
GGCCGCCAGTGTGCTGGAATTCGGCTTAAAGGTACCCAGAGCAGACAGCC
GCCACCATGGAGTCTCCCTCGGCCCCTCCCCACAGATGGTGCATCCCTG
GCAGAGGCTCCTGCTCACAGCCTCACTTCTAACCTTCTGGAACCCGCCCA
CCACTGCCAAGCTCACTATTGAATCCACGCCGTTCAATGTCGCAGAGGGG
AAGGAGGTGCTTCTACTTGTCCACAATCTGCCCCAGCATCTTTTTGGCTA
CAGCTGGTACAAAGGTGAAAGAGTGGATGGCAACCGTCAAATTATAGGAT
ATGTAATAGGAACTCAACAAGCTACCCCAGGGCCCGCATACAGTGGTCGA
GAGATAATATACCCCAATGCATCCCTGCTGATCCAGAACATCATCCAGAA
TGACACAGGATTCTACACCCTACACGTCATAAAGTCAGATCTTGTGAATG
AAGAAGCAACTGGCCAGTTCCGGGTATACCCGGAGCTGCCCAAGCCCTCC
ATCTCCAGCAACAACTCCAAACCCGTGGAGGACAAGGATGCTGTGGCCTT
CACCTGTGAACCTGAGACTCAGGACGCAACCTACCTGTGGTGGGTAAACA
ATCAGAGCCTCCCGGTCAGTCCCAGGCTGCAGCTGTCCAATGGCAACAGG
ACCCTCACTCTATTCAATGTCACAAGAAATGACACAGCAAGCTACAAATG
```

```
TGAAACCCAGAACCCAGTGAGTGCCAGGCGCAGTGATTCAGTCATCCTGA
ATGTCCTCTATGGCCCGGATGCCCCCACCATTTCCCCTCTAAACACATCT
TACAGATCAGGGGAAAATCTGAACCTCTCCTGCCACGCAGCCTCTAACCC
ACCTGCACAGTACTCTTGGTTTGTCAATGGGACTTTCCAGCAATCCACCC
AAGAGCTCTTTATCCCCAACATCACTGTGAATAATAGTGGATCCTATACG
TGCCAAGCCCATAACTCAGACACTGGCCTCAATAGGACCACAGTCACGAC
GATCACAGTCTATGCAGAGCCACCCAAACCCTTCATCACCAGCAACAACT
CCAACCCCGTGGAGGATGAGGATGCTGTAGCCTTAACCTGTGAACCTGAG
ATTCAGAACACAACCTACCTGTGGTGGGTAAATAATCAGAGCCTCCCGGT
CAGTCCCAGGCTGCAGCTGTCCAATGACAACAGGACCCTCACTCTACTCA
GTGTCACAAGGAATGATGTAGGACCCTATGAGTGTGGAATCCAGAACGAA
TTAAGTGTTGACCACAGCGACCCAGTCATCCTGAATGTCCTCTATGGCCC
AGACGACCCCACCATTTCCCCCTCATACACCTATTACCGTCCAGGGGTGA
ACCTCAGCCTCTCCTGCCATGCAGCCTCTAACCCACCTGCACAGTATTCT
TGGCTGATTGATGGGAACATCCAGCAACACACACAAGAGCTCTTTATCTC
CAACATCACTGAGAAGAACAGCGGACTCTATACCTGCCAGGCCAATAACT
CAGCCAGTGGCCACAGCAGGACTACAGTCAAGACAATCACAGTCTCTGCG
GAGCTGCCCAAGCCCTCCATCTCCAGCAACAACTCCAAACCCGTGGAGGA
CAAGGATGCTGTGGCCTTCACCTGTGAACCTGAGGCTCAGAACACAACCT
ACCTGTGGTGGGTAAATGGTCAGAGCCTCCCAGTCAGTCCCAGGCTGCAG
CTGTCCAATGGCAACAGGACCCTCACTCTATTCAATGTCACAAGAAATGA
CGCAAGAGCCTATGTATGTGGAATCCAGAACTCAGTGAGTGCAAACCGCA
GTGACCCAGTCACCCTGGATGTCCTCTATGGGCCGGACACCCCCATCATT
TCCCCCCCAGACTCGTCTTACCTTTCGGGAGCGGACCTCAACCTCTCCTG
CCACTCGGCCTCTAACCCATCCCCGCAGTATTCTTGGCGTATCAATGGGA
TACCGCAGCAACACACACAAGTTCTCTTTATCGCCAAAATCACGCCAAAT
AATAACGGGACCTATGCCTGTTTTGTCTCTAACTTGGCTACTGGCCGCAA
TAATTCCATAGTCAAGAGCATCACAGTCTCTGCATCTGGAACTTCTCCTG
GTCTCTCAGCTGGGGCACTGTCGGCATCATGATTGGAGTGCTGGTTGGG
GTTGCTCTGATATAGCAGCCCTGGTGTAGTTTCTTCATTTCAGGAAGACT
GACAGTTGTTTGCTTCTTCCTTAAAGCATTTGCAACAGCTACAGTCTAA
AATTGCTTCTTTACCAAGGATATTTACAGAAAAGACTCTGACCAGAGATC
GAGACCATCCTCTAGATAAGATATCCGATCCACCGGATCTAGATAACTGA
TCATAATCAGCCATACCACATTTGTAGAGGTTTTACTTGCTTTAAAAAAC
CTCCCACACCTCCCCCTGAACCTGAAACATAAAATGAATGCAATTGTTGT
TGTTAACTTGTTTATTGCAGCTTATAATGGTTACAAATAAAGCAATAGCA
TCACAAATTTCACAAATAAAGCATTTTTTCACTGCATTCTAGTTGTGGT
TTGTCCAAACTCATCAATGTATCTTAACGCGGATCTGGGCGTGGTTAAGG
GTGGGAAAGAATATATAAGGTGGGGGTCTTATGTAGTTTTGTATCTGTTT
TGCAGCAGCCGCCGCCGCCATGAGCACCAACTCGTTTGATGGAAGCATTG
TGAGCTCATATTTGACAACGCGCATGCCCCATGGGCCGGGGTGCGTCAG
```

```
AATGTGATGGGCTCCAGCATTGATGGTCGCCCCGTCCTGCCCGCAAACTC
TACTACCTTGACCTACGAGACCGTGTCTGGAACGCCGTTGGAGACTGCAG
CCTCCGCCGCCGCTTCAGCCGCTGCAGCCACCGCCCGCGGGATTGTGACT
GACTTTGCTTTCCTGAGCCCGCTTGCAAGCAGTGCAGCTTCCCGTTCATC
CGCCCGCGATGACAAGTTGACGGCTCTTTTGGCACAATTGGATTCTTTGA
CCCGGGAACTTAATGTCGTTTCTCAGCAGCTGTTGGATCTGCGCCAGCAG
GTTTCTGCCCTGAAGGCTTCCTCCCCTCCCAATGCGGTTTAAAACATAAA
TAAAAACCAGACTCTGTTTGGATTTGGATCAAGCAAGTGTCTTGCTGTC
TTTATTTAGGGGTTTTGCGCGCGCGGTAGGCCCGGGACCAGCGGTCTCGG
TCGTTGAGGGTCCTGTGTATTTTTTCCAGGACGTGGTAAAGGTGACTCTG
GATGTTCAGATACATGGGCATAAGCCCGTCTCTGGGGTGGAGGTAGCACC
ACTGCAGAGCTTCATGCTGCGGGGTGGTGTTGTAGATGATCCAGTCGTAG
CAGGAGCGCTGGGCGTGGTGCCTAAAAATGTCTTTCAGTAGCAAGCTGAT
TGCCAGGGGCAGGCCCTTGGTGTAAGTGTTTACAAAGCGGTTAAGCTGGG
ATGGGTGCATACGTGGGGATATGAGATGCATCTTGGACTGTATTTTTAGG
TTGGCTATGTTCCCAGCCATATCCCTCCGGGGATTCATGTTGTGCAGAAC
CACCAGCACAGTGTATCCGGTGCACTTGGGAAATTTGTCATGTAGCTTAG
AAGGAAATGCGTGGAAGAACTTGGAGACGCCCTTGTGACCTCCAAGATTT
TCCATGCATTCGTCCATAATGATGGCAATGGGCCCACGGGCGGCGGCCTG
GGCGAAGATATTTCTGGGATCACTAACGTCATAGTTGTGTTCCAGGATGA
GATCGTCATAGGCCATTTTTACAAAGCGCGGGCGGAGGGTGCCAGACTGC
GGTATAATGGTTCCATCCGGCCCAGGGGCGTAGTTACCCTCACAGATTTG
CATTTCCCACGCTTTGAGTTCAGATGGGGGGATCATGTCTACCTGCGGGG
CGATGAAGAAAACGGTTTCCGGGGTAGGGGAGATCAGCTGGGAAGAAAGC
AGGTTCCTGAGCAGCTGCGACTTACCGCAGCCGGTGGGCCCGTAAATCAC
ACCTATTACCGGCTGCAACTGGTAGTTAAGAGAGCTGCAGCTGCCGTCAT
CCCTGAGCAGGGGGGCACTTCGTTAAGCATGTCCCTGACTCGCATGTTT
TCCCTGACCAAATCCGCCAGAAGGCGCTCGCCGCCCAGCGATAGCAGTTC
TTGCAAGGAAGCAAAGTTTTTCAACGGTTTGAGACCGTCCGCCGTAGGCA
TGCTTTTGAGCGTTTGACCAAGCAGTTCCAGGCGGTCCCACAGCTCGGTC
ACCTGCTCTACGGCATCTCGATCCAGCATATCTCCTCGTTTCGCGGGTTG
GGGCGGCTTTCGCTGTACGGCAGTAGTCGGTGCTCGTCCAGACGGGCCAG
GGTCATGTCTTTCCACGGGCGCAGGGTCCTCGTCAGCGTAGTCTGGGTCA
CGGTGAAGGGGTGCGCTCCGGGCTGCGCGCTGGCCAGGGTGCGCTTGAGG
CTGGTCCTGCTGGTGCTGAAGCGCTGCCGGTCTTCGCCCTGCGCGTCGGC
CAGGTAGCATTTGACCATGGTGTCATAGTCCAGCCCCTCCGCGGCGTGGC
CCTTGGCGCGCAGCTTGCCCTTGGAGGAGGCGCCGCACGAGGGGCAGTGC
AGACTTTTGAGGGCGTAGAGCTTGGGCGCGAGAAATACCGATTCCGGGGA
GTAGGCATCCGCGCCGCAGGCCCCGCAGACGGTCTCGCATTCCACGAGCC
AGGTGAGCTCTGGCCGTTCGGGGTCAAAAACCAGGTTTCCCCCATGCTTT
```

```
TTGATGCGTTTCTTACCTCTGGTTTCCATGAGCCGGTGTCCACGCTCGGT
GACGAAAAGGCTGTCCGTGTCCCCGTATACAGACTTGAGAGGCCTGTCCT
CGAGCGGTGTTCCGCGGTCCTCCTCGTATAGAAACTCGGACCACTCTGAG
ACAAAGGCTCGCGTCCAGGCCAGCACGAAGGAGGCTAAGTGGGAGGGGTA
GCGGTCGTTGTCCACTAGGGGTCCACTCGCTCCAGGGTGTGAAGACACA
TGTCGCCCTCTTCGGCATCAAGGAAGGTGATTGGTTTGTAGGTGTAGGCC
ACGTGACCGGGTGTTCCTGAAGGGGGCTATAAAAGGGGGTGGGGCGCG
TTCGTCCTCACTCTCTTCCGCATCGCTGTCTGCGAGGGCCAGCTGTTGGG
GTGAGTACTCCCTCTGAAAAGCGGGCATGACTTCTGCGCTAAGATTGTCA
GTTTCCAAAAACGAGGAGGATTTGATATTCACCTGGCCCGCGGTGATGCC
TTTGAGGGTGGCCGCATCCATCTGGTCAGAAAAGACAATCTTTTTGTTGT
CAAGCTTGGTGGCAAACGACCCGTAGAGGGCGTTGGACAGCAACTTGGCG
ATGGAGCGCAGGGTTTGGTTTTTGTCGCGATCGGCGCGCTCCTTGGCCGC
GATGTTTAGCTGCACGTATTCGCGCGCAACGCACCGCCATTCGGGAAAGA
CGGTGGTGCGCTCGTCGGGCACCAGGTGCACGCGCCAACCGCGGTTGTGC
AGGGTGACAAGGTCAACGCTGGTGGCTACCTCTCCGCGTAGGCGCTCGTT
GGTCCAGCAGAGGCGGCCGCCCTTGCGCGAGCAGAATGGCGGTAGGGGT
CTAGCTGCGTCTCGTCCGGGGGTCTGCGTCCACGGTAAAGACCCCGGGC
AGCAGGCGCGCGTCGAAGTAGTCTATCTTGCATCCTTGCAAGTCTAGCGC
CTGCTGCCATGCGCGGGCGGCAAGCGCGCGCTCGTATGGGTTGAGTGGGG
GACCCCATGGCATGGGTGGGTGAGCGCGGAGGCGTACATGCCGCAAATG
TCGTAAACGTAGAGGGGCTCTCTGAGTATTCCAAGATATGTAGGGTAGCA
TCTTCCACCGCGGATGCTGGCGCGCACGTAATCGTATAGTTCGTGCGAGG
GAGCGAGGAGGTCGGGACCGAGGTTGCTACGGGCGGGCTGCTCTGCTCGG
AAGACTATCTGCCTGAAGATGGCATGTGAGTTGGATGATATGGTTGGACG
CTGGAAGACGTTGAAGCTGGCGTCTGTGAGACCTACCGCGTCACGCACGA
AGGAGGCGTAGGAGTCGCGCAGCTTGTTGACCAGCTCGGCGGTGACCTGC
ACGTCTAGGGCGCAGTAGTCCAGGGTTTCCTTGATGATGTCATACTTATC
CTGTCCCTTTTTTTTCCACAGCTCGCGGTTGAGGACAAACTCTTCGCGGT
CTTTCCAGTACTCTTGGATCGGAAACCCGTCGGCCTCCGAACGGTAAGAG
CCTAGCATGTAGAACTGGTTGACGGCCTGGTAGGCGCAGCATCCCTTTTC
TACGGGTAGCGCGTATGCCTGCGCGGCCTTCCGGCATGACCAGCATGAAG
GGCACGAGCTGCTTCCCAAAGGCCCCCATCCAAGTATAGGTCTCTACATC
GTAGGTGACAAAGAGACGCTCGGTGCGAGGATGCGAGCCGATCGGGAAGA
ACTGGATCTCCCGCCACCAATTGGAGGAGTGGCTATTGATGTGGTGAAAG
TAGAAGTCCCTGCGACGGGCCGAACACTCGTGCTGGCTTTTGTAAAAACG
TGCGCAGTACTGGCAGCGGTGCACGGGCTGTACATCCTGCACGAGGTTGA
CCTGACGACCGCGCACAAGGAAGCAGAGTGGGAATTTGAGCCCCTCGCCT
GGCGGGTTTGGCTGGTGGTCTTCTACTTCGGCTGCTTGTCCTTGACCGTC
TGGCTGCTCGAGGGGAGTTACGGTGGATCGGACCACCACGCCGCGCAGC
CCAAAGTCCAGATGTCCGCGCGCGGCGGTCGGAGCTTGATGACAACATCG

CGCAGATGGGAGCTGTCCATGGTCTGGAGCTCCCGCGGCGTCAGGTCAGG
CGGGAGCTCCTGCAGGTTTACCTCGCATAGACGGGTCAGGGCGCGGGCTA
GATCCAGGTGATACCTAATTTCCAGGGGCTGGTTGGTGGCGGCGTCGATG
GCTTGCAAGAGGCCGCATCCCCGCGGCGCGACTACGGTACCGCGCGGCGG
GCGGTGGGCCGCGGGGGTGTCCTTGGATGATGCATCTAAAAGCGGTGACG
CGGGCGAGCCCCCGGAGGTAGGGGGGGCTCCGGACCCGCCGGGAGAGGGG
GCAGGGGCACGTCGGCGCCGCGCGCGGGCAGGAGCTGGTGCTGCGCGCGT
AGGTTGCTGGCGAACGCGACGACGCGGCGGTTGATCTCCTGAATCTGGCG
CCTCTGCGTGAAGACGACGGGCCCGGTGAGCTTGAACCTGAAAGAGAGTT
CGACAGAATCAATTTCGGTGTCGTTGACGGCGGCCTGGCGCAAAATCTCC
TGCACGTCTCCTGAGTTGTCTTGATAGGCGATCTCGGCCATGAACTGCTC
GATCTCTTCCTCCTGGAGATCTCCGCGTCCGGCTCGCTCCACGGTGGCGG
CGAGGTCGTTGGAAATGCGGGCCATGAGCTGCGAGAAGGCGTTGAGGCCT
CCCTCGTTCCAGACGCGGCTGTAGACCACGCCCCCTTCGGCATCGCGGGC
GCGCATGACCACCTGCGCGAGATTGAGCTCCACGTGCCGGGCGAAGACGG
CGTAGTTTCGCAGGCGCTGAAAGAGGTAGTTGAGGGTGGTGGCGGTGTGT
TCTGCCACGAAGAAGTACATAACCCAGCGTCGCAACGTGGATTCGTTGAT
AATTGTTGTGTAGGTACTCCGCCGCCGAGGGACCTGAGCGAGTCCGCATC
GACCGGATCGGAAAACCTCTCGAGAAAGGCGTCTAACCAGTCACAGTCGC
AAGGTAGGCTGAGCACCGTGGCGGGCGGCAGCGGGCGGCGGTCGGGGTTG
TTTCTGGCGGAGGTGCTGCTGATGATGTAATTAAAGTAGGCGGTCTTGAG
ACGGCGGATGGTCGACAGAAGCACCATGTCCTTGGGTCCGGCCTGCTGAA
TGCGCAGGCGGTCGGCCATGCCCCAGGCTTCGTTTTGACATCGGCGCAGG
TCTTTGTAGTAGTCTTGCATGAGCCTTTCTACCGGCACTTCTTCTTCTCC
TTCCTCTTGTCCTGCATCTCTTGCATCTATCGCTGCGGCGGCGGCGGAGT
TTGGCCGTAGGTGGCGCCCTCTTCCTCCCATGCGTGTGACCCCGAAGCCC
CTCATCGGCTGAAGCAGGGCTAGGTCGGCGACAACGCGCTCGGCTAATAT
GGCCTGCTGCACCTGCGTGAGGGTAGACTGGAAGTCATCCATGTCCACAA
AGCGGTGGTATGCGCCCGTGTTGATGGTGTAAGTGCAGTTGGCCATAACG
GACCAGTTAACGGTCTGGTGACCCGGCTGCGAGAGCTCGGTGTACCTGAG
ACGCGAGTAAGCCCTCGAGTCAAATACGTAGTCGTTGCAAGTCCGCACCA
GGTACTGGTATCCCACCAAAAAGTGCGGCGGCGGCTGGCGGTAGAGGGGC
CAGCGTAGGGTGGCCGGGGCTCCGGGGGCGAGATCTTCCAACATAAGGCG
ATGATATCCGTAGATGTACCTGGACATCCAGGTGATGCCGGCGGCGGTGG
TGGAGGCGCGCGGAAAGTCGCGGACGCGGTTCCAGATGTTGCGCAGCGGC
AAAAAGTGCTCCATGGTCGGGACGCTCTGGCCGGTCAGGCGCGCGCAATC
GTTGACGCTCTAGCGTGCAAAAGGAGAGCCTGTAAGCGGGCACTCTTCCG
TGGTCTGGTGGATAAATTCGCAAGGGTATCATGGCGGACGACCGGGGTTC
GAGCCCCGTATCCGGCCGTCCGCCGTGATCCATGCGGTTACCGCCCGCGT
GTCGAACCCAGGTGTGCGACGTCAGACAACGGGGAGTGCTCCTTTTGGC
```

-continued

```
TTCCTTCCAGGCGCGGCGGCTGCTGCGCTAGCTTTTTTGGCCACTGGCCG
CGCGCAGCGTAAGCGGTTAGGCTGGAAAGCGAAAGCATTAAGTGGCTCGC
TCCCTGTAGCCGGAGGGTTATTTTCCAAGGGTTGAGTCGCGGGACCCCCG
GTTCGAGTCTCGGACCGGCCGGACTGCGGCGAACGGGGGTTTGCCTCCCC
GTCATGCAAGACCCCGCTTGCAAATTCCTCCGGAAACAGGGACGAGCCCC
TTTTTTGCTTTTCCCAGATGCATCCGGTGCTGCGGCAGATGCGCCCCCCT
CCTCAGCAGCGGCAAGAGCAAGAGCAGCGGCAGACATGCAGGGCACCCTC
CCCTCCTCCTACCGCGTCAGGAGGGGCGACATCCGCGGTTGACGCGGCAG
CAGATGGTGATTACGAACCCCCGCGGCGCCGGGCCCGGCACTACCTGGAC
TTGGAGGAGGGCGAGGGCCTGGCGCGGCTAGGAGCGCCCTCTCCTGAGCG
GCACCCAAGGGTGCAGCTGAAGCGTGATACGCGTGAGGCGTACGTGCCGC
GGCAGAACCTGTTTCGCGACCGCGAGGGAGAGGAGCCCGAGGAGATGCGG
GATCGAAAGTTCCACGCAGGGCGCGAGCTGCGGCATGGCCTGAATCGCGA
GCGGTTGCTGCGCGAGGAGGACTTTGAGCCCGACGCGCGAACCGGGATTA
GTCCCGCGCGCACACGTGGCGGCCGCCGACCTGGTAACCGCATACGAG
CAGACGGTGAACCAGGAGATTAACTTTCAAAAAGCTTTAACAACCACGT
GCGTACGCTTGTGGCGCGCGAGGAGGTGGCTATAGGACTGATGCATCTGT
GGGACTTTGTAAGCGCGCTGGAGCAAAACCCAAATAGCAAGCCGCTCATG
GCGCAGCTGTTCCTTATAGTGCAGCACAGCAGGGACAACGAGGCATTCAG
GGATGCGCTGCTAAACATAGTAGAGCCCGAGGGCCGCTGGCTGCTCGATT
TGATAAACATCCTGCAGAGCATAGTGGTGCAGGAGCGCAGCTTGAGCCTG
GCTGACAAGGTGGCCGCCATCAACTATTCCATGCTTAGCCTGGGCAAGTT
TTACGCCCGCAAGATATACCATACCCCTTACGTTCCCATAGACAAGGAGG
TAAAGATCGAGGGGTTCTACATGCGCATGGCGCTGAAGGTGCTTACCTTG
AGCGACGACCTGGGCGTTTATCGCAACGAGCGCATCCACAAGGCCGTGAG
CGTGAGCCGGCGGCGCGAGCTCAGCGACCGCGAGCTGATGCACAGCCTGC
AAAGGGCCCTGGCTGGCACGGGCAGCGGCGATAGAGAGGCCGAGTCCTAC
TTTGACGCGGGCGCTGACCTGCGCTGGGCCCAAGCCGACGCGCCCTGGA
GGCAGCTGGGGCCGGACCTGGGCTGGCGGTGGCACCCGCGCGCGCTGGCA
ACGTCGGCGGCGTGGAGGAATATGACGAGGACGATGAGTACGAGCCAGAG
GACGGCGAGTACTAAGCGGTGATGTTTCTGATCAGATGATGCAAGACGCA
ACGGACCCGGCGGTGCGGGCGGCGCTGCAGAGCCAGCCGTCCGGCCTTAA
CTCCACGGACGACTGGCGCCAGGTCATGGACCGCATCATGTCGCTGACTG
CGCGCAATCCTGACGCGTTCCGGCAGCAGCCGCAGGCCAACCGGCTCTCC
GCAATTCTGGAAGCGGTGGTCCCGGCGCGCGCAAACCCCACGCACGAGAA
GGTGCTGGCGATCGTAAACGCGCTGGCCGAAAACAGGGCCATCCGGCCCG
ACGAGGCCGGCCTGGTCTACGACGCGCTGCTTCAGCGCGTGGCTCGTTAC
AACAGCGGCAACGTGCAGACCAACCTGGACCGGCTGGTGGGGGATGTGCG
CGAGGCCGTGGCGCAGCGTGAGCGCGCGCAGCAGCAGGGCAACCTGGGCT
CCATGGTTGCACTAAACGCCTTCCTGAGTACACAGCCCGCCAACGTGCCG
CGGGGACAGGAGGACTACACCAACTTTGTGAGCGCACTGCGGCTAATGGT
```

```
GACTGAGACACCGCAAAGTGAGGTGTACCAGTCTGGGCCAGACTATTTTT
TCCAGACCAGTAGACAAGGCCTGCAGACCGTAAACCTGAGCCAGGCTTTC
AAAAACTTGCAGGGGCTGTGGGGGGTGCGGGCTCCCACAGGCGACCGCGC
GACCGTGTCTAGCTTGCTGACGCCCAACTCGCGCCTGTTGCTGCTGCTAA
TAGCGCCCTTCACGGACAGTGGCAGCGTGTCCCGGGACACATACCTAGGT
CACTTGCTGACACTGTACCGCGAGGCCATAGGTCAGGCGCATGTGGACGA
GCATACTTTCCAGGAGATTACAAGTGTCAGCCGCGCGCTGGGGCAGGAGG
ACACGGGCAGCCTGGAGGCAACCCTAAACTACCTGCTGACCAACCGGCGG
CAGAAGATCCCCTCGTTGCACAGTTTAAACAGCGAGGAGGAGCGCATTTT
GCGCTACGTGCAGCAGAGCGTGAGCCTTAACCTGATGCGCGACGGGGTAA
CGCCCAGCGTGGCGCTGGACATGACCGCGCGCAACATGGAACCGGGCATG
TATGCCTCAAACCGGCCGTTTATCAACCGCCTAATGGACTACTTGCATCG
CGCGGCCGCCGTGAACCCCGAGTATTTCACCAATGCCATCTTGAACCCGC
ACTGGCTACCGCCCCCTGGTTTCTACACCGGGGGATTCGAGGTGCCCGAG
GGTAACGATGGATTCCTCTGGGACGACATAGACGACAGCGTGTTTTCCCC
GCAACCGCAGACCCTGCTAGAGTTGCAACAGCGCGAGCAGGCAGAGGCGG
CGCTGCGAAAGGAAAGCTTCCGCAGGCCAAGCAGCTTGTCCGATCTAGGC
GCTGCGGCCCCGCGGTCAGATGCTAGTAGCCCATTTCCAAGCTTGATAGG
GTCTCTTACCAGCACTCGCACCACCCGCCCGCGCCTGCTGGGCGAGGAGG
AGTACCTAAACAACTCGCTGCTGCAGCCGCAGCGCGAAAAAAACCTGCCT
CCGGCATTTCCCAACAACGGGATAGAGAGCCTAGTGGACAAGATGAGTAG
ATGGAAGACGTACGCGCAGGAGCACAGGGACGTGCCAGGCCCGCGCCCGC
CCACCCGTCGTCAAAGGCACGACCGTCAGCGGGGTCTGGTGTGGGAGGAC
GATGACTCGGCAGACGACAGCAGCGTCCTGGATTTGGGAGGGAGTGGCAA
CCCGTTTGCGCACCTTCGCCCCAGGCTGGGGAGAATGTTTTAAAAAAAAA
AAAGCATGATGCAAAATAAAAAACTCACCAAGGCCATGGCACCGAGCGTT
GGTTTTCTTGTATTCCCCTTAGTATGCGGCGCGCGGCGATGTATGAGGAA
GGTCCTCCTCCCTCCTACGAGAGTGTGGTGAGCGCGGCGCCAGTGGCGGC
GGCGCTGGGTTCTCCCTTCGATGCTCCCCTGGACCCGCCGTTTGTGCCTC
CGCGGTACCTGCGGCCTACCGGGGGAGAAACAGCATCCGTTACTCTGAG
TTGGCACCCCTATTCGACACCACCCGTGTGTACCTGGTGGACAACAAGTC
AACGGATGTGGCATCCCTGAACTACCAGAACGACCACAGCAACTTTCTGA
CCACGGTCATTCAAAACAATGACTACAGCCCGGGGGAGGCAAGCACACAG
ACCATCAATCTTGACGACCGGTCGCACTGGGGCGGCGACCTGAAAACCAT
CCTGCATACCAACATGCCAAATGTGAACGAGTTCATGTTTACCAATAAGT
TTAAGGCGCGGGTGATGGTGTCGCGCTTGCCTACTAAGGACAATCAGGTG
GAGCTGAAATACGAGTGGGTGGAGTTCACGCTGCCCGAGGGCAACTACTC
CGAGACCATGACCATAGACCTTATGAACAACGCGATCGTGGAGCACTACT
TGAAAGTGGGCAGACAGAACGGGGTTCTGGAAAGCGACATCGGGGTAAAG
TTTGACACCCGCAACTTCAGACTGGGGTTTGACCCCGTCACTGGTCTTGT
```

-continued

CATGCCTGGGGTATATACAAACGAAGCCTTCCATCCAGACATCATTTTGC
TGCCAGGATGCGGGGTGGACTTCACCCACAGCCGCCTGAGCAACTTGTTG
GGCATCCGCAAGCGGCAACCCTTCCAGGAGGGCTTTAGGATCACCTACGA
TGATCTGGAGGGTGGTAACATTCCCGCACTGTTGGATGTGGACGCCTACC
AGGCGAGCTTGAAAGATGACACCGAACAGGGCGGGGGTGGCGCAGGCGGC
AGCAACAGCAGTGGCAGCGGCGCGAAGAGAACTCCAACGCGGCAGCCGC
GGCAATGCAGCCGGTGGAGGACATGAACGATCATGCCATTCGCGGCGACA
CCTTTGCCACACGGGCTGAGGAGAAGCGCGCTGAGGCCGAAGCAGCGGCC
GAAGCTGCCGCCCCCGCTGCGCAACCCGAGGTCGAGAAGCCTCAGAAGAA
ACCGGTGATCAAACCCCTGACAGAGGACAGCAAGAAACGCAGTTACAACC
TAATAAGCAATGACAGCACCTTCACCCAGTACCGCAGCTGGTACCTTGCA
TACAACTACGGCGACCCTCAGACCGGAATCCGCTCATGGACCCTGCTTTG
CACTCCTGACGTAACCTGCGGCTCGGAGCAGGTCTACTGGTCGTTGCCAG
ACATGATGCAAGACCCCGTGACCTTCCGCTCCACGCGCCAGATCAGCAAC
TTTCCGGTGGTGGGCGCCGAGCTGTTGCCCGTGCACTCCAAGAGCTTCTA
CAACGACCAGGCCGTCTACTCCCAACTCATCCGCCAGTTTACCTCTCTGA
CCCACGTGTTCAATCGCTTTCCCGAGAACCAGATTTTGGCGCGCCCGCCA
GCCCCCACCATCACCACCGTCAGTGAAAACGTTCCTGCTCTCACAGATCA
CGGGACGCTACCGCTGCGCAACAGCATCGGAGGAGTCCAGCGAGTGACCA
TTACTGACGCCAGACGCCGCACCTGCCCCTACGTTTACAAGGCCCTGGGC
ATAGTCTCGCCGCGCGTCCTATCGAGCCGCACTTTTTGAGCAAGCATGTC
CATCCTTATATCGCCCAGCAATAACACAGGCTGGGGCCTGCGCTTCCCAA
GCAAGATGTTTGGCGGGGCCAAGAAGCGCTCCGACCAACACCCAGTGCGC
GTGCGCGGGCACTACCGCGCGCCCTGGGGCGCGCACAAACGCGGCCGCAC
TGGGCGCACCACCGTCGATGACGCCATCGACGCGGTGGTGGAGGAGGCGC
GCAACTACACGCCCACGCCGCCACCAGTGTCCACAGTGGACGCGGCCATT
CAGACCGTGGTGCGCGGAGCCCGGCGCTATGCTAAAATGAAGAGACGGCG
GAGGCGCGTAGCACGTCGCCACCGCCGCCGACCCGGCACTGCCGCCCAAC
GCGCGGCGGCGGCCCTGCTTAACCGCGCACGTCGCACCGGCCGACGGGCG
GCCATGCGGGCCGCTCGAAGGCTGGCCGCGGGTATTGTCACTGTGCCCCC
CAGGTCCAGGCGACGAGCGGCCGCCGCAGCAGCCGCGGCCATTAGTGCTA
TGACTCAGGGTCGCAGGGGCAACGTGTATTGGGTGCGCGACTCGGTTAGC
GGCCTGCGCGTGCCCGTGCGCACCCGCCCCCCGCGCAACTAGATTGCAAG
AAAAAACTACTTAGACTCGTACTGTTGTATGTATCCAGCGGCGGCGGCGC
GCAACGAAGCTATGTCCAAGCGCAAAATCAAAGAAGAGATGCTCCAGGTC
ATCGCGCCGGAGATCTATGGCCCCCCGAAGAAGGAAGAGCAGGATTACAA
GCCCCGAAAGCTAAAGCGGGTCAAAAAGAAAAAGAAAGATGATGATGATG
AACTTGACGACGAGGTGGAACTGCTGCACGCTACCGCGCCCAGGCGACGG
GTACAGTGGAAAGGTCGACGCGTAAAACGTGTTTTGCGACCCGGCACCAC
CGTAGTCTTTACGCCCGGTGAGCGCTCCACCCGCACCTACAAGCGCGTGT
ATGATGAGGTGTACGGCGACGAGGACCTGCTTGAGCAGGCCAACGAGCGC

-continued

CTCGGGGAGTTTGCCTACGGAAAGCGGCATAAGGACATGCTGGCGTTGCC
GCTGGACGAGGGCAACCCAACACCTAGCCTAAAGCCCGTAACACTGCAGC
AGGTGCTGCCCGCGCTTGCACCGTCCGAAGAAAAGCGCGGCCTAAAGCGC
GAGTCTGGTGACTTGGCACCCACCGTGCAGCTGATGGTACCCAAGCGCCA
GCGACTGGAAGATGTCTTGGAAAAAATGACCGTGGAACCTGGGCTGGAGC
CCGAGGTCCGCGTGCGGCCAATCAAGCAGGTGGCGCCGGGACTGGGCGTG
CAGACCGTGGACGTTCAGATACCCACTACCAGTAGCACCAGTATTGCCAC
CGCCACAGAGGGCATGGAGACACAAACGTCCCCGGTTGCCTCAGCGGTGG
CGGATGCCGCGGTGCAGGCGGTCGCTGCGGCCGCGTCCAAGACCTCTACG
GAGGTGCAAACGGACCCGTGGATGTTTCGCGTTTCAGCCCCCCGGCGCCC
GCGCCGTTCGAGGAAGTACGGCGCCGCCAGCGCGCTACTGCCCGAATATG
CCCTACATCCTTCCATTGCGCCTACCCCCGGCTATCGTGGCTACACCTAC
CGCCCCAGAAGACGAGCAACTACCCGACGCCGAACCACCACTGGAACCCG
CCGCCGCCGTCGCCGTCGCCAGCCCGTGCTGGCCCCGATTTCCGTGCGCA
GGGTGGCTCGCGAAGGAGGCAGGACCCTGGTGCTGCCAACAGCGCGCTAC
CACCCCAGCATCGTTTAAAAGCCGGTCTTTGTGGTTCTTGCAGATATGGC
CCTCACCTGCCGCCTCCGTTTCCCGGTGCCGGGATTCCGAGGAAGAATGC
ACCGTAGGAGGGGCATGGCCGGCCACGGCCTGACGGGCGGCATGCGTCGT
GCGCACCACCGGCGGCGGCGCGCGTCGCACCGTCGCATGCGCGGCGGTAT
CCTGCCCCTCCTTATTCCACTGATCGCCGCGGCGATTGGCGCCGTGCCCG
GAATTGCATCCGTGGCCTTGCAGGCGCAGAGACACTGATTAAAAACAAGT
TGCATGTGGAAAAATCAAAATAAAAAGTCTGGACTCTCACGCTCGCTTGG
TCCTGTAACTATTTTGTAGAATGGAAGACATCAACTTTGCGTCTCTGGCC
CCGCGACACGGCTCGCGCCCGTTCATGGGAAACTGGCAAGATATCGGCAC
CAGCAATATGAGCGGTGGCGCCTTCAGCTGGGGCTCGCTGTGGAGCGGCA
TTAAAAATTTCGGTTCCACCGTTAAGAACTATGGCAGCAAGGCCTGGAAC
AGCAGCACAGGCCAGATGCTGAGGGATAAGTTGAAAGAGCAAAATTTCCA
ACAAAAGGTGGTAGATGGCCTGGCCTCTGGCATTAGCGGGGTGGTGGACC
TGGCCAACCAGGCAGTGCAAAATAAGATTAACAGTAAGCTTGATCCCCGC
CCTCCCGTAGAGGAGCCTCCACCGGCCGTGGAGACAGTGTCTCCAGAGGG
GCGTGGCGAAAAGCGTCCGCGCCCCGACAGGGAAGAAACTCTGGTGACGC
AAATAGACGAGCCTCCCTCGTACGAGGAGGCACTAAAGCAAGGCCTGCCC
ACCACCCGTCCCATCGCGCCCATGGCTACCGGAGTGCTGGGCCAGCACAC
ACCCGTAACGCTGGACCTGCCTCCCCCCGCCGACACCCAGCAGAAACCTG
TGCTGCCAGGCCCGACCGCCGTTGTTGTAACCCGTCCTAGCCGCGCGTCC
CTGCGCCGCGCCGCCAGCGGTCCGCGATCGTTGCGGCCCGTAGCCAGTGG
CAACTGGCAAAGCACACTGAACAGCATCGTGGGTCTGGGGGTGCAATCCC
TGAAGCGCCGACGATGCTTCTGATAGCTAACGTGTCGTATGTGTGTCATG
TATGCGTCCATGTCGCCGCCAGAGGAGCTGCTGAGCCGCCGCGCGCCCGC
TTTCCAAGATGGCTACCCCTTCGATGATGCCGCAGTGGTCTTACATGCAC

-continued

```
ATCTCGGGCCAGGACGCCTCGGAGTACCTGAGCCCCGGGCTGGTGCAGTT
TGCCCGCGCCACCGAGACGTACTTCAGCCTGAATAACAAGTTTAGAAACC
CCACGGTGGCGCCTACGCACGACGTGACCACAGACCGGTCCCAGCGTTTG
ACGCTGCGGTTCATCCCTGTGGACCGTGAGGATACTGCGTACTCGTACAA
GGCGCGGTTCACCCTAGCTGTGGGTGATAACCGTGTGCTGGACATGGCTT
CCACGTACTTTGACATCCGCGGCGTGCTGGACAGGGGCCCTACTTTTAAG
CCCTACTCTGGCACTGCCTACAACGCCCTGGCTCCCAAGGGTGCCCCAAA
TCCTTGCGAATGGGATGAAGCTGCTACTGCTCTTGAAATAAACCTAGAAG
AAGAGGACGATGACAACGAAGACGAAGTAGACGAGCAAGCTGAGCAGCAA
AAAACTCACGTATTTGGGCAGGCGCCTTATTCTGGTATAAATATTACAAA
GGAGGGTATTCAAATAGGTGTCGAAGGTCAAACACCTAAATATGCCGATA
AAACATTTCAACCTGAACCTCAAATAGGAGAATCTCAGTGGTACGAAACA
GAAATTAATCATGCAGCTGGGAGAGTCCTAAAAAGACTACCCCAATGAA
ACCATGTTACGGTTCATATGCAAAACCCACAAATGAAATGGAGGGCAAG
GCATTCTTGTAAAGCAACAAAATGGAAAGCTAGAAAGTCAAGTGGAAATG
CAATTTTTCTCAACTACTGAGGCAGCCGCAGGCAATGGTGATAACTTGAC
TCCTAAAGTGGTATTGTACAGTGAAGATGTAGATATAGAAACCCCAGACA
CTCATATTTCTTACATGCCCACTATTAAGGAAGGTAACTCACGAGAACTA
ATGGGCCAACAATCTATGCCCAACAGGCCTAATTACATTGCTTTTAGGGA
CAATTTTATTGGTCTAATGTATTACAACAGCACGGGTAATATGGGTGTTC
TGGCGGGCCAAGCATCGCAGTTGAATGCTGTTGTAGATTTGCAAGACAGA
AACACAGAGCTTTCATACCAGCTTTTGCTTGATTCCATTGGTGATAGAAC
CAGGTACTTTTCTATGTGGAATCAGGCTGTTGACAGCTATGATCCAGATG
TTAGAATTATTGAAAATCATGGAACTGAAGATGAACTTCCAAATTACTGC
TTTCCACTGGGAGGTGTGATTAATACAGAGACTCTTACCAAGGTAAAACC
TAAAACAGGTCAGGAAAATGGATGGGAAAAAGATGCTACAGAATTTTCAG
ATAAAAATGAAATAAGAGTTGGAAATAATTTTGCCATGGAAATCAATCTA
AATGCCAACCTGTGGAGAAATTTCCTGTACTCCAACATAGCGCTGTATTT
GCCCGACAAGCTAAAGTACAGTCCTTCCAACGTAAAAATTTCTGATAACC
CAAACACCTACGACTACATGAACAAGCGAGTGGTGGCTCCCGGGCTAGTG
GACTGCTACATTAACCTTGGAGCACGCTGGTCCCTTGACTATATGGACAA
CGTCAACCCATTTAACCACCACCGCAATGCTGGCCTGCGCTACCGCTCAA
TGTTGCTGGCAATGGTCGCTATGTGCCCTTCCACATCCAGGTGCCTCAG
AAGTTCTTTGCCATTAAAAACCTCCTTCTCCTGCCGGGCTCATACACCTA
CGAGTGGAACTTCAGGAAGGATGTTAACATGGTTCTGCAGAGCTCCCTAG
GAAATGACCTAAGGGTTGACGGAGCCAGCATTAAGTTTGATAGCATTTGC
CTTTACGCCACCTTCTTCCCCATGGCCCACAACACCGCCTCCACGCTTGA
GGCCATGCTTAGAAACGACACCAACGACCAGTCCTTTAACGACTATCTCT
CCGCCGCCAACATGCTCTACCCTATACCCGCCAACGCTACCAACGTGCCC
ATATCCATCCCCTCCCGCAACTGGGCGGCTTTCCGCGGCTGGGCCTTCAC
GCGCCTTAAGACTAAGGAAACCCCATCACTGGGCTCGGGCTACGACCCTT
ATTACACCTACTCTGGCTCTATACCCTACCTAGATGGAACCTTTTACCTC
AACCACACCTTTAAGAAGGTGGCCATTACCTTTGACTCTTCTGTCAGCTG
GCCTGGCAATGACCGCCTGCTTACCCCCAACGAGTTTGAAATTAAGCGCT
CAGTTGACGGGGAGGGTTACAACGTTGCCCAGTGTAACATGACCAAAGAC
TGGTTCCTGGTACAAATGCTAGCTAACTATAACATTGGCTACCAGGGCTT
CTATATCCCAGAGAGCTACAAGGACCGCATGTACTCCTTCTTTAGAAACT
TCCAGCCCATGAGCCGTCAGGTGGTGGATGATACTAAATACAAGGACTAC
CAACAGGTGGGCATCCTACACCAACACAACAACTCTGGATTTGTTGGCTA
CCTTGCCCCCACCATGCGCGAAGGACAGGCCTACCCTGCTAACTTCCCCT
ATCCGCTTATAGGCAAGACCGCAGTTGACAGCATTACCCAGAAAAAGTTT
CTTTGCGATCGCACCCTTTGGCGCATCCCATTCTCCAGTAACTTTATGTC
CATGGGCGCACTCACAGACCTGGGCCAAAACCTTCTCTACGCCAACTCCG
CCCACGCGCTAGACATGACTTTTGAGGTGGATCCCATGGACGAGCCCACC
CTTCTTTATGTTTGTTTGAAGTCTTTGACGTGGTCCGTGTGCACCAGCC
GCACCGCGGCGTCATCGAAACCGTGTACCTGCGCACGCCCTTCTCGGCCG
GCAACGCCACAACATAAAGAAGCAAGCAACATCAACAACAGCTGCCGCCA
TGGGCTCCAGTGAGCAGGAACTGAAAGCCATTGTCAAAGATCTTGGTTGT
GGGCCATATTTTTGGGCACCTATGACAAGCGCTTTCCAGGCTTTGTTTC
TCCACACAAGCTCGCCTGCGCCATAGTCAATACGGCCGGTCGCGAGACTG
GGGGCGTACACTGGATGGCCTTTGCCTGGAACCCGCACTCAAAAACATGC
TACCTCTTTGAGCCCTTTGGCTTTTCTGACCAGCGACTCAAGCAGGTTTA
CCAGTTTGAGTACGAGTCACTCCTGCGCCGTAGCGCCATTGCTTCTTCCC
CCGACCGCTGTATAACGCTGGAAAAGTCCACCCAAAGCGTACAGGGGCCC
AACTCGGCCGCCTGTGGACTATTCTGCTGCATGTTTCTCCACGCCTTTGC
CAACTGGCCCCAAACTCCCATGGATCACAACCCCACCATGAACCTTATTA
CCGGGGTACCCAACTCCATGCTCAACAGTCCCCAGGTACAGCCCACCCTG
CGTCGCAACCAGGAACAGCTCTACAGCTTCCTGGAGCGCCACTCGCCCTA
CTTCCGCAGCCACAGTGCGCAGATTAGGAGCGCCACTTCTTTTTGTCACT
TGAAAAACATGTAAAAATAATGTACTAGAGACACTTTCAATAAAGGCAAA
TGCTTTTATTTGTACACTCTCGGGTGATTATTTACCCCCACCCTTGCCGT
CTGCGCCGTTTAAAAATCAAAGGGGTTCTGCCGCGCATCGCTATGCGCCA
CTGGCAGGGACACGTTGCGATACTGGTGTTTAGTGCTCCACTTAAACTCA
GGCACAACCATCCGCGGCAGCTCGGTGAAGTTTTCACTCCACAGGCTGCG
CACCATCACCAACGCGTTTAGCAGGTCGGGCGCCGATATCTTGAAGTCGC
AGTTGGGGCCTCCGCCCTGCGCGCGCGAGTTGCGATACACAGGGTTGCAG
CACTGGAACACTATCAGCGCCGGGTGGTGCACGCTGGCCAGCACGCTCTT
GTCGGAGATCAGATCCGCGTCCAGGTCCTCCGCGTTGCTCAGGGCGAACG
GAGTCAACTTTGGTAGCTGCCTTCCCAAAAAGGGCGCGTGCCCAGGCTTT
GAGTTGCACTCGCACCGTAGTGGCATCAAAAGGTGACCGTGCCCGGTCTG
GGCGTTAGGATACAGCGCCTGCATAAAAGCCTTGATCTGCTTAAAAGCCA
```

-continued

```
CCTGAGCCTTTGCGCCTTCAGAGAAGAACATGCCGCAAGACTTGCCGGAA
AACTGATTGGCCGGACAGGCCGCGTCGTGCACGCAGCACCTTGCGTCGGT
GTTGGAGATCTGCACCACATTTCGGCCCCACCGGTTCTTCACGATCTTGG
CCTTGCTAGACTGCTCCTTCAGCGCGCGCTGCCCGTTTTCGCTCGTCACA
TCCATTTCAATCACGTGCTCCTTATTTATCATAATGCTTCCGTGTAGACA
CTTAAGCTCGCCTTCGATCTCAGCGCAGCGGTGCAGCCACAACGCGCAGC
CCGTGGGCTCGTGATGCTTGTAGGTCACCTCTGCAAACGACTGCAGGTAC
GCCTGCAGGAATCGCCCCATCATCGTCACAAAGGTCTTGTTGCTGGTGAA
GGTCAGCTGCAACCCGCGGTGCTCCTCGTTCAGCCAGGTCTTGCATACGG
CCGCCAGAGCTTCCACTTGGTCAGGCAGTAGTTTGAAGTTCGCCTTTAGA
TCGTTATCCACGTGGTACTTGTCCATCAGCGCGCGCAGCCTCCATGCC
CTTCTCCCACGCAGACACGATCGGCACACTCAGCGGGTTCATCACCGTAA
TTTCACTTTCCGCTTCGCTGGGCTCTTCCTCTTCCTCTTGCGTCCGCATA
CCACGCGCCACTGGGTCGTCTTCATTCAGCCGCCGCACTGTGCGCTTACC
TCCTTTGCCATGCTTGATTAGCACCGGTGGGTTGCTGAAACCCACCATTT
GTAGCGCCACATCTTCTCTTTCTTCCTCGCTGTCCACGATTACCTCTGGT
GATGGCGGGCGCTCGGGCTTGGAGAAGGGCGCTTCTTTTTCTTCTTGGG
CGCAATGGCCAAATCCGCCGCCGAGGTCGATGGCCGCGGGCTGGGTGTGC
GCGGCACCAGCGCGTCTTGTGATGAGTCTTCCTCGTCCTCGGACTCGATA
CGCCGCCTCATCCGCTTTTTTGGGGCGCCCGGGGAGGCGGCGGCGACGG
GGACGGGGACGACACGTCCTCCATGGTTGGGGACGTCGCGCCGCACCGC
GTCCGCGCTCGGGGGTGGTTTCGCGCTGCTCCTCTTCCCGACTGGCCATT
TCCTTCTCCTATAGGCAGAAAAAGATCATGGAGTCAGTCGAGAAGAAGGA
CAGCCTAACCGCCCCCTCTGAGTTCGCCACCACCGCCTCCACCGATGCCG
CCAACGCGCCTACCACCTTCCCCGTCGAGGCACCCCCGCTTGAGGAGGAG
GAAGTGATTATCGAGCAGGACCCAGGTTTTGTAAGCGAAGACGACGAGGA
CCGCTCAGTACCAACAGAGGATAAAAAGCAAGACCAGGACAACGCAGAGG
CAAACGAGGAACAAGTCGGGCGGGGGGACGAAAGGCATGGCGACTACCTA
GATGTGGGAGACGACGTGCTGTTGAAGCATCTGCAGCGCCAGTGCGCCAT
TATCTGCGACGCGTTGCAAGAGCGCAGCGATGTGCCCCTCGCCATAGCGG
ATGTCAGCCTTGCCTACGAACGCCACCTATTCTCACCGCGCGTACCCCCC
AAACGCCAAGAAAACGGCACATGCGAGCCCAACCCGCGCCTCAACTTCTA
CCCCGTATTTGCCGTGCCAGAGGTGCTTGCCACCTATCACATCTTTTTCC
AAAACTGCAAGATACCCCTATCCTGCCGTGCCAACCGCAGCCGAGCGGAC
AAGCAGCTGGCCTTGCGGCAGGGCGCTGTCATACCTGATATCGCCTCGCT
CAACGAAGTGCCAAAAATCTTTGAGGGTCTTGGACGCGACGAGAAGCGCG
CGGCAAACGCTCTGCAACAGGAAAACAGCGAAAATGAAAGTCACTCTGGA
GTGTTGGTGGAACTCGAGGGTGACAACGCGCGCCTAGCCGTACTAAAACG
CAGCATCGAGGTCACCCACTTTGCCTACCCGGCACTTAACCTACCCCCCA
AGGTCATGAGCACAGTCATGAGTGAGCTGATCGTGCGCCGTGCGCAGCCC
CTGGAGAGGGATGCAAATTTGCAAGAACAAACAGAGGAGGGCCTACCCGC
```

```
AGTTGGCGACGAGCAGCTAGCGCGCTGGCTTCAAACGCGCGAGCCTGCCG
ACTTGGAGGAGCGACGCAAACTAATGATGGCCGCAGTGCTCGTTACCGTG
GAGCTTGAGTGCATGCAGCGGTTCTTTGCTGACCCGGAGATGCAGCGCAA
GCTAGAGGAAACATTGCACTACACCTTTCGACAGGGCTACGTACGCCAGG
CCTGCAAGATCTCCAACGTGGAGCTCTGCAACCTGGTCTCCTACCTTGGA
ATTTTGCACGAAAACCGCCTTGGGCAAAACGTGCTTCATTCCACGCTCAA
GGGCGAGGCGCGCCGCGACTACGTCCGCGACTGCGTTTACTTATTTCTAT
GCTACACCTGGCAGACGGCCATGGGCGTTTGGCAGCAGTGCTTGGAGGAG
TGCAACCTCAAGGAGCTGCAGAAACTGCTAAAGCAAACTTGAAGGACCT
ATGGACGGCCTCAACGAGCGCTCCGTGGCCGCGCACCTGGCGGACATCA
TTTTCCCCGAACGCCTGCTTAAAACCCTGCAACAGGGTCTGCCAGACTTC
ACCAGTCAAAGCATGTTGCAGAACTTTAGGAACTTTATCCTAGAGCGCTC
AGGAATCTTGCCCGCCACCTGCTGTGCACTTCCTAGCGACTTTGTGCCCA
TTAAGTACCGCGAATGCCCTCCGCCGCTTTGGGGCCACTGCTACCTTCTG
CAGCTAGCCAACTACCTTGCCTACCACTCTGACATAATGGAAGACGTGAG
CGGTGACGGTCTACTGGAGTGTCACTGTCGCTGCAACCTATGCACCCCGC
ACCGCTCCCTGGTTTGCAATTCGCAGCTGCTTAACGAAAGTCAAATTATC
GGTACCTTTGAGCTGCAGGGTCCCTCGCCTGACGAAAGTCCGCGGCTCC
GGGGTTGAAACTCACTCCGGGGCTGTGGACGTCGGCTTACCTTCGCAAAT
TTGTACCTGAGGACTACCACGCCCACGAGATTAGGTTCTACGAAGACCAA
TCCCGCCCGCCTAATGCGGAGCTTACCGCCTGCGTCATTACCCAGGGCCA
CATTCTTGGCCAATTGCAAGCCATCAACAAAGCCCGCCAAGAGTTTCTGC
TACGAAAGGGACGGGGGGTTTACTTGGACCCCCAGTCCGGCGAGGAGCTC
AACCCAATCCCCCGCCGCCGCAGCCCTATCAGCAGCAGCCGCGGGCCCT
TGCTTCCCAGGATGGCACCCAAAAAGAAGCTGCAGCTGCCGCCGCCACCC
ACGGACGAGGAGGAATACTGGGACAGTCAGGCAGAGGAGGTTTTGGACGA
GGAGGAGGAGGACATGATGGAAGACTGGGAGAGCCTAGACGAGGAAGCTT
CCGAGGTCGAAGAGGTGTCAGACGAAACACCGTCACCCTCGGTCGCATTC
CCCTCGCCGGCGCCCCAGAAATCGGCAACCGGTTCCAGCATGGCTACAAC
CTCCGCTCCTCAGGCGCCGCCGGCACTGCCCGTTCGCCGACCCAACCGTA
GATGGGACACCACTGGAACCAGGGCCGGTAAGTCCAAGCAGCCGCCGCCG
TTAGCCCAAGAGCAACAACAGCGCCAAGGCTACCGCTCATGGCGCGGGCA
CAAGAACGCCATAGTTGCTTGCTTGCAAGACTGTGGGGGCAACATCTCCT
TCGCCCGCCGCTTTCTTCTCTACCATCACGGCGTGGCCTTCCCCCGTAAC
ATCCTGCATTACTACCGTCATCTCTACGCCCATACTGCACCGGCGGCAG
CGGCAGCAACAGCAGCGGCCACACAGAAGCAAAGGCGACCGGATAGCAAG
ACTCTGACAAAGCCCAAGAAATCCACAGCGGCGGCAGCAGCAGGAGGAGG
AGCGCTGCGTCTGGCGCCCAACGAACCCGTATCGACCCGCGAGCTTAGAA
ACAGGATTTTCCCACTCTGTATGCTATATTTCAACAGAGCAGGGCCAA
GAACAAGAGCTGAAAATAAAAAACAGGTCTCTGCGATCCCTCACCCGCAG
```

CTGCCTGTATCACAAAAGCGAAGATCAGCTTCGGCGCACGCTGGAAGACG

CGGAGGCTCTCTTCAGTAAATACTGCGCGCTGACTCTTAAGGACTAGTTT

CGCGCCCTTTCTCAAATTTAAGCGCGAAAACTACGTCATCTCCAGCGGCC

ACACCCGGCGCCAGCACCTGTTGTCAGCGCCATTATGAGCAAGGAAATTC

CCACGCCCTACATGTGGAGTTACCAGCCACAAATGGGACTTGCGGCTGGA

GCTGCCCAAGACTACTCAACCCGAATAAACTACATGAGCGCGGGACCCCA

CATGATATCCCGGGTCAACGGAATACGCGCCCACCGAAACCGAATTCTCC

TGGAACAGGCGGCTATTACCACCACACCTCGTAATAACCTTAATCCCCGT

AGTTGGCCCGCTGCCCTGGTGTACCAGGAAAGTCCCGCTCCCACCACTGT

GGTACTTCCCAGAGACGCCCAGGCCGAAGTTCAGATGACTAACTCAGGGG

CGCAGCTTGCGGGCGGCTTTCGTCACAGGGTGCGGTCGCCCGGGCAGGGT

ATAACTCACCTGACAATCAGAGGGCGAGGTATTCAGCTCAACGACGAGTC

GGTGAGCTCCTCGCTTGGTCTCCGTCCGGACGGGACATTTCAGATCGGCG

GCGCCGGCCGCTCTTCATTCACGCCTCGTCAGGCAATCCTAACTCTGCAG

ACCTCGTCCTCTGAGCCGCGCTCTGGAGGCATTGGAACTCTGCAATTTAT

TGAGGAGTTTGTGCCATCGGTCTACTTTAACCCCTTCTCGGGACCTCCCG

GCCACTATCCGGATCAATTTATTCCTAACTTTGACGCGGTAAAGGACTCG

GCGGACGGCTACGACTGAATGTTAAGTGGAGAGGCAGAGCAACTGCGCCT

GAAACACCTGGTCCACTGTCGCCGCCACAAGTGCTTTGCCCGCGACTCCG

GTGAGTTTTGCTACTTTGAATTGCCCGAGGATCATATCGAGGGCCCGGCG

CACGGCGTCCGCTTACCGCCCAGGGAGAGCTTGCCCGTAGCCTGATTCG

GGAGTTTACCCAGCGCCCCCTGCTAGTTGAGCGGGACAGGGGACCCTGTG

TTCTCACTGTGATTTGCAACTGTCCTAACCCTGGATTACATCAAGATCCT

CTAGTTAATGTCAGGTCGCCTAAGTCGATTAACTAGAGTACCCGGGGATC

TTATTCCCTTTAACTAATAAAAAAAATAATAAAGCATCACTTACTTAAA

ATCAGTTAGCAAATTTCTGTCCAGTTTATTCAGCAGCACCTCCTTGCCCT

CCTCCCAGCTCTGGTATTGCAGCTTCCTCCTGGCTGCAAACTTTCTCCAC

AATCTAAATGGAATGTCAGTTTCCTCCTGTTCCTGTCCATCCGCACCCAC

TATCTTCATGTTGTTGCAGATGAAGCGCGCAAGACCGTCTGAAGATACCT

TCAACCCCGTGTATCCATATGACACGGAAACCGGTCCTCCAACTGTGCCT

TTTCTTACTCCTCCCTTTGTATCCCCCAATGGGTTTCAAGAGAGTCCCCC

TGGGGTACTCTCTTTGCGCCTATCCGAACCTCTAGTTACCTCCAATGGCA

TGCTTGCGCTCAAAATGGGCAACGGCTCTCTCTGGACGAGGCCGGCAAC

CTTACCTCCCAAAATGTAACCACTGTGAGCCCACCTCTCAAAAAAACCAA

GTCAAACATAAACCTGGAAATATCTGCACCCCTCACAGTTACCTCAGAAG

CCCTAACTGTGGCTGCCGCCGCACCTCTAATGGTCGCGGGCAACACACTC

ACCATGCAATCACAGGCCCCGCTAACCGTGCACGACTCCAAACTTAGCAT

TGCCACCCAAGGACCCCTCACAGTGTCAGAAGGAAAGCTAGCCCTGCAAA

CATCAGGCCCCCTCACCACCACCGATAGCAGTACCCTTACTATCACTGCC

TCACCCCCTCTAACTACTGCCACTGGTAGCTTGGGCATTGACTTGAAAGA

GCCCATTTATACACAAAATGGAAAACTAGGACTAAAGTACGGGGCTCCTT

TGCATGTAACAGACGACCTAAACACTTTGACCGTAGCAACTGGTCCAGGT

GTGACTATTAATAATACTTCCTTGCAAACTAAAGTTACTGGAGCCTTGGG

TTTTGATTCACAAGGCAATATGCAACTTAATGTAGCAGGAGGACTAAGGA

TTGATTCTCAAAACAGACGCCTTATACTTGATGTTAGTTATCCGTTTGAT

GCTCAAAACCAACTAAATCTAAGACTAGGACAGGGCCCTCTTTTTATAAA

CTCAGCCCACAACTTGGATATTAACTACAACAAAGGCCTTTACTTGTTTA

CAGCTTCAAACAATTCCAAAAAGCTTGAGGTTAACCTAAGCACTGCCAAG

GGGTTGATGTTTGACGCTACAGCCATAGCCATTAATGCAGGAGATGGGCT

TGAATTTGGTTCACCTAATGCACCAAACACAAATCCCCTCAAAACAAAAA

TTGGCCATGGCCTAGAATTTGATTCAAACAAGGCTATGGTTCCTAAACTA

GGAACTGGCCTTAGTTTTGACAGCACAGGTGCCATTACAGTAGGAAACAA

AAATAATGATAAGCTAACTTTGTGGACCACACCAGCTCCATCTCCTAACT

GTAGACTAAATGCAGAGAAAGATGCTAAACTCACTTTGGTCTTAACAAAA

TGTGGCAGTCAAATACTTGCTACAGTTTCAGTTTTGGCTGTTAAAGGCAG

TTTGGCTCCAATATCTGGAACAGTTCAAAGTGCTCATCTTATTATAAGAT

TTGACGAAAATGGAGTGCTACTAAACAATTCCTTCCTGGACCCAGAATAT

TGGAACTTTAGAAATGGAGATCTTACTGAAGGCACAGCCTATACAAACGC

TGTTGGATTTATGCCTAACCTATCAGCTTATCCAAAATCTCACGGTAAAA

CTGCCAAAAGTAACATTGTCAGTCAAGTTTACTTAAACGGAGACAAAACT

AAACCTGTAACACTAACCATTACACTAAACGGTACACAGGAAACAGGAGA

CACAACTCCAAGTGCATACTCTATGTCATTTTCATGGGACTGGTCTGGCC

ACAACTACATTAATGAAATATTTGCCACATCCTCTTACACTTTTTCATAC

ATTGCCCAAGAATAAAGAATCGTTTGTGTTATGTTTCAACGTGTTTATTT

TTCAATTGCAGAAAATTTCAAGTCATTTTTCATTCAGTAGTATAGCCCCA

CCACCACATAGCTTATACAGATCACCGTACCTTAATCAAACTCACAGAAC

CCTAGTATTCAACCTGCCACCTCCCTCCCAACACACAGAGTACACAGTCC

TTTCTCCCCGGCTGGCCTTAAAAAGCATCATATCATGGGTAACAGACATA

TTCTTAGGTGTTATATTCCACACGGTTTCCTGTCGAGCCAAACGCTCATC

AGTGATATTAATAAACTCCCCGGGCAGCTCACTTAAGTTCATGTCGCTGT

CCAGCTGCTGAGCCACAGGCTGCTGTCCAACTTGCGGTTGCTTAACGGGC

GGCGAAGGAGAAGTCCACGCCTACATGGGGGTAGAGTCATAATCGTGCAT

CAGGATAGGCGGTGGTGCTGCAGCAGCGCGCGAATAAACTGCTGCCGCC

GCCGCTCCGTCCTGCAGGAATACAACATGGCAGTGGTCTCCTCAGCGATG

ATTCGCACCGCCCGCAGCATAAGGCGCCTTGTCCTCCGGGCACAGCAGCG

CACCCTGATCTCACTTAAATCAGCACAGTAACTGCAGCACAGCACCACAA

TATTGTTCAAAATCCCACAGTGCAAGGCGCTGTATCCAAAGCTCATGGCG

GGGACCACAGAACCCACGTGGCCATCATACCACAAGCGCAGGTAGATTAA

GTGGCGACCCCTCATAAACACGCTGGACATAAACATTACCTCTTTTGGCA

TGTTGTAATTCACCACCTCCCGGTACCATATAAACCTCTGATTAAACATG

GCGCCATCCACCACCATCCTAAACCAGCTGGCCAAAACCTGCCCGCCGGC

-continued
```
TATACACTGCAGGGAACCGGGACTGGAACAATGACAGTGGAGAGCCCAGG
ACTCGTAACCATGGATCATCATGCTCGTCATGATATCAATGTTGGCACAA
CACAGGCACACGTGCATACACTTCCTCAGGATTACAAGCTCCTCCCGCGT
TAGAACCATATCCCAGGGAACAACCCATTCCTGAATCAGCGTAAATCCCA
CACTGCAGGGAAGACCTCGCACGTAACTCACGTTGTGCATTGTCAAAGTG
TTACATTCGGGCAGCAGCGGATGATCCTCCAGTATGGTAGCGCGGGTTTC
TGTCTCAAAAGGAGGTAGACGATCCCTACTGTACGGAGTGCGCCGAGACA
ACCGAGATCGTGTTGGTCGTAGTGTCATGCCAAATGGAACGCCGGACGTA
GTCATATTTCCTGAAGCAAAACCAGGTGCGGGCGTGACAAACAGATCTGC
GTCTCCGGTCTCGCCGCTTAGATCGCTCTGTGTAGTAGTTGTAGTATATC
CACTCTCTCAAAGCATCCAGGCGCCCCCTGGCTTCGGGTTCTATGTAAAC
TCCTTCATGCGCCGCTGCCCTGATAACATCCACCACCGCAGAATAAGCCA
CACCCAGCCAACCTACACATTCGTTCTGCGAGTCACACACGGGAGGAGCG
GGAAGAGCTGGAAGAACCATGTTTTTTTTTTATTCCAAAAGATTATCCA
AAACCTCAAAATGAAGATCTATTAAGTGAACGCGCTCCCCTCCGGTGGCG
TGGTCAAACTCTACAGCCAAAGAACAGATAATGGCATTTGTAAGATGTTG
CACAATGGCTTCCAAAAGGCAAACGGCCCTCACGTCCAAGTGGACGTAAA
GGCTAAACCCTTCAGGGTGAATCTCCTCTATAAACATTCCAGCACCTTCA
ACCATGCCCAAATAATTCTCATCTCGCCACCTTCTCAATATATCTCTAAG
CAAATCCCGAATATTAAGTCCGGCCATTGTAAAAATCTGCTCCAGAGCGC
CCTCCACCTTCAGCCTCAAGCAGCGAATCATGATTGCAAAAATTCAGGTT
CCTCACAGACCTGTATAAGATTCAAAAGCGGAACATTAACAAAAATACCG
CGATCCCGTAGGTCCCTTCGCAGGGCCAGCTGAACATAATCGTGCAGGTC
TGCACGGACCAGCGCGGCCACTTCCCCGCCAGGAACCATGACAAAAGAAC
CCACACTGATTATGACACGCATACTCGGAGCTATGCTAACCAGCGTAGCC
CCGATGTAAGCTTGTTGCATGGGCGGCGATATAAAATGCAAGGTGCTGCT
CAAAAAATCAGGCAAAGCCTCGCGCAAAAAAGAAAGCACATCGTAGTCAT
GCTCATGCAGATAAAGGCAGGTAAGCTCCGGAACCACCACAGAAAAAGAC
ACCATTTTCTCTCAAACATGTCTGCGGGTTTCTGCATAAACACAAAATA
AAATAACAAAAAAACATTTAAACATTAGAAGCCTGTCTTACAACAGGAAA
AACAACCCTTATAAGCATAAGACGGACTACGGCCATGCCGGCGTGACCGT
AAAAAAACTGGTCACCGTGATTAAAAAGCACCACCGACAGCTCCTCGGTC
ATGTCCGGAGTCATAATGTAAGACTCGGTAAACACATCAGGTTGATTCAC
ATCGGTCAGTGCTAAAAAGCGACCGAAATAGCCCGGGGAATACATACCC
GCAGGCGTAGAGACAACATTACAGCCCCCATAGGAGGTATAACAAAATTA
ATAGGAGAGAAAAACACATAAACACCTGAAAAACCCTCCTGCCTAGGCAA
AATAGCACCCTCCCGCTCCAGAACAACATACAGCGCTTCCACAGCGGCAG
CCATAACAGTCAGCCTTACCAGTAAAAAAGAAAACCTATTAAAAAAACAC
CACTCGACACGGCACCAGCTCAATCAGTCACAGTGTAAAAAGGGCCAAG
TGCAGAGCGAGTATATATAGGACTAAAAAATGACGTAACGGTTAAAGTCC
ACAAAAAACACCCAGAAAACCGCACGCGAACCTACGCCCAGAAACGAAAG
CCAAAAAACCCACAACTTCCTCAAATCGTCACTTCCGTTTTCCCACGTTA
CGTCACTTCCCATTTTAAGAAAACTACAATTCCCAACACATACAAGTTAC
TCCGCCCTAAAACCTACGTCACCCGCCCCGTTCCCACGCCCCGCGCCACG
TCACAAACTCCACCCCCTCATTATCATATTGGCTTCAATCCAAAATAAGG
TATATTATTGATGAT,
```

In some embodiments, an adenovirus-derived vector, optionally relating to a replication defective adenovirus, comprises a sequence with at least 75%, 80%, 85%, 90%, 95%, 98%, 99%, 99.5%, 99.8%, 99.9% identity to SEQ. ID. NO: 3 or a sequence generated from SEQ. ID. NO: 3 by alternative codon replacements. In various embodiments, the adenovirus-derived vectors described herein have a deletion in the E2b region, and optionally, in the E1 region, the deletion conferring a variety of advantages to the use of the vectors in immunotherapy as described herein.

Certain regions within the adenovirus genome serve essential functions and may need to be substantially conserved when constructing the replication defective adenovirus vectors of the invention. These regions are further described in Lauer (Lauer et al. Natural variation among human adenoviruses: genome sequence and annotation of human adenovirus serotype I. Journal of General Virology (2004), 85, 2615-2625), Leza (Leza et al. Cellular Transcription Factor Binds to Adenovirus Early Region PromotersandtoaCyclicAMPResponseElement. Journal OF VIROLOGY, August 1988, p. 3003-3013), and Miralles (Miralles et al. The Adenovirus Inverted Terminal Repeat Functions as an Enhancer in a Cell-free System. THE JOURNAL OF BIOLOGICAL CHEMISTRY. Vol. 264, No. 18, Issue of June 25, pp. 10763-10772, 1983), which are each herein incorporate by reference in their entirety. Recombinant nucleic acid vectors comprising a sequence with identity values of at least 75%, 80%, 85%, 90%, 95%, 98%, 99%, 99.5%, 99.8%, 99.9% to a portion of SEQ. ID. NO: 3 are within the bounds of the invention.

First generation, E1-deleted Adenovirus subtype 5 (Ad5)-based vectors, although promising platforms for use as cancer vaccines, are impeded in activity by naturally occurring or induced Ad-specific neutralizing antibodies. Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded tumor antigen transgene in Ad-immune hosts. Indeed, multiple homologous immunizations with Ad5 [E1-, E2b-]-CEA(6D), encoding a variant of the tumor antigen CEA, induced CEA-specific cell-mediated immune (CMI) responses with antitumor activity in mice despite the presence of pre-existing or induced Ad5-neutralizing antibody. In a phase I/II study, cohorts of patients with advanced colorectal cancer were immunized with escalating doses of Ad5 [E1-, E2b-]-CEA (6D). CEA-specific CMI responses were observed despite the presence of pre-existing Ad5 immunity in a majority (61.3%) of patients. Importantly, there was minimal toxicity, and overall patient survival (48% at 12 months) was similar regardless of pre-existing Ad5 neutralizing antibody titers. The results demonstrated that, in cancer patients, the novel Ad5 [E1-, E2b-] gene delivery platform generates significant CMI responses to the tumor antigen CEA in the setting of both naturally acquired and immunization-induced Ad5 specific immunity. CEA antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). Thus, the methods and compositions of the invention relate to a recombinant nucleic acid vector, wherein the recombinant nucleic acid vector comprises a replication defective adenovirus vector, and wherein upon administration to a human, the composition is capable of inducing an immune response directed towards cells expressing CEA antigen in said human. The immune response may be induced even in the presence of preexisting immunity against Ad5. In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000 or higher. The immune response may comprise a cell-mediated immunity and/or a humoral immunity as described herein. The immune response may be measured by one or more of intracellular cytokine staining (ICS), ELISpot, proliferation assays, cytotoxic T cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

While cancer immunotherapy achieved by delivering tumor-associated antigens (TAA) provides survival benefits, limitations to these strategies exist and more immunologically potent vaccines are needed. To address the low immunogenicity of self-tumor antigens, a variety of advanced, multi-component vaccination strategies including co-administration of adjuvants and immune stimulating cytokines are provided. The invention relates to recombinant viral vectors that inherently provide innate pro-inflammatory signals, while simultaneously engineered to express the antigen of interest. Of particular interest are adenovirus serotype-5 (Ad5)-based immunotherapeutics that have been repeatedly used in humans to induce robust T cell-mediated immune (CMI) responses, all while maintaining an extensive safety profile. In addition, Ad5 vectors can be reliably manufactured in large quantities and are stable for storage and delivery for outpatient administration. Nonetheless, a major obstacle to the use of first generation (E1-deleted) Ad5-based vectors is the high frequency of pre-existing anti-adenovirus type 5 neutralizing antibodies. These antibodies can be present in a potential vaccinee due to either prior wild type adenovirus infection and/or induction of adenovirus neutralizing antibodies by repeated injections with Ad5-based vaccines, each resulting in inadequate immune stimulation against the target TAA.

Attempts to overcome anti-Ad immunity have included use of alternative Ad serotypes and/or alternations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform has been previously reported to successfully induce CMI responses in animal models of cancer and infectious disease and more importantly, this recombinant Ad5 gene delivery platform overcomes the barrier of Ad5 immunity and can be used in the setting of pre-existing and/or vector-induced Ad immunity thus enabling multiple homologous administrations of the vaccine. We have constructed and tested an Ad5 [E1-, E2b-] platform containing a gene insert for the tumor antigen carcinoembryonic antigen (CEA) with a modification that enhances T cell responses (Ad5 [E1-, E2b-]-CEA(6D) and is used in various embodiments of the invention for therapies raising an immune response against CEA. Multiple immunizations with this Ad5 platform induced CEA-specific CMI responses with antitumor activity despite the presence of existing Ad5 immunity in mice. The results of a first-in-man, phase I/II clinical trial demonstrate safety and immunogenicity in humans. A dose escalation of the Ad5 [E1-, E2b-]-CEA(6D) vector in advanced stage colorectal cancer patients demonstrates that CMI can be induced without a substantial effect on clinical outcome relative to the existence of pre-existing Ad5-immunity.

CEA as Target for Immune Response

CEA represents an attractive target antigen for immunotherapy since it is over-expressed in nearly all colorectal cancers and pancreatic cancers, and is also expressed by some lung and breast cancers, and uncommon tumors such as medullary thyroid cancer, but is not expressed in other cells of the body except for low-level expression in gastrointestinal epithelium (Berinstein, N. L. 2002. Carcinoembryonic antigen as a target for therapeutic anticancer vaccines: a review. *J Clin Oncol* 20:2197-2207.). CEA contains epitopes that may be recognized in an MHC restricted fashion by T cells.

Members of the CEA gene family are subdivided into three subgroups based on sequence similarity, developmental expression patterns and their biological functions: the CEA-related Cell Adhesion Molecule (CEACAM) subgroup containing twelve genes (CEACAM1, CEACAM3-CEACAM8, CEACAM16 and CEACAM18-CEACAM21), the Pregnancy Specific Glycoprotein (PSG) subgroup containing eleven closely related genes (PSG1-PSG11) and a subgroup of eleven pseudogenes (CEACAMP1-CEACAMP11) (Zhou et al. 2000; Gray-Owen and Blumberg 2006; FIGS. 1.4-1.5). Most members of the CEACAM subgroup have similar structures consist of an extracellular Ig-like domains composed of a single N-terminal V-set domain, with structural homology to the immunoglobulin variable domains, followed by varying numbers of C2-set domains of A or B subtypes, a transmembrane domain and a cytoplasmic domain (Bcauchemin et al. 1999; Kammerer et al., 2007). There are two members of CEACAM subgroup (CEACAM16 and CEACAM20) that show a few exceptions in the organization of their structures. CEACAM16 contains two Ig-like V-type domains at its N and C termini and CEACAM20 contains a truncated Ig-like V-type 1 domain (FIG. 1.4). The CEACAM molecules can be anchored to the cell surface via their transmembrane domains (CEACAM5 thought CEACAM8) or directly linked to glycophosphatidylinositol (GPI) lipid moiety (CEACAM5, CEACAM18 thought CEACAM21).

Members of CEA family are known to be expressed in different cell types and have a wide range of biological functions. CEACAMs are found prominently on most epithelial cells and are present on different leucocytes. In humans, CEACAM1, the ancestor member of CEA family, is expressed on the apical side of epithelial and endothelial cells as well as on lymphoid and myeloid cells. CEACAM1 mediates cell-cell adhesion through homophilic (CEACAM1 to CEACAM1) as well as heterophilic (e.g. CEACAM1 to CEACAM5) interactions (Kuespert et al. 2006; Gray-Owen and Blumberg 2006). In addition, CEACAM1 is involved in many other biological processes, such as angiogenesis, cell migration, and immune functions (Gray-Owen and Blumberg 2006). CEACAM3 and CEACAM4 expression is largely restricted to granulocytes, and they are able to convey uptake and destruction of several bacterial pathogens including *Neisseria, Moraxella*, and *Haemophilus* species (Schmitter et al. 2004).

Thus, in various embodiments, compositions and methods of the invention relate to raising an immune response against a CEA, selected from the group consisting of CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, and PSG11. An immune response may be raised against cells, e.g. cancer cells, expressing or overexpressing one or more of the CEAs, using the methods and compositions of the invention. In some embodiments, the overexpression of the one or more CEAs in such cancer cells is over 5, 10, 20, 30, 40, 50, 60, 70, 80, 90, 100 fold or more compared to non-cancer cells.

Further, compositions and methods of the invention, in various embodiments, take advantage of human cytolytic T cells (CTLs), specifically those that recognize CEA epitopes which bind to selected MHC molecules, e.g. HLA-A2, A3, and A24. Individuals expressing MHC molecules of certain serotypes, e.g. HLA-A2, A3, and A24 may be selected for therapy using the methods and compositions of the invention. For example, individuals expressing MHC molecules of certain serotypes, e.g. HLA-A2, A3, and A24, may be selected for a therapy including raising an immune response against CEA, using the methods and compositions described herein.

In various embodiments, these T cells can be generated by in vitro cultures using antigen-presenting cells pulsed with the epitope of interest to stimulate peripheral blood mononuclear cells. In addition, T cell lines can also be generated after stimulation with CEA latex beads, CEA protein-pulsed plastic adherent peripheral blood mononuclear cells, or DCs sensitized with CEA RNA. T cells can also be generated from patients immunized with a vaccine vector encoding CEA immunogen. HLA A2-presented peptides from CEA can further be found in primary gastrointestinal tumors. In various embodiments, the invention relates to an HLA A2 restricted epitope of CEA, CAP-1, a nine amino acid sequence (YLSGANLNL; SEQ. ID. NO.: 4), with ability to stimulate CTLs from cancer patients immunized with vaccine-CEA. Cap-1(6D) (YLSGADLNL; SEQ. ID. NO.: 5) is a peptide analog of CAP-1. Its sequence includes a heteroclitic (nonanchor position) mutation, resulting in an amino acid change from Asn to Asp, enhancing recognition by the T-cell receptor. The Asn to Asp mutation appears to not cause any change in the binding of the peptide to HLA A2. Compared with the non-mutated CAP-1 epitope, Cap-1(6D) can enhance the sensitization of CTLs by 100 to 1,000 times (Tsang, K. Y., Zhu, M., Nieroda, C. A., Correale, P., Zaremba, S., Hamilton, J. M., Cole, D., Lam, C., and Schlom, J. 1997. Phenotypic stability of a cytotoxic T-cell line directed against an immunodominant epitope of human carcinoembryonic antigen. *Clin Cancer Res* 3:2439-2449; Zaremba, S., Barzaga, E., Zhu, M., Soares, N., Tsang, K. Y., and Schlom, J. 1997. Identification of an enhancer agonist cytotoxic T lymphocyte peptide from human carcinoembryonic antigen. *Cancer Res* 57:4570-4577; Tangri, S., Ishioka, G. Y., Huang, X., Sidney, J., Southwood, S., Fikes, J., and Sette, A. 2001. Structural features of peptide analogs of human histocompatibility leukocyte antigen class 1 epitopes that are more potent and immunogenic than wild-type peptide. *J Exp Med* 194:833-846). CTL lines can be elicited from peripheral blood mononuclear cells of healthy volunteers by in vitro sensitization to the Cap-1(6D) peptide, but not significantly to the CAP-1 peptide. These cell lines can lyse human tumor cells expressing endogenous CEA. Thus, polypeptide sequences comprising CAP-1 or CAP-1(6D), nucleic acid sequences encoding such sequences, an adenovirus vectors; for example replication defective adenovirus vectors, comprising such nucleic acid sequences are within the bounds of the invention.

Clinical Trials of Vaccines Targeting CEA

Although CEA can serve as a T cell target and CEA-specific T cell precursors exist in humans, their frequency is quite low (<1/100,000). The invention, in various embodiments relates to increasing their numbers sufficiently and harnessing them to lyse CEA—expressing tumor cells. Several phase I clinical trials assessing various vaccine approaches for activating CEA-specific T cells were performed. Early studies were based on vaccination using protein with adjuvant (Samanci, A., Yi, Q., Fagerberg, J., Strigård, K., Smith, G., Rudén, U., Wahren, B., and Mellstedt, H. 1998. Pharmacological administration of granulocyte/macrophage-colony-stimulating factor is of significant importance for the induction of a strong humoral and cellular response in patients immunized with recombinant carcinoembryonic antigen. *Cancer Immunol Immunother* 47:131-142), or in the form of anti-idiotype vaccines (Foon, K. A., John, W. J., Chakraborty, M., Das, R., Teitelbaum, A., Garrison, J., Kashala, O., Chatterjee, S. K., and Bhattacharya-Chatterjee, M. 1999. Clinical and immune responses in resected colon cancer patients treated with anti-idiotype monoclonal antibody vaccine that mimics the carcinoembryonic antigen. *J Clin Oncol* 17:2889-2885; Foon, K. A., John, W. J., Chakraborty, M., Sherratt, A., Garrison, J., Flett, M., and Bhattacharya-Chatterjee, M. 1997. Clinical and immune responses in advanced colorectal cancer patients treated with anti-idiotype monoclonal antibody vaccine that mimics the carcinoembryonic antigen. *Clin Cancer Res* 3:1267-1276). CEA-specific T cell proliferative responses were observed in a substantial proportion of the patients in these studies; although the magnitude of the immune responses was modest. In order to improve upon these results, poxviruses engineered to express tumor antigens have been developed (Paoletti, E. 1996. Applications of pox virus vectors to vaccination: an update. *Proc Natl Acad Sci USA* 93:11349-11353; Cox, W. I., Tartaglia, J., and Paoletti, E. 1993. Induction of cytotoxic T lymphocytes by recombinant canarypox (ALVAC) and attenuated vaccinia (NYVAC) viruses expressing the HIV-1 envelope glycoprotein. *Virology* 195:845-850; Taylor, J., Trimarchi, C., Weinberg, R., Languet, B., Guillemin, F., Desmettre, P., and Paoletti, E. 1991. Efficacy studies on a canarypox-rabies recombinant virus. *Vaccine* 9:190-193). Both the vaccinia poxvirus and ALVAC, a variant of the canary poxvirus, have been genetically engineered to contain the genes that encode for various antigens, so that when the virus is injected into the body, it enters the host's cells and induces them to produce the antigen of interest. Because these vectors do not integrate into the genome, there is no risk of insertional mutagenesis, and expression of viral products and transgenes is transient, lasting only 10 to 14 days. Various immunization schemes against CEA utilizing such vectors were previously studied, but showed limited to no clinical response.

The compositions and methods of the invention, in various embodiments, provide adenovirus based vectors expressing a variant CEA for immunization against CEA. These vectors can raise an immune response against CEA. Further, in various embodiments, the composition and methods of the invention lead to clinical responses, such as altered disease progression or life expectancy.

Ad5 Vaccines

Adenoviruses are a family of DNA viruses characterized by an icosohedral, non-enveloped capsid containing a linear double-stranded genome. Of the human Ads, none are associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without bound by theory, this is likely due to a replication dependent cis-activation of the Ad5 major late promoter (MLP), preventing late gene expression (primarily the Ad5 capsid proteins) until replicated genomes are present to be encapsulated. The composition and methods of the invention take advantage of feature in the development of advanced generation Ad vectors/vaccines.

Ad5 Vectors

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells not expressing the Ad5 E1 genes. The recombinant Ad5 [E1-] vectors are propagated in human cells (typically 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germline transmission is extremely low if at all. Conventional Ad5 [E1-] vectors have a carrying capacity that approaches 7 kb.

Ad5 [E1-] Vectors Used as a Cancer Vaccine:

Arthur et. al. demonstrated that Ad5 [E1-] vectors encoding a variety of antigens could efficiently transduce 95% of ex vivo exposed DC's to high titers of the vector (Arthur, J. F., Butterfield, L. H., Roth, M. D., Bui, L. A., Kiertscher, S. M., Lau, R., Dubinett, S., Glaspy, J., McBride, W. H., and Economou, J. S. 1997. A comparison of gene transfer methods in human dendritic cells. *Cancer Gene Ther* 4:17-25). Importantly, increasing levels of foreign gene expression were noted in the DC with increasing multiplicities of infection (MOI) with the vector, a finding repeated by others, as well as reproduced in our preliminary studies (Diao, J., Smythe, J. A., Smyth, C., Rowe, P. B., and Alexander, I. E. 1999. Human PBMC-derived dendritic cells transduced with an adenovirus vector induce cytotoxic T-lymphocyte responses against a vector-encoded antigen in vitro. *Gene Ther* 6:845-853). It has been demonstrated that DC infected with Ad5 [E1-] vectors encoding a variety of antigens (including the tumor antigens MART-1, MAGE-A4, DF3/MUC1, p53, hugp100 melanoma antigen, polyoma virus middle −T antigen,) have the propensity to induce antigen specific CTL responses, have an enhanced antigen presentation capacity, and have an improved ability to initiate T-cell proliferation in mixed lymphocyte reactions (Arthur, J. F., Butterfield, L. H., Roth, M. D., Bui, L. A., Kiertscher, S. M., Lau, R., Dubinett, S., Glaspy, J., McBride, W. H., and Economou, J. S. 1997. A comparison of gene transfer methods in human dendritic cells. *Cancer Gene Ther* 4:17-25; Diao, J., Smythe, J. A., Smyth, C., Rowe, P. B., and Alexander, I. E. 1999. Human PBMC-derived dendritic cells transduced with an adenovirus vector induce cytotoxic T-lymphocyte responses against a vector-encoded antigen in vitro. *Gene Ther* 6:845-853; Brossart, P., Goldrath, A. W., Butz, E. A., Martin, S., and Bevan, M. J. 1997. Virus-mediated delivery of antigenic epitopes into dendritic cells as a means to induce CTL. *J Immunol* 158:3270-3276; Butterfield, L. H., Jilani, S. M., Chakraborty, N. G., Bui, L. A., Ribas, A., Dissette, V. B., Lau, R., Gamradt, S. C., Glaspy, J. A., McBride, W. H., et al. 1998. Generation of melanoma-specific cytotoxic T lymphocytes by dendritic cells transduced with a MART-1 adenovirus. *J Immunol* 161:5607-5613; Bregni, M., Shammah, S., Malaffo, F., Di Nicola, M., Milanesi, M., Magni, M., Matteucci, P., Ravagnani, F., Jordan, C. T., Siena, S., et al. 1998. Adenovirus vectors for gene transduction into mobilized blood CD34+ cells. *Gene Ther* 5:465-472; Dietz, A. B., and Vuk-Pavlovic, S. 1998. High efficiency adenovirus-mediated gene transfer to human dendritic cells. *Blood* 91:392-398; Ishida, T., Chada, S., Stipanov, M., Nadaf, S., Ciernik, F. I., Gabrilovich, D. I., and Carbone, D. P. 1999. Dendritic cells transduced with wild-type p53 gene elicit potent anti-tumour immune responses. *Clin Exp Immunol* 117:244-251; Ribas, A., Butterfield, L. H., McBride, W. H., Jilani, S. M., Bui, L. A., Vollmer, C. M., Lau, R., Dissette, V. B., Hu, B., Chen, A. Y., et al. 1997. Genetic immunization for the melanoma antigen MART-1/Melan-A using recombinant adenovirus-transduced murine dendritic cells. *Cancer Res* 57:2865-2869). Immunization of animals with DC's previously transduced by Ad5 vectors encoding tumor specific antigens has been demonstrated to result in significant levels of protection for the animals when challenged with tumor cells expressing the respective antigen (Wan, Y., Bramson, J., Carter, R., Graham, F., and Gauldic, J. 1997. Dendritic cells transduced with an adenoviral vector encoding a model tumor-associated antigen for tumor vaccination. *Hum Gene Ther* 8:1355-1363; Wan, Y., Emtage, P., Foley, R., Carter, R., and Gauldie, J. 1999. Murine dendritic cells transduced with an adenoviral vector expressing a defined tumor antigen can overcome anti-adenovirus neutralizing immunity and induce effective tumor regression. *Int J Oncol* 14:771-776). Interestingly, intra-tumoral injection of Ads encoding IL-7 was less effective than injection of DCs transduced with IL-7 encoding Ad5 vectors at inducing antitumor immunity, further heightening the interest in ex vivo transduction of DCs by Ad5 vectors (Miller, P. W., Sharma, S., Stolina, M., Butterfield, L. H., Luo, J., Lin, Y., Dohadwala, M., Batra, R.

K., Wu, L., Economou, J. S., et al. 2000. Intratumoral administration of adenoviral interleukin 7 gene-modified dendritic cells augments specific antitumor immunity and achieves tumor eradication. *Hum Gene Ther* 11:53-65). Ex vivo DC transduction strategies have also been used to attempt to induce tolerance in recipient hosts, for example, by Ad5 mediated delivery of the CTLA4Ig into DCs, blocking interactions of the DCs CD80 with the CD28 molecule present on T-cells (Lu, L., Gambotto, A., Lee, W. C., Qian, S., Bonham, C. A., Robbins, P. D., and Thomson, A. W. 1999. Adenoviral delivery of CTLA4Ig into myeloid dendritic cells promotes their in vitro tolerogenicity and survival in allogeneic recipients. *Gene Ther* 6:554-563).

Ad5 vector capsid interactions with DCs in and of themselves may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods of the invention take advantage of an Ad5 infection resulting in direct induction of DC maturation (Rea, D., Schagen, F. H., Hoeben, R. C., Mehtali, M., Havenga, M. J., Toes, R. E., Melief, C. J., and Offringa, R. 1999. Adenoviruses activate human dendritic cells without polarization toward a T-helper type 1-inducing subset. *J Virol* 73:10245-10253; Hirschowitz, E. A., Weaver, J. D., Hidalgo, G. E., and Doherty, D. E. 2000. Murine dendritic cells infected with adenovirus vectors show signs of activation. *Gene Ther* 7:1112-1120). Studies of immature bone marrow derived DCs from mice suggest that Ad vector infection of immature bone marrow derived DCs from mice resulted may upregulate cell surface markers normally associated with DC maturation (MHC I and II, CD40, CD80, CD86, and ICAM-1) as well as down-regulation of CD11c, an integrin known to be down regulated upon myeloid DC maturation. In some instances, Ad vector infection triggers IL-12 production by DCs, a marker of DC maturation (Hirschowitz, E. A., Weaver, J. D., Hidalgo, G. E., and Doherty, D. E. 2000. Murine dendritic cells infected with adenovirus vectors show signs of activation. *Gene Ther* 7:1112-1120). Without being bound by theory, these events may possibly be due to Ad5 triggered activation of NF-κB pathways (Hirschowitz, E. A., Weaver, J. D., Hidalgo, G. E., and Doherty, D. E. 2000. Murine dendritic cells infected with adenovirus vectors show signs of activation. *Gene Ther* 7:1112-1120; Loser, P., Jennings, G. S., Strauss, M., and Sandig, V. 1998. Reactivation of the previously silenced cytomegalovirus major immediate-early promoter in the mouse liver: involvement of NF-κB. *J Virol* 72:180-190; Morelli, A. E., Larregina, A. T., Ganster, R. W., Zahorchak, A. F., Plowey, J. M., Takayama, T., Logar, A. J., Robbins, P. D., Falo, L. D., and Thomson, A. W. 2000. Recombinant adenovirus induces maturation of dendritic cells via an NF-κB-dependent pathway. *J Virol* 74:9617-9628). Mature DCs can be efficiently transduced by Ad vectors, and did not lose their functional potential to stimulate the proliferation of naive T-cells at lower MOI, as demonstrated by mature CD83+ human DC (derived from peripheral blood monocytes. However, mature DCs may also be less infectable than immature ones (Rea, D., Schagen, F. H., Hoeben, R. C., Mehtali, M., Havenga, M. J., Toes, R. E., Melief, C. J., and Offringa, R. 1999. Adenoviruses activate human dendritic cells without polarization toward a T-helper type 1-inducing subset. *J Virol* 73:10245-10253; Jonuleit, H., Tilting, T., Steitz, J., Bruck, J., Giesecke, A., Steinbrink, K., Knop, J., and Enk, A. H. 2000. Efficient transduction of mature CD83+ dendritic cells using recombinant adenovirus suppressed T cell stimulatory capacity. *Gene Ther* 7:249-254). Modification of capsid proteins can be used as a strategy to optimize infection of DC by Ad vectors, as well as enhancing functional maturation, for example using the CD40L receptor as a viral vector receptor, rather than using the normal CAR receptor infection mechanisms (Tillman, B. W., Hayes, T. L., DeGruijl, T. D., Douglas, J. T., and Curiel, D. T. 2000. Adenoviral vectors targeted to CD40 enhance the efficacy of dendritic cell-based vaccination against human papillomavirus 16-induced tumor cells in a murine model. *Cancer Res* 60:5456-5463).

Most dramatically, when the potential of non-viral vectors to induce anti-HIV immune responses was directly compared to Ad5 based vectoring systems, the Ad5 based systems were found to be far superior (Shiver, J. W., Fu, T. M., Chen, L., Casimiro, D. R., Davies, M. E., Evans, R. K., Zhang, Z. Q., Simon, A. J., Trigona, W. L., Dubey, S. A., et al. 2002. Replication-incompetent adenoviral vaccine vector elicits effective anti-immunodeficiency-virus immunity. *Nature* 415:331-335). For example, in Ad5 naïve primate models, vaccination with a Ad5 [E1-] expressing the HIV gag was superior in protecting the animals from SHIV infections as compared to similar efforts utilizing naked DNA vaccines expressing HIV-gag. Thus, viral vectors can be superior to naked DNA approaches (Shiver, J. W., Fu, T. M., Chen, L., Casimiro, D. R., Davies, M. E., Evans, R. K., Zhang, Z. Q., Simon, A. J., Trigona, W. L., Dubey, S. A., et al. 2002. Replication-incompetent adenoviral vaccine vector elicits effective anti-immunodeficiency-virus immunity. *Nature* 415:331-335). Combined strategies (building upon their clinical experiences with naked DNA-gag vectors alone) using naked DNA-gag vaccines as a priming vaccination, followed by boosting with the Ad5 [E1-]-gag vaccine further improved T cell responses in human trials than those previously noted with the DNA-HIV-gag encoding vector alone (HVTN working group meeting, Alexandria, Va.: 2002).

In summary, Ad5 vectors appear to offer a unique opportunity to allow for high level and efficient transduction of TAAs such as CEA. One of the major problems facing Ad5 based vectors is the high propensity of pre-existing immunity to Ads in the human population, and how this may preclude the use of conventional, Ad5 [E1-] deleted (first generation Ads) in most human populations, for any additional vaccine application.

Ad5 [E1-, E2B-]-CEA(6D) Vaccine: The Use of Ad5 [E1-, E2b-] Vaccines to Overcome the Challenge of Pre-Existing Anti-Ad5 Immunity Studies in humans and animals have demonstrated that pre-existing immunity against Ad5 can be an inhibitory factor to commercial use of Ad-based vaccines (Yang, Z. Y., Wyatt, L. S., Kong, W. P., Moodie, Z., Moss, B., and Nabel, G. J. 2003. Overcoming immunity to a viral vaccine by DNA priming before vector boosting. *J Virol* 77:799-803; Casimiro, D. R., Chen, L., Fu, T. M., Evans, R. K., Caulfield, M. J., Davies, M. E., Tang, A., Chen, M., Huang, L., Harris, V., et al. 2003. Comparative immunogenicity in rhesus monkeys of DNA plasmid, recombinant vaccinia virus, and replication-defective adenovirus vectors expressing a human immunodeficiency virus type 1 gag gene. *J Virol* 77:6305-6313). The preponderance of humans have antibody against Ad5, the most widely used subtype for human vaccines, with two-thirds of humans studied having lympho-proliferative responses against Ad5 (Chirmule, N., Propert, K., Magosin, S., Qian, Y., Qian, R., and Wilson, J. 1999. Immune responses to adenovirus and adeno-associated virus in humans. *Gene Ther* 6:1574-1583). This pre-existing immunity can inhibit immunization or re-immunization using typical Ad5 vaccines and may preclude the immunization of a vaccinee against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype. To avoid the Ad5 immunization barrier, and improve upon the limited efficacy of first generation Ad5 [E1-] vectors to induce optimal immune responses, various embodiments of the invention relate to a next generation Ad5 vector based vaccine platform. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes (Hartigan-O'Connor, D., Barjot, C., Salvatori, G., and Chamberlain, J. S. 2002. Generation and growth of gutted adenoviral vectors. *Methods Enzymol* 346:224-246). Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors of the invention, often eliciting potent immune responses to target transgene antigens while minimizing the immune responses to Ad viral proteins.

In various embodiments, Ad5 [E1-, E2b-] vectors of the invention induce a potent CMI, as well as antibodies against the vector expressed vaccine antigens even in the presence of Ad immunity (Harui, A., Roth, M. D., Kiertscher, S. M., Mitani, K., and Basak, S. K. 2004. Vaccination with helper-dependent adenovirus enhances the generation of transgene-specific CTL. *Gene Ther* 11:1617-1626). Ad5 [E1-, E2b-] vectors also have reduced adverse reactions as compared to Ad5 [E1-] vectors, in particular the appearance of hepatotoxicity and tissue damage (Hodges, B. L., Serra, D., Hu, H., Begy, C. A., Chamberlain, J. S., and Amalfitano, A. 2000. Multiply deleted [E1, polymerase-, and pTP-] adenovirus vector persists despite deletion of the preterminal protein. *J Gene Med* 2:250-259; Morral, N., Parks, R. J., Zhou, H., Langston, C., Schiedner, G., Quinones, J., Graham, F. L., Kochanek, S., and Beaudet, A. L. 1998. High doses of a helper-dependent adenoviral vector yield supraphysiological levels of alpha1-antitrypsin with negligible toxicity. *Hum Gene Ther* 9:2709-2716; DelloRusso, C., Scott, J. M., Hartigan-O'Connor, D., Salvatori, G., Barjot, C., Robinson, A. S., Crawford, R. W., Brooks, S. V., and Chamberlain, J. S. 2002. Functional correction of adult mdx mouse muscle using gutted adenoviral vectors expressing full-length dystrophin. *Proc Natl Acad Sci USA* 99:12979-12984; Reddy, P. S., Sakhuja, K., Ganesh, S., Yang, L., Kayda, D., Brann, T., Pattison, S., Golightly, D., Idamakanti, N., Pinkstaff, A., et al. 2002. Sustained human factor VIII expression in hemophilia A mice following systemic delivery of a gutless adenoviral vector. *Mol Ther* 5:63-73). A key aspect of these Ad5 vectors is that expression of Ad late genes is greatly reduced (Hodges, B. L., Serra, D., Hu, H., Begy, C. A., Chamberlain, J. S., and Amalfitano, A. 2000. Multiply deleted [E1, polymerase-, and pTP-] adenovirus vector persists despite deletion of the preterminal protein. *J Gene Med* 2:250-259; Amalfitano, A., Hauser, M. A., Hu, H., Serra, D., Begy, C. R., and Chamberlain, J. S. 1998. Production and characterization of improved adenovirus vectors with the E1, E2b, and E3 genes deleted. *J Virol* 72:926-933; Hartigan-O'Connor, D., Kirk, C. J., Crawford, R., Mule, J. J., and Chamberlain, J. S. 2001. Immune evasion by muscle-specific gene expression in dystrophic muscle. *Mol Ther* 4:525-533). For example, production of the capsid fiber proteins could be detected in vivo for Ad5 [E1-] vectors, while fiber expression was ablated from Ad5 [E1-, E2b-] vector vaccines (Hu, H., Serra, D., and Amalfitano, A. 1999. Persistence of an [E1-, polymerase-] adenovirus vector despite transduction of a neoantigen into immune-competent mice. *Hum Gene Ther* 10:355-364; DelloRusso, C., Scott, J. M., Hartigan-O'Connor, D., Salvatori, G., Barjot, C., Robinson, A. S., Crawford, R. W., Brooks, S. V., and Chamberlain, J. S. 2002. Functional correction of adult mdx mouse muscle using gutted adenoviral vectors expressing full-length dystrophin. *Proc Natl Acad Sci USA* 99:12979-12984; Reddy, P. S., Sakhuja, K., Ganesh, S., Yang, L., Kayda, D., Brann, T., Pattison, S., Golightly, D., Idamakanti, N., Pinkstaff, A., et al. 2002. Sustained human factor VIII expression in hemophilia A mice following systemic delivery of a gutless adenoviral vector. *Mol Ther* 5:63-73). The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 hours following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Various embodiments of the invention contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

In some cases, this immune induction may take months. Ad5 [E1-, E2b-] vectors not only are safer than, but appear to be superior to Ad5 [E1-] vectors in regard to induction of antigen specific immune responses, making them much better suitable as a platform to deliver CEA vaccines that can result in a clinical response.

Various embodiments of the invention, by taking advantage of the new Ad5 [E1-, E2b-] vector system in delivering a long sought-after need for a develop a therapeutic vaccine against CEA, overcome barriers found with other Ad5 systems and permit the immunization of people who have previously been exposed to Ad5.

In various embodiments the compositions and methods of the invention comprising an Ad5 [E1-, E2b-] vector CEA vaccine effect of increased overall survival (OS) within the bounds of technical safety.

Adenovirus Vectors

Compared to First Generation adenovirus vectors, certain embodiments of the Second Generation E2b deleted adenovirus vectors of the present invention contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens. The E2b deleted adenovirus vectors also have reduced adverse reactions as compared to First Generation adenovirus vectors (Morral, et al Hum Gene Ther 9/2709-2716 (1998); Hodges, et al. J Gene Med 2/250-259 (2000); DelloRusso, et al. Proc Natl Acad Sci USA 99/12979-12984 (2002); Reddy, et al. Mol Ther 5/63-73 (2002); (Amalfitano and Parks, et al. Curr Gene Ther 2/111-133 (2002); Amalfitano Curr Opin Mol Ther 5/362-366 (2003); Everett, et al. Human Gene Ther 14/1715-1726 (2003)) E2b deleted vectors have reduced expression of viral genes (Hodges, et al. J Gene Med 2/250-259 (2000); Amalfitano, et al. J Virol 72/926-933 (1998); Hartigan-O'Connor, et al. Mol Ther 4/525-533 (2001)), and this characteristic has been reported to lead to extended transgene expression in vivo (Hu, et al. Hum Gene Ther 10/355-364 (1999); DelloRusso, et al. Proc Natl Acad Sci USA 99/12979-12984 (2002); Reddy, et al. Mol Ther 5/63-73 (2002); (Amalfitano and Parks, et al. Curr Gene Ther 2/111-133 (2002); Amalfitano Curr Opin Mol Ther 5/362-366 (2003); Everett, et al. Human Gene Ther 14/1715-1726 (2003)).

The innate immune response to wild type Ad can be complex, and it appears that Ad proteins expressed from adenovirus vectors play an important role (Moorhead, et al. J Virol 73/1046-1053 (1999); Nazir, et al. J Investig Med 53/292-304 (2005); Schaack, et al. Proc Natl Acad Sci USA 101/3124-3129 (2004); Schaack, et al. Viral Immunol 18/79-88 (2005); Kiang, et al. Mol Ther 14/588-598 (2006); Hartman, et al. J Virol 81/1796-1812 (2007); Hartman, et al. Virology 358/357-372 (2007)). Specifically, the deletions of pre-terminal protein and DNA polymerase in the E2b deleted vectors appear to reduce inflammation during the first 24 to 72 hours following injection, whereas First Generation adenovirus vectors stimulate inflammation during this period (Schaack, et al. Proc Natl Acad Sci USA 101/3124-3129 (2004); Schaack, et al. Viral Immunol 18/79-88 (2005); Kiang, et al. Mol Ther 14/588-598 (2006); Hartman, et al. J Virol 81/1796-1812 (2007); Hartman, et al. Virology 358/357-372 (2007)). In addition, it has been reported that the additional replication block created by E2b deletion also leads to a 10,000 fold reduction in expression of Ad late genes, well beyond that afforded by E1, E3 deletions alone (Amalfitano et al. J. Virol. 72/926-933 (1998); Hodges et al. J. Gene Med. 2/250-259 (2000)). The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by Second Generation E2b deleted vectors results in increased potential for the vectors to express desired vaccine antigens during the infection of antigen presenting cells (i.e. dendritic cells), decreasing the potential for antigenic competition, resulting in greater immunization of the vaccine to the desired antigen relative to identical attempts with First Generation adenovirus vectors. E2b deleted adenovirus vectors provide an improved Ad-based vaccine candidate that is safer, more effective, and more versatile than previously described vaccine candidates using First Generation adenovirus vectors.

Thus, first generation, E1-deleted Adenovirus subtype 5 (Ad5)-based vectors, although promising platforms for use as cancer vaccines, are impeded in activity by naturally occurring or induced Ad-specific neutralizing antibodies. Without being bound by theory, Ad5-based vectors with deletions of the E1 and the E2b regions (Ad5 [E1-, E2b-]), the latter encoding the DNA polymerase and the pre-terminal protein, for example by virtue of diminished late phase viral protein expression, may avoid immunological clearance and induce more potent immune responses against the encoded tumor antigen transgene in Ad-immune hosts. Indeed, multiple homologous immunizations with Ad5 [E1-, E2b-]-CEA(6D), encoding the tumor antigen CEA, induced CEA-specific cell-mediated immune (CMI) responses with antitumor activity in mice despite the presence of pre-existing or induced Ad5-neutralizing antibody. In the present phase I/II study, cohorts of patients with advanced colorectal cancer were immunized with escalating doses of Ad5 [E1-, E2b-]-CEA(6D). CEA-specific CMI responses were observed despite the presence of pre-existing Ad5 immunity in a majority (61.3%) of patients. Importantly, there was minimal toxicity, and overall patient survival (48% at 12 months) was similar regardless of pre-existing Ad5 neutralizing antibody titers. The results demonstrate that, in cancer patients, the novel Ad5 [E1-, E2b-] gene delivery platform generates significant CMI responses to the tumor antigen CEA in the setting of both naturally acquired and immunization-induced Ad5 specific immunity.

The present invention contemplates the use of E2b deleted adenovirus vectors, such as those described in U.S. Pat. Nos. 6,063,622; 6,451,596; 6,057,158; 6,083,750; and 8,298,549, which are each incorporated herein by reference in their entirety. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. The present invention also provides such packaging cell lines; for example E.C7 (formally called C-7), derived from the HEK-203 cell line (Amalfitano, et al. Proc Natl Acad Sci USA 93/3352-3356 (1996); Amalfitano, et al. Gene Ther 4/258-263 (1997)).

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in the present invention can enable the propagation of adenovirus vectors with a carrying capacity approaching 13 kb, without the need for a contaminating helper virus [Mitani et al. (1995) Proc. Natl. Acad. Sci. USA 92:3854; Hodges, et al., 2000 J Gene Med 2:250-259; (Amalfitano and Parks, Curr Gene Ther 2/111-133 (2002)]. In addition, when genes critical to the viral life cycle are deleted (e.g., the E2b genes), a further crippling of Ad to replicate or express other viral gene proteins occurs. This can decrease immune recognition of virally infected cells, and allow for extended durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5 [Doerfler, In Adenovirus DNA, The Viral Genome and Its Expression (Martinus Nijhoff Publishing Boston, 1986)]. Though the MLP is minimally active prior to Ad genome replication, the highly toxic Ad late genes are primarily transcribed and translated from the MLP only after viral genome replication has occurred [Thomas and Mathews (1980) Cell 22:523]. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

In certain embodiments, the adenovirus vectors contemplated for use in the present invention include E2b deleted adenovirus vectors that have a deletion in the E2b region of the Ad genome and, optionally, the E1 region. In some cases, such vectors do not have any other regions of the Ad genome deleted. In another embodiment, the adenovirus vectors contemplated for use in the present invention include E2b deleted adenovirus vectors that have a deletion in the E2b region of the Ad genome and, optionally, deletions in the E1 and E3 regions. In some cases, such vectors have no other regions deleted. In a further embodiment, the adenovirus vectors contemplated for use in the present invention include adenovirus vectors that have a deletion in the E2b region of the Ad genome and, optionally, deletions in the E1, E3 and, also optionally, partial or complete removal of the E4 regions. In some cases, such vectors have no other deletions. In another embodiment, the adenovirus vectors contemplated for use in the present invention include adenovirus vectors that have a deletion in the E2b region of the Ad genome and, optionally deletions in the E1 and/or E4 regions. In some cases, such vectors contain no other deletions. In an additional embodiment, the adenovirus vectors contemplated for use in the present invention include adenovirus vectors that have a deletion in the E1a, E2b and/or E4 regions of the Ad genome. In some cases, such vectors have no other deletions. In one embodiment, the adenovirus vectors for use herein comprise vectors having the E1 and/or DNA polymerase functions of the E2b region deleted. In some cases, such vectors have no other deletions. In a further embodiment, the adenovirus vectors for use herein have the E1 and/or the preterminal protein functions of the E2b region deleted. In some cases, such vectors have no other deletions. In another embodiment, the adenovirus vectors for use herein have the E1, DNA polymerase and/or the preterminal protein functions deleted. In some cases, such vectors have no other deletions. In one particular embodiment, the adenovirus vectors contemplated for use herein are deleted for at least a portion of the E2b region and/or the E1 region. In some cases, such vectors are not "gutted" adenovirus vectors. In this regard, the vectors may be deleted for both the DNA polymerase and the preterminal protein functions of the E2b region. In an additional embodiment, the adenovirus vectors for use in the present invention include adenovirus vectors that have a deletion in the E1, E2b and/or 100K regions of the adenovirus genome. In one embodiment, the adenovirus vectors for use herein comprise vectors having the E1, E2b and/or protease functions deleted. In some cases, such vectors have no other deletions. In a further embodiment, the adenovirus vectors for use herein have the E1 and/or the E2b regions deleted, while the fiber genes have been modified by mutation or other alterations (for example to alter Ad tropism). Removal of genes from the E3 or E4 regions may be added to any of the mentioned adenovirus vectors. In certain embodiments, the adenovirus vector may be a "gutted" adenovirus vector.

The term "E2b deleted", as used herein, refers to a specific DNA sequence that is mutated in such a way so as to prevent expression and/or function of at least one E2b gene product. Thus, in certain embodiments, "E2b deleted" is used in relation to a specific DNA sequence that is deleted (removed) from the Ad genome. E2b deleted or "containing a deletion within the E2b region" refers to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

The term "E1 deleted", as used herein, refers to a specific DNA sequence that is mutated in such a way so as to prevent expression and/or function of at least one E1 gene product. Thus, in certain embodiments, "E1 deleted" is used in relation to a specific DNA sequence that is deleted (removed) from the Ad genome. E1 deleted or "containing a deletion within the E1 region" refers to a deletion of at least one base pair within the E1 region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E1 region of the Ad genome. An E1 deletion may be a deletion that prevents expression and/or function of at least one E1 gene product and therefore, encompasses deletions within exons of encoding portions of E1-specific proteins as well as deletions within promoter and leader sequences. In certain embodiments, an E1 deletion is a deletion that prevents expression and/or function of one or both of a trans-acting transcriptional regulatory factor of the E1 region. In a further embodiment, "E1 deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

As would be understood by the skilled artisan upon reading the present disclosure, other regions of the Ad genome can be deleted. Thus to be "deleted" in a particular region of the Ad genome, as used herein, refers to a specific DNA sequence that is mutated in such a way so as to prevent expression and/or function of at least one gene product encoded by that region. In certain embodiments, to be "deleted" in a particular region refers to a specific DNA sequence that is deleted (removed) from the Ad genome in such a way so as to prevent the expression and/or the function encoded by that region (e.g., E2b functions of DNA polymerase or preterminal protein function). "Deleted" or "containing a deletion" within a particular region refers to a deletion of at least one base pair within that region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted from a particular region. In another embodiment, the deletion is more than 150, 160, 170, 180, 190, 200, 250, or 300 base pairs within a particular region of the Ad genome. These deletions are such that expression and/or function of the gene product encoded by the region is prevented. Thus deletions encompass deletions within exons encoding portions of proteins as well as deletions within promoter and leader sequences. In a further embodiment, "deleted" in a particular region of the Ad genome refers to one or more point mutations in the DNA sequence of this region of an Ad genome such that one or more encoded proteins is non-functional. Such mutations include residues that are replaced with a different residue leading to a change in the amino acid sequence that result in a nonfunctional protein. Deletions or mutations in the Ad genome can be within one or more of E1a, E1b, E2a, E2b, E3, E4, L1, L2, L3, L4, L5, TP, POL, IV, and VA regions.

The deleted adenovirus vectors of the present invention can be generated using recombinant techniques known in the art (see e.g., Amalfitano et al., 1998 J. Virol. 72:926-933; Hodges, et al., 2000 J Gene Med 2:250-259).

As would be recognized by the skilled artisan, the adenovirus vectors for use in the present invention can be successfully grown to high titers using an appropriate packaging cell line that constitutively expresses E2b gene products and products of any of the necessary genes that may have been deleted. In certain embodiments, HEK-293-derived cells that not only constitutively express the E1 and DNA polymerase proteins, but also the Ad-preterminal protein, can be used. In one embodiment, E.C7 cells are used to successfully grow high titer stocks of the adenovirus vectors (see e.g., Amalfitano et al., J. Virol. 1998 72:926-933; Hodges, et al. J Gene Med 2/250-259 (2000)).

In order to delete critical genes from self-propagating adenovirus vectors, the proteins encoded by the targeted genes can first be coexpressed in HEK-293 cells, or similar, along with the E1 proteins. For example, only those proteins which are non-toxic when coexpressed constitutively (or toxic proteins inducibly-expressed) can be selectively utilized. Coexpression in HEK-293 cells of the E1 and E4 genes is possible (for example utilizing inducible, not constitutive, promoters) according to the methods in Yeh et al. (1996) J. Virol. 70:559; Wang et al. (1995) Gene Therapy 2:775; and Gorziglia et al. (1996) J. Virol. 70:4173. The E1 and protein IX genes, a virion structural protein, can be coexpressed [Caravokyri and Leppard (1995) J. Virol. 69:6627. Further coexpression of the E1, E4, and protein IX genes is also possible as described in Krougliak and Graham (1995) Hum. Gene Ther. 6:1575. The E1 and 100 k genes can be successfully expressed in transcomplementing cell lines, as can E1 and protease genes (Oualikene, et al. Hum Gene Ther 11/1341-1353 (2000); Hodges, et al. J. Virol 75/5913-5920 (2001)).

Cell lines coexpressing E1 and E2b gene products for use in growing high titers of E2b deleted Ad particles are described in U.S. Pat. No. 6,063,622. The E2b region encodes viral replication proteins, which are essential for Ad genome replication [Doerfler, supra and Pronk et al. (1992) Chromosoma 102:S39-S45]. Useful cell lines constitutively express the approximately 140 kD Ad-DNA polymerase and/or the approximately 90 kD preterminal protein. In particular, cell lines that have high-level, constitutive coexpression of the E1, DNA polymerase, and preterminal proteins, without toxicity (e.g. E.C7), are desirable for use in propagating Ad for use in multiple vaccinations. These cell lines permit the propagation of adenovirus vectors deleted for the E1, DNA polymerase, and preterminal proteins.

The recombinant Ad of the present invention can be propagated using techniques known in the art. For example, tissue culture plates containing E.C7 cells can be infected with the adenovirus vector virus stocks at an appropriate MOI (e.g., 5) and incubated at 37.0.degree. C. for 40-96 h. The infected cells can be harvested, resuspended in 10 mM Tris-Cl (pH 8.0), and sonicated, and the virus is purified by two rounds of cesium chloride density centrifugation. In certain techniques, the virus containing band is desalted over a Sephadex CL-6B column (Pharmacia Biotech, Piscataway, N.J.), sucrose or glycerol is added, and aliquots are stored at −80.degree. C. In some embodiments, the virus is placed in a solution designed to enhance its stability, such as A195 (Evans, et al. J Pharm Sci 93/2458-2475 (2004)). The titer of the stock can be measured (e.g., by measurement of the optical density at 260 nm of an aliquot of the virus after SDS lysis). In another embodiment, plasmid DNA, either linear or circular, encompassing the entire recombinant E2b deleted adenovirus vector is transfected into E.C7, or similar cells, and incubated at 37.0.degree. C. until evidence of viral production is present (e.g. the cytopathic effect). The conditioned media from these cells can be used to infect more E.C7, or similar cells, to expand the amount of virus produced, before purification. Purification can be accomplished, for example, by two rounds of cesium chloride density centrifugation or selective filtration. In certain embodiments, the virus may be purified by column chromatography, using commercially available products (e.g. Adenopure from Puresyn, Inc., Malvern, Pa.) or custom made chromatographic columns.

Generally, the compositions of the present invention comprises enough of the virus to ensure that the cells to be infected are confronted with a certain number of viruses. Thus, in various embodiments, the present invention provides a stock of recombinant Ad, preferably an RCA-free stock of recombinant Ad. The preparation and analysis of Ad stocks is well known in the art. Viral stocks can vary considerably in titer, depending largely on viral genotype and the protocol and cell lines used to prepare them. The viral stocks of the present invention can have a titer of at least about $10^6$, $10^7$, or $10^8$ pfu/ml, and many such stocks can have higher titers, such as at least about $10^9$, $10^{10}$, $10^{11}$, or $10^{12}$ pfu/ml. Depending on the nature of the recombinant virus and the packaging cell line, it is possible that a viral stock of the present invention can have a titer of even about $10^{13}$ particles/ml or higher.

Further information on viral delivery systems is known in the art and can be found, for example, in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993, which are each herein incorporated by reference in their entirety.

Heterologous Nucleic Acid

The adenovirus vectors of the present invention typically comprise heterologous nucleic acid sequences that encode one or more target antigens of interest, or variants, fragments or fusions thereof, against which it is desired to generate an immune response. In some embodiments, the adenovirus vectors of the present invention comprise heterologous nucleic acid sequences that encode one or more proteins, variants thereof, fusions thereof, or fragments thereof, that can modulate the immune response. In a further embodiment of the invention, the adenovirus vector of the present invention encodes one or more antibodies against specific antigens, such as anthrax protective antigen, permitting passive immunotherapy. In certain embodiments, the adenovirus vectors of the present invention comprise heterologous nucleic acid sequences encoding one or more proteins having therapeutic effect (e.g., anti-viral, antibacterial, antiparasitic, or anti-tumor function). Thus the present invention provides the Second Generation E2b deleted adenovirus vectors that comprise a heterologous nucleic acid sequence. In some embodiments, the heterologous nucleic acid sequence is colorectal embryonic antigen (CEA) or a variant, a part, or a variant part thereof.

As such, the present invention further provides nucleic acid sequences, also referred to herein as polynucleotides, that encode one or more target antigens of interest, or fragments or variants thereof. As such, the present invention provides polynucleotides that encode target antigens from any source as described further herein, vectors comprising such polynucleotides and host cells transformed or transfected with such expression vectors. The terms "nucleic acid" and "polynucleotide" are used essentially interchangeably herein. As will be also recognized by the skilled artisan, polynucleotides of the invention may be single-stranded (coding or antisense) or double-stranded, and may be DNA (e.g. genomic, cDNA, or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. This refers to the DNA molecule as originally isolated, and does not exclude genes or coding regions later added to the segment recombinantly in the laboratory.

As will be understood by those skilled in the art, the polynucleotides of this invention can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

Polynucleotides may comprise a native sequence (i.e., an endogenous sequence that encodes a target antigen polypeptide/protein/epitope of the invention or a portion thereof) or may comprise a sequence that encodes a variant, fragment, or derivative of such a sequence. In certain embodiments, the polynucleotide sequences set forth herein encode target antigen proteins as described herein. In some embodiments, polynucleotides represent a novel gene sequence that has been optimized for expression in specific cell types (i.e. human cell lines) that may substantially vary from the native nucleotide sequence or variant but encode a similar protein antigen.

In other related embodiments, the present invention provides polynucleotide variants having substantial identity to native sequences encoding proteins (e.g., target antigens of interest) as described herein, for example those comprising at least 70% sequence identity, preferably at least 75%, 80%, 85%, 90%, 95%, 96%, 97%, 98%, or 99% or higher, sequence identity compared to a native polynucleotide sequence encoding the polypeptides of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like. In some embodiments, the present invention provides polynucleotides encoding a protein comprising for example at least 70% sequence identity, preferably at least 75%, 80%, 85%, 90%, 95%, 96%, 97%, 98%, or 99% or higher, sequence identity compared to a protein sequence encoded by a native polynucleotide sequence of this invention using the methods described herein.

Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. In some cases, said one or more substitutions, additions, deletions and/or insertions may result in an increased immunogenicity of the epitope of the polypeptide encoded by the variant polynucleotide. As described elsewhere herein, the polynucleotide variants preferably encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished, but optionally substantially increased, relative to the native polypeptide. The term "variants" should also be understood to encompass homologous genes of xenogenic origin. In particular embodiments, variants or fragments of target antigens are modified such that they have one or more reduced biological activities. For example, an oncogenic protein target antigen may be modified to reduce or eliminate the oncogenic activity of the protein, or a viral protein may be modified to reduce or eliminate one or more activities or the viral protein. An example of a modified CEA protein is a CEA having a N610D mutation, resulting in a variant protein with increased immunogenicity.

The present invention provides polynucleotides that comprise or consist of at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide, including target protein antigens, as described herein, as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described herein may be extended at one or both ends by additional nucleotides not found in the native sequence encoding a polypeptide as described herein, such as an epitope or heterologous target protein. This additional sequence may consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides of the present invention, or fragments thereof, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., Unified Approach to Alignment and Phylogenes, pp. 626-645 (1990); Methods in Enzymology vol. 183, Academic Press, Inc., San Diego, Calif.; Higgins, D. G. and Sharp, P. M., CABIOS 5:151-153 (1989); Myers, E. W. and Muller W., CABIOS 4:11-17 (1988); Robinson, E. D., Comb. Theor 11:105 (1971); Saitou, N. Nei, M., Mol. Biol. Evol. 4:406-425 (1987); Sneath, P. H. A. and Sokal, R. R., Numerical Taxonomy—the Principles and Practice of Numerical Taxonomy, Freeman Press, San Francisco, Calif. (1973); Wilbur, W. J. and Lipman, D. J., Proc. Natl. Acad., Sci. USA 80:726-730 (1983).

Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al., Nucl. Acids Res. 25:3389-3402 (1977), and Altschul et al., J. Mol. Biol. 215:403-410 (1990), respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, Proc. Natl. Acad. Sci. USA 89:10915 (1989)) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In another embodiment of the invention, a mutagenesis approach, such as site-specific mutagenesis, is employed for the preparation of variants and/or derivatives of the target antigen sequences, or fragments thereof, as described herein. By this approach, specific modifications in a polypeptide sequence can be made through mutagenesis of the underlying polynucleotides that encode them. These techniques provide a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of an epitope comprised in a polypeptide or the oncogenicity of a target antigen. Assays to test the immunogenicity of a polypeptide or variant thereof are well known in the art and include, but are not limited to, T cell cytotoxicity assays (CTL/chromium release assays), T cell proliferation assays, intracellular cytokine staining, ELISA, ELISpot, etc. The techniques of site-specific mutagenesis are well known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

The preparation of sequence variants of the selected peptide-encoding DNA segments using site-directed mutagenesis provides a means of producing potentially useful species and is not meant to be limiting, as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982.

Polynucleotide segments or fragments encoding the polypeptides of the present invention may be readily prepared by, for example, directly synthesizing the fragment by chemical means, as is commonly practiced using an automated oligonucleotide synthesizer. Also, fragments may be obtained by application of nucleic acid reproduction technology, such as the PCR. technology of U.S. Pat. No. 4,683,202, by introducing selected sequences into recombinant vectors for recombinant production, and by other recombinant DNA techniques generally known to those of skill in the art of molecular biology (see for example, Current Protocols in Molecular Biology, John Wiley and Sons, NY, N.Y.).

In order to express a desired target antigen polypeptide or fragment or variant thereof, or fusion protein comprising any of the above, as described herein, the nucleotide sequences encoding the polypeptide, or functional equivalents, are inserted into an appropriate Ad as described elsewhere herein using recombinant techniques known in the art. The appropriate adenovirus vector may contain the necessary elements for the transcription and translation of the inserted coding sequence and any desired linkers. Methods which are well known to those skilled in the art may be used to construct these adenovirus vectors containing sequences encoding a polypeptide of interest and appropriate transcriptional and translational control elements. These methods include in vitro recombinant DNA techniques, synthetic techniques, and in vivo genetic recombination.

Such techniques are described, for example, in Amalfitano et al., 1998 J. Virol. 72:926-933; Hodges, et al., 2000 J Gene Med 2:250-259; Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of vector/host systems may be utilized to contain and produce polynucleotide sequences. These include, but are not limited to, microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

The "control elements" or "regulatory sequences" present in an adenovirus vector may include those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, sequences encoding a polypeptide of interest may be ligated into an Ad transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon can be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162). Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., target antigens of interest), using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

The adenovirus vectors of the present invention comprise nucleic acid sequences encoding one or more antigens of interest, or variants or fragments thereof. The nucleic acid sequence may also contain a product that can be detected or selected for. As referred to herein, a "reporter" gene is one whose product can be detected, such as by fluorescence, enzyme activity on a chromogenic or fluorescent substrate, and the like or selected for by growth conditions. Such reporter genes include, without limitation, green fluorescent protein (GFP), 0-galactosidase, chloramphenicol acetyltransferase (CAT), luciferase, neomycin phosphotransferase, secreted alkaline phosphatase (SEAP), and human growth hormone (HGH). Selectable markers include drug resistances, such as neomycin (G418), hygromycin, and the like.

The nucleic acid encoding an antigen of interest may also comprise a promoter or expression control sequence. This is a nucleic acid sequence that controls expression of the nucleic acid sequence encoding a target antigen and generally is active or activatable in the targeted cell. The choice of the promoter will depend in part upon the targeted cell type and the degree or type of control desired. Promoters that are suitable within the context of the present invention include, without limitation, constitutive, inducible, tissue specific, cell type specific, temporal specific, or event-specific.

Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), bovine papilloma virus promoter, and adenovirus promoter. In addition to viral promoters, cellular promoters are also amenable within the context of this invention. In particular, cellular promoters for the so-called housekeeping genes are useful (e.g., β-actin). Viral promoters are generally stronger promoters than cellular promoters.

Inducible promoters may also be used. These promoters include MMTV LTR (PCT WO 91/13160), inducible by dexamethasone, metallothionein, inducible by heavy metals, and promoters with cAMP response elements, inducible by cAMP, heat shock, promoter. By using an inducible promoter, the nucleic acid may be delivered to a cell and will remain quiescent until the addition of the inducer. This allows further control on the timing of production of the protein of interest.

Event-type specific promoters are active or upregulated only upon the occurrence of an event, such as tumorigenicity or viral infection, for example. The HIV LTR is a well-known example of an event-specific promoter. The promoter is inactive unless the tat gene product is present, which occurs upon viral infection. Some event-type promoters are also tissue-specific. Preferred event-type specific promoters include promoters activated upon viral infection.

Examples of promoters discussed herein include, but are not limited to, promoters for alphafetoprotein, alpha actin, myo D, carcinoembryonic antigen, VEGF-receptor (GenBank Accession No. X89776); FGF receptor; TEK or tic 2 (GenBank Accession No. L06139); tic (GenBank Accession Nos. X60954; S89716); urokinase receptor (GenBank Accession No. S78532); E- and P-selectins (GenBank Accession Nos. M64485; L01874); VCAM-1 (GenBank Accession No. M92431); endoglin (GenBank Accession No. HSENDOG); endosialin (Rettig et al., PNAS 89:10832, 1992); alpha V-beta3 integrin (Villa-Garcia et al., Blood 3:668, 1994; Donahue et al., BBA 1219:228, 1994); endothelin-1 (GenBank Accession Nos. M25377; J04819; J05489); ICAM-3 (GenBank Accession No. S50015); E9 antigen (Wang et al., Int. J. Cancer 54:363, 1993); von Willebrand factor (GenBank Accession Nos. HUMVWFI; HUMVWFA); CD44 (GenBank Accession No. HUMCD44B); CD40 (GenBank Accession Nos. HACD40L; HSCD405FR); vascular-endothelial cadherin (Martin-Padura et al., J. Pathol. 175:51, 1995); notch 4 (Uyttendaele et al., Development 122:2251, 1996) high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, alpha-crystallin, PDGF receptor, integrin receptor, α-actin, SM1 and SM2 myosin heavy chains, calponin-hl, SM22 alpha angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, CD4, and the like are useful within the context of this invention.

In addition to the promoter, repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription (Dunaway et al., Mol Cell Biol 17: 182-9, 1997; Gdula et al., Proc Natl Acad Sci USA 93:9378-83, 1996, Chan et al., J Virol 70: 5312-28, 1996; Scott and Geyer, EMBO J. 14: 6258-67, 1995; Kalos and Fournier, Mol Cell Biol 15: 198-207, 1995; Chung et al., Cell 74: 505-14, 1993) and can silence background transcription.

Negative regulatory elements can be located in the promoter regions of a number of different genes. The repressor element can function as a repressor of transcription in the absence of factors, such as steroids, as does the NSE in the promoter region of the ovalbumin gene (Haecker et al., Mol. Endocrinology. 9:1113-1126, 1995). These negative regulatory elements can bind specific protein complexes from oviduct, none of which are sensitive to steroids. Three different elements are located in the promoter of the ovalbumin gene. Oligonucleotides corresponding to portions of these elements can repress viral transcription of the TK reporter. One of the silencer elements shares sequence identity with silencers in other genes (TCTCTCCNA (SEQ ID NO: 6)).

Further, repressor elements can be located in the promoter region of a variety of genes, including the collagen II gene, for example. Nuclear factors from HeLa cells can bind specifically to DNA fragments containing the silencer region (Savanger et al., J. Biol. Chem. 265(12):6669-6674, 1990). Repressor elements may play a role regulating transcription in the carbamyl phosphate synthetase gene (Goping et al., Nucleic Acid Research 23(10):1717-1721, 1995). This gene is expressed in only two different cell types, hepatocytes and epithelial cells of the intestinal mucosa. Negative regulatory regions are also found in the promoter region of the choline acetyltransferase gene, the albumin promoter (Hu et al., J. Cell Growth Differ. 3(9):577-588, 1992), phosphoglycerate kinase (PGK-2) gene promoter (Misuno et al., Gene 119(2): 293-297, 1992), and in the 6-phosphofructo-2-kinase/fructose-2, 6-bisphosphatase gene, in which the negative regulatory element inhibits transcription in non-hepatic cell lines (Lemaigre et al., Mol. Cell. Biol. 11(2):1099-1106). Furthermore, the negative regulatory element Tse-1 is located in a number of liver specific genes, including tyrosine aminotransferase (TAT). TAT gene expression is liver specific and inducible by both glucocorticoids and the cAMP signaling pathway. The cAMP response element (CRE) can ask as the target for repression by Tse-1 and hepatocyte-specific elements (Boshart et al., Cell 61(5):905-916, 1990). Accordingly, it is clear that varieties of such elements are known or are readily identified.

In certain embodiments, elements that increase the expression of the desired target antigen are incorporated into the nucleic acid sequence of the adenovirus vectors described herein. Such elements include, but are not limited to internal ribosome binding sites (IRES; Wang and Siddiqui, Curr. Top. Microbiol. Immunol 203:99, 1995; Ehrenfeld and Semler, Curr. Top. Microbiol. Immunol. 203:65, 1995; Rees et al., Biotechniques 20:102, 1996; Sugimoto et al., Biotechnology 12:694, 1994). IRES can increase translation efficiency. As well, other sequences may enhance expression. For some genes, sequences especially at the 5' end may inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels may be assayed by any known method, including Northern blot hybridization, RNase probe protection and the like. Protein levels may be assayed by any known method, including ELISA.

As would be recognized by the skilled artisan, the adenovirus vectors of the present invention comprising heterologous nucleic acid sequences can be generated using recombinant techniques known in the art, such as those described in Maionc et al., 2001 Proc Natl Acad Sci USA, 98:5986-5991; Maionc et al., 2000 Hum Gene Ther 11:859-868; Sandig et al. 2000 Proc Natl Acad Sci USA, 97:1002-1007; Harui et al. 2004 Gene Therapy, 11:1617-1626; Parks et al., 1996 Proc Natl Acad Sci USA, 93:13565-13570; DelloRusso et al., 2002 Proc Natl Acad Sci USA, 99:12979-12984; Current Protocols in Molecular Biology, John Wiley and Sons, NY, N.Y.).

As noted above, the adenovirus vectors of the present invention comprise nucleic acid sequences that encode one or more target proteins or antigens of interest. In this regard, the vectors may contain nucleic acid encoding 1, 2, 3, 4, 5, 6, 7, 8, 9, 10, 11, 12, 13, 14, 15, 16, 17, 18, 19, 20 or more different target antigens of interest. The target antigens may be a full length protein or may be a fragment (e.g., an epitope) thereof. The adenovirus vectors may contain nucleic acid sequences encoding multiple fragments or epitopes from one target protein of interest or may contain one or more fragments or epitopes from numerous different target proteins of interest. In some embodiments, the target antigen or protein comprises CEA.

The term "target antigen" or "target protein" as used herein refers to a molecule, such as a protein, against which an immune response is to be directed. The target antigen may comprise any substance against which it is desirable to generate an immune response but generally, the target antigen is a protein. A target antigen may comprise a full length protein or a fragment thereof that induces an immune response (i.e., an immunogenic fragment). A target antigen or fragment thereof may be modified, e.g., to reduce one or more biological activities of the target antigen or to enhance its immunogenicity. In some embodiments, the target antigen or target protein is CEA.

An "immunogenic fragment", as used herein is a fragment of a polypeptide that is specifically recognized (i.e., specifically bound) by a B-cell and/or T-cell surface antigen receptor resulting in the generation of an immune response specifically against the fragment. In certain embodiments, immunogenic fragments bind to an MHC class I or class II molecule. As used herein, an immunogenic fragment is said to "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β.2-microglobulin (β2m) into MEC class I/β2m/peptide heterotrimeric complexes (see Parker et al., J. Immunol. 152:163, 1994). Alternatively, functional peptide competition assays that are known in the art may be employed. Immunogenic fragments of polypeptides may generally be identified using well known techniques, such as those summarized in Paul, Fundamental Immunology, 3rd ed., 243-247 (Raven Press, 1993) and references cited therein. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full length target polypeptide (e.g., in an ELISA and/or T-cell reactivity assay). In other words, an immunogenic fragment may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988.

Target antigens of the present invention include but are not limited to antigens derived from any of a variety of infectious agents or cancer cells. An infectious agent may refer to any living organism capable of infecting a host. Cancer typically includes a neoplastic cell. Infectious agents include, for example, bacteria, any variety of viruses, such as, single stranded RNA viruses, single stranded DNA viruses, fungi, parasites, and protozoa. Examples of infectious agents include, but are not limited to, *Actinobacillus* spp., *Actinomyces* spp., Adenovirus (types 1, 2, 3, 4, 5 et 7), Adenovirus (types 40 and 41), *Aerococcus* spp., *Aeromonas hydrophila, Ancylostoma duodenale, Angiostrongylus cantonensis, Ascaris lumbricoides, Ascaris* spp., *Aspergillus* spp., *Babesia* spp, *B. microti, Bacillus anthracis, Bacillus cereus, Bacteroides* spp., *Balantidium coli, Bartonella bacilliformis, Blastomyces dermatitidis, Bluetongue virus, Bordetella bronchiseptica, Bordetella pertussis, Borrelia afzelii, Borrelia burgdorferi, Borrelia garinii, Branhamella catarrhalis, Brucella* spp. (*B. abortus, B. canis, B. melitensis, B. suis*), *Brugia* spp., *Burkholderia,* (*Pseudomonas*) *mallei, Burkholderia* (*Pseudomonas*) *pseudomallei, California serogroup, Campylobacter fetus* subsp. *Fetus, Campylobacter jejuni, C. coli, C. fetus* subsp. *Jejuni, Candida albicans, Capnocytophaga* spp., Chikungunya virus, *Chlamydia psittaci, Chlamydia trachomatis, Citrobacter* spp., *Clonorchis sinensis, Clostridium botulinum, Clostridium difficile, Clostridium perfringens, Clostridium tetani, Clostridium* spp. (with the exception of those species listed above), *Coccidioides immitis,* Colorado tick fever virus, *Corynebacterium diphtheriae, Coxiella burnetii,* Coxsackievirus, Creutzfeldt-Jakob agent, Kuru agent, Crimean-Congo hemorrhagic fever virus, *Cryptococcus neoformans, Cryptosporidium parvum*, Cytomegalovirus, *Cyclospora cayatanesis*, Dengue virus (1, 2, 3, 4), Diphtheroids, Eastern (Western) equine encephalitis virus, Ebola virus, *Echinococcus granulosus, Echinococcus multilocularis*, Echovirus, *Edwardsiella tarda, Entamoeba histolytica, Enterobacter* spp., Enterovirus 70, *Epidermophyton floccosum, Ehrlichia* spp, *Ehrlichia sennetsu, Microsporum* spp. *Trichophyton* spp., Epstein-Barr virus, *Escherichia coli*, enterohemorrhagic, *Escherichia coli*, enteroinvasive, *Escherichia coli*, enteropathogenic, *Escherichia coli*, enterotoxigenic, *Fasciola hepatica, Francisella tularensis, Fusobacterium* spp., *Gemella hacmolysans, Giardia lamblia*, Guanarito virus, *Haemophilus duercyi, Haemophilus influenzae* (group b), Hantavirus, Hepatitis A virus, Hepatitis B virus, Hepatitis C virus, Hepatitis D virus, Hepatitis E virus, Herpes simplex virus, Herpesvirus simiae, *Histoplasma capsulatum*, Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila, Leishmania major, Leishmania infantum, Leishmania* spp., *Leptospira interrogans, Listeria monocytogenes*, Lymphocytic choriomeningitis virus, Machupo virus, Marburg virus, Measles virus, *Micrococcus* spp., *Moraxella* spp., *Mycobacterium* spp. (other than *M. bovis, M. tuberculosis, M. avium, M. leprae*), *Mycobacterium tuberculosis, M. bovis, Mycoplasma hominis, M. orale, M. salivarium, M. fermentans, Mycoplasma pneumoniae, Naegleria fowleri, Necator americanus, Neisseria gonorrhoeae, Neisseria meningitides, Neisseria* spp. (other than *N. gonorrhoeae* and *N. meningitidis*), *Nocardia* spp., Norwalk virus, Omsk hemorrhagic fever virus, *Onchocerca volvulus, Opisthorchis* spp., Parvovirus B19, *Pasteurella* spp., *Peptococcus* spp., *Peptostreptococcus* spp., *Plasmodium falciparum, Plasmodium vivax, Plasmodium* spp., *Plesiomonas shigelloides*, Powassan encephalitis virus, *Proteus* spp., *Pseudomonas* spp. (other than *P. mallei, P. pseudomallei*), Rabies virus, Respiratory syncytial virus, Rhinovirus, *Rickettsia akari, Rickettsia prowazekii, R. Canada, Rickettsia rickettsii*, Rift Valley virus, Ross river virus/O'Nyong-Nyong virus, Rubella virus, *Salmonella choleraesuis, Salmonella paratyphi, Salmonella typhi, Salmonella* spp. (with the exception of those species listed above), *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus, Streptobacillus moniliformis, Streptococcus agalactiae, Streptococcus faecalis, Streptococcus pneumoniae, Streptococcus pyogenes, Streptococcus salivarius, Taenia saginata, Taenia solium, Toxocara canis, T. cati, T. cruzi, Toxoplasma gondii, Treponema pallidum, Trichinella* spp., *Trichomonas vaginalis, Trichuris trichiura, Trypanosoma brucei, Trypanosoma cruzi, Ureaplasma urealyticum*, Vaccinia virus, Varicella-zoster virus, eastern equine encephalitis virus (EEEV), severe acute respiratory virus (SARS), Venezuelan equine encephalitis virus (VEEV), Vesicular stomatitis virus, *Vibrio cholerae*, serovar 01, *Vibrio parahaemolyticus*, West Nile virus, *Wuchereria bancrofti*, Yellow fever virus, *Yersinia enterocolitica, Yersinia pseudotuberculosis*, and *Yersinia pestis*.

Examples of infectious agents associated with human malignancies include Epstein-Barr virus, *Helicobacter pylori*, Hepatitis B virus, Hepatitis C virus, Human heresvirus-8, Human immunodeficiency virus, Human papillomavirus, Human T cell leukemia virus, liver flukes, and *Schistosoma* hacmatobium.

A number of viruses are associated with viral hemorrhagic fever, including filoviruses (e.g., Ebola, Marburg, and Reston), arenaviruses (e.g. Lassa, Junin, and Machupo), and bunyaviruses. In addition, phlcboviruses, including, for example, Rift Valley fever virus, have been identified as etiologic agents of viral hemorrhagic fever. Etiological agents of hemorrhagic fever and associated inflammation may also include paramyxoviruses, particularly respiratory syncytial virus (Feldmann, H. et al. (1993) Arch Virol Suppl. 7:81-100). In addition, other viruses causing hemorrhagic fevers in man have been identified as belonging to the following virus groups: togavirus (Chikungunya), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens may include proteins, or variants or fragments thereof, produced by any of the infectious organisms described herein, such as, but not limited to, viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens may also include bacterial surface proteins including pneumococcal PsaA, PspA, LytA, surface or virulence associated proteins of bacterial pathogens such as Nisseria gonnorhea, outer membrane proteins or surface proteases.

Target antigens may also include proteins, or variants or fragments thereof, of infectious agents associated with human malignancies such as the human papillomavirus (HPV) oncoproteins E6 and E7. In certain embodiments, the oncoprotein may be modified to produce a non-oncogenic variant or a variant having reduced oncogenicity relative to the wild type protein. For example, the portion of the peptide that is responsible for binding a tumor suppressor protein (e.g., p53 and pRb) may be deleted or modified so that it no longer interacts with the tumor suppressor protein. As another example, an oncoprotein that is a kinase, such as Her2/neu, may be kinase-inactivated, e.g., by point mutation. In some instances, two or more target antigens may be used during immunization. For example, the E6 and E7 antigens can be combined in a fusion protein, or separate vectors containing heterologous nucleotides encoding the modified or unmodified E6 and E7 target antigens are used in combination. For example, an Ad5-E6 vector can be administered with an Ad5-E7 vector. In this example, the Ad5-E6 vector and Ad5-E7 vector may be administered simultaneously or they may be administered sequentially.

Target antigens of the present invention include but are not limited to antigens derived from a variety of tumor proteins. Illustrative tumor proteins useful in the present invention include, but are not limited to any one or more of, WT1, HPV E6, HPV E7, p53, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, BRCA1, hTERT, hTRT, iCE, MUC1, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mber-abl, ETV6/AML, LDLR/FUT, Pml/RARα, and TEL/AML1. These and other tumor proteins are known to the skilled artisan. In some embodiments, parts or variants of tumor proteins are employed as target antigens. In some embodiments, parts or variants of tumor proteins being employed as target antigens have a modified, for example, increased ability to effect and immune response against the tumor protein or cells containing the same.

In some embodiments, a replication defective adenovirus vector, e.g. the vector identified by SEQ. ID. NO.:3, comprises a sequence encoding a target antigen described herein, or a fragment, a variant, or a variant fragment thereof, at a suitable position on the sequence, for example at a position replacing the nucleic acid sequence encoding a CEA or a variant CEA, e.g. the sequence identified by SEQ. ID. NO.:1.

In certain embodiments tumor antigens may be identified directly from an individual with cancer. In this regard, screens can be carried out using a variety of known technologies. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed and purified using techniques known in the art. This target molecule is then linked to one or more epitopes/cassettes of the present invention as described herein and administered to the cancer patient in order to alter the immune response to the target molecule isolated from the tumor. In this manner, "personalized vaccines" are contemplated within the context of the invention. In certain embodiments, cancers may include carcinomas or sarcomas. In some embodiments, a personalized tumor antigen related to CEA is characterized from a patient and further utilized as the target antigen as a whole, in part or as a variant.

The adenovirus vectors of the present invention may also include nucleic acid sequences that encode proteins that increase the immunogenicity of the target antigen. In this regard, the protein produced following immunization with the adenovirus vector containing such a protein may be a fusion protein comprising the target antigen of interest fused to a protein that increases the immunogenicity of the target antigen of interest.

In one embodiment, such an "immunological fusion partner" is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences are described in U.S. Patent Application 60/158,585 and U.S. Pat. No. 7,009,042, which are herein incorporated by reference in their entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., Infection and Immun. 67:3998-4007 (1999), incorporated herein by reference in their entirety). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One Ra12 fusion polypeptide comprises a 14 KD C-terminal fragment corresponding to amino acid residues 192 to 323 of MTB32A. Other Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within another embodiment, an immunological fusion partner is derived from protein D, a surface protein of the gram-negative bacterium *Haemophilus* influenza B (WO 91/18926). In some cases, a protein D derivative comprises approximately the first third of the protein (e.g., the first N-terminal 100-110 amino acids). A protein D derivative may be lipidated. Within certain embodiments, the first 109 residues of a Lipoprotein D fusion partner is included on the N-terminus to provide the polypeptide with additional exogenous T-cell epitopes, which may increase the expression level in *E. coli* and may function as an expression enhancer. The lipid tail may ensure optimal presentation of the antigen to antigen presenting cells. Other fusion partners include the non-structural protein from influenzae virus, NS1 (hemagglutinin) Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within another embodiment, a repeat portion of LYTA may be incorporated into a fusion polypeptide. A repeat portion can, for example, be found in the C-terminal region starting at residue 178. One particular repeat portion incorporates residues 188-305.

Methods of Use

The adenovirus vectors of the present invention can be used in a number of vaccine settings for generating an immune response against one or more target antigens as described herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

Generally, generating an immune response comprises an induction of a humoral response and/or a cell-mediated response. In certain embodiments, it is desirable to increase an immune response against a target antigen of interest. In certain circumstances, generating an immune response may involve a decrease in the activity and/or number of certain cells of the immune system or a decrease in the level and/or activity of certain cytokines or other effector molecules. As such "generating an immune response" or "inducing an immune response" comprises any statistically significant change, e.g. increase or decrease, in the number of one or more immune cells (T cells, B cells, antigen-presenting cells, dendritic cells, neutrophils, and the like) or in the activity of one or more of these immune cells (CTL activity, HTL activity, cytokine secretion, change in profile of cytokine secretion, etc.).

The skilled artisan would readily appreciate that a number of methods for establishing whether an alteration in the immune response has taken place are available. A variety of methods for detecting alterations in an immune response (e.g. cell numbers, cytokine expression, cell activity) are known in the art and are useful in the context of the instant invention. Illustrative methods are described in Current Protocols in Immunology, Edited by: John E. Coligan, Ada M. Kruisbeek, David H. Margulies, Ethan M. Shevach, Warren Strober (2001 John Wiley & Sons, NY, N.Y.) Ausubel et al. (2001 Current Protocols in Molecular Biology, Greene Publ. Assoc. Inc. & John Wiley & Sons, Inc., NY, N.Y.); Sambrook et al. (1989 Molecular Cloning, Second Ed., Cold Spring Harbor Laboratory, Plainview, N.Y.); Maniatis et al. (1982 Molecular Cloning, Cold Spring Harbor Laboratory, Plainview, N.Y.) and elsewhere.

Illustrative methods useful in this context include intracellular cytokine staining (ICS), ELISpot, proliferation assays, cytotoxic T cell assays including chromium release or equivalent assays, and gene expression analysis using any number of polymerase chain reaction (PCR) or RT-PCR based assays.

In certain embodiments, generating an immune response comprises an increase in target antigen-specific CTL activity of between 1.5 and 5 fold in a subject administered the adenovirus vectors of the invention as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

In a further embodiment, generating an immune response comprises an increase in target antigen-specific HTL activity, such as proliferation of helper T cells, of between 1.5 and 5 fold in a subject administered the adenovirus vectors of the invention that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-gamma (IFN-γ), interleukin-1 (IL-1), IL-2, IL-3, IL-6, IL-7, IL-12, IL-15, tumor necrosis factor-alpha (TNF-α), granulocyte macrophage colony-stimulating factor (GM-CSF), granulocyte-colony stimulating factor (G-CSF), or other cytokine. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

In a further embodiment, generating an immune response comprises an increase in target-specific antibody production of between 1.5 and 5 fold in a subject administered the adenovirus vectors of the present invention as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

Thus the present invention provides methods for generating an immune response against a target antigen of interest comprising administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In certain embodiments, the present invention provides methods wherein the vector administered is not a gutted vector. In particular embodiments, the target antigen may be a wild-type protein, a fragment, a variant, or a variant fragment thereof. In some embodiments, the target antigen comprises CEA, a fragment, a variant, or a variant fragment thereof.

In a further embodiment, the present invention provides methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, a fragment, a variant, or a variant fragment thereof. In some embodiments, the target antigen comprises CEA, a fragment, a variant, or a variant fragment thereof.

With regard to preexisting immunity to Ad, this can be determined using methods known in the art, such as antibody-based assays to test for the presence of Ad antibodies. Further, in certain embodiments, the methods of the present invention include first determining that an individual has preexisting immunity to Ad then administering the E2b deleted adenovirus vectors of the invention as described herein.

One embodiment of the invention provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, a fragment, a variant, or a variant fragment thereof. In some embodiments, the target antigen comprises CEA, a fragment, a variant, or a variant fragment thereof.

Thus, the present invention contemplates multiple immunizations with the same E2b deleted adenovirus vector or multiple immunizations with different E2b deleted adenovirus vectors. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen. In some embodiments, the target antigen comprises CEA, a fragment, a variant, or a variant fragment thereof.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially. In some embodiments, the target antigen comprises CEA, a fragment, a variant, or a variant fragment thereof.

As would be readily understood by the skilled artisan, more than two adenovirus vectors may be used in the methods of the present invention. Three, 4, 5, 6, 7, 8, 9, 10 or more different adenovirus vectors may be used in the methods of the invention. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more target antigens. In some embodiments, the one or more target antigen comprises CEA, a fragment, a variant, or a variant fragment thereof.

The present invention provides methods of generating an immune response against any target antigen, such as those described elsewhere herein.

In certain embodiments, the adenovirus vectors are used to generate an immune response against a cancer. In this regard, the methods include generating an immune response against carcinomas or sarcomas such as solid tumors, lymphomas or leukemias. Thus, the adenovirus vectors described herein are used to generate an immune response against a cancer including but not limited to carcinomas or sarcomas such as neurologic cancers, melanoma, non-Hodgkin's lymphoma, Hodgkin's disease, leukemias, plasmocytomas, adenomas, gliomas, thymomas, breast cancer, prostate cancer, colo-rectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers. In some embodiments, the target antigen comprises CEA, a fragment, a variant, or a variant fragment thereof.

Further, in this regard, the cancer target antigens may include but are not limited to antigens derived from a variety of tumor proteins. Illustrative tumor proteins useful in the present invention include, but are not limited to any one or more of, p53, HPV E6, HPV E7, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PSA, PSM, Tyrosinase, TRP-1, TRP-2, ART-4, CAMEL, CEA, Cyp-B, Her2/neu, hTERT, hTRT, iCE, MUC1, MUC2, PRAME, P15, RU1, RU2, SART-1, SART-3, WT1, AFP, β-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mber-abl, ETV6/AML, LDLR/FUT, Pml/RARα, and TEL/AML1. These and other tumor proteins are known to the skilled artisan. In particular embodiments, the target antigen may be one of these and other tumor proteins, a fragment, a variant, or a variant fragment thereof.

Methods are also provided for treating or ameliorating the symptoms of any of the infectious diseases or cancers as described herein. The methods of treatment comprise administering the adenovirus vectors one or more times to individuals suffering from or at risk from suffering from an infectious disease or cancer as described herein. As such, the present invention provides methods for vaccinating against infectious diseases or cancers in individuals who are at risk of developing such a disease. Individuals at risk may be individuals who may be exposed to an infectious agent at some time or have been previously exposed but do not yet have symptoms of infection or individuals having a genetic predisposition to developing a cancer or being particularly susceptible to an infectious agent. Individuals suffering from an infectious disease or cancer described herein may be determined to express and/or present a target antigen, which may be use to guide the therapies herein. For example, an example can be found to express and/or present a target antigen and an adenovirus vector encoding the target antigen, a variant, a fragment or a variant fragment thereof may be administered subsequently.

The present invention contemplates the use of adenovirus vectors for the in vivo delivery of nucleic acids encoding a target antigen, or a fragment, a variant, or a variant fragment thereof. Once injected into a subject, the nucleic acid sequence is expressed resulting in an immune response against the antigen encoded by the sequence. The adenovirus vector vaccine is administered in an "effective amount", that is, an amount of adenovirus vector that is effective in a selected route or routes of administration to elicit an immune response as described elsewhere herein. In certain embodiments, an effective amount is one that induces an immune response effective to facilitate protection or treatment of the host against the target infectious agent or cancer. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

The adenovirus vectors of the invention are generally prepared as known in the art (see e.g., Hodges et al., 2000 supra; or Amalfitano et al., 1998 supra). For example, in certain embodiments, tissue culture plates containing E.C7 or C-7 cells are infected with the adenovirus vector virus stocks at an appropriate MOI (e.g., 5) and incubated at 37° C. for 40 h. The infected cells are harvested, resuspended in an appropriate buffer such as 10 mM Tris-Cl (pH 8.0), and sonicated, and the virus is purified by two rounds of cesium chloride density centrifugation. In certain techniques, the virus containing band is desalted over a Sephadex CL-6B column (Pharmacia Biotech, Piscataway, N.J.), glycerol is added to a concentration of 12%, and aliquots are stored at −80° C. The titer of the stock is measured (e.g. by measurement of the optical density at 260 nm of an aliquot of the virus after SDS lysis). GMP procedures for producing appropriate Ad stocks for human administration are used where appropriate.

For administration, the adenovirus vector stock is combined with an appropriate buffer, physiologically acceptable carrier, excipient or the like. In certain embodiments, an appropriate number of adenovirus vector particles are administered in an appropriate buffer, such as, sterile PBS. In certain circumstances it will be desirable to deliver the adenovirus vector compositions disclosed herein subcutaneously, parenterally, intravenously, intramuscularly, or even intraperitoneally. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. In other embodiments, E2b deleted adenovirus vectors may be delivered in pill form, delivered by swallowing or by suppository.

Illustrative pharmaceutical forms suitable for injectable use include sterile aqueous solutions or dispersions and sterile powders for the extemporaneous preparation of sterile injectable solutions or dispersions, for example, see U.S. Pat. No. 5,466,468, which is herein incorporated by reference in its entirety. Fluid forms to the extent that easy syringability exists may be preferred. Forms that are stable under the conditions of manufacture and storage are within the bounds of this invention. In various embodiments, forms are preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (sec for example, "Remington's Pharmaceutical Sciences" 15th Edition, pages 1035-1038 and 1570-1580, which is herein incorporated by reference in its entirety). Some variation in dosage will necessarily occur depending on the condition of the subject being treated. Moreover, for human administration, preparations will preferably meet sterility, pyrogenicity, and the general safety and purity standards as required by FDA Office of Biologics standards.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" relates to molecular entities and compositions that do not produce an allergic or similar untoward reaction when administered to a human.

In certain embodiments, the adenovirus vectors of the invention may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, IFN-γ, TNFα, IL-2, IL-8, IL-12, IL-18, IL-7, IL-3, IL-4, IL-5, IL-6, IL-9, IL-10, and/or IL-13, and others, like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient may support an immune response that includes Th1- and/or Th2-type responses. Within certain embodiments, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989. Thus, various embodiments of the invention relate to therapies raising an immune response against a target antigen, for example CEA, using cytokines, e.g. IFN-γ, TNFα IL-2, IL-8, IL-12, IL-18, IL-7, IL-3, IL-4, IL-5, IL-6, IL-9, IL-10, and/or IL-13 supplied concurrently with a replication defective adenovirus vector treatment. In some embodiments, a cytokine or a nucleic acid encoding a cytokine, is administered together with a replication defective adenovirus described herein. In some embodiments, cytokine administration is performed prior or subsequent to adenovirus vector administration. In some embodiments, a replication defective adenovirus vector capable of raising an immune response against a target antigen, for example CEA, further comprises a sequence encoding a cytokine.

Certain illustrative adjuvants for eliciting a predominantly Th1-type response include, for example, a combination of monophosphoryl lipid A, preferably 3-de-O-acylated monophosphoryl lipid A, together with an aluminum salt. MPL® adjuvants are available from GlaxoSmithKlein (Research Triangle Park, N.C.; see, for example, U.S. Pat. Nos. 4,436,727; 4,877,611; 4,866,034 and 4,912,094, each incorporated herein by reference in its entirety). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462, each incorporated herein by reference in its entirety. Immunostimulatory DNA sequences are also described, for example, by Sato et al., Science 273:352, 1996. Another adjuvant for use in the present invention comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other formulations may include more than one saponin in the adjuvant combinations of the present invention, for example combinations of at least two of the following group comprising QS21, QS7, Quil A, β-escin, or digitonin.

In certain embodiments, the compositions may be delivered by intranasal sprays, inhalation, and/or other aerosol delivery vehicles. The delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871, incorporated herein by reference in its entirety) are well-known in the pharmaceutical arts. Likewise, illustrative transmucosal drug delivery in the form of a polytetrafluoroetheylene support matrix is described in U.S. Pat. No. 5,780,045, incorporated herein by reference in its entirety.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like.

Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit. Rev Ther Drug Carrier Syst. 1995; 12(2-3):233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol. Chem. 1990 Sep. 25; 265(27):16337-42; Muller et al., DNA Cell Biol. 1990 April; 9(3):221-9). Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28, incorporated herein by reference in its entirety). To avoid side effects due to intracellular polymeric overloading, such ultrafine particles (sized around 0.1 µm) may be designed using polymers able to be degraded in vivo. Such particles can be made as described, for example, by Couvreur et al., Crit. Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684, each incorporated herein by reference in its entirety.

Routes and frequency of administration of the therapeutic compositions described herein, as well as dosage, may vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g. swallowing, suppository for vaginal or rectal delivery). In certain embodiments, between 1 and 10 doses may be administered over a 52 week period. In certain embodiments, 6 doses are administered, at intervals of 1 month, and further booster vaccinations may be given periodically thereafter. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95 or 100 week periods. Doses may be administered at 1, 2, 3, 4, 5, or 6 week intervals or longer intervals.

A suitable dose is an amount of an adenovirus vector that, when administered as described above, is capable of promoting a target antigen immune response as described elsewhere herein. In certain embodiments, the immune response is at least 10-50% above the basal (i.e., untreated) level. In certain embodiments, the immune response is at least 2, 3, 4, 5, 6, 7, 8, 9, 10, 12, 15, 20, 25, 30, 35, 40, 45, 50, 55, 60, 65, 70, 75, 80, 85, 90, 100, 110, 125, 150, 200, 250, 300, 400, 500 or more over the basal level. Such response can be monitored by measuring the target antigen(s) antibodies in a patient or by vaccine-dependent generation of cytolytic effector cells capable of killing patient tumor or infected cells in vitro, or other methods known in the art for monitoring immune responses. Such vaccines should also be capable of causing an immune response that leads to an improved clinical outcome of the disease in question in vaccinated patients as compared to non-vaccinated patients. In some embodiments, the improved clinical outcome comprises treating disease, reducing the symptoms of a disease, changing the progression of a disease, or extending life.

In general, an appropriate dosage and treatment regimen provides the adenovirus vectors in an amount sufficient to provide therapeutic and/or prophylactic benefit. Such a response can be monitored by establishing an improved clinical outcome for the particular disease being treated in treated patients as compared to non-treated patients. The monitoring data can be evaluated over time. In some embodiments, the progression of a disease over time is altered. Such improvements in clinical outcome would be readily recognized by a treating physician. Increases in preexisting immune responses to a target protein can generally correlate with an improved clinical outcome. Such immune responses may generally be evaluated using standard proliferation, cytotoxicity or cytokine assays, which may be performed using samples obtained from a patient before and after treatment.

While one advantage of the present invention is the capability to administer multiple vaccinations with the same or different adenovirus vectors, particularly in individuals with preexisting immunity to Ad, the adenoviral vaccines of this invention may also be administered as part of a prime and boost regimen. A mixed modality priming and booster inoculation scheme may result in an enhanced immune response. Thus, one aspect of this invention is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-4, may be employed, although more may be used. The length of time between priming and boost may typically vary from about four months to a year, but other time frames may be used. In certain embodiments, subjects may be primed 1, 2, 3, 4, 5, 6, 7, 8, 9, 10, or more times with plasmid vaccines, and then boosted 4 months later with the adenovirus vector.

Patient Selection

Various embodiments of the invention relate to compositions and methods for raising an immune response against one or more CEA antigens in selected patient populations. Accordingly, methods and compositions of the invention may target patients with a cancer including but not limited to carcinomas or sarcomas such as neurologic cancers, melanoma, non-Hodgkin's lymphoma, Hodgkin's disease, leukemias, plasmocytomas, adenomas, gliomas, thymomas, breast cancer, prostate cancer, colo-rectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers can be targeted for therapy. In some cases, the targeted patient population may be limited to individuals having colorectal adenocarcinoma, metastatic colorectal cancer, advanced CEA expressing colorectal cancer breast cancer, lung cancer, bladder cancer, or pancreas cancer. A histologically confirmed diagnosis of a selected cancer, for example colorectal adenocarcinoma, may be used. A particular disease stage or progression may be selected, for example, patients with one or more of a metastatic, recurrent, stage III, or stage IV cancer may be selected for therapy with the methods and compositions of the invention. In some embodiments, patients may be required to have received and, optionally, progressed through other therapies including but not limited to fluoropyrimidine, irinotccan, oxaliplatin, bevacizumab, cetuximab, or panitumumab containing therapies. In some cases, individual's refusal to accept such therapies may allow the patient to be included in a therapy eligible pool with methods and compositions of the invention. In some embodiments, individuals to receive therapy using the methods and compositions of the invention may be required to have an estimated life expectancy of at least, 1, 2, 3, 4, 5, 6, 7, 8, 9, 10, 11, 12, 14, 15, 18, 21, or 24 months. The patient pool to receive a therapy using the methods and compositions of the invention may be limited by age. For example, individuals who are older than 2, 3, 4, 5, 6, 7, 8, 9, 10, 11, 12, 13, 14, 15, 16, 17, 18, 19, 20, 21, 25, 30, 35, 40, 50, 60, or more years old can be eligible for therapy with methods and compositions of the invention. For another example, individuals who are younger than 75, 70, 65, 60, 55, 50, 40, 35, 30, 25, 20, or fewer years old can be eligible for therapy with methods and compositions of the invention.

In some embodiments, patients receiving therapy using the methods and compositions of the invention are limited to individuals with adequate hematologic function, for example with one or more of a WBC count of at least 1000, 1500, 2000, 2500, 3000, 3500, 4000, 4500, 5000 or more per microliter, a hemoglobin level of at least 5, 6, 7, 8, 9, 10, 11, 12, 13, 14 or higher g/dL, a platelet count of at least 50,000; 60,000; 70,000; 75,000; 90,000; 100,000; 110,000; 120,000; 130,000; 140,000; 150,000 or more per microliter; with a PT-INR value of less than or equal to 0.8, 1.0, 1.2, 1.3, 1.4, 1.5, 1.6, 1.8, 2.0, 2.5, 3.0, or higher, a PTT value of less than or equal to 1.2, 1.4, 1.5, 1.6, 1.8, 2.0×ULN or more. In various embodiments, hematologic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, patients receiving therapy using the methods and compositions of the invention are limited to individuals with adequate renal and/or hepatic function, for example with one or more of a serum creatinine level of less than or equal to 0.8, 0.9, 1.0, 1.1, 1.2, 1.3, 1.4, 1.5, 1.6, 1.7, 1.8, 1.9, 2.0, 2.1, 2.2 mg/dL or more, a bilirubin level of 0.8, 0.9, 1.0, 1.1, 1.2, 1.3, 1.4, 1.5, 1.6, 1.7, 1.8, 1.9, 2.0, 2.1, 2.2 mg/dL or more, while allowing a higher limit for Gilbert's syndrome, for example, less than or equal to 1.5, 1.6, 1.8, 1.9, 2.0, 2.1, 2.2, 2.3, or 2.4 mg/dL, an ALT and AST value of less than or equal to less than or equal to 1.5, 2.0, 2.5, 3.0×upper limit of normal (ULN) or more. In various embodiments, renal or hepatic function indicator limits are chosen differently for individuals in different gender and age groups, for example 0-5, 5-10, 10-15, 15-18, 18-21, 21-30, 30-40, 40-50, 50-60, 60-70, 70-80 or older than 80.

In some embodiments, the K-ras mutation status of individuals who are candidates for a therapy using the methods and compositions of the invention can be determined. Individuals with a preselected K-ras mutational status can be included in an eligible patient pool for therapies using the methods and compositions of the invention.

In various embodiments, patients receiving therapy using the methods and compositions of the invention are limited to individuals without concurrent cytotoxic chemotherapy or radiation therapy, a history of, or current, brain metastases, a history of autoimmune disease, such as but not restricted to, inflammatory bowel disease, systemic lupus erythematosus, ankylosing spondylitis, scleroderma, multiple sclerosis, thyroid disease and vitiligo, serious intercurrent chronic or acute illness, such as cardiac disease (NYHA class III or IV), or hepatic disease, a medical or psychological impediment to probable compliance with the protocol, concurrent (or within the last 5 years) second malignancy other than non-melanoma skin cancer, cervical carcinoma in situ, controlled superficial bladder cancer, or other carcinoma in situ that has been treated, an active acute or chronic infection including: a urinary tract infection, HIV (e.g. as determined by ELISA and confirmed by Western Blot), and chronic hepatitis, or concurrent steroid therapy (or other immunosuppressives, such as azathioprine or cyclosporin A). In some cases, patients with at least 3, 4, 5, 6, 7, 8, 9, or 10 weeks of discontinuation of any steroid therapy (except that used as pre-medication for chemotherapy or contrast-enhanced studies) may be included in a pool of eligible individuals for therapy using the methods and compositions of the invention.

In some embodiments, patients receiving therapy using the methods and compositions of the invention include individuals with thyroid disease and vitiligo.

Pre-Treatment Evaluation

In various embodiments, samples, for example serum or urine samples, from the individuals or candidate individuals for a therapy using the methods and compositions of the invention may be collected. Samples may be collected before, during, and/or after the therapy for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer. The samples may be tested for any of the hematologic, renal, or hepatic function indicators described herein as well as suitable others known in the art, for example a B-HCG for women with childbearing potential. In that regard, hematologic and biochemical tests, including cell blood counts with differential, PT, INR and PTT, tests measuring Na, K, Cl, $CO_2$, BUN, creatinine, Ca, total protein, albumin, total bilirubin, alkaline phosphatase, AST, ALT and glucose are within the bounds of the invention. In some embodiments, the presence or the amount of HIV antibody, Hepatitis BsAg, or Hepatitis C antibody are determined in a sample from individuals or candidate individuals for a therapy using the methods and compositions of the invention. Biological markers, such as antibodies to CEA or the neutralizing antibodies to Ad5 vector can be tested in a sample, such as serum, from individuals or candidate individuals for a therapy using the methods and compositions of the invention. In some cases, one or more samples, such as a blood sample can be collected and archived from an individuals or candidate individuals for a therapy using the methods and compositions of the invention. Collected samples can be assayed for immunologic evaluation. Individuals or candidate individuals for a therapy using the methods and compositions of the invention can be evaluated in imaging studies, for example using CT scans or MRI of the chest, abdomen, or pelvis. Imaging studies can be performed before, during, or after therapy using the methods and compositions of the invention, during, and/or after the therapy, for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years or longer.

Treatment Plans

Dosage and Administration

Compositions and methods of the invention contemplate various dosage and administration regimens during therapy. Patients may receive a replication defective adenovirus or adenovirus vector, for example Ad5 [E1-, E2B-]-CEA(6D), that is capable of raising an immune response in an individual against a target antigen described herein, for example CEA. In various embodiments, the replication defective adenovirus is administered at a dose that suitable for effecting such immune response. In some cases, the replication defective adenovirus is administered at a dose that is greater than or equal to $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, or more virus particles (VP) per immunization. In some cases, the replication defective adenovirus is administered at a dose that is less than or equal to $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, or more virus particles per immunization. In various embodiments, a desired dose described herein is administered in a suitable volume of formulation buffer, for example a volume of about 0.1-10 ml, 0.2-8 ml, 0.3-7 ml, 0.4-6 ml, 0.5-5 ml, 0.6-4 ml, 0.7-3 ml, 0.8-2 ml, 0.9-1.5 ml, 0.95-1.2 ml, 1.0-1.1 ml. Those of skill in the art appreciate that the volume may fall within any range bounded by any of these values (e.g., about 0.5 ml to about 1.1 ml. The administration of the virus particles can be through a variety of suitable paths for delivery, for example it can be by injection (e.g., intracutaneous, intramuscular, intravenous or subcutaneous), intranasally (e.g., by aspiration), in pill form (e.g. swallowing, suppository for vaginal or rectal delivery. In some embodiments, a subcutaneous delivery may be preferred and can offer greater access to dendritic cells.

The administration of the virus particles to an individual may be repeated. The repeated deliveries of virus particles may follow a schedule or alternatively, may be performed on an as needed basis. For example, the individual's immunity against a target antigen, for example CEA, may be tested and replenished as necessary with additional deliveries. In some embodiments, schedules for delivery include administrations of virus particles at regular intervals. Joint delivery regimens may be designed comprising one or more of a period with a schedule and/or a period of need based administration assessed prior to administration. For example, a therapy regimen may include an administration, for example subcutaneous administration once every three weeks then another immunotherapy treatment every three months until removed from therapy for any reason including death. Another example regimen comprises three administrations every three weeks then another set of three immunotherapy treatments every three months. Another example regimen comprises a first period with a first number of administrations at a first frequency, a second period with a second number of administrations at a second frequency, a third period with a third number of administrations at a third frequency etc. and optionally one or more periods with undetermined number of administrations on an as needed basis. The number of administrations in each period can be independently selected and can for example be 1, 2, 3, 4, 5, 6, 7, 8, 9, 10, 11, 12, 13, 14, 15, 16, 17, 18, 19, 20 or more. The frequency of the administration in each period can also be independently selected, can for example be about every day, every other day, every third day, twice a week, once a week, once every other week, every three weeks, every month, every six weeks, every other month, every third month, every fourth month, every fifth month, every sixth month, once a year etc. The therapy can take a total period of up to 1, 2, 3, 4, 5, 6, 7, 8, 9, 10, 11, 12, 13, 14, 15, 16, 17, 18, 19, 20, 21, 22, 23, 24, 30, 36 months or more. The scheduled interval between immunizations may be modified so that the interval between immunizations is revised by up to a fifth, a fourth, a third, or half of the interval. For example, for a 3-week interval schedule, an immunization may be repeated between 20 and 28 days (3 weeks −1 day to 3 weeks +7 days). For the first 3 immunizations, if the second and/or third immunization is delayed, the subsequent immunizations may be shifted allowing a minimum amount of buffer between immunizations. For example, for a three week interval schedule, if an immunization is delayed, the subsequent immunization may be scheduled to occur no earlier than 17, 18, 19, or 20 days after the previous immunization.

Compositions of the invention, such as Ad5 [E1-, E2b-]-CEA(6D) virus particles, can be provided in various states, for example, at room temperature, on ice, or frozen. Compositions may be provided in a container of a suitable size, for example a vial of 2 ml vial. In one embodiment, 1 2 ml vial with 1.0 ml of extractable vaccine contains $5 \times 10^{11}$ total virus particles/mL. Storage conditions including temperature and humidity may vary. For example, compositions for use in therapy may be stored at room temperature, 4° C.−20° C. or lower until used.

General Evaluations

In various embodiments, general evaluations are performed on the individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

General evaluations may include one or more of medical history, ECOG Performance Score, Karnofsky performance status, and complete physical examination with weight by the attending physician. Any other treatments, medications, biologics, or blood products that the patient is receiving or has received since the last visit may be recorded. Patients may be followed at the clinic for a suitable period, for example approximately 30 minutes, following receipt of vaccine to monitor for any adverse reactions. Local and systemic reactogenicity after each dose of vaccine will may be assessed daily for a selected time, for example for 3 days (on the day of immunization and 2 days thereafter). Diary cards may be used to report symptoms and a ruler may be used to measure local reactogenicity. Immunization injection sites may be assessed. CT scans or MRI of the chest, abdomen, and pelvis may be performed.

Hematological and Biochemical Assessment

In various embodiments, hematological and biochemical evaluations are performed on the individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Hematological and biochemical evaluations may include one or more of blood test for chemistry and hematology, CBC with differential, Na, K, Cl, $CO_2$, BUN, creatinine, Ca, total protein, albumin, total bilirubin, alkaline phosphatase, AST, ALT, glucose, and ANA.

Biological Markers

In various embodiments, biological markers are evaluated on individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Biological marker evaluations may include one or more of measuring antibodies to CEA or the Ad5 vector, from a serum sample of adequate volume, for example about 5 ml Biomarkers (e.g., CEA or CA15-3) may be reviewed if determined and available Immunological Assessment In various embodiments, an immunological assessment is performed on individuals receiving treatment according to the methods and compositions of the invention. One or more of any tests may be performed as needed or in a scheduled basis, such as on weeks 0, 3, 6 etc. A different set of tests may be performed concurrent with immunization vs. at time points without immunization.

Peripheral blood, for example about 90 mL may be drawn prior to each immunization and at a time after at least some of the immunizations, to determine whether there is an effect on the immune response at specific time points during the study and/or after a specific number of immunizations. Immunological assessment may include one or more of assaying peripheral blood mononuclear cells (PBMC) for T cell responses to CEA using ELISpot, proliferation assays, multi-parameter flow cytometric analysis, and cytoxicity assays. Serum from each blood draw may be archived and sent and determined.

Tumor Assessment

In various embodiments, a tumor assessment is performed on individuals receiving treatment according to the methods and compositions of the invention. One or more of any tests may be performed as needed or in a scheduled basis, such as prior to treatment, on weeks 0, 3, 6 etc. A different set of tests may be performed concurrent with immunization vs. at time points without immunization.

Tumor assessment may include one or more of CT or MRI scans of chest, abdomen, or pelvis performed prior to treatment, at a time after at least some of the immunizations and at approximately every three months following the completion of a selected number, for example 2, 3, or 4, of first treatments and for example until removal from treatment.

Rate of Immune Response

Immune responses against a target antigen described herein, such as CEA, may be evaluated from a sample, such as a peripheral blood sample of an individual using one or more suitable tests for immune response, such as ELISpot, cytokine flow cytometry, or antibody response. A positive immune response by ELISpot is described at the 2002 Society of Biologic Therapy Workshop on "Immunologic Monitoring of Cancer Vaccine Therapy", i.e. a T cell response is considered positive if the mean number of spots adjusted for background in six wells with antigen exceeds the number of spots in six control wells by 10 and the difference between single values of the six wells containing antigen and the six control wells is statistically significant at a level of $p \leq 0.05$ using the Student's t test. Immunogenicity assays may occur prior to each immunization and at scheduled timepoints during the period of the treatment. For example, a timepoint for an immunugenecity assay at around week 1, 2, 3, 4, 5, 6, 7, 8, 9, 10, 11, 12, 13, 14, 15, 18, 20, 24, 30, 36, or 48 of a treatment may be scheduled even without a scheduled immunization at this time. In some cases, an individual may be considered evaluable for immune response if they receive at least a minimum number of immunizations, for example 1, 2, 3, 4, 5, 6, 7, 8, 9, or more immunizations.

Determination of Clinical Response

In some embodiments, disease progression or clinical response determination is made according to the RECIST 1.1 criteria among patients with measurable/evaluable disease.

In some embodiments, therapies using the methods and compositions of the invention affect a Complete Response (CR; disappearance of all target lesions for target lesions or disappearance of all non-target lesions and normalization of tumor marker level for non-target lesions) in an individual receiving the therapy.

In some embodiments, therapies using the methods and compositions of the invention affect a Partial Response (PR; at least a 30% decrease in the sum of the LD of target lesions, taking as reference the baseline sum LD for target lesions) in an individual receiving the therapy.

In some embodiments, therapies using the methods and compositions of the invention affect a Stable Disease (SD; neither sufficient shrinkage to qualify for PR nor sufficient increase to qualify for PD, taking as reference the smallest sum LD since the treatment started for target lesions) in an individual receiving the therapy.

In some embodiments, therapies using the methods and compositions of the invention affect an Incomplete Response/Stable Disease (SD; persistence of one or more non-target lesion(s) or/and maintenance of tumor marker level above the normal limits for non-target lesions) in an individual receiving the therapy.

In some embodiments, therapies using the methods and compositions of the invention affect a Progressive Disease (PD; at least a 20% increase in the sum of the LD of target lesions, taking as reference the smallest sum LD recorded since the treatment started or the appearance of one or more new lesions for target lesions or persistence of one or more non-target lesion(s) or/and maintenance of tumor marker level above the normal limits for non-target lesions) in an individual receiving the therapy.

EXAMPLES

Example 1: Multiple Injections of Ad5Null Adenovirus Vector Produces Anti-Adenovirus Antibodies This example shows that multiple injections of Ad5-null results in the production of anti-adenovirus antibodies in the injected subjects It was demonstrated that the Ad5Null adenovirus vector that does not contain any heterologous nucleic acid sequences, generates a neutralizing immune response in mice. In particular, in one experiment, female Balb/c mice aged 5-7 weeks were immunized with Ad5Null viral particles at 14 day intervals. To determine the presence of anti-adenovirus antibodies, an enzyme linked immunosorbent assay (ELISA) was used. For this ELISA, $10^9$ viral particles were coated onto microtiter wells in 100 μL of 0.05M carbonate/bicarbonate buffer, pH 9.6, and incubated overnight at room temperature. For a standard immunoglobulin G (IgG) reference curve, 200 ng, 100 ng, 50 ng, 25 ng, and 0 ng of purified mouse IgG (Sigma Chemicals) were coated onto microtiter wells as described above. After incubation, all wells were washed 3 times with 250 μL of 1% bovine serum albumin (BSA) in phosphate buffered saline (PBS), pH 7.4. After washing, 250 μL of BSA/PBS was added to all and incubated for 30 minutes at room temperature to block unbound sites. After incubation, all wells were washed 3 times with 250 μL of BSA/PBS. After washing, 200 μL of a 1/100 serum dilution in BSA/PBS was added to wells and incubated for 1 hour at room temperature. For a positive control, 200 μL of a 1/10000 dilution of anti-adenovirus antiserum (Biodesign International) in BSA/PBS were added to wells. Control wells contained BSA/PBS only. After incubation, all wells were washed 3 times with 250 μL of BSA/PBS. After washing, 200 μL of a 1/10000 dilution of peroxidase conjugated gamma chain specific goat anti-mouse IgG (Sigma Chemicals) in BSA/PBS were added to each well and incubated for 1 hour at room temperature. After incubation, all wells were washed 3 times with 250 μL of BSA/PBS. After washing, 200 .mu.L of developing reagent (0.5 mg/mL 1,2 phenylenediamine in 0.2M potassium phosphate buffer, pH 5.0, containing 0.06% hydrogen peroxide) was added to each well and incubated for 30-40 minutes at room temperature. After incubation, the color reaction was stopped by addition of 50 .mu.L 5N HCl to each well. All wells were then read in a microwell plate reader at 492 nm. After readings were obtained, the optical density readings of unknown samples were correlated with the standard IgG curve to obtain the nanograms of IgG bound per well. This was performed using the INSTAT statistical package.

As shown in FIG. 1, significant levels (P<0.001) of anti-adenovirus IgG antibody were detected in mice 2 weeks after a first injection with $10^{10}$ Ad-5-null. A significantly higher level (P<0.001) was observed 2 weeks after a second injection with $10^{10}$ adenovirus. Significantly higher (P<0.001) levels of antibody were continued to be observed 2 weeks after a third injection with $10^{10}$ Ad5-null. Each value represents the average of triplicate determinations from pooled sera of 5 mice in each group. These results indicate that multiple injections of Ad5-null results in the production of anti-adenovirus antibodies in the injected subjects.

To determine the presence of neutralizing antibody to Ad, the following assay was utilized. A HEK-293T cell line was cultured in 200 .mu.L of culture medium consisting of DMEM containing 10% fetal calf serum (DMEM/FCS) in microwell tissue culture plates at a cell concentration of $2 \times 10^3$ cells per well for 24 hours at 37 C in 5% $CO_2$. After incubation, 100 .mu.L of culture medium was removed from triplicate wells and mixed with 20 .mu.L of DMEM/FCS containing viral particles (VP). After mixing, the 120 .mu.L mixture was added back to the respective microwells. In another set of triplicate wells, 100 .mu.L of culture medium was removed and mixed with 20 .mu.L of heat inactivated (56 C for 1 hour) Ad immune mouse serum previously incubated with VP for one hour at room temperature. After mixing, the 120 .mu.L mixture was added back to the respective wells. In triplicate cell control wells, 20 .mu.L of DMEM/FCS was added to control for total culture medium volume. Triplicate medium only control wells contained 220 .mu.L of DMEM/FCS. The tissue culture plate was incubated for an additional 3 days at 37 C in 5% $CO_2$. After incubation, 40 .mu.L of PROMEGA cell viability reagent (Owen's reagent) was added to all wells and incubated for 75 minutes at 37 C in 5% $CO_2$. In this assay, the Owen's reagent (MTS tetrazolium compound) is bioreduced by viable cells into a colored formazan product that is soluble in tissue culture medium. The quantity of formazan product as measured by absorbance at 490 nm is directly proportional to the number of living cells in culture. After incubation, 150 .mu.L was removed from each well and transferred to another microwell plate for optical density readings. Optical density readings at 492 nm were subsequently obtained using a microwell plate reader.

Figure 2:
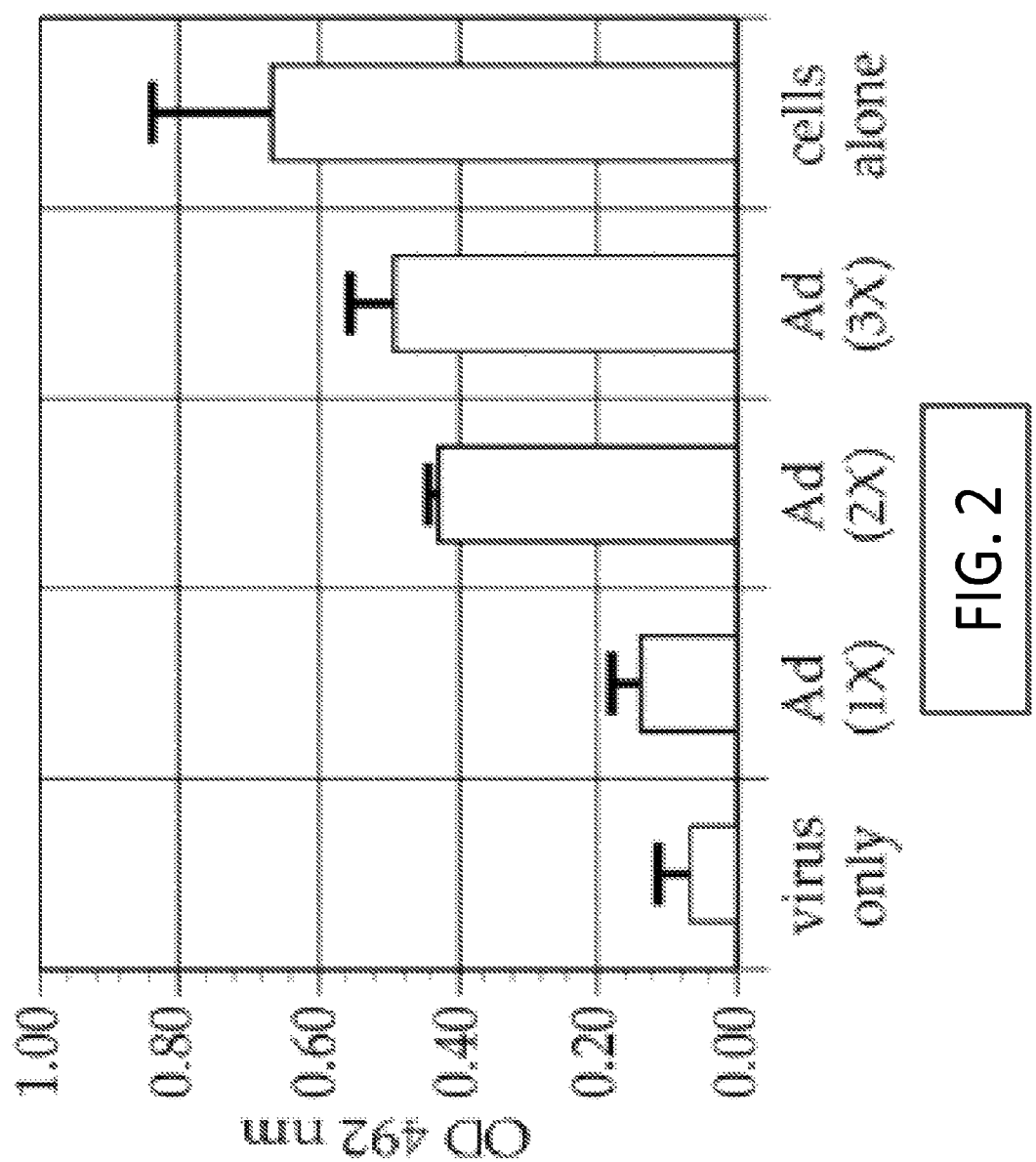
FIG. 2 is a bar graph showing neutralizing antibody levels from mice immunized with Ad5Null. Mice were immunized three times with Ad5Null viral particles at 14 day intervals. Note the presence of increasing neutralizing antibodies after each immunization. Optical density readings indicate the presence of viable target cells.

In an experiment to detect the presence of neutralizing antibodies to Ad, groups of 5 mice each were injected once, twice, or three times with $10^{10}$ Ad5null at two week intervals. Two weeks after the final injection of virus, mice were bled, pooled, and assessed for neutralizing antibody as described above using $4 \times 10^7$ VP incubated with or without heat inactivated sera. Cells cultured alone served as a control group. As shown in FIG. 2, normal mice and mice injected one time with Ad5null did not exhibit significant levels of neutralizing antibody. Mice injected two times with Ad exhibited significant ($P<0.05$) levels of neutralizing antibody as compared with cells incubated with virus only. Mice injected three times with Ads-null also exhibited significant ($P<0.01$) levels of neutralizing antibody as compared with cells incubated with virus only.

Example 2: The Ad5 [E1-]-CEA Vector Vaccine Induces CEA Specific Immune Response Upon Re-Immunization in Ad5 Immune Mice This example shows that the Ad5 [E1-, E2b-] vector platform induces CMI responses against the tumor associated antigen (TAA) carcinoembryonic antigen (CEA) in the presence of pre-existing Ad5 immunity in mice.

Characterization of Ad5 CEA Vectors

Initial studies were performed to confirm CEA gene expression of two Ad5-CEA vector platforms. It was first determined that the CEA antigen could be expressed on cells transfected with the vaccine vector platforms. A549 cells were obtained from ATCC and transfected with Ad5 [E1-]-CEA or Ad5 [E1-, E2b-]-CEA. Western blot analysis revealed that cells transfected with the vector platforms expressed CEA antigen.

Induction of Ad5 Immunity in Mice

Figure 3:
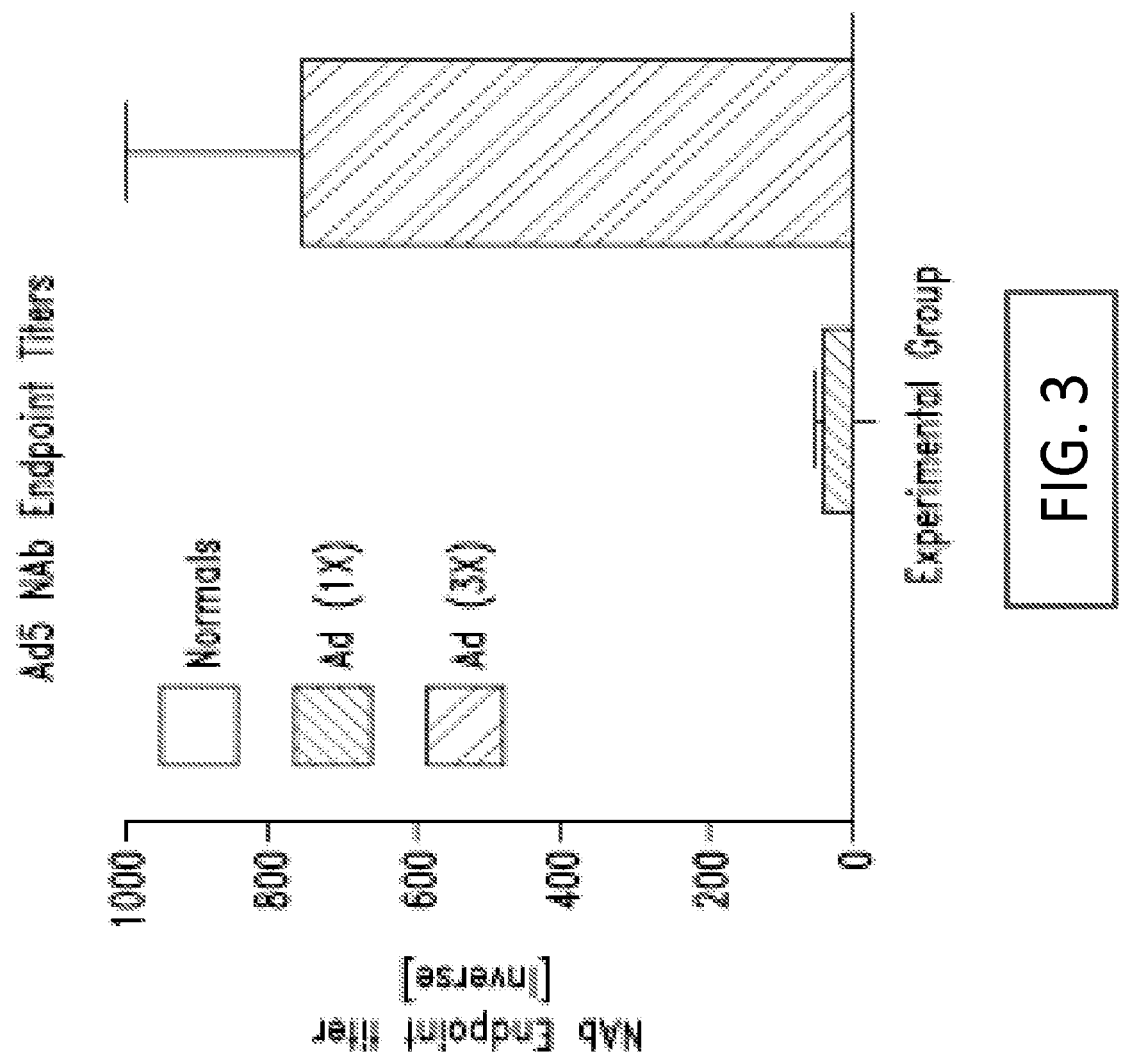
FIG. 3 is a bar graph showing the induction of NAb in C57Bl/6 mice after injections with Ad5-Null vector platform (VP). Note the increasing levels of NAb induced in mice after repeated injections with Ad particles. Values represent mean±SEM.

To assess the levels of Ad5 immunity that could be induced, groups of Ad5 naive C57Bl/6 mice were injected subcutaneously with the Ad5 vector platform (VP). Twenty eight to forty two days later, serum samples were collected and assessed for endpoint Ad5 NAb titers. As shown in FIG. 3, undetectable Ad5 NAb titers (endpoint Ad5 NAb titer <1/25) were observed in normal control mice. Ad5 NAb (endpoint titers of 1/25 to 1/50) was detectable after one injection but dramatically increased after three injections of $10^{10}$ Ad5. Therefore, in additional Ad5 immune studies, mice were injected twice with $10^{10}$ Ad5 VP to render the animals Ad5 immune.

Immunization of Ad5 Immune Mice with Ad5 [E1-]-CEA or Ad5 [E1-, E2b-]-CEA.

These experiments were designed to determine and compare the immunization induction potential of Ad5 [E1-]-CEA and Ad5 [E1-, E2b-]-CEA vaccines in Ad5 immune mice. Groups of female C57Bl/6 mice, 4 to 8 weeks old, were immunized 2 times at 2 week intervals with $10^{10}$ Ad5-null VP. Two weeks following the last Ad5-null immunization, the mice were immunized 3 times at weekly intervals with $10^{10}$ VP of Ad5 [E1-]-CEA or Ad5 [E1-, E2b-]-CEA. Two weeks following the last immunization, mice were euthanized and their spleens and sera harvested for analyses.

CMI responses were assessed by ELISpot assays performed on splenocytes exposed to intact CEA antigen. Splenocytes from Ad5 immune C57Bl/6 mice that were immunized subcutaneously with Ad5 E1-]-CEA or Ad5 [E1-, E2b-]-CEA were harvested and assessed for the number of IFN-γ and IL-2 secreting cells as described above. As shown in FIGS. 4A and 4B, significantly elevated numbers of both IFN-γ and IL-2 secreting cells were observed in spleens assayed from mice immunized with Ad5 [E1-, E2b-]-CEA as compared to immunized Ad5 [E1-]-CEA mice. Specificity studies revealed that immunizations with Ad5 CEA vectors induced specific CEA associated CMI responses and not responses against other irrelevant antigens such as the HIV-gag protein or β-galactosidase. These results demonstrate that immunization of Ad5 immune mice with Ad5 [E1-, E2b-]-CEA induce significantly higher CMI responses.

Lack of Adverse Liver Effects in Immunized Mice

Figure 5:
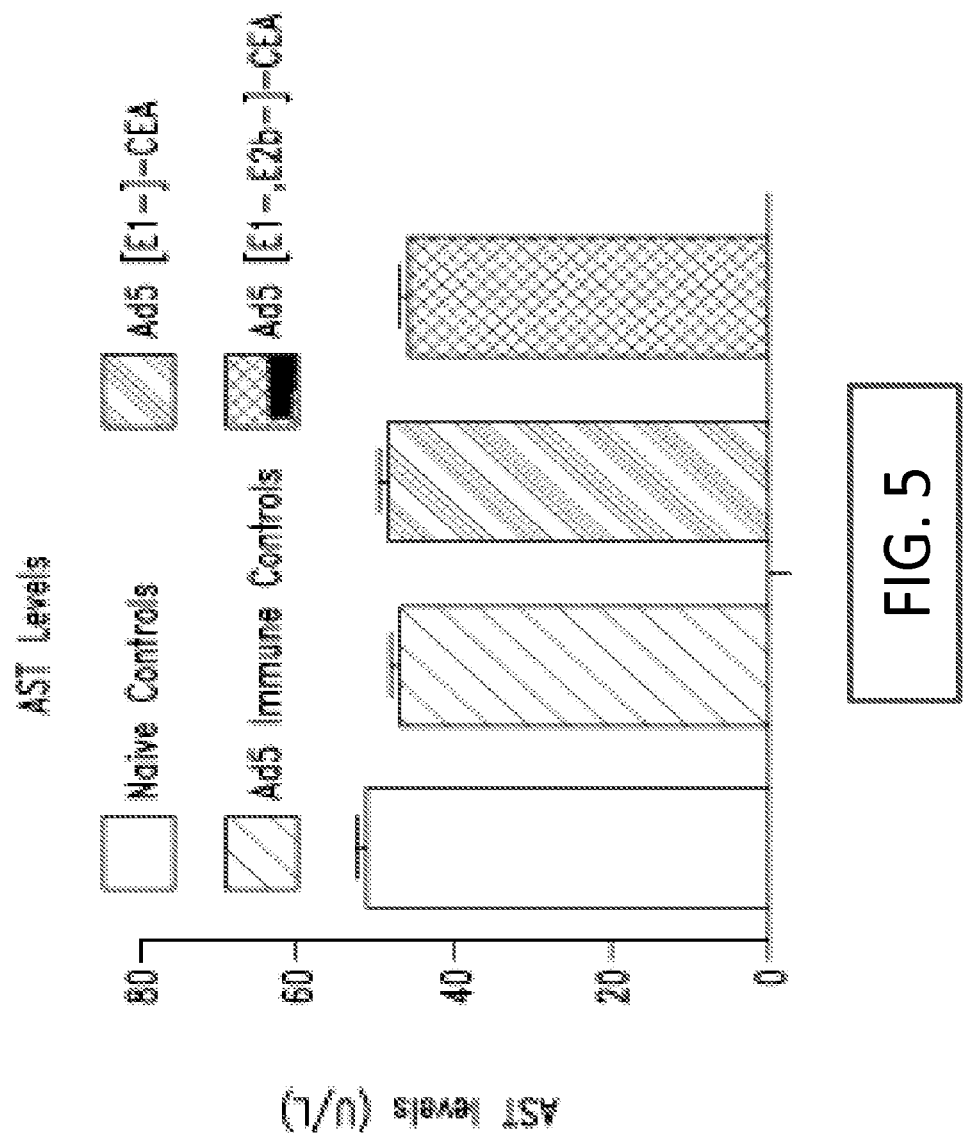
FIG. 5 is a bar graph showing serum AST levels in control mice and mice vaccinated with $10^{10}$ viral particles of Ad5 [E1-]-CEA or Ad5 [E1-, E2b-]-CEA. Values represent mean±SEM.

Toxicity studies were performed on serum from Ad5 immune female C57Bl/6 mice immunized with Ad5 [E1-]-CEA, Ad5 [E1-, E2b-]-CEA as described above. Ad5 naive or Ad5 immune mice injected with buffer alone served as controls. Three days after the third immunization, aspartate aminotransferase (AST) levels were assessed on the blood samples to determine liver toxicity due to the treatment. AST levels were not elevated over controls following immunization with either vector (FIG. 5). Alanine aminotransferase (ALT) levels were also assessed and similar results were observed.

Ad5 [E1-, E2b-]-CEA Immunotherapy in Ad5 Immune Tumor Bearing Mice

Based upon the successful immunological results observed above, studies in which MC38 tumors were established in mice and then treated were performed as described below. For these studies a CEA expressing MC38 murine cell line was used. This cell line has been genetically modified to express human CEA and can be implanted into C57Bl/6 mice. After tumor establishment, the mice were treated with the novel Ad5 [E1-, E2b-]-CEA vector platform. To determine if Ad5 immune tumor bearing mice could be treated with the Ad5 [E1-, E2b-]-CEA vector, C57Bl/6 mice were injected two times subcutaneously with $10^{10}$ Ad5

[E1-]-null VP at 14 day intervals to render the mice Ad5 immune. Two weeks after the last injection, two groups of 7 C57Bl/6 mice were injected subcutaneously with $10^6$ CEA expressing MC38 tumor cells. Seven days later, when tumors were palpable, one group of mice was treated by distal subcutaneous injection with $10^{10}$ VP of Ad5 [E1-, E2b-]-CEA on days 7, 13 and 19. A group of 7 injection buffer only treated C57Bl/6 mice served as untreated controls. All mice were monitored for tumor size over a 21 day period and tumor volumes were determined as previously described.

Figure 6:
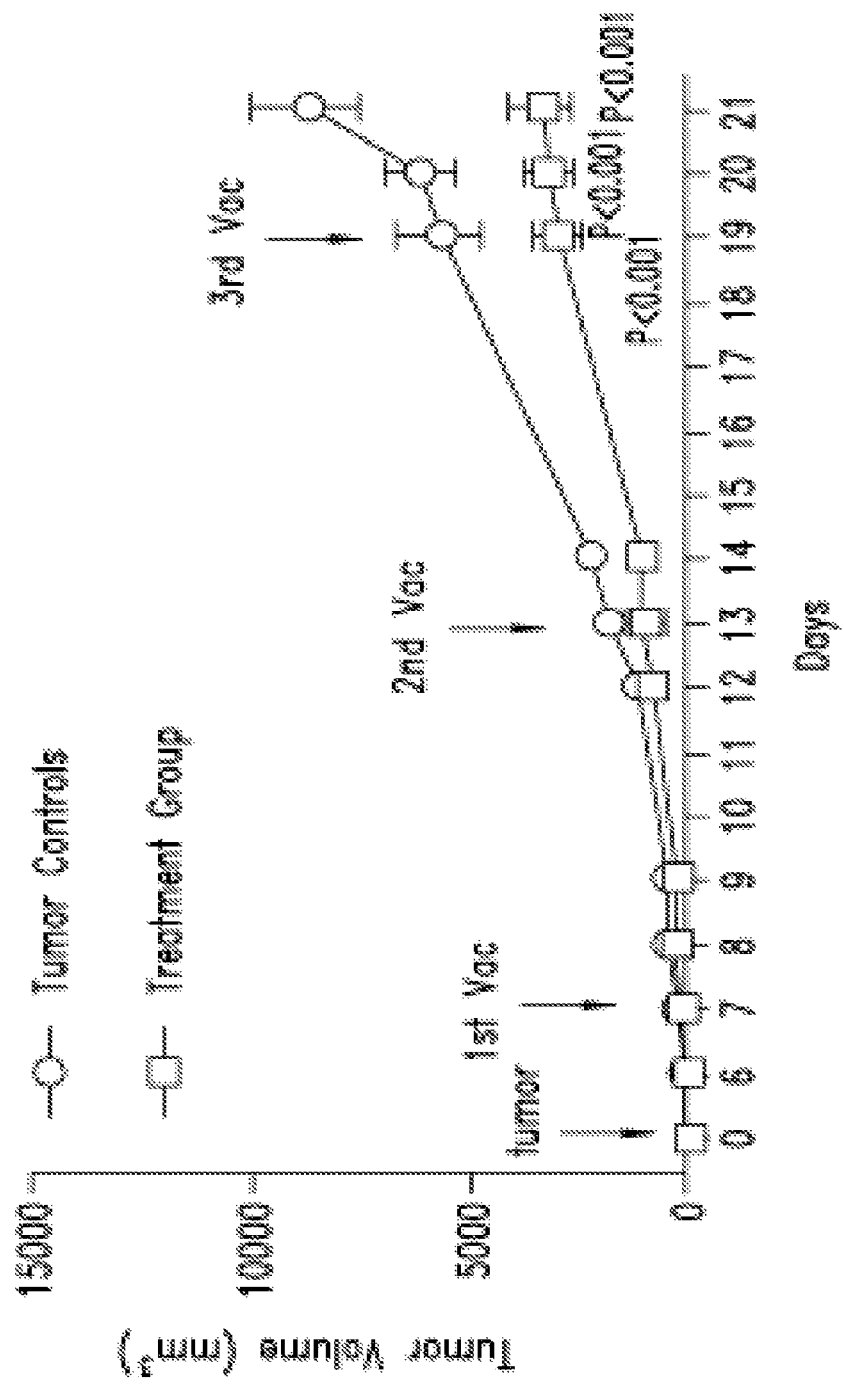
FIG. 6 is a line graph showing tumor volume. Ad5 immune C57Bl/6 mice were injected with MC38 CEA expressing tumor cells and subsequently treated (Vac) with Ad5 [E1-, E2b-]-CEA vaccine as described. Note the significant reduction in tumor size by days 19-21 as compared to untreated control tumor bearing mice. Tumor measurements were taken and volumes were determined. Statistical analysis was performed using the Bonferroni post-tests analysis with PRISM software. Values represent mean±SEM.
Figure 7:
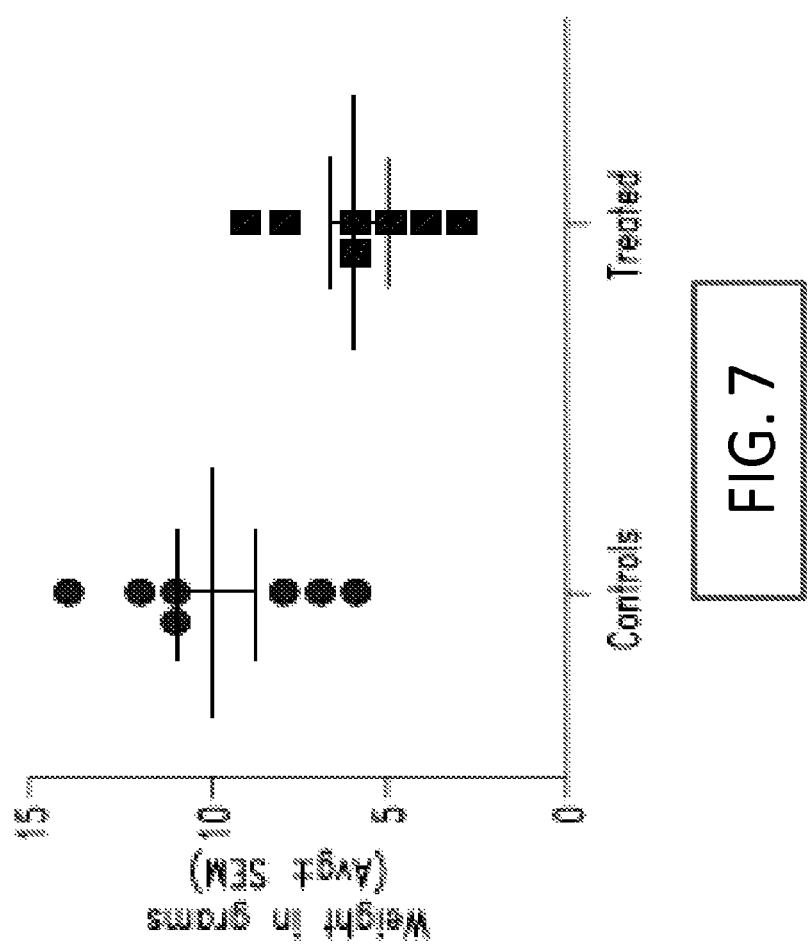
FIG. 7 is a graph showing tumor weights from treated and untreated Ad5 immune MC38 tumor bearing mice. Note the significant (p=0.0124) reduction in tumor weights from the mice treated with Ad5 [E1-, E2b-]-CEA. Values represent mean±SEM.

As shown in FIG. 6, the tumor growth by day 19 was significantly reduced in the Ad5 [E1-, E2b-]-CEA treated mice and remained so. At the end of the study (Day 22), the mice were sacrificed and the tumors were excised and weighed. As shown in FIG. 7, the tumors in the mice treated with Ad5 [E1-, E2b-]-CEA were significantly ($P<0.05$) smaller in weight than the untreated controls.

At the termination of the study, spleens were collected from mice and the CEA specific CMI response was determined by ELISpot assay. CEA specific IFN-γ secretion response was significantly higher in mice immunized with Ad5 [E1-, E2b-]-CEA than in mice who received MC-38 tumor cells alone. These results indicate that treatment of CEA expressing tumors in Ad5 immunized mice using the Ad5 [E1-, E2b-]-CEA vaccine can significantly decrease tumor growth progression.

Example 3: Quantitative ELISA for CEA Expression on A549 Cells after Infection

Experimental Design

On day one, of the assay a BD Falcon Tissue Culture 96-well plate was seeded with A549 cells passaged three days prior (lot #30Jul02, passage p+23), ($7.7\times10^3$ cells/well) and placed into a $37\pm2°$ C. incubator with a $5\pm2\%$ $CO_2$ atmosphere overnight. The next day, a dilution series of the test article were prepared and replicate wells were inoculated at levels ranging from $1.56\times10^3$ to $2.5\times10^4$ viral particles/well. Untreated A549 cells were used to serve as the mock sample. On day four of the assay wells were treated with a 10% Triton X-100 solution for analysis by ELISA to measure CEA concentration.

For the ELISA, a microtiter plate was coated overnight with an anti-CEA capture antibody (abcam Carcino embryonic antigen CEA antibody [(NCRC16(AKA161)] catalog number ab2077, lot #201993. The wells were washed to remove unbound reactants, and the plate was blocked with a Phosphate Buffered Saline (PBS) solution containing 1% Tween 20. to fall within the range of the standard curve. After the blocking period, the wells were washed, and samples, controls, and standards were incubated in assigned triplicate wells. Unbound reactants were removed by washing, and a rabbit polyclonal to CEA detection antibody (abcam carcino embryonic antigen CEA antibody catalog # ab15987, lot #898335) was added. After incubation, the wells were washed and incubated with 3,31',5,5'-tetramethylbenzidine (TMB), the peroxidase substrate. The substrate formed a colored product in the presence of the enzyme, reaction was stopped with 1M phosphoric acid solution, and the absorbance was determined on a calibrated microplate reader. A calibration curve was generated from standards containing known concentrations of CEA, and the curve was used to determine the concentration of CEA in the samples Test Evaluation The quantity of CEA produced per virus particle was calculated from the concentration of CEA measured by ELISA, after adjusting for dilution and multiplicity of infection (MOI). The value determined in a similar manner for culture media alone was subtracted to compensate for background levels present in the media. The sample analysis is shown in Table 1.

TABLE 1

Sample Analysis

| Sample ID | $A_{450}$-$A_{540}$ Rep 1 | Rep 2 | Mean | SD | RSD | Blank Subtr | ELISA Dil'n Fact | CEA ng/ml | AVG CEA ng/ml | Total CEA ng/ml | CEA Ng/vp |
|---|---|---|---|---|---|---|---|---|---|---|---|
| 10-002917 Well 1 at 2.5E+04 vp | 1.3387 | 1.2977 | 1.318 | 0.029 | 2.2% | 1.244 | 1000 | 7,731 | 7,691 | 7,621 | 0.30 |
| | 0.7121 | 0.6789 | 0.693 | 0.023 | 3.4% | 0.622 | 2000 | 7,797 | | | |
| 10-002917 Well 2 at 2.5E+04 vp | 1.1717 | 1.1329 | 1.152 | 0.027 | 2.4% | 1.078 | 1000 | 6,563 | | | |
| | 0.6222 | 0.6151 | 0.619 | 0.005 | 0.8% | 0.545 | 2000 | 6,975 | | | |
| 10-002917 Well 3 at 2.5E+04 vp | 1.1659 | 2.0492 | 1.608 | 0.625 | 38.9% | 1.534 | 1000 | 10,264 | | | |
| | 0.6131 | 0.5946 | 0.604 | 0.013 | 2.2% | 0.530 | 2000 | 6,815 | | | |
| 10-002917 Well 1 at 1.25E+04 vp | 1.1051 | 1.0759 | 1.091 | 0.021 | 1.9% | 1.017 | 1000 | 6,169 | 6,049 | 5,979 | 0.48 |
| | 0.5970 | 0.5716 | 0.584 | 0.018 | 3.1% | 0.510 | 2000 | 6,602 | | | |
| 10-002917 Well 2 at 1.25E+04 vp | 1.0652 | 1.0376 | 1.051 | 0.020 | 1.9% | 0.977 | 1000 | 5,919 | | | |
| | 0.5726 | 0.5770 | 0.575 | 0.003 | 0.5% | 0.501 | 2000 | 6,506 | | | |
| 10-002917 Well 3 at 1.25E+04 vp | 0.9731 | 0.9514 | 0.962 | 0.015 | 1.6% | 0.888 | 1000 | 5,383 | | | |
| | 0.5049 | 0.4970 | 0.501 | 0.006 | 1.1% | 0.427 | 2000 | 5,716 | | | |
| 10-002917 Well 1 at 6.25E+03 vp | 0.7601 | 0.7210 | 0.741 | 0.028 | 3.7% | 0.667 | 1000 | 4,141 | 4,286 | 4,216 | 0.67 |
| | 0.4041 | 0.3881 | 0.396 | 0.011 | 2.9% | 0.322 | 2000 | 4,566 | | | |
| 10-002917 Well 2 at 6.25E+03 vp | 0.7157 | 0.7068 | 0.711 | 0.006 | 0.9% | 0.637 | 1000 | 3,979 | | | |
| | 0.3893 | 0.3843 | 0.387 | 0.004 | 0.9% | 0.313 | 2000 | 4,465 | | | |
| 10-002917 Well 3 at 6.25E+03 vp | 0.7360 | 0.7188 | 0.727 | 0.012 | 1.7% | 0.653 | 1000 | 4,065 | | | |
| | 0.3995 | 0.3807 | 0.390 | 0.013 | 3.4% | 0.316 | 2000 | 4,499 | | | |
| 10-002917 Well 1 at 3.13E+03 vp | 0.8920 | 0.8878 | 0.890 | 0.003 | 0.3% | 0.816 | 500 | 2,483 | 2,690 | 2,620 | 0.84 |
| | 0.4573 | 0.4613 | 0.459 | 0.003 | 0.6% | 0.385 | 1000 | 2,631 | | | |
| 10-002917 Well 2 at 3.13E+03 vp | 0.8615 | 0.8544 | 0.858 | 0.005 | 0.6% | 0.784 | 500 | 2,393 | | | |
| | 0.4425 | 0.4406 | 0.442 | 0.001 | 0.3% | 0.368 | 1000 | 2,538 | | | |
| 10-002917 Well 3 at 3.13E+03 vp | 1.0518 | 1.0464 | 1.049 | 0.004 | 0.4% | 0.975 | 500 | 2,953 | | | |
| | 0.5519 | 0.5565 | 0.554 | 0.003 | 0.6% | 0.480 | 1000 | 3,141 | | | |
| 10-002917 Well 1 at 1.56E+03 vp | 1.8771 | 1.8616 | 1.869 | 0.011 | 0.6% | 1.795 | 100 | 1,351 | 1,271 | 1,201 | 0.77 |
| | 1.1963 | 1.1695 | 1.183 | 0.019 | 1.6% | 1.109 | 200 | 1,354 | | | |
| 10-002917 Well 2 at 1.56E+03 vp | 1.7435 | 1.7436 | 1.744 | 0.000 | 0.0% | 1.670 | 100 | 1,179 | | | |
| | 1.0960 | 1.0788 | 1.087 | 0.012 | 1.1% | 1.013 | 200 | 1,229 | | | |

TABLE 1-continued

Sample Analysis

| Sample ID | $A_{450}$-$A_{540}$ Rep 1 | Rep 2 | Mean | SD | RSD | Blank Subtr | ELISA Dil'n Fact | CEA ng/ml | AVG CEA ng/ml | Total CEA ng/ml | CEA Ng/vp |
|---|---|---|---|---|---|---|---|---|---|---|---|
| 10-002917 Well 3 at 1.56E+03 vp | 1.7801 1.1041 | 1.8098 1.1263 | 1.795 1.115 | 0.021 0.016 | 1.2% 1.4% | 1.721 1.041 | 100 200 | 1,245 1,264 | | | |
| 10-002917 Well 1 | 1.2509 | 1.2278 | 1.239 | 0.016 | 1.3% | 1.165 | 10 | 72 | 70 | 0 | — |
| Mock | 0.7146 | 0.6952 | 0.705 | 0.014 | 1.9% | 0.631 | 20 | 79 | | | |
| 10-002917 Well 2 | 1.2290 | 1.2382 | 1.234 | 0.007 | 0.5% | 1.160 | 10 | 71 | | | |
| Mock | 0.7246 | 0.7133 | 0.719 | 0.008 | 1.1% | 0.645 | 20 | 80 | | | |
| 10-002917 Well 3 | 0.9769 | 0.9750 | 0.976 | 0.001 | 0.1% | 0.902 | 10 | 55 | | | |
| Mock | 0.5579 | 0.5454 | 0.552 | 0.009 | 1.6% | 0.478 | 20 | 63 | | | |

Example 4: Schedule, Dose, Route of Immunization Safety Data

Figure 8:
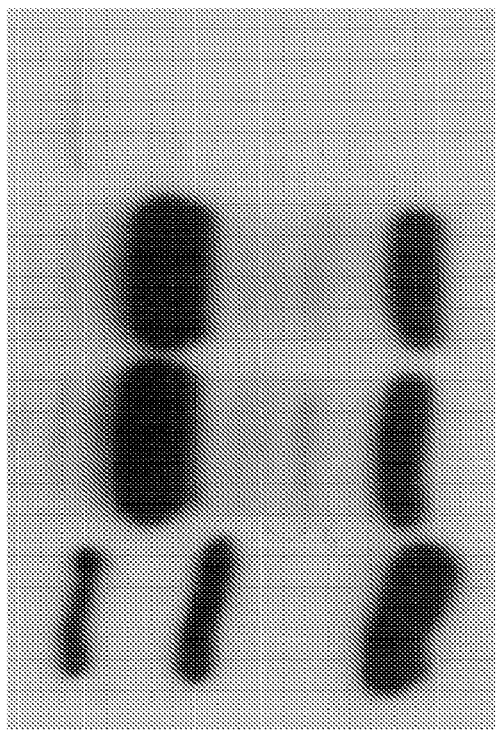
FIG. 8 is a representative immunoblot demonstrating Gag production by A-549 cells infected with Ad5 [E1-, E2b-]-gag. A-549 whole cell lysate was infected at a MOI of 200 of Ad5 [E1-, E2b-]-gag or Ad5-null for 44 h. The blot was stained with a mouse monoclonal antibody against Gag. Lane 1, Magic Mark XP Western Standard (Invitrogen, CA), Lanes 2 and 3, Ad5 [E1-, E2b-]-gag, Lane 4, Ad5-null (empty). The upper band (55 kDa) comprises the gag precursor and the lower band (41 kDa) comprises the p17/p24 gag complex.

Initial studies were performed to evaluate and confirm that an Ad5 [E1-, E2b-] vector platform could express the antigen proteins on transfected cells. A-549 cells were transfected with vaccine platforms and analyzed by Western Blot Analysis. Antigen proteins such as HIV-gag, HIV-pol, or HIV-nef were observed to be expressed on cells once they were transfected with the Ad5 [E1-, E2b-] vector platforms. A representative Western Blot is presented in FIG. 8.

Figure 9:
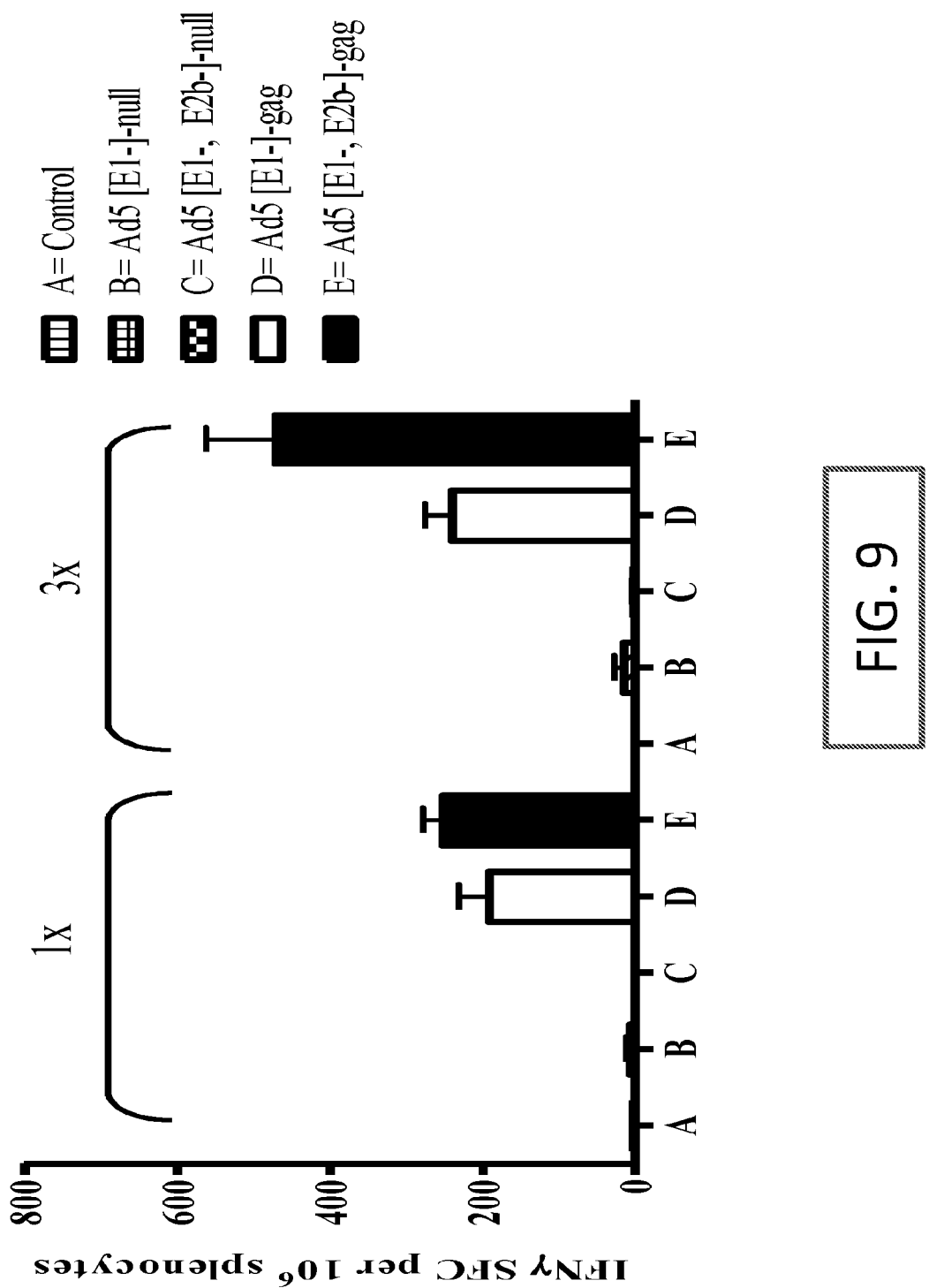
FIG. 9 demonstrates the effect of multiple immunizations on inducing a greater CMI (IFN-γ ELISpot) response. Ad5 Naïve BALB/C mice (n=5/group) were immunized once or three times at fourteen day intervals with $10^{10}$ VP of Ad5 [E1-]-null, Ad5 [E1-, E2b-]-null, Ad5 [E1-]-gag, Ad5 [E1-, E2b-]-gag, or injection buffer alone (control). Fourteen days after the final immunization splenocytes were assessed for IFN-γ secreting splenocytes by ELISpot analysis. For positive controls, splenocytes were exposed to Concanavalin A (Con A) (data not shown). The error bars depict the SEM

A dose response evaluation was performed using the Ad5 [E1-, E2b-] vector platform and demonstrated that $10^{10}$ virus particles (VP) is a dose that results in a desired CMI response against a transgene product in a murine model. CMI responses were assessed by utilizing an ELISpot assay to detect interferon-gamma (IFN-γ) and IL-2 secreting cells (splenocytes) from spleens of mice. Furthermore, in murine and non-human primate (NHP) models, three immunizations using $10^{10}$ VP separated by two weeks to four weeks, respectively, resulted in the desired CMI responses. In mice, a greater degree of CM1 responses were observed after multiple immunizations as compared with one immunization only (FIG. 9).

Figure 10:
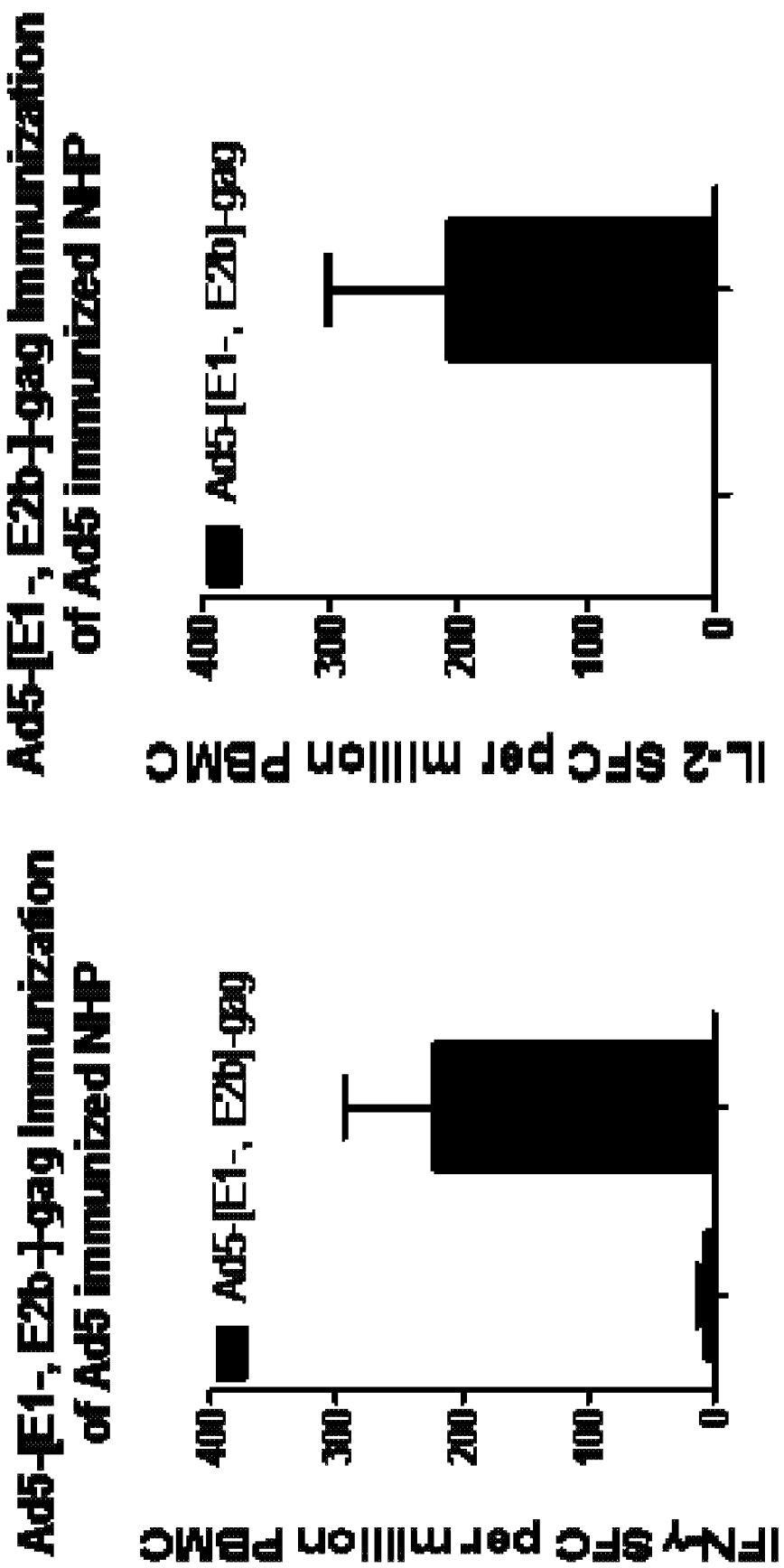
FIG. 10 shows the results of ELISpot INF-γ (A) and 1L-2 (B) analysis of PBMC from Cynomolgus Macaques (N=3) pre-immunized against Wild Type Ad5. When Ad5 neutralizing antibody titers reached 1:50 or greater they were immunized intradermally three times at 30 day intervals with Ad5-[E1-, E2b-]-gag at a dose of $10^{10}$ VP. The first immunization (Wild Type Ad5) was on day 1 and 124 days later (32 days after last vaccination) the NAb titers were equal to or greater than 1:1000. Note the presence of significantly elevated values (P<0.05) in the Dec. 17, 2007 samples. For positive controls, splenocytes were exposed to Concanavalin A (Con A) (data not shown). Values represent mean±SEM.

In a NHP model, the animals were rendered Ad5 immune by injection with wild type Ad5 virus. After detection of the presence of Ad5 neutralizing antibody, which confirmed that the animals were immune to Ad5, the animals were vaccinated with an Ad5 [E1-, E2b-] vector platform three times at monthly intervals. As shown in FIG. 10, after immunizations, the presence of robust CMI responses was detected, when peripheral blood mononuclear cells (PBMCs) of animals were assessed for IFN-γ and IL-2 secreting cells.

In addition to the preliminary immunology studies performed in the initial vaccine trial in 3 NHP shown above, toxicity studies were also performed on the same NHP vaccinated with Ad5 [E1-, E2b-]-HIV gag. Animal temperatures and weights were assessed during the study period. The animals gained weight as they grew during the study period. No temperature differences were observed during the study period. Hematology studies were also performed on the vaccinated NHP.

There appeared to be a small increase in the white blood cell count 2 weeks after the second vaccination that normalized thereafter.

Other than fluctuation in values, there appeared to be no other differences in hematology values during the course of the study. Chemistry values were also determined in the NHP during the course of the study. Alkaline phosphatase levels declined slightly during the course of the study but remained in the normal range. Albumin levels declined slightly during the course of the study but remained in the normal. There were no other differences observed in the blood chemistries during the course of the study. The route of immunization in this clinical study is chosen since the preponderance of DC reside in the dermis.

Figure 11:
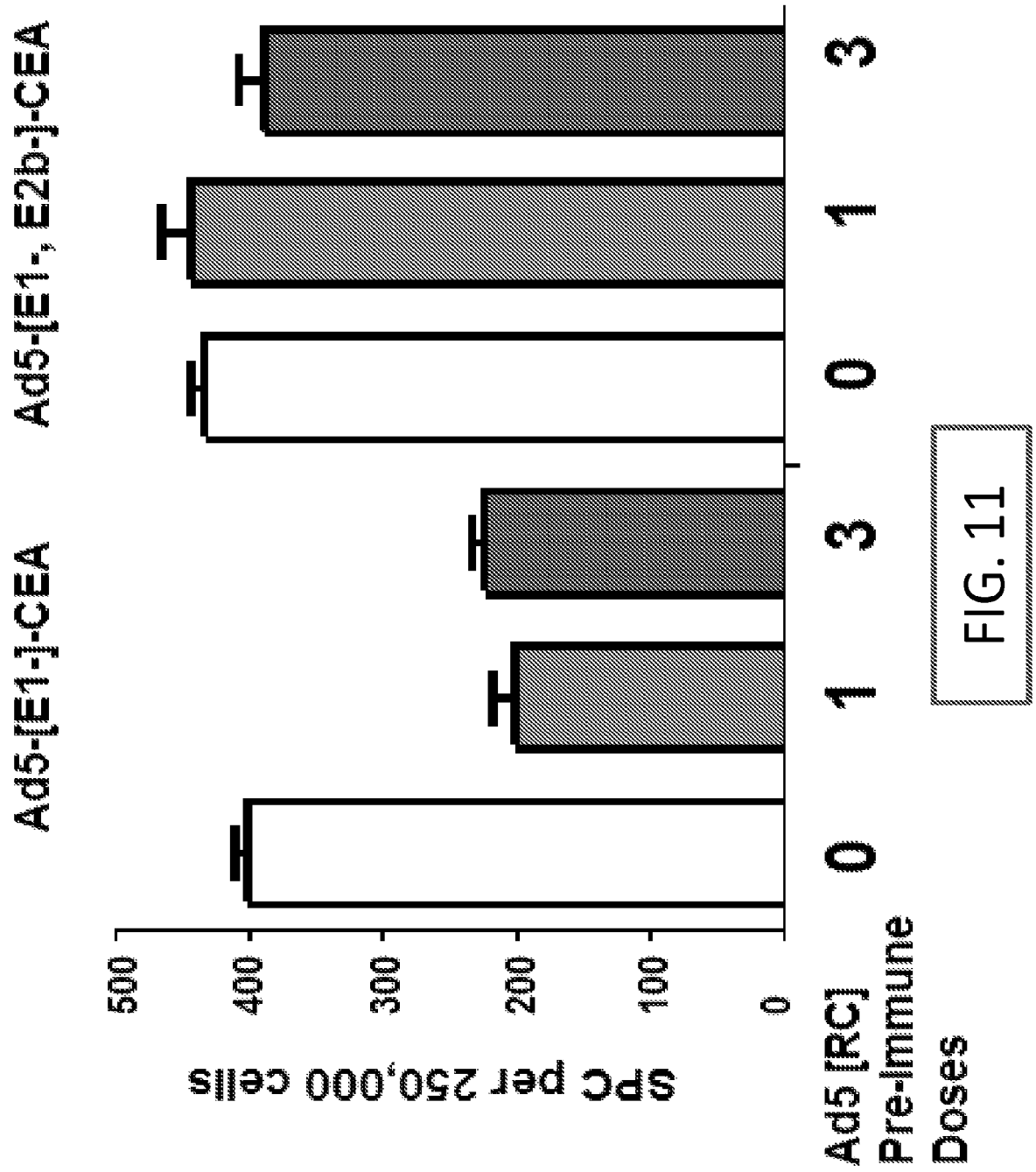
FIG. 11 ELISpot interferon-γ secreting SPC from mice vaccinated with recombinant Ad5 CEA expression vectors. Graph shows lack of reduction in SPC from mice vaccinated with Ad5 [[E1-, E2b-]-CEA as compared with the reductions in SPC from Ad5 [E1-]-CEA vaccinated mice.

A desired level of CMI response was induced using the Ad5 [E1-, E2b-] platform employing CEA and other transgenes. Using an Ad5 [E1-, E2b-]-CEA vector platform, both non-Ad5 immune and Ad5 pre-immunized mice were injected three times with the vaccine. After immunizations, the splenocytes from mice were assessed by ELISpot for IFN-γ secreting cells. As shown in FIG. 11, elevated CMI responses were observed after immunizations and the levels of CMI responses were similar in both non-Ad5 immune and Ad5 pre-immunized mice. These results indicate that robust CMI responses can be induced despite the presence of pre-existing Ad5 immunity. A III clinical study was designed using three immunizations separated by three weeks via a needle subcutaneous delivery method.

Rationale for Schedule, Dose, Route of Administration

A clinical study design flowed from pre-clinical and clinical studies in animals and humans using the Ad5 [E1-, E2b-] vector platform. A dose response evaluation using the Ad5 [E1-, E2b-] vector platform was performed demonstrating that $10^{10}$ virus particles (VP) is a dose which results in a desired CMI response against a transgene product in a murine model. Furthermore, in murine and non-human primate (NHP) models three immunizations using $10^{10}$ VP separated by two to four weeks respectively resulted in the desired CMI. The route of immunization is chosen since a preponderance of dendritic cells (DC) reside in the dermis. Using this premise, multiple murine and NHP studies were performed using a sub-cutaneous injection protocol. A desired level of circulating CMI was induced using the Ad5 [E1-, E2b-] platform employing CEA and other transgenes. A phase III clinical study followed using three immunizations separated by three weeks via a needle subcutaneous (SQ) delivery method continuing immunotherapy treatment every three months until removed from study for any reason including death.

Construction and Production of Ad5 [E1-, E2b-]-CEA (6D).

The cDNA sequence containing the modified CEA with the CAP1(6D) mutation was produced. Clinical grade Ad5 [E1-, E2b-]-CEA(6D) was constructed as previously described (Gabitzsch et al. (2010) Anti-tumor immunity despite immunity to adenovirus using a novel adenoviral vector Ad5 [E1-, E2b-]-CEA. Cancer Immunol Immunoother 59:1131-1135) and manufactured using the E.C7 cell line.

Summary

A total of 34 patients (32 colorectal cancer patients, one bladder cancer patient, and one lung cancer patient) were entered into the Phase 1/II clinical study under IND14325. The majority received all three scheduled immunotherapy treatments with ETBX-011(Ad5 [E1-, E2b-]-CEA(6D)). Five patients who stopped immunotherapy early did so due to significant disease progression. RECIST 1.0 criteria using CT or MRI scans obtained at baseline and after treatments were completed. Toxicity was assessed according to the National Cancer Institute Common Terminology Criteria for Adverse Events (CTCAE) version 4.0. Peripheral blood carcinoembryonic antigen (CEA) levels, hematology, serum chemistries, and anti-nuclear antibody titers were compared between baseline and 9 weeks following the initiation of immunotherapy. Survival was measured from the day of the first immunization until death from any cause.

A total of 94 treatments were administered to patients. No dose limiting toxicity or serious adverse events (SAE) that resulted in treatment discontinuation at any treatment dose level. There was only one significant change in a blood hematology value. As a group, the basophil count was significantly lower at week 9, three weeks after treatment ended. However, this value remained in the normal range for basophil counts and, overall, there appeared to be no significant biological effect. With a median follow-up of 7.4 months, all 34 patients as a group (cohorts 1, 2, 3/phase II, and cohort 5) experienced a 12-month survival proportion of 41.4%. Of the 34 patients entered into the study, 28 patients received the three immunotherapy treatments and experienced a 12-month survival proportion of 55%. For the colorectal adenocarcinoma patients, 27 patients received the three immunotherapy treatments and experienced a 12-month survival proportion of 53%. A dose response to increasing levels of ETBX-011 was observed with the highest cell-mediated immune (CMI) responses occurring in patients that received the highest dose of $5 \times 10^{11}$ VP of ETBX-011. When the highest CEA specific CMI responses were compared with pre-existing or vector induced Ad5 NAb activity, there was no correlation between levels of CEA specific CMI and Ad5 neutralizing antibody (NAb) level. These clinical trial data lead us to believe that there is sufficient data to advance to a randomized Phase III trial for the treatment of metastatic colorectal adenocarcinoma with overall survival as the clinical endpoint.

Protocol Schema and Patient Treatment.

The clinical study was performed under an FDA-approved Investigational New Drug Exemption and registered at ClinicalTrials.gov. Participants were recruited from medical oncology clinics at Duke University Medical Center, Durham, N.C. and Medical Oncology Associates, Spokane, Wash. Patients provided informed consent approved by the respective Institutional Review Boards (IRB). Eligibility requirements included metastatic cancer expressing CEA and adequate hematologic, renal, and hepatic function. Trial participants were required to have received treatment with standard therapy known to have a possible overall survival benefit or refused such therapy. Exclusion criteria included chemotherapy or radiation within the prior 4 weeks, history of autoimmune disease, viral hepatitis, HIV, or use of immunosuppressives. Patients who had been receiving bevacizumab or cetuximab for at least 3 months prior to enrollment were permitted to continue receiving these antibodies. Prior CEA immunotherapy was permitted. The study employed a standard 3+3 dose escalation strategy with dose limiting toxicities (DLT) defined as grade 3 or 4 major organ toxicity. The Ad5 [E1-, E2b-]-CEA(6D) doses were delivered to patients as follows: cohort 1: dose of $1 \times 10^9$ VP in 0.5 ml subcutaneously (SQ) in the same thigh every 3 weeks for 3 immunizations; cohort 2: dose of $1 \times 10^{10}$ VP in 0.5 ml SQ every 3 weeks for 3 treatments; cohort 3: dose of $1 \times 10^{11}$ in 0.5 ml SQ every 3 weeks for 3 treatments. Following establishment of the dose of $1 \times 10^{11}$ VP as safe, an additional 12 patients received Ad5 [E1-, E2b-]-CEA(6D) at this dose and schedule (phase II cohort). After completing the phase II cohort, an additional cohort (cohort 5) of six (6) patients received a dose of $5 \times 10^{11}$ VP in 2.5 ml SQ every 3 weeks for 3 treatments to determine safety of the highest achievable dose. PMBC were collected from patients just prior to the immunizations at weeks 0, 3, 6, and three weeks following the last treatment. The PBMC were frozen in liquid nitrogen until ELISpot assays were performed. In cohort 5, fresh PBMC were analyzed in preliminary flow cytometry assays for polyfunctional CD8+T lymphocytes.

Assessment of Clinical Activity.

Clinical activity was assessed according to Response Evaluation Criteria in Solid Tumors (RECIST 1.0 criteria) using computed tomography (CT) or magnetic resonance imaging (MRI) scans obtained at baseline and after treatments were completed. Toxicity was assessed according to the National Cancer Institute Common Terminology Criteria for Adverse Events (CTCAE) version 4. Peripheral blood CEA levels, hematology, serum chemistries, and anti-nuclear antibody titers were compared at baseline and 3 weeks following the final treatment. Survival was measured from the day of the first immunization until death from any cause.

Analysis of CMI Responses by ELISpot Assay.

An ELISpot assay for IFN-γ secreting lymphocytes was adapted from our previous animal studies and performed as described (Gabitzsch et al. (2010) Anti-tumor immunity despite immunity to adenovirus using a novel adenoviral vector Ad5 [E1-, E2b-]-CEA. Cancer Immunol Immunother 59:1131-1135). Briefly, isolated PBMCs ($2 \times 10^5$ cells/well) from individual patient samples were incubated 36-40 hours with a CEA peptide pool (15 mers with 11aa overlap covering full length CEA with the 6D modification; 0.1 µg/well) to stimulate IFN-γ producing T cells. CMI responses to Ad5 were determined after exposure of patient PBMC to Ad5-null (empty vector). Cells stimulated with concanavalin A (Con A) at a concentration of 0.25 µg/well served as positive controls. Colored spot-forming cells (SFC) were counted using an Immunospot ELISpot plate reader (Cellular Technology, Shaker Heights, Ohio) and responses were considered to be positive if 50 SFC were detected/106 cells after subtraction of the negative control and SFC were ≥2-fold higher than those in the negative control wells.

Determination of Ad5 Neutralizing Antibody (NAb) Titers.

Endpoint Ad5 NAb titers were determined. Briefly, dilutions of heat inactivated test sera in 100 µL of DMEM containing 10% fetal calf serum were mixed with 4×107 VP of Ad5 [E1-]-null and incubated for 60 minutes at room temperature. The samples were added to microwells containing HEK293 cells cultured in DMEM containing 10% heat inactivated calf serum at 2×103 cells/well for 24 hours at 37° C. in 5% CO2. The mixture was incubated for an additional 72 hours at 37° C. in 5% CO2. An MTS tetrazolium bioreduction assay (Promega Corp. Madison, Wis.) was used to measure cell killing and endpoint Ad5 NAb titers. Endpoint titers with a value less than 1:25 were assigned a value of 0.

Statistics.

Statistical analyses comparing immune responses were performed employing the Mann-Whitney test (PRISM, Graph Pad). Survival comparisons were performed employing Kaplan-Meier plots (PRISM, Graph Pad). Ad5 NAb titer and CEA-specific CMI were analyzed as continuous variables. The association of Ad5 NAb titer with change in CEA-specific CMI was tested with the Spearman correlation coefficient. The association of Ad5 NAb titer with survival was tested with the Wald test of the proportional hazards model. All tests used a 2-sided alpha of 0.05.

Demographics: All Patients

Thirty two patients with metastatic colorectal cancer, one with lung cancer and one with bladder cancer, median age 58 (range 38-77), who had failed a median of three prior chemotherapeutic regimens (range: 2→5), had a median performance status of 90% (range 70-100%), and had a median of three sites of metastatic disease (range 1-5), were enrolled (Table 2). The majority of patients was able to receive all three immunizations. Five patients who stopped immunizations prior to completion of all three treatments did so due to significant disease progression.

Demographics: Colorectal Adenocarcinoma Patients

Thirty two patients, median age 57.5 (range 38-77) with metastatic colorectal cancer, who had failed a median of three prior chemotherapeutic regimens (range: 2→5), had a median performance status of 90% (range 70-100%), and had a median of three sites of metastatic disease (range 1-5), were enrolled (Table 2). The majority was able to receive all three immunizations. Four patients who stopped immunization early did so due to significant disease progression. The colorectal adenocarcinoma patient demographics, albeit limited in size, compares favorably with previously published studies of patients with chemotherapy-refractory colorectal cancer (3-5).

Adverse Effects

A total of 94 immunization treatments were administered to all patients. There was no dose limiting toxicity and no serious adverse events that resulted in treatment discontinuation at any vaccine dose level. The most common toxicity (Table 3) was a self-limited, injection site reaction. Other reactions that occurred at a low frequency include fever, flu-like symptoms, anorexia, chills, nausea, and headache.

TABLE 2

Patient Demographics

| Patient ID/ Cohort | Dose (VP) | Dx | Age | Sex | KPS | # prior CTx | Mets (# of sites) | # of doses | ++ Disease status after tx | Survival (Months) | CEA Baseline | CEA Week 9 |
|---|---|---|---|---|---|---|---|---|---|---|---|---|
| 002/1 | $10^9$ | C | 67 | M | 70 | >3 | 4 | 3 | PD | 3 (−) | 98.8 | 867.4 |
| 003/1 | $10^9$ | R | 63 | M | 100 | 5 | 2 | 3 | PD | 9 (−) | 195.1 | 472.2 |
| 004/1 | $10^9$ | C | 53 | F | 100 | 2 | 3 | 3 | PD | 11 (−) | 65.4 | 196.8 |
| 005/2 | $10^{10}$ | C | 60 | M | 100 | 3 | 3 | 3 | SD | 12 (+) | 2.5 | 3.7 (7 month follow-up) |
| 007/2 | $10^{10}$ | C | 52 | M | 80 | 2 | 5 | 1 | PD | 1 (−) | 120.7 | Not Done |
| 008/2 | $10^{10}$ | C | 42 | F | 100 | 3 | 3 | 3 | PD | 12 (+) | 3.0 | 3.1 |
| 010/2 | $10^{10}$ | C | 58 | M | 90 | 3 | 3 | 3 | PD | 12 (−) | 7.1 | 5.8 |
| 011/3 | $10^{11}$ | R | 50 | M | 100 | 5 | 1 | 3 | PD | 12 (+) | 21.0 | 25.9 |
| 012/3 | $10^{11}$ | C | 48 | M | 100 | 1 | 2 | 3 | PD | 12 (+) | 5.8 | 18.4 |
| 013/3 | $10^{11}$ | R | 62 | M | 100 | 3 | 2 | 2 | PD | 4 (−) | 172.9 | Not Done |
| 500/3 | $10^{11}$ | C | 55 | M | 80 | 4 | 3 | 3 | PD | 12 (+) | 3.2 | 11.5 |
| 015/3 | $10^{11}$ | C | 58 | F | 80 | 3 | 4 | 3 | PD | 10 (−) | 2.0 | 2.4 |
| 016/3 | $10^{11}$ | C | 53 | F | 100 | 3 | 4 | 3 | PD | 6 (−) | 6.1 | 12.7 |
| 017/3* | $10^{11}$ | R | 52 | F | 90 | 3 | 2 | 3 | PD | 3 (−) | 204.8 | Not Done |
| 501/II | $10^{11}$ | R | 54 | M | 90 | 1 | 1 | 3 | PD | 12 (+) | 17.1 | 96.4 |
| 502/II | $10^{11}$ | C | 66 | F | 80 | 1 | 2 | 2 | PD | 3 (−) | 2549.5 | Not Done |
| 503/II | $10^{11}$ | Bl | 73 | M | 70 | 4 | 5 | 1 | PD | 0.25 (−) | Not Done | Not Done |
| 019/II | $10^{11}$ | C | 69 | M | 90 | 1 | 3 | 3 | PD | 12 (+) | 264.3 | 638.0 |
| 020/II^ | $10^{11}$ | C | 59 | M | 100 | 5 | 4 | 3 | SD | 12 (+) | 2.2 | 2.2 |
| 021/II^ | $10^{11}$ | C | 51 | F | 100 | 4 | 3 | 3 | PD | 12 (+) | 2.0 | 2.7 |
| 506/II | $10^{11}$ | C | 77 | F | 80 | 2 | 2 | 3 | PD | 3 (−) | 16.5 | 38.2 |
| 023/II | $10^{11}$ | C | 51 | F | 100 | 3 | 4 | 3 | PD | 4 (−) | 32.4 | 211.4 |
| 504/II | $10^{11}$ | C | 57 | M | 90 | 3 | 3 | 3 | PD | 12 (+) | 424.7 | 2073.6 |
| 507/II | $10^{11}$ | R | 58 | M | 90 | 2 | 2 | 3 | PD | 12 (+) | <0.5 | 0.6 |
| 508/II | $10^{11}$ | L | 67 | M | 100 | 2 | 0 | 3 | Unknown | 12 (+) | 109.2 | Not Done |
| 024/II | $10^{11}$ | C | 67 | M | 90 | 2 | 3 | 3 | PD | 12 (+) | 7.8 | 6.4 |
| 025/II | $10^{11}$ | C | 62 | F | 100 | 2 | 4 | 3 | PD | 7 (−) | 391.2 | Not Done |
| 026/II | $10^{11}$ | C | 53 | M | 100 | 3 | 2 | 2 | PD | 4 (−) | 4057.5 | 7859.1 (treatment #2) |
| 030/5 | $5 \times 10^{11}$ | C | 38 | M | 90 | 4 | 3 | 3 | PD | 8 (+) | 9.2 | 18.7 |
| 031/5 | $5 \times 10^{11}$ | R | 72 | F | 90 | 4 | 2 | 3 | SD | 7 (+) | 3.9 | 5.6 |
| 032/5 @ | $5 \times 10^{11}$ | R | 53 | M | 90 | 4 | 3 | 3 | PD | 6 (−) | 31.9 | 75.4 |
| 033/5 @ | $5 \times 10^{11}$ | R | 48 | F | 90 | >3 | 2 | 3 | PD | 5 (−) | 21.3 | 21.1 |
| 034/5 | $5 \times 10^{11}$ | C | 62 | M | 100 | 5 | 4 | 3 | PD | 6 (+) | 1.9 | 2.4 |
| 035/5 | $5 \times 10^{11}$ | C | 60 | F | 90 | 3 | 5 | 2 | PD | 2 (−) | 9.5 | Not Done |

Dx = diagnosis (Bl = bladder cancer; C = colon cancer; L = lung cancer; R = rectal cancer) KPS = Karnofsky Performance Status
*concurrent cetuximab; ^concurrent bevacizumab; @ concurrent panitumumab
++ Represents disease status at 9 weeks post-initiation of immunizations
PD = Progressive Disease; SD = Stable Disease
(+) Alive; (−) Dead at last follow-up; survival rounded off to nearest month These symptoms were also self-limiting and did not require intervention other than symptomatic measures such as acetaminophen.

Summary of Hematology, Chemistry, and ANA Values Pre and Post Treatment

Biological effects of ETBX-011 injections were monitored by recording blood hematology, chemistry, and antinuclear antibody (ANA) values of individual patients in case record forms (CRFs). Of 34 total patients entered into the trial, 28 received all three treatments with ETBX-011. For the 28 patients which received all three treatments, the blood hematology, chemistry, and ANA values at week 0 (prior to first treatment) were compared with those obtained at week 9 (three weeks after the third treatment). As shown in Table 4 below, there were no significant changes in chemistry or ANA values after treatments with ETBX-011. There was only one significant change in the blood hematology values. The basophil count was significantly (P=0.0403) lower at week 9 after treatments. However, this value remained in the normal range for basophil counts and, overall, there appeared to be no significant biological effects.

Clinical Outcomes

CEA levels at baseline and week 9 were assessed in patients. Among those with CEA levels available at baseline and follow-up, three (patients 010, 020, and 024) had no increase in CEA levels at the end of the immunization period while the remaining patients showed increased CEA levels. There were three patients with stable disease who remained so during the 9 week study period. All other patients experienced some level of progressive disease (Table 2). Of the seven patients in cohorts 1 and 2, there were five deaths and two patients remained alive at 12 months following the initiation of immunization. Of the 21 patients in cohort 3 and phase II, there were 10 deaths and all the remaining 11 patients were alive at 12 months, respectively. Of the six patients in cohort 5, there were three deaths and three patients were alive at 6, 7, and 8 months, respectively.

Of the 34 patients enrolled into the study, two patients received one treatment, four patients received two immunization treatments, and the remaining 28 patients received all three immunization treatments. All patients were followed for survival and Kaplan-Meier plots and survival proportions performed (PRISM software). Patient deaths were determined by information gathered from the social security death index (SSDI) database and clinical charts.

Figure 12:
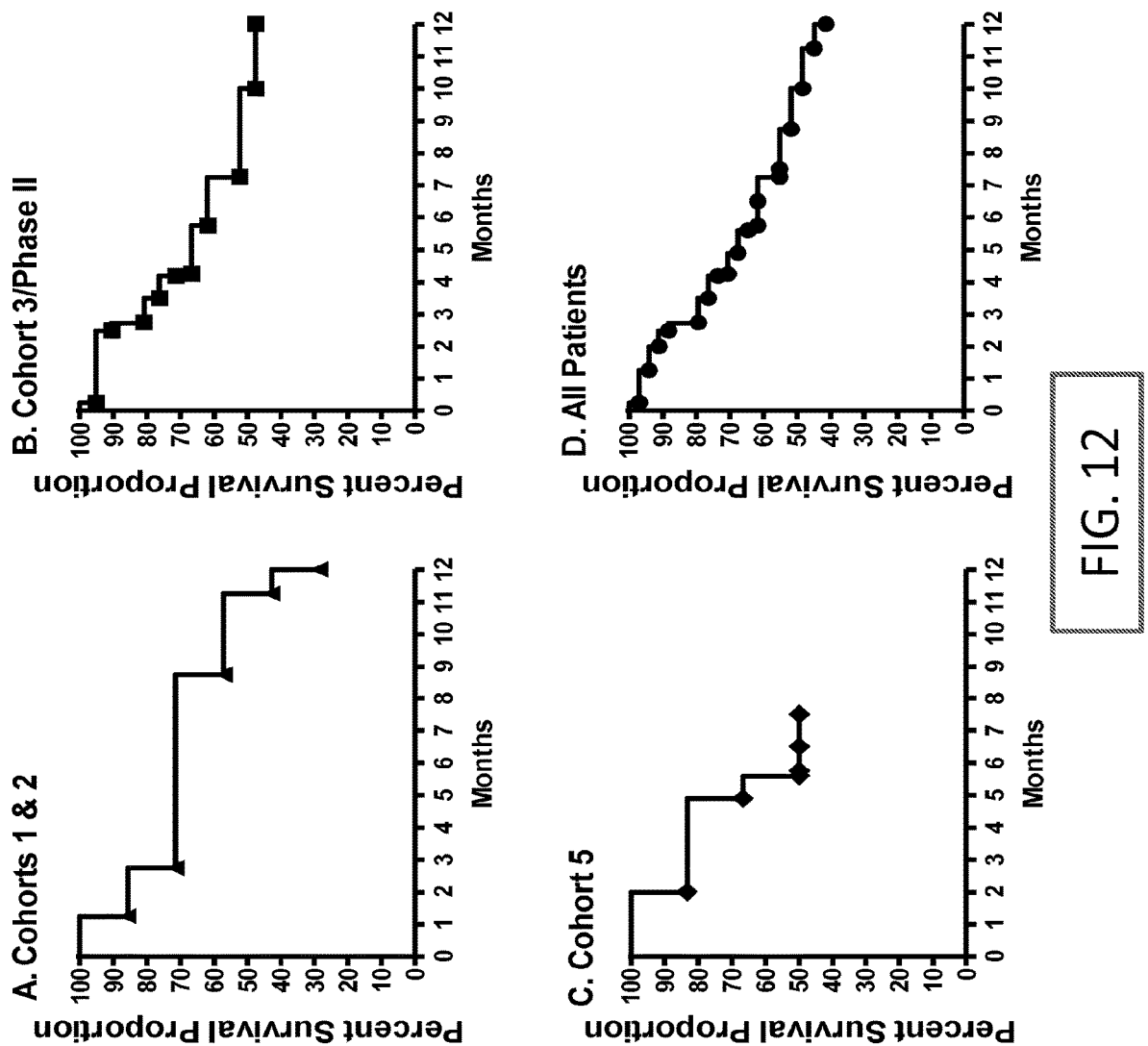
FIG. 12 demonstrates Kaplan-Meier survival plots of patients treated with Ad5 [E1-, E2b-]-CEA(6D). Patients treated with Ad5 [E1-, E2b-]-CEA(6D) were followed for survival. Panel A represents 7 patients in cohorts 1 and 2 that were followed for survival. There were 5 events in this group. Panel B represents 21 patients in cohort 3 and Ph II that were followed for survival. There were 11 events in this group. Panel C represents 6 patients in cohort 5 that were followed for survival. There were 3 events in this group. Panel D represents all 34 that were followed for survival. There were 19 events in this group.

The seven patients in cohorts 1 and 2 experienced a 12-month survival proportion of 29% (FIG. 12A). Of the patients in cohorts 1 and 2, patient 004 survived 11 months and received additional post-immunization treatments with bevacizumab, folfox, and xeloda. Patient 003 survived nine months and received irradiation treatment after ETBX-011 immunizations. Patient 005, alive at 12+ months, received irradiation treatment and entered another clinical trial after immunizations. Patient 010 survived up to 12 months and entered two clinical trials after immunizations. Patients 002, 007, and 008 received no further treatments after immunizations and survived 3, 1, and 12+ months, respectively.

The 21 patients in cohort 3 and phase II experienced a 12-month survival proportion of 48% (FIG. 12B). Of the patients in cohort 3 and phase II, one patient (017) received concurrent cetuximab during immunizations. Patients 020 and 021 received concurrent bevacizumab during immunizations. Patient 011 surviving over 12 months received radiation treatment after ETBX-011 immunizations. Patients 012 and 016 survived over 12 months and 6 months, respectively, and received additional chemotherapy treatment after immunizations. Patient 013 survived 4 months and received treatment with nexavar after immunizations. Patient 015 survived 10 months and received follow-on treatment with cetuximab. Patient 019 survived over 12 months and received treatment with bevacizumab and xeliri after protocol immunizations. Patient 020 survived over 12 months and received treatment with bevacizumab after immunizations. Patient 021 survived over 12 months and received follow-on treatment with bevacizumab and xeloda. Patient 500 survived over 12 months and received treatment with cetuximab and xeloda and entered a clinical trial after immunizations. Patient 501 survived over 12 months and received treatment with cetuximab and irinotecan after ETBX-011 immunizations. Patient 508 has survived over 12 months; however, we have been unable to obtain further data on the characteristics of this patient. Patients 017, 023, 024, 025, 026, 502, 504, 506, and 507 received no further treatment after immunizations and survived 3, 4, 12+, 7, 4, 3, 12+, 3, and 12+ months, respectively (+means still alive at the time of writing).

The six patients in cohort 5 experienced a 12-month survival proportion of 50% (FIG. 12C). Of the patients in this cohort, one patient (030) is currently alive at 8 months and received treatment with pazopanib and threshold 302 chemotherapy after ETBX-011 immunizations. Patient 031 is currently alive at 7 months and has not received further treatment after immunizations. Patient 032 received concurrent panitumumab, survived 6 months, and received treatment with folfox after immunizations. Patient 033 received concurrent panitumumab, survived 5 months with no additional therapy after immunizations. Patient 034 is currently alive at 6+ months and received radiation and treatment with xeloda after immunizations. Patient 035 received two treatments and survived 2 months.

Figure 13:
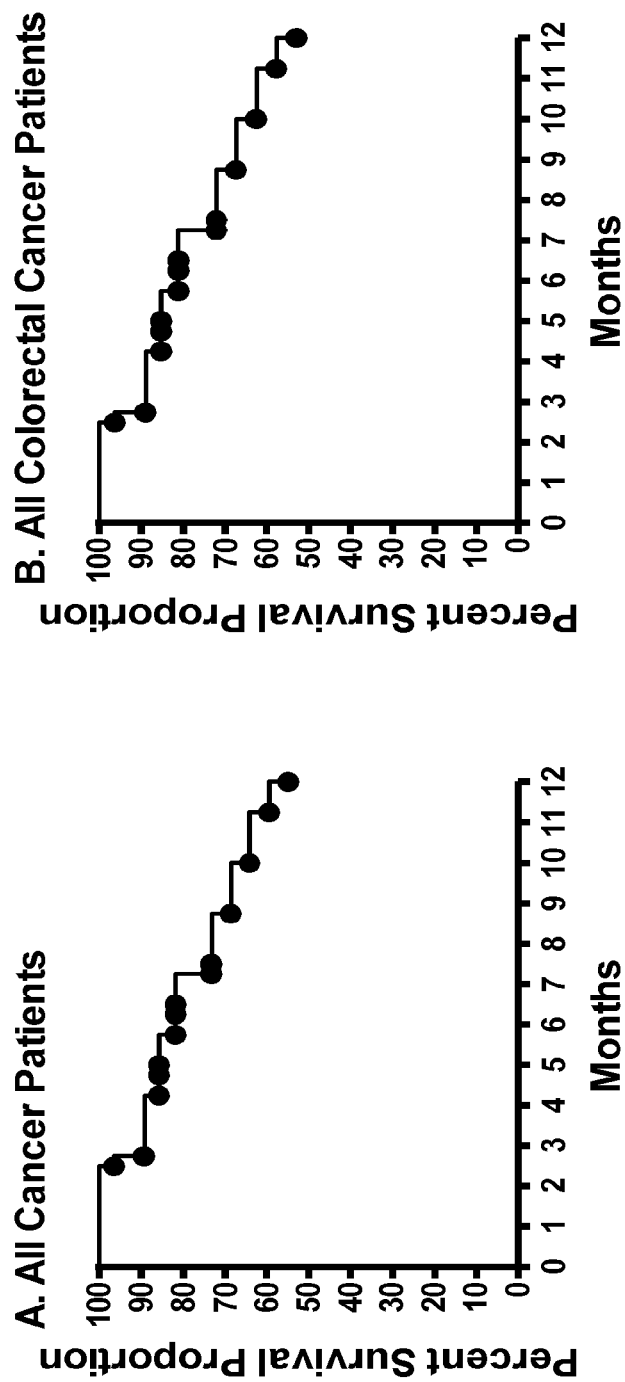
FIG. 13 demonstrates Kaplan-Meier survival plots of patients treated with Ad5 [E1-, E2b-]-CEA(6D). Patients treated three times with Ad5 [E1-, E2b-]-CEA(6D) were followed for survival. Panel A represents 28 patients that were followed for survival. There were 11 events in this group. Panel B represents 27 patients that were followed for survival. There were 11 events in this group.

With a median survival of 7.4 months, all 34 patients as a group (cohorts 1, 2, 3/phase II, and cohort 5) experienced a 12-month survival proportion of 41% (FIG. 12D). Of the 34 patients entered in to the study, 28 patients received the three immunization treatments and experienced a 12-month survival proportion of 55% (FIG. 13A) with a median survival of 10.625 months. For the colorectal adenocarcinoma patients, 27 patients received the three immunization treatments and experienced a 12-month survival proportion of 53% (FIG. 13B) with a median survival of 10.00 months.

Figure 14:
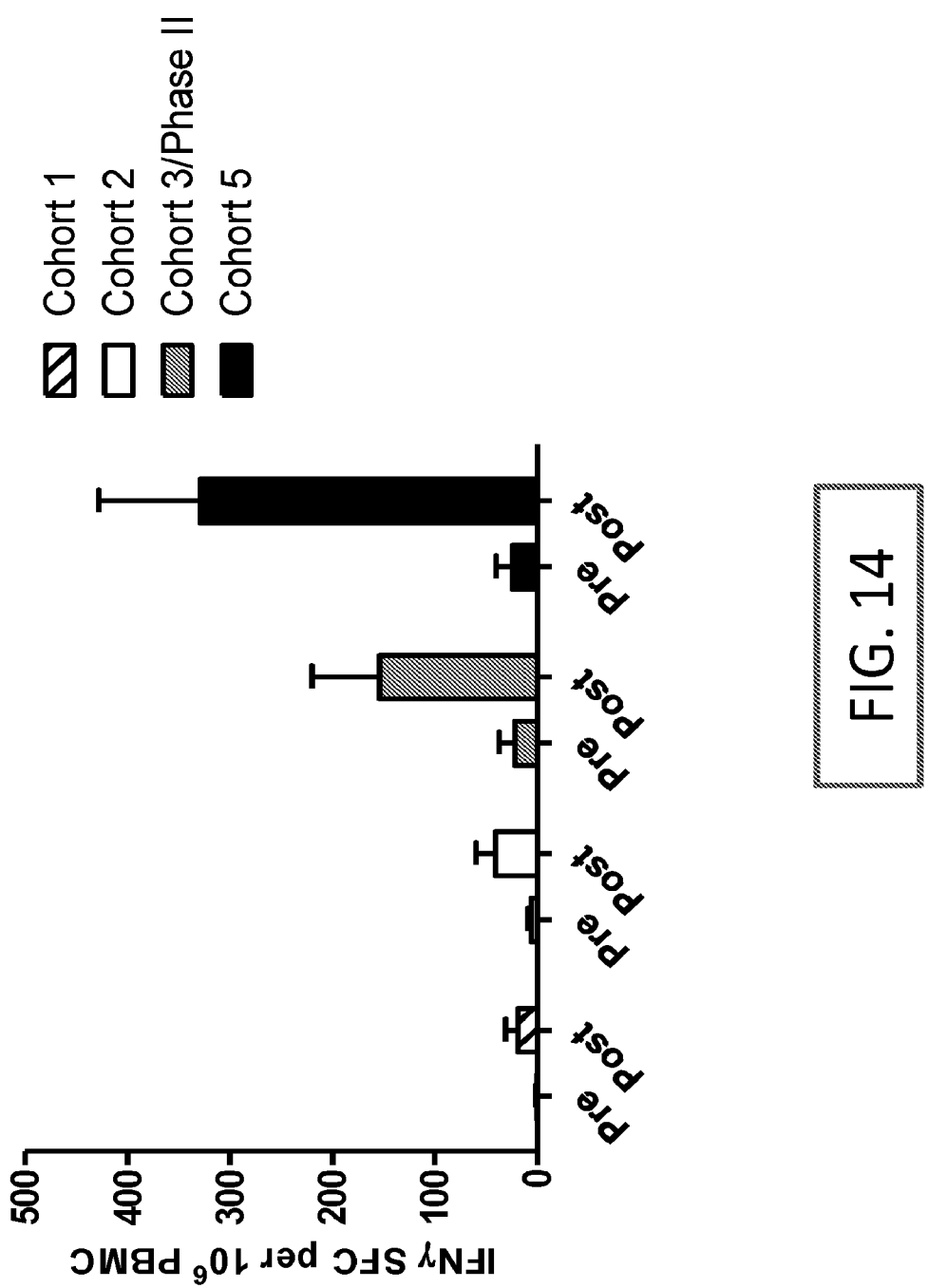
FIG. 14 demonstrates CEA-directed CMI responses in treated patients. CMI (IFN-γ secretion) was assessed at baseline (Pre) and after administrations of Ad5 [E1-, E2b-]-CEA(6D) (Post). The highest CMI responses (regardless of time point) observed in the patients after treatment revealed a dose response. The highest CMI levels occurred in patients that received the highest dose of $5\times10^{11}$ VP (Cohort 5). The CMI responses for Cohort 3/Phase II and Cohort 5 were significantly elevated (P=0.0002 and P=0.0317, respectively; Mann-Whitney test) as compared to their baseline (Pre) values. Specificity of the responses was demonstrated by the lack of reactivity with the irrelevant antigens β-galactosidase and HIV-gag (data not shown). For positive controls, PBMCs were exposed to concanavalin A (data not shown). Values=Mean±SEM for each Cohort.

Evaluation of Immune Parameters in Treated Metastatic Colorectal Cancer Patients A secondary objective was to evaluate CEA specific immune responses following immunization treatments with the product. As determined by ELISA, we observed no antibody activity directed against CEA. We assessed CMI responses in colorectal cancer patients treated in cohort 1, cohort 2, cohort 3/Phase II, and cohort 5. PBMCs were isolated prior to ETBX-011 treatment and after all treatments as well as three weeks following the last treatment from patients. CEA specific ELISpot assays were performed on PBMC as previously described (6) to determine the numbers of interferon gamma (IFN-γ) secreting lymphocytes after exposure to CEA peptides in vitro. We determined the highest CMI responses during immunizations, regardless of time point (weeks 3, 6, or 9) in the patients treated in cohort 1, cohort 2, cohort 3/Phase II, and cohort 5. As shown in FIG. 14, this analysis revealed a dose response to increasing levels of product. The highest CMI levels occurred in patients that received the highest dose of $5 \times 10^{11}$ VP (Cohort 5).

Determination of Induced CMI Responses to CEA.

Figure 15:
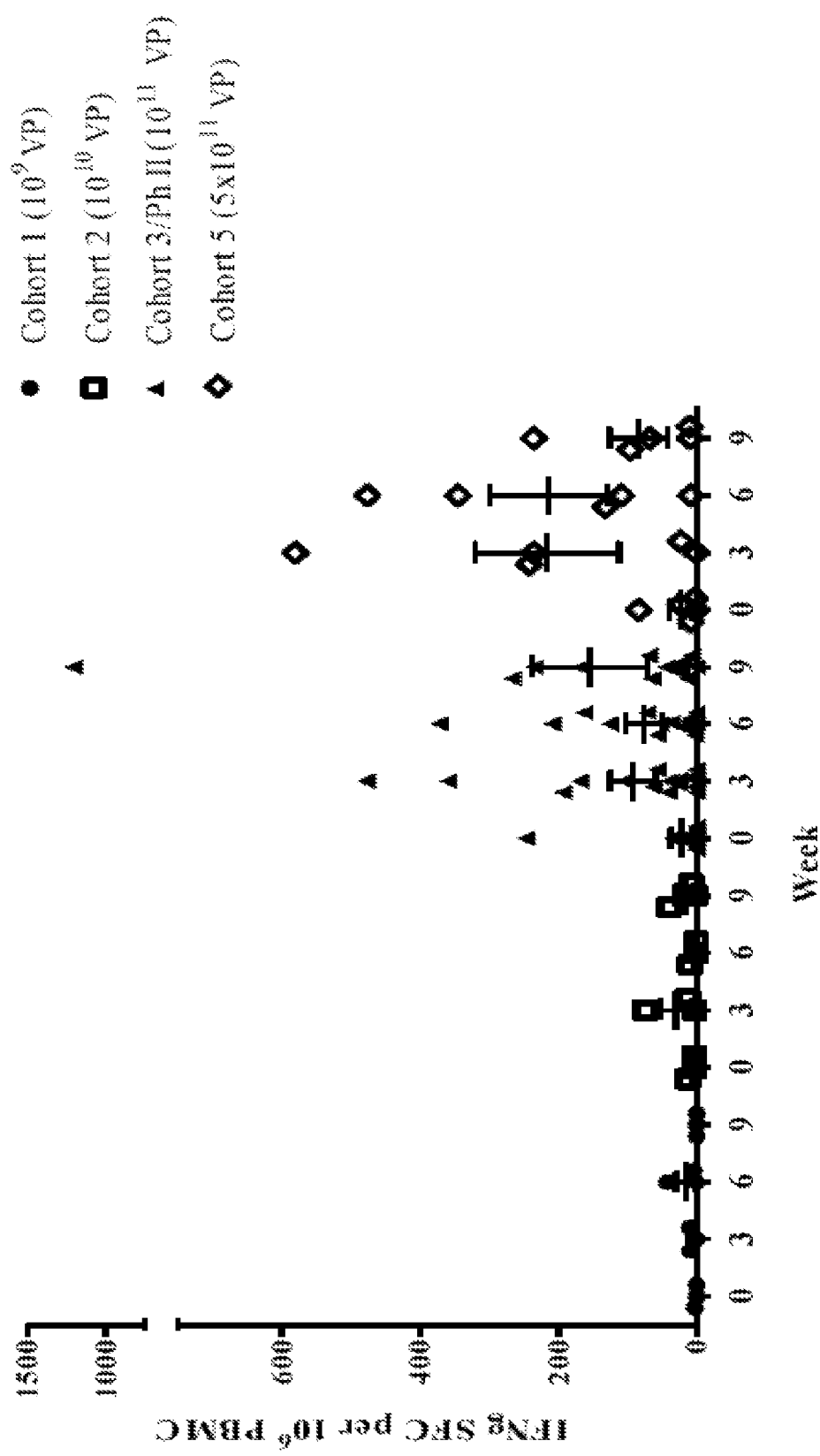
FIG. 15 demonstrates CEA directed CMI responses in treated patients. CMI (IFN-γ secretion) was assessed at baseline (week 0) and 3 weeks after the last immunotherapy (week 9) for patients in all 4-dose cohorts. A dose response was observed and the highest CMI level occurred in patients that received the highest dose. The CMI response with the highest dose was significantly elevated (P<0.02; Mann-Whitney test). Specificity of the responses was demonstrated by the lack of reactivity with the irrelevant antigens β-galactosidase and HIV-gag (data not shown). For positive controls, PBMCs were exposed to concanavalin A (data not shown). Horizontal line and error bar indicate the mean±SEM.

ELISpot analysis was performed on cryopreserved PBMC samples drawn before each immunization and after completion of the final immunization to assess CEA-specific CMI responses. We observed a dose response effect with the highest magnitude CEA-specific CMI responses occurring in patients who received the highest dose of Ad5 [E1-, E2b-]-CEA(6D) (FIG. 14). Of the doses received, 0/3 (0%) patients in cohort 1 exhibited positive CEA-directed CMI responses, 1/4 (25%) patients in cohort 2 exhibited positive CEA-directed CMI responses, 10/19 (53%) patients in cohort 3/phase II exhibited positive CEA-directed CMI responses, and 4/6 (67%) patients in cohort 5 exhibited positive CEA-directed CMI responses. The time course of induction of CEA-specific CMI (FIG. 15) demonstrated that there may be plateau in the magnitude of CEA CMI prior to the last dose. In the largest group of patients who received the same dose (cohort 3 plus phase II), we observed a significant increase over baseline in the average CEA-directed CMI responses at the 6 week evaluation (P<0.05, Mann-Whitney test), averaging 94 SFC/$10^6$ PBMC, which increased further by the 9 week evaluation (FIG. 15). One patient (patient ID 13) had a highly elevated baseline CEA-specific immune response (1100 SFC) and had elevated CMI at week six (2305 SFC) but did not return for 9-week evaluation and therefore, was not included in CEA CMI data analysis.

Figure 16:
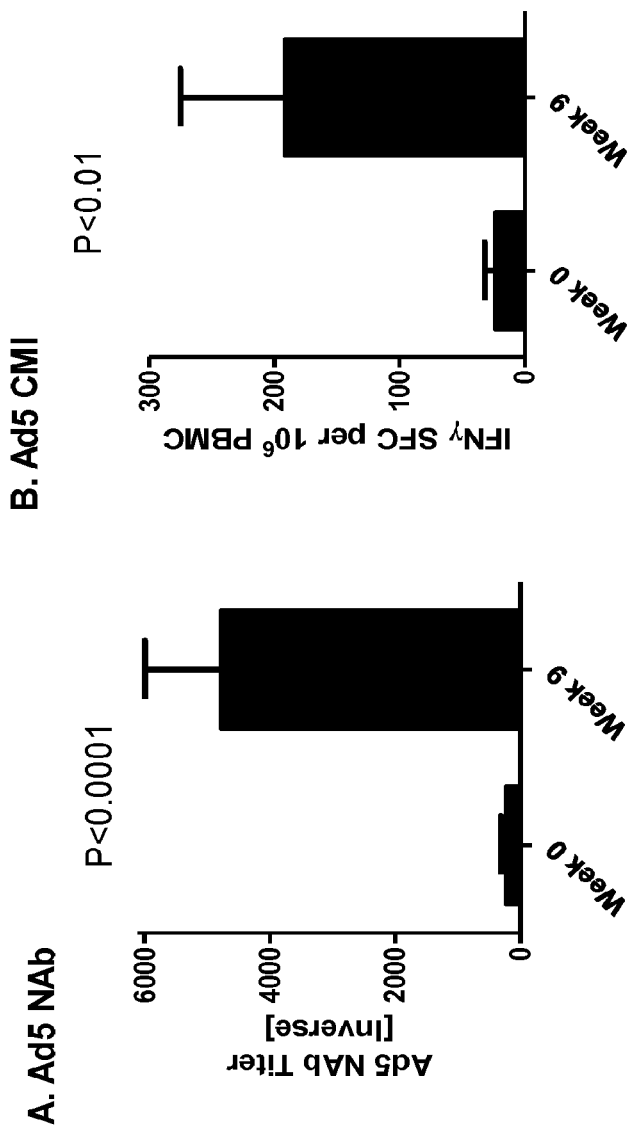
FIG. 16 demonstrates Ad5 immune responses in patients receiving immunizations with Ad5 [E1-, E2b-]-CEA(6D) vaccine. Ad5 NAb titers (A) and CMI responses (B) to Ad5 were determined in patients at baseline (week 0) and 3 weeks (week 9) after the third immunization. The number of IFN-γ secreting PBMCs from patients that were specific for Ad5 was determined by ELISpot. Both the Ad5 NAb titers and Ad5 CMI responses were significantly elevated at week 9 (P<0.0001 and P<0.01, respectively; Mann-Whitney test) Values=Mean±SEM.

We also measured Ad5 NAb and CMI against Ad5 and correlated it with CEA-specific CMI. Each patient had their serum and PBMC sample tested at baseline (prior to treatment) and at 9 weeks after completion of 3 treatments. Nineteen of 31 colorectal cancer patients (61%) tested in this study had Ad5 neutralizing activity in serum samples prior to the onset of treatment with ETBX-011. The mean pre-treatment Ad5 NAb titer value obtained among all patients was 1:189±1:71 SEM (geometric mean 1:21) and the mean pre-treatment Ad5 NAb titer among seropositive patients was 1:308±1:108 (geometric mean 1:146). Analysis of serum samples from patients who received 3 immunizations revealed Ad5 NAb titers that were significantly increased (P<0.0001, Mann-Whitney test) by week 9 (mean 1:4767±1:1225 SEM (geometric mean 1:1541) when compared with their respective baseline values (FIG. 16). Analysis of PBMC for CMI responses to Ad5 also revealed a significant increase (P<0.01, Mann-Whitney test) in Ad5 directed CMI responses after immunizations with ETBX-011 (FIG. 16).

Figure 17:
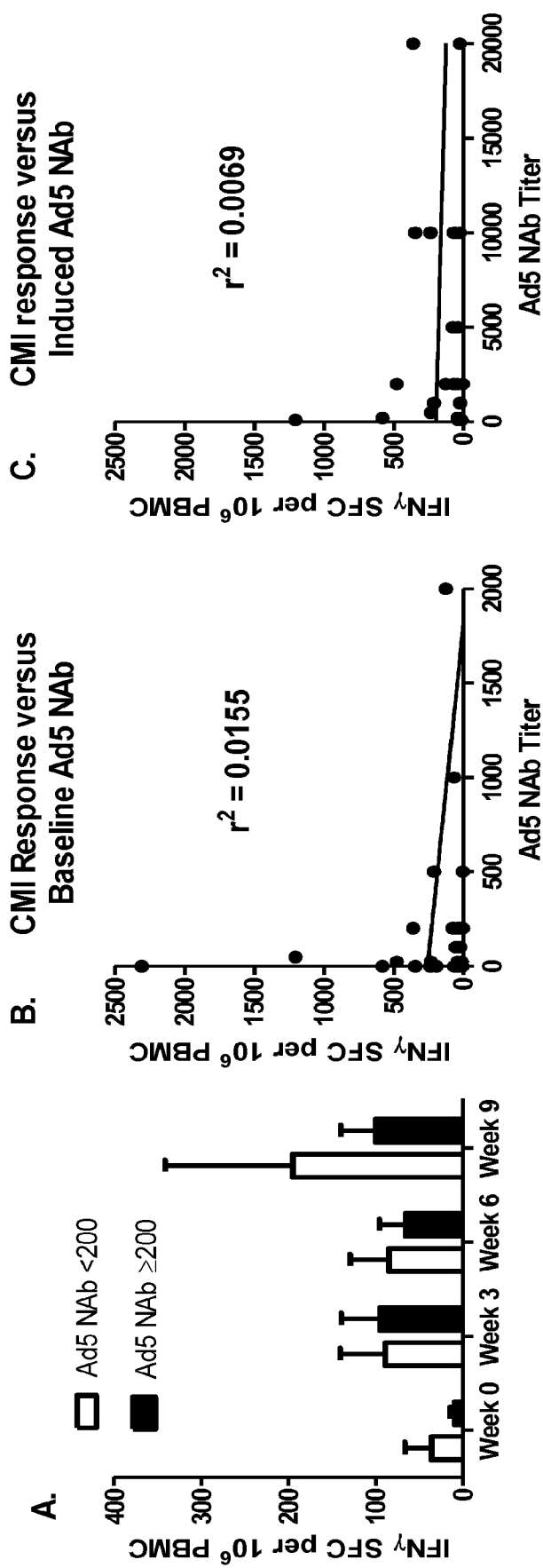
FIG. 17 demonstrates CEA-specific immunity in patients receiving immunizations with Ad5 [E1-, E2b-]-CEA(6D) vaccine and comparisons with Ad5 immunity. (A) The mean CEA specific immune responses in patients (n=19) who received $1\times10^{11}$VP of Ad5 [E1-, E2b-]-CEA(6D) as measured by IFN-γ secretion of PBMC in patients with none to low pre-existing Ad5 immunity (NAb<200, white bars) as compared to the CEA specific immune response of patients with high pre-existing Ad5 immunity (NAb titer ≥200, black bars) prior to the initiation of treatment with Ad5 [E1-, E2b-]-CEA(6D). There was no significant difference between the two groups at any time point tested (P>0.4, Mann-Whitney test) (Values=Mean±SEM). (B) Correlation between pre-existing Ad5 NAb activity and highest levels of induced CEA CMI responses. (C) Correlation between vector induced Ad5 NAb activity and CEA CMI responses. The $r^2$ values in B and C revealed no correlation between pre-existing or vector induced Ad5 NAb activity and CEA CMI ELISpot responses.

Comparison of week 9 CEA-directed CMI responses from patients with low baseline pre-existing Ad5 immunity (Ad5 NAb≥200) verses those with high baseline Ad5 immunity (Ad5 NAb>200) revealed no significant difference in immune responses (P>0.4, Mann Whitney test) (FIG. 17). Further, when the highest CEA specific CMI responses were compared with pre-existing or vector induced Ad5 NAb activity, there was no correlation between levels of CEA CMI and Ad5 NAb activity (FIG. 17). These data indicate that immunizations with ETBX-011 were not only able to overcome self-tolerance, but were also able to induce CEA-specific immune responses in colorectal cancer patients despite the presence of pre-existing and/or immunization induced Ad5 immunity. Together these clinical trial data support the advancement to a Phase III clinical trial with overall survival as the primary endpoint

DISCUSSION

Adenoviral vectors have significant potential for use as cancer therapeutic vaccines because of their propensity to induce robust adaptive immune responses specifically against transgene products in general. However, recombinant first generation Ad5 [E1-] vectors used in homologous prime/boost regimens have been greatly limited in their potential efficacy due to the presence of pre-existing Ad5 immunity as well as vector induced immunity. Specifically, Ad5-directed immunity mitigates immune responses to TAA that have been incorporated into earlier generation Ad5 [E1-] based platforms. The Ad5 [E1-, E2b-] platform utilized in the present study was intended to accommodate a homologous prime-boost regimen, by avoiding presentation of antigens that are the targets of pre-existing Ad5 immunity. Since CEA has been identified as one of the priority cancer antigens by the National Cancer Institute, we investigated this TAA as a transgene to be incorporated into the new Ad5 [E1-, E2b-] vector platform for use as a cancer therapeutic vaccine. CEA expression in adults is normally limited to low levels in the gastrointestinal epithelium, whereas, CEA is over-expressed in adenocarcinomas of the colon and rectum and in many breast, lung, and pancreas cancers. We chose the HLA A2 restricted CAP1(6D) modification of CEA because, compared with the wild type CAP1 epitope, CAP1 (6D) can enhance the sensitization of CTLs and has been included in our recent CEA-based vaccine constructs. Although we did not test for HLA type because we used full length CEA that is not HLA-restricted, A*0201 is the allele observed most frequently in Caucasians (allele frequency 0.2717) and is common in other populations. However, it is possible to test patients for HLA type and utilize the relationship between HLA type and clinical and/or CMI responses.

Previously, we tested multiple subcutaneous immunizations employing three administrations of a single dose level ($1 \times 10^{10}$ VP) of this class of Ad5 vaccine expressing the TAA CEA, (Ad5 [E1-, E2b-]-CEA(6D)) in a pre-clinical murine model of CEA expressing cancer. In mice with pre-existing Ad5 immunity, we demonstrated the induction of potent CEA directed CMI responses that resulted in anti-tumor activity and noted that these CMI and anti-tumor responses were significantly greater than those responses induced by a current generation Ad5 [E1-] based vector vaccine. We have also demonstrated in additional animal models (both cancer and infectious disease targeted) that multiple subcutaneous immunizations with vaccines based on the new Ad5 [E1-, E2b-] platform induce CMI responses that were superior to those of current generation Ad5 [E1-] based vaccines, can overcome the barrier of Ad5 immunity, and can be utilized in multiple immunization regimens requiring a generation of robust CMI responses. In our present report, the greatest magnitude of CEA-directed CMI responses occurred in patients receiving the highest dose of the vector. We observed that a CEA-directed CMI response was induced in a dose-responsive manner despite the presence of pre-existing and/or vector induced Ad5 immunity. No CEA directed antibody responses were observed either pre- or post-vaccination employing an ELISA technique. In a preliminary analysis (data not shown), we also observed a population of polyfunctional CD8+ T cells (those that secrete more than one cytokine when activated) after immunizations, a sign of greater functionality of T cells induced by the vaccine. These data support the use of the Ad5 [E1, E2b-]-CEA(6D) vector in homologous prime-boost regimens designed to induce and increase CEA-directed CMI responses in patients with advanced colorectal adenocarcinoma, as well as any number of other vaccine amenable diseases or applications.

We believe there are factors that contribute to the favorable activity of this new platform. As compared to earlier generation Ad5 [E1-] vectors containing deletion in the early 1 (E1) gene region, the Ad5 [E1-, E2b-] vector platform with additional deletions in the early 2b (E2b) gene region exhibits significantly reduced inflammatory responses directed at the vector. This can result in longer transgene expression and a reduction in elimination of transgene expressing cells (e.g., antigen presenting cells) that would otherwise occur due to induced inflammatory responses. Since Ad5 late gene antigen expression is significantly reduced as compared to earlier generation Ad5 platforms, this could enable the Ad5 [E1-, E2b-] platform to evade Ad5 immune mediated neutralizing activity for significantly longer periods of time resulting in greater longevity and amplification of TAA expression. In addition, a E2b gene product, a polymerase, is a known target of human cellular memory immune responses to Ad5 infection and its elimination from the vaccine could be furthering its capability in the setting of pre-existing Ad5 immunity. Without being bound by theory, the extended and/or greater expression of TAA by the vector in this milieu could result in a more effective immune response against the target antigen. However, it is also possible that this vector configuration produces better transgene expression, different biodistribution, or different innate/adaptive immune effects that impact the effectiveness of this vector, rather than escape from pre-existing immunity.

Of interest is the observation that treated patients in our study exhibited favorable survival probability. Overall, all 25 patients treated at least 2 times with Ad5 [E1-, E2b-]-CEA(6D) exhibited a 12-month survival probability of 48% and this was achieved despite the presence of significant levels of pre-existing Ad5 neutralizing antibody titers.

In other clinical trials, immunotherapeutic agents have been found to increase overall survival without having a direct impact on time to objective disease progression, a trend noted in our study as well. Without being bound by theory, by engaging the patient's immune system, active immunotherapeutics, such as Ad5 [E1-, E2b-]-CEA(6D), could induce continuous immunologic anti-tumor responses over a long period of time that could result in a "deceleration" or alteration in specific aspects of the rapid growth rate or spread of the tumor not measured by standard response assessments. Indeed, we have observed slower tumor progression in Ad5 immune mice harboring established CEA-expressing tumors following treatment with Ad5 [E1-, E2b-]-CEA(6D). Moreover, it has been noted that overall survival might be the only true parameter for determination of clinical efficacy of any potential cancer (immune) therapy.

As with any new treatment modality, safety is an important factor. In this Phase I/II trial, we demonstrated that the Ad5 [E1-, E2b-]-CEA(6D) could be manufactured to scale, as well be easily and repeatedly administered by conventional subcutaneous injection techniques. The most common adverse effects were site of injection reactions and flu-like symptoms consisting of fever, chills, headache, and nausea. There was no impact on blood hematology or serum chemistries and, overall, the treatments were well tolerated. Specifically, no SAE were noted, and no treatments were stopped due to adverse events, indicating that a dose limitation to use of Ad5 [E1-, E2b-]-CEA(6D) in this clinical application had not been met.

These data suggest that patients with advanced colorectal cancer which are treated with Ad5 [E1-, E2b-]-CEA(6D) do not have serious adverse effects and may experience extension of life even if they have pre-existing immunity to Ad5. The results of this trial are encouraging enough to advance to a large, randomized, single agent trial. The observation that some of the patients experienced an increase of CMI which is dose dependent, could be an indication that this may play a role in their clinical outcome.

TABLE 3

Adverse Events

| Adverse Events | # Of Events | Unrelated/ Unlikely | Possible | Probably/ Definite | *Grade (G1, G2, or G3) | % Incidence (Based on 94 treatments) |
|---|---|---|---|---|---|---|
| Injection Site Reaction | 21 | | | 21 | G1(19); G2 (2) | 22.3 |
| Pain (all types) | 17 | 17 | | | G1 (8); G2 (7); G3 (2) | 18.1 |
| Fever | 10 | 4 | 2 | 4 | G1 (7); G2 (3) | 10.6 |
| Flu-like symptoms | 10 | 3 | 5 | 2 | G1 (9); G2 (1) | 10.6 |
| Fatigue | 8 | 6 | 2 | | G1 (5); G2 (2); G3 (1) | 8.5 |
| Shortness of Breath | 6 | 6 | | | G1 (3); G2 (3) | 6.4 |
| Anorexia | 5 | 4 | 1 | | G1 (3); G2 (2) | 5.3 |
| Chills | 5 | 1 | 1 | 3 | G1 (5) | 5.3 |
| Nausea | 5 | 4 | 1 | | G1 (5) | 5.3 |
| Constipation | 5 | 5 | | | G1 (3); G2 (2) | 5.3 |
| Edema | 5 | 5 | | | G1 (3); G2 (2) | 5.3 |
| Vomiting | 4 | 4 | | | G1 (4) | 4.3 |
| Hypertension | 3 | 3 | | | G1 (2); G2 (1) | 3.2 |
| Anemia | 3 | 3 | | | G1 (1); G2 (1); G3 (1) | 3.2 |
| Cough | 2 | 2 | | | G1 (2) | 2.1 |
| Depression | 2 | 2 | | | G1 (2) | 2.1 |
| Diarrhea | 2 | 2 | | | G1 (2) | 2.1 |
| Headache | 2 | 1 | 1 | | G1 (2) | 2.1 |
| Hypoalbuminemia | 2 | 2 | | | G1(1); G2 (1) | 2.1 |
| Hypokalemia | 2 | 2 | | | G1 (1); G2 (1) | 2.1 |
| Pleural Effusion | 2 | 2 | | | G2 (1); G3 (1) | 2.1 |
| Alkaline Phosphatase Increase | 2 | 2 | | | G1(1); G3 (1) | 2.1 |
| Myalgia | 2 | | 2 | | G1 (2) | 2.1 |
| Night Sweats | 2 | 2 | | | G1 (1); G2 (1) | 2.1 |
| Sleep | 2 | 2 | | | G1 (2) | 2.1 |
| Low Magnesium | 2 | 2 | | | G1 (2) | 2.1 |
| Abdominal Bloating | 1 | 1 | | | G1 (1) | 1.1 |
| Abdominal Distention | 1 | 1 | | | G3 (1) | 1.1 |
| Abdominal Swelling | 1 | 1 | | | G2 (1) | 1.1 |
| Abdominal Wound | 1 | 1 | | | G2 (1) | 1.1 |

TABLE 3-continued

Adverse Events

| Adverse Events | # Of Events | Unrelated/ Unlikely | Possible | Probably/ Definite | *Grade (G1, G2, or G3) | % Incidence (Based on 94 treatments) |
|---|---|---|---|---|---|---|
| ALT Increase | 1 | 1 | | | G1 (1) | 1.1 |
| AST Increase | 1 | 1 | | | G2 (1) | 1.1 |
| Biliary Obstruction | 1 | 1 | | | G3 (1) | 1.1 |
| Bowel Obstruction | 1 | 1 | | | G3 (1) | 1.1 |
| Cold | 1 | 1 | | | G1 (1) | 1.1 |
| Dyspnea | 1 | 1 | | | G3 (1) | 1.1 |
| Dysuria | 1 | 1 | | | G1 (1) | 1.1 |
| Frequent Urination | 1 | 1 | | | G1 (1) | 1.1 |
| GI Disorder | 1 | 1 | | | G3 (1) | 1.1 |
| Extra Pyramidial Movements | 1 | 1 | | | G1 (1) | 1.1 |
| Insomnia | 1 | 1 | | | G1 (1) | 1.1 |
| Herpes Simplex | 1 | 1 | | | G1 (1) | 1.1 |
| Hypotension | 1 | 1 | | | G1 (1) | 1.1 |
| Loss of Appetite | 1 | 1 | | | G1 (1) | 1.1 |
| Low White Blood Cells | 1 | 1 | | | G1 (1) | 1.1 |
| Numbness/Sensation in Fingertips | 1 | 1 | | | G1 (1) | 1.1 |
| Onset of Menses | 1 | 1 | | | G1 (1) | 1.1 |
| Poor Quality Sleep | 1 | 1 | | | G1 (1) | 1.1 |
| Presyncope | 1 | 1 | | | G2 (1) | 1.1 |
| Pruritis | 1 | 1 | | | G1 (1) | 1.1 |
| Rash-Right Lower Eye Lid | 1 | 1 | | | G1 (1) | 1.1 |
| Red/Swelling Right Upper Eyelid | 1 | 1 | | | G1 (1) | 1.1 |
| Renal Calculi | 1 | 1 | | | G2 (1) | 1.1 |
| Runny Nose | 1 | | 1 | | G1 (1) | 1.1 |
| Shallow Breathing | 1 | 1 | | | G1 (1) | 1.1 |
| Skin Rash | 1 | 1 | | | G1 (1) | 1.1 |
| Vaginal Discharge | 1 | 1 | | | G1 (1) | 1.1 |
| Concentration | 1 | | | | G1 (1) | 1.1 |
| Weight Loss | 1 | 1 | | | G2 (1) | 1.1 |
| Arthritis Joint inflammation | 1 | 1 | | | G1 (1) | 1.1 |
| Flushing | 1 | | 1 | | G1 (1) | 1.1 |
| Acute Renal Failure | Disease progression | | | | G3 (1) | 1.1 |

*Parenthesis ( ) indicates numbers of events.

TABLE 4

Hematology, Chemistry, and ANA values

| | Week 0 value (Mean ± SEM) | Week 9 value (Mean ± SEM) |
|---|---|---|
| Hematology Test | | |
| Hgb (g/dL) | 13.09 ± 0.313 | 12.48 ± 0.413 |
| Hct (%) | 39.63 ± 0.875 | 37.92 ± 1.140 |
| Plts (×109/L) | 225.1 ± 20.76 | 247.3 ± 23.57 |
| WBC (×103/mm3) | 6.81 ± 0.532 | 8.21 ± 0.741 |
| Neutrophils (%) | 64.46 ± 2.068 | 67.28 ± 3.268 |
| Lymphocytes (%) | 23.23 ± 1.874 | 18.34 ± 2.071 |
| Monocytes (%) | 8.86 ± 0.462 | 7.68 ± 0.569 |
| Eosinophils (%) | 3.97 ± 0.677 | 3.16 ± 0.685 |
| Basophils (%) | 0.52 ± 0.056 | 0.38 ± 0.048 |
| Chemistry Test | | |
| Na (mEq/L) | 139.2 ± 0.424 | 137.9 ± 0.718 |
| K (mEq/L) | 3.90 ± 0.085 | 3.80 ± 0.073 |
| Cl (mEq/L) | 105.0 ± 0.561 | 103.3 ± 1.061 |
| CO2 (mEq/L) | 27.8 ± 0.374 | 27.63 ± 0.458 |
| BUN (mg/dL) | 17.0 ± 1.136 | 17.1 ± 1.611 |
| Creatinine (mg/dL) | 0.81 ± 0.046 | 0.86 ± 0.054 |
| Glucose (mg/dL) | 121.8 ± 7.458 | 123.5 ± 7.885 |
| Ca (mg/dL) | 8.84 ± 0.075 | 8.87 ± 0.073 |
| Total protein (g/dL) | 6.95 ± 0.078 | 6.67 ± 0.100 |
| Albumin (g/dL) | 3.78 ± 0.085 | 3.62 ± 0.113 |
| AST (U/L) | 31.71 ± 3.846 | 31.88 ± 3.506 |
| ALT (U/L) | 27.83 ± 4.228 | 25.67 ± 3.414 |
| Alkaline phosphatase (U/L) | 107.0 ± 13.30 | 124.0 ± 17.40 |
| Bilirubin (mg/dL) | 0.78 ± 0.071 | 0.75 ± 0.079 |
| *ANA Test* | | |
| Titer | 103.3 ± 51.04 | 123.3 ± 50.56 |

*Values represent inverse of the titer and are from patients with positive values.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A composition comprising a single dose of a pharmaceutical composition comprising from $1 \times 10^9$ to $5 \times 10^{11}$ viral particles of a replication-defective vector comprising a nucleic acid sequence encoding an amino acid sequence according to SEQ ID NO:5.

2. The composition of claim 1, wherein the replication-defective vector is a replication-defective adenoviral vector.

3. The composition of claim 2, wherein the replication-defective adenoviral vector has a deletion in an early 2b (E2b) gene region.

4. The composition of claim 3, wherein the replication-defective adenoviral vector further comprises a deletion in an early 1 (E1) gene region, a deletion in an early 3 (E3) gene region, a deletion in an early 4 (E4) gene region, or a combination thereof.

5. The composition of claim 1, wherein the single dose of the pharmaceutical composition comprises a dose of at least $10^9$ replication-defective viral particles.

6. The composition of claim 1, wherein the single dose of the pharmaceutical composition comprises a dose of at least $10^{11}$ replication-defective viral particles.

7. The composition of claim 1, further comprising an additional composition.

8. The composition of claim 7, wherein the additional composition comprises an immunostimulant.

9. The composition of claim 7, wherein the additional composition comprises a vector encoding an antigen selected from p53, HPV E6, HPV E7, MAGE-A1, MAGE-A2, MAGE-A3, MAGE-A4, MAGE-A6, MAGE-A10, MAGE-A12, BAGE, DAM-6, -10, GAGE-1, -2, -8, GAGE-3, -4, -5, -6, -7B, NA88-A, NY-ESO-1, MART-1, MC1R, Gp100, PSA, PSM, Tyrosinase, TRP-1, TRP-2, ART-4, CAMEL, Cyp-B, Her2/neu, hTERT, hTRT, iCE, MUC1, MUC2, PRAME, P15, RU1, RU2, SART-1, SART-3, WT1, AFP, 13-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mber-abl, ETV6/AML, LDLR/FUT, Pml/RARa, TEL/AML1, or any combination thereof.

10. The composition of claim 7, wherein the additional composition further comprises a vector encoding an antigen selected from HPV E6, HPV E7, Her2/neu, MUC1, PSA, PSM, or any combination thereof.

11. The composition of claim 1, wherein the pharmaceutical composition is formulated as an aerosol for delivery by intranasal spray or inhalation, as a powder for preparation of solutions or dispersions, in a pill for oral deliver, in a suppository for vaginal or rectal delivery, or in a polytetrafluoroethylene support matrix for transmucosal delivery.

12. The composition of claim 11, wherein the solutions or dispersions are injectable by parenteral delivery via intravenous injection, intraperitoneal injection, subcutaneous injection, or intramuscular injection.

13. The composition of claim 1, wherein the replication-defective vector is encapsulated in a lipid particle, a liposome, a vesicle, a nanosphere, or a nanoparticle.

14. The composition of claim 1, wherein the replication-defective vector is covalently or non-covalently bound to a lipid particle, a liposome, a vesicle, a nanosphere, or a nanoparticle.

15. The composition of claim 1, wherein the pharmaceutical composition comprises a dose of replication-defective vectors capable of promoting a target antigen immune response.

16. The composition of claim 1, wherein the pharmaceutical composition comprises a dose of replication-defective vectors sufficient to provide a therapeutic benefit, a prophylactic benefit, or a combination thereof.

17. The composition of claim 7, wherein the additional composition further comprises chemotherapy or a dose of radiation.

18. The composition of claim 17, wherein the chemotherapy comprises fluoropyrimidine, irinotecan, oxaliplatin, bevacizunab, Capecitabine, Mitomycin, Regorafenib, cetuxinab, panitumumab, acetinophen, or any combination thereof.

* * * * *

SEQUENCE LISTING

<160> NUMBER OF SEQ ID NOS: 6

<210> SEQ ID NO 1
<211> LENGTH: 2109
<212> TYPE: DNA
<213> ORGANISM: Homo sapiens

<400> SEQUENCE: 1

```
atggagtctc cctcggcccc tccccacaga tggtgcatcc cctggcagag gctcctgctc      60
acagcctcac ttctaacctt ctggaacccg cccaccactg ccaagctcac tattgaatcc     120
acgccgttca atgtcgcaga ggggaaggag gtgcttctac ttgtccacaa tctgccccag     180
catcttttg gctacagctg gtacaaaggt gaaagagtgg atggcaaccg tcaaattata      240
ggatatgtaa taggaactca acaagctacc ccagggcccg catacagtgg tcgagagata     300
atataccca atgcatccct gctgatccag aacatcatcc agaatgacac aggattctac     360
accctacacg tcataaagtc agatcttgtg aatgaagaag caactggcca gttccggta     420
tacccggagc tgcccaagcc ctccatctcc agcaacaact ccaaacccgt ggaggacaag     480
gatgctgtgg ccttcacctg tgaacctgag actcaggacg caacctacct gtggtgggta     540
aacaatcaga gcctcccggt cagtcccagg ctgcagctgt ccaatggcaa caggaccctc     600
actctattca atgtcacaag aaatgacaca gcaagctaca atgtgaaaac cagaacccca     660
gtgagtgcca ggcgcagtga ttcagtcatc ctgaatgtcc tctatggccc ggatgccccc     720
accatttccc ctctaaacac atcttacaga tcaggggaaa atctgaacct ctcctgccac     780
gcagcctcta ccacctgc acagtactct tggtttgtca atgggacttt ccagcaatcc     840
acccaagagc tctttatccc caacatcact gtgaataata gtggatccta cgtgccaa      900
gcccataact cagacactgg cctcaatagg accacagtca cgacgatcac agtctatgca     960
gagccaccca aaccttcat caccagcaac aactccaacc ccgtggagga tgaggatgct    1020
gtagccttaa cctgtgaacc tgagattcag aacacaacct acctgtggtg ggtaaataat    1080
cagagcctcc cggtcagtcc caggctgcag ctgtccaatg caacaggac cctcactcta    1140
ctcagtgtca caaggaatga tgtaggaccc tatgagtgtg aatccagaa cgaattaagt    1200
gttgaccaca gcgacccagt catcctgaat gtcctctatg gcccagacga ccccaccatt    1260
tcccctcat acacctatta ccgtccaggg gtgaacctca gcctctcctg ccatgcagcc    1320
tctaacccac ctgcacagta ttcttggctg attgatggga acatccagca acacacacaa    1380
gagctcttta tctccaacat cactgagaag acagcggac tctataccctg ccaggccaat    1440
aactcagcca gtggccacag caggactaca gtcaagacaa tcacagtctc tgcggagctg    1500
cccaagccct ccatctccag caacaactcc aaacccgtgg aggacaagga tgctgtggcc    1560
ttcacctgtg aacctgaggc tcagaacaca acctacctgt ggtgggtaaa tggtcagagc    1620
ctcccagtca gtcccaggct gcagctgtcc aatggcaaca ggaccctcac tctattcaat    1680
gtcacaagaa atgacgcaag agcctatgta tgtggaatcc agaactcagt gagtgcaaac    1740
cgcagtgacc cagtcacccc tggatgtcct catgggccgg acaccccat catttccccc    1800
ccagactcgt cttacctttc gggagcgaac ctcaacctct cctgccactc ggcctctaac    1860
ccatccccgc agtattcttg gcgtatcaat gggataccgc agcaacacac acaagttctc    1920
tttatcgcca aaatcacgcc aaataataac gggacctatg cctgttttgt ctctaacttg    1980
```

| | | | | |
|---|---|---|---|---|
| gctactggcc | gcaataattc | catagtcaag | agcatcacag | tctctgcatc | tggaacttct | 2040 |
| cctggtctct | cagctggggc | cactgtcggc | atcatgattg | gagtgctggt | tggggttgct | 2100 |
| ctgatatag | | | | | 2109 |

<210> SEQ ID NO 2
<211> LENGTH: 2109
<212> TYPE: DNA
<213> ORGANISM: Homo sapiens

<400> SEQUENCE: 2

| | | | | | |
|---|---|---|---|---|---|---|
| atggagtctc | cctcggcccc | tccccacaga | tggtgcatcc | cctggcagag | gctcctgctc | 60 |
| acagcctcac | ttctaacctt | ctggaacccg | cccaccactg | ccaagctcac | tattgaatcc | 120 |
| acgccgttca | atgtcgcaga | ggggaaggag | gtgcttctac | ttgtccacaa | tctgccccag | 180 |
| catcttttg | gctacagctg | gtacaaaggt | gaaagagtgg | atggcaaccg | tcaaattata | 240 |
| ggatatgtaa | taggaactca | acaagctacc | ccagggcccg | catacagtgg | tcgagagata | 300 |
| atataccccca | atgcatccct | gctgatccag | aacatcatcc | agaatgacac | aggattctac | 360 |
| accctacacg | tcataaagtc | agatcttgtg | aatgaagaag | caactggcca | gttccgggta | 420 |
| tacccggagc | tgcccaagcc | ctccatctcc | agcaacaact | ccaaacccgt | ggaggacaag | 480 |
| gatgctgtgg | ccttcacctg | tgaacctgag | actcaggacg | caacctacct | gtggtgggta | 540 |
| aacaatcaga | gcctcccggt | cagtcccagg | ctgcagctgt | ccaatggcaa | caggaccctc | 600 |
| actctattca | atgtcacaag | aaatgacaca | gcaagctaca | atgtgaaac | ccagaaccca | 660 |
| gtgagtgcca | ggcgcagtga | ttcagtcatc | ctgaatgtcc | tctatggccc | ggatgccccc | 720 |
| accatttccc | ctctaaacac | atcttacaga | tcaggggaaa | atctgaacct | ctcctgccac | 780 |
| gcagcctcta | acccacctgc | acagtactct | tggtttgtca | atgggacttt | ccagcaatcc | 840 |
| acccaagagc | tctttatccc | caacatcact | gtgaataata | gtggatccta | acgtgccaa | 900 |
| gcccataact | cagacactgg | cctcaatagg | accacagtca | cgacgatcac | agtctatgca | 960 |
| gagccaccca | aacccttcat | caccagcaac | aactccaacc | ccgtggagga | tgaggatgct | 1020 |
| gtagccttaa | cctgtgaacc | tgagattcag | aacacaacct | acctgtggtg | ggtaaataat | 1080 |
| cagagcctcc | cggtcagtcc | caggctgcag | ctgtccaatg | acaacaggac | cctcactcta | 1140 |
| ctcagtgtca | caaggaatga | tgtaggaccc | tatgagtgtg | aatccagaa | cgaattaagt | 1200 |
| gttgaccaca | gcgacccagt | catcctgaat | gtcctctatg | gcccagacga | ccccaccatt | 1260 |
| tcccctcat | acacctatta | ccgtccaggg | gtgaacctca | gcctctcctg | ccatgcagcc | 1320 |
| tctaacccac | ctgcacagta | ttcttggctg | attgatggga | acatccagca | acacacacaa | 1380 |
| gagctcttta | tctccaacat | cactgagaag | aacagcggac | tctatacctg | ccaggccaat | 1440 |
| aactcagcca | gtggccacag | caggactaca | gtcaagacaa | tcacagtctc | tgcggagctg | 1500 |
| cccaagccct | ccatctccag | caacaactcc | aaacccgtgg | aggacaagga | tgctgtggcc | 1560 |
| ttcacctgtg | aacctgaggc | tcagaacaca | acctacctgt | ggtgggtaaa | tggtcagagc | 1620 |
| ctcccagtca | gtcccaggct | gcagctgtcc | aatggcaaca | ggaccctcac | tctattcaat | 1680 |
| gtcacaagaa | atgacgcaag | agcctatgta | tgtggaatcc | agaactcagt | gagtgcaaac | 1740 |
| cgcagtgacc | cagtcacccct | ggatgtcctc | tatgggccgg | acacccccat | catttccccc | 1800 |
| ccagactcgt | cttaccttc | gggagcgaac | ctcaacctct | cctgccactc | ggcctctaac | 1860 |
| ccatccccgc | agtattcttg | gcgtatcaat | gggataccgc | agcaacacac | acaagttctc | 1920 |
| tttatcgcca | aaatcacgcc | aaataataac | gggacctatg | cctgttttgt | ctctaacttg | 1980 |

| | |
|---|---|
| gctactggcc gcaataattc catagtcaag agcatcacag tctctgcatc tggaacttct | 2040 |
| cctggtctct cagctggggc cactgtcggc atcatgattg agtgctggt tggggttgct | 2100 |
| ctgatatag | 2109 |

<210> SEQ ID NO 3
<211> LENGTH: 32315
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| catcatcaat aatatacctt attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tactgtaata gtaatcaatt | 360 |
| acggggtcat tagttcatag cccatatatg gagttccgcg ttacataact tacggtaaat | 420 |
| ggcccgcctg gctgaccgcc caacgacccc cgcccattga cgtcaataat gacgtatgtt | 480 |
| cccatagtaa cgccaatagg gactttccat tgacgtcaat gggtggagta tttacggtaa | 540 |
| actgcccact tggcagtaca tcaagtgtat catatgccaa gtacgccccc tattgacgtc | 600 |
| aatgacggta aatggcccgc ctggcattat gcccagtaca tgaccttatg gactttcct | 660 |
| acttggcagt acatctacgt attagtcatc gctattacca tggtgatgcg gttttggcag | 720 |
| tacatcaatg ggcgtggata gcggtttgac tcacggggat ttccaagtct ccaccccatt | 780 |
| gacgtcaatg ggagtttgtt ttggcaccaa aatcaacggg actttccaaa atgtcgtaac | 840 |
| aactccgccc cattgacgca aatgggcggt aggcgtgtac ggtgggaggt ctatataagc | 900 |
| agagctggtt tagtgaaccg tcagatccgc tagagatctg gtaccgtcga cgcggccgct | 960 |
| cgagcctaag cttggtaccg agctcggatc cactagtaac ggccgccagt gtgctggaat | 1020 |
| tcggcttaaa ggtacccaga gcagacagcc gccaccatgg agtctccctc ggcccctccc | 1080 |
| cacagatggt gcatcccctg cagaggctc ctgctcacag cctcacttct aaccttctgg | 1140 |
| aacccgccca ccactgccaa gctcactatt gaatccacgc cgttcaatgt cgcagagggg | 1200 |
| aaggaggtgc ttctacttgt ccacaatctg ccccagcatc ttttggcta cagctggtac | 1260 |
| aaaggtgaaa gagtggatgg caaccgtcaa attataggat atgtaatagg aactcaacaa | 1320 |
| gctaccccag ggcccgcata cagtggtcga gagataatat accccaatgc atccctgctg | 1380 |
| atccagaaca tcatccagaa tgacacagga ttctacaccc tacacgtcat aaagtcagat | 1440 |
| cttgtgaatg aagaagcaac tggccagttc cgggtatacc cggagctgcc caagccctcc | 1500 |
| atctccagca caactccaa acccgtggag acaaggatg ctgtggcctt cacctgtgaa | 1560 |
| cctgagactc aggacgcaac ctacctgtgg tgggtaaaca atcagagcct cccggtcagt | 1620 |
| cccaggctgc agctgtccaa tggcaacagg accctcactc tattcaatgt cacaagaaat | 1680 |
| gacacagcaa gctacaaatg tgaaacccag aacccagtga gtgccaggcg cagtgattca | 1740 |
| gtcatcctga atgtcctcta tggccccgat gccccacca tttcccctct aaacacatct | 1800 |
| tacagatcag gggaaaatct gaacctctcc tgccacgcag cctctaaccc acctgcacag | 1860 |

```
tactcttggt tgtcaatgg gactttccag caatccaccc aagagctctt tatcccaac      1920
atcactgtga ataatagtgg atcctatacg tgccaagccc ataactcaga cactggcctc   1980
aataggacca cagtcacgac gatcacagtc tatgcagagc cacccaaacc cttcatcacc   2040
agcaacaact ccaaccccgt ggaggatgag gatgctgtag ccttaacctg tgaacctgag   2100
attcagaaca caacctacct gtggtgggta ataatcaga gcctcccggt cagtcccagg    2160
ctgcagctgt ccaatgacaa caggaccctc actctactca gtgtcacaag gaatgatgta   2220
ggaccctatg agtgtggaat ccagaacgaa ttaagtgttg accacagcga cccagtcatc   2280
ctgaatgtcc tctatggccc agacgacccc accatttccc cctcatacac ctattaccgt   2340
ccaggggtga acctcagcct ctcctgccat gcagcctcta acccacctgc acagtattct   2400
tggctgattg atgggaacat ccagcaacac acacaagagc tctttatctc caacatcact   2460
gagaagaaca gcggactcta tacctgccag gccaataact cagccagtgg ccacagcagg   2520
actacagtca agacaatcac agtctctgcg gagctgccca gccctccat ctccagcaac    2580
aactccaaac ccgtggagga caaggatgct gtggccttca cctgtgaacc tgaggctcag   2640
aacacaacct acctgtggtg ggtaaatggt cagagcctcc cagtcagtcc caggctgcag   2700
ctgtccaatg gcaacaggac cctcactcta ttcaatgtca caagaaatga cgcaagagcc   2760
tatgtatgtg gaatccagaa ctcagtgagt gcaaaccgca gtgacccagt caccctggat   2820
gtcctctatg gccggacac cccatcatt tcccccccag actcgtctta cctttcggga    2880
gcggacctca acctctcctg ccactcggcc tctaacccat ccccgcagta ttcttggcgt   2940
atcaatggga taccgcagca acacacacaa gttctcttta tcgccaaaat cacgccaaat   3000
aataacggga cctatgcctg ttttgtctct aacttggcta ctggccgcaa taattccata   3060
gtcaagagca tcacagtctc tgcatctgga acttctcctg gtctctcagc tggggccact   3120
gtcggcatca tgattggagt gctggttggg gttgctctga tatagcagcc ctggtgtagt   3180
ttcttcattt caggaagact gacagttgtt ttgcttcttc cttaaagcat ttgcaacagc   3240
tacagtctaa aattgcttct ttaccaagga tatttacaga aaagactctg accagagatc   3300
gagaccatcc tctagataag atatccgatc caccggatct agataactga tcataatcag   3360
ccataccaca tttgtagagg ttttacttgc tttaaaaaac ctcccacacc tcccctgaa    3420
cctgaaacat aaaatgaatg caattgttgt tgttaacttg tttattgcag cttataatgg   3480
ttacaaataa agcaatagca tcacaaattt cacaaataaa gcattttttt cactgcattc   3540
tagttgtggt ttgtccaaac tcatcaatgt atcttaacgc ggatctgggc gtggttaagg   3600
gtgggaaaga atatataagg tgggggtctt atgtagtttt gtatctgttt gcagcagcc    3660
gccgccgcca tgagcaccaa ctcgtttgat ggaagcattg tgagctcata tttgacaacg   3720
cgcatgcccc catgggccgg ggtgcgtcag aatgtgatgg gctccagcat tgatggtcgc   3780
cccgtcctgc ccgcaaactc tactaccttg acctacgaga ccgtgtctgg aacgccgttg   3840
gagactgcag cctccgccgc cgcttcagcc gctgcagcca ccgccgcgg gattgtgact   3900
gactttgctt tcctgagccc gcttgcaagc agtgcagctt cccgttcatc cgcccgcgat   3960
gacaagttga cggctctttt ggcacaattg gattctttga cccgggaact taatgtcgtt   4020
tctcagcagc tgttggatct gcgccagcag gtttctgccc tgaaggcttc ctcccctccc   4080
aatgcggttt aaaacataaa taaaaaacca gactctgttt ggatttggat caagcaagtg   4140
tcttgctgtc tttatttagg ggtttgcgc gcgcggtagg cccgggacca gcggtctcgg   4200
```

```
tcgttgaggg tcctgtgtat tttttccagg acgtggtaaa ggtgactctg gatgttcaga    4260
tacatgggca taagcccgtc tctggggtgg aggtagcacc actgcagagc ttcatgctgc    4320
ggggtggtgt tgtagatgat ccagtcgtag caggagcgct gggcgtggtg cctaaaaatg    4380
tctttcagta gcaagctgat tgccaggggc aggcccttgg tgtaagtgtt tacaaagcgg    4440
ttaagctggg atgggtgcat acgtggggat atgagatgca tcttggactg tattttttagg   4500
ttggctatgt tcccagccat atccctccgg ggattcatgt tgtgcagaac caccagcaca    4560
gtgtatccgg tgcacttggg aaatttgtca tgtagcttag aaggaaatgc gtggaagaac    4620
ttggagacgc ccttgtgacc tccaagattt tccatgcatt cgtccataat gatggcaatg    4680
ggcccacggg cggcggcctg ggcgaagata tttctgggat cactaacgtc atagttgtgt    4740
tccaggatga gatcgtcata ggccattttt acaaagcgcg ggcggagggt gccagactgc    4800
ggtataatgg ttccatccgg cccagggggcg tagttaccct cacagatttg catttcccac   4860
gctttgagtt cagatggggg gatcatgtct acctgcgggg cgatgaagaa aacggtttcc    4920
ggggtagggg agatcagctg ggaagaaagc aggttcctga gcagctgcga cttaccgcag    4980
ccggtgggcc cgtaaatcac acctattacc ggctgcaact ggtagttaag agagctgcag    5040
ctgccgtcat ccctgagcag gggggccact tcgttaagca tgtccctgac tcgcatgttt    5100
tccctgacca aatccgccag aaggcgctcg ccgcccagcg atagcagttc ttgcaaggaa    5160
gcaaagtttt tcaacggttt gagaccgtcc gccgtaggca tgcttttgag cgtttgacca    5220
agcagttcca ggcggtccca cagctcggtc acctgctcta cggcatctcg atccagcata    5280
tctcctcgtt tcgcggggttg gggcggcttt cgctgtacgg cagtagtcgg tgctcgtcca    5340
gacgggccag ggtcatgtct ttccacgggc gcagggtcct cgtcagcgta gtctgggtca    5400
cggtgaaggg gtgcgctccg ggctgcgcgc tggccagggt gcgcttgagg ctggtcctgc    5460
tggtgctgaa gcgctgccgg tcttcgccct gcgcgtcggc caggtagcat ttgaccatgg    5520
tgtcatagtc cagccccctcc gcggcgtggc ccttggcgcg cagcttgccc ttggaggagg    5580
cgccgcacga ggggcagtgc agacttttga gggcgtagag cttgggcgcg agaaataccg    5640
attccgggga gtaggcatcc gcgccgcagg ccccgcagac ggtctcgcat tccacgagcc    5700
aggtgagctc tggccgttcg gggtcaaaaa ccaggtttcc cccatgcttt tgatgcgtt    5760
tcttacctct ggtttccatg agccggtgtc cacgctcggt gacgaaaagg ctgtccgtgt    5820
ccccgtatac agacttgaga ggcctgtcct cgagcggtgt tccgcggtcc tcctcgtata    5880
gaaactcgga ccactctgag acaaaggctc gcgtccaggc cagcacgaag gaggctaagt    5940
gggaggggta gcggtcgttg tccactaggg ggtccactcg ctccagggtg tgaagacaca    6000
tgtcgccctc ttcggcatca aggaaggtga ttggtttgta ggtgtaggcc acgtgaccgg    6060
gtgttcctga agggggggcta taaaagggggg tgggggcgcg ttcgtcctca ctctcttccg    6120
catcgctgtc tgcgagggcc agctgttggg gtgagtactc cctctgaaaa gcggcatga    6180
cttctgcgct aagattgtca gtttccaaaa acgaggagga tttgatattc acctggcccg    6240
cggtgatgcc tttgagggtg gccgcatcca tctggtcaga aaagacaatc ttttgttgt    6300
caagcttggt ggcaaacgac ccgtagaggg cgttggacag caacttggcg atggagcgca    6360
gggtttggtt tttgtcgcga tcggcgcgct ccttggccgc gatgtttagc tgcacgtatt    6420
cgcgcgcaac gcaccgccat tcgggaaaga cggtggtgcg ctcgtcgggc accaggtgca    6480
cgcgccaacc gcggttgtgc agggtgacaa ggtcaacgct ggtggctacc tctccgtgta    6540
ggcgctcgtt ggtccagcag aggcggccgc ccttgcgcga gcagaatggc ggtagggggt    6600
```

```
ctagctgcgt ctcgtccggg gggtctgcgt ccacggtaaa gaccccgggc agcaggcgcg    6660
cgtcgaagta gtctatcttg catccttgca agtctagcgc ctgctgccat gcgcgggcgc    6720
caagcgcgcg ctcgtatggg ttgagtgggg gaccccatgg catggggtgg gtgagcgcgg    6780
aggcgtacat gccgcaaatg tcgtaaacgt agaggggctc tctgagtatt ccaagatatg    6840
tagggtagca tcttccaccg cggatgctgg cgcgcacgta atcgtatagt tcgtgcgagg    6900
gagcgaggag gtcgggaccg aggttgctac gggcgggctg ctctgctcgg aagactatct    6960
gcctgaagat ggcatgtgag ttggatgata tggttggacg ctggaagacg ttgaagctgg    7020
cgtctgtgag acctaccgcg tcacgcacga aggaggcgta ggagtcgcgc agcttgttga    7080
ccagctcggc ggtgacctgc acgtctaggg cgcagtagtc cagggtttcc ttgatgatgt    7140
catacttatc ctgtcccttt tttttccaca gctcgcggtt gaggacaaac tcttcgcggt    7200
ctttccagta ctcttggatc ggaaacccgt cggcctccga acggtaagag cctagcatgt    7260
agaactggtt gacggcctgg taggcgcagc atccctttc tacgggtagc gcgtatgcct    7320
gcgcggcctt ccggcatgac cagcatgaag ggcacgagct gcttcccaaa ggcccccatc    7380
caagtatagg tctctacatc gtaggtgaca aagagacgct cggtgcgagg atgcgagccg    7440
atcgggaaga actggatctc ccgccaccaa ttggaggagt ggctattgat gtggtgaaag    7500
tagaagtccc tgcgacgggc cgaacactcg tgctggcttt tgtaaaaacg tgcgcagtac    7560
tggcagcggt gcacgggctg tacatcctgc acgaggttga cctgacgacc gcgcacaagg    7620
aagcagagtg ggaatttgag cccctcgcct ggcgggtttg gctggtggtc ttctacttcg    7680
gctgcttgtc cttgaccgtc tggctgctcg aggggagtta cggtggatcg gaccaccacg    7740
ccgcgcgagc ccaaagtcca gatgtccgcg cgcggcggtc ggagcttgat gacaacatcg    7800
cgcagatggg agctgtccat ggtctggagc tcccgcggcg tcaggtcagg cgggagctcc    7860
tgcaggttta cctcgcatag acgggtcagg gcgcgggcta gatccaggtg atacctaatt    7920
tccaggggct ggttggtggc ggcgtcgatg gcttgcaaga ggccgcatcc ccgcggcgcg    7980
actacggtac cgcgcggcgg gcggtgggcc gcggggtgt ccttggatga tgcatctaaa    8040
agcggtgacg cgggcgagcc cccggaggta gggggggctc cggacccgcc gggagagggg    8100
gcaggggcac gtcggcgccg cgcgcgggca ggagctggtg ctgcgcgcgt aggttgctgg    8160
cgaacgcgac gacgcggcgg ttgatctcct gaatctggcg cctctgcgtg aagacgacgg    8220
gcccggtgag cttgaacctg aaagagagtt cgacagaatc aatttcggtg tcgttgacgg    8280
cggcctggcg caaaatctcc tgcacgtctc ctgagttgtc ttgataggcg atctcggcca    8340
tgaactgctc gatctcttcc tcctggagat ctccgcgtcc ggctcgctcc acggtggcgg    8400
cgaggtcgtt ggaaatgcgg gccatgagct gcgagaaggc gttgaggcct ccctcgttcc    8460
agacgcggct gtagaccacg ccccccttcgg catcgcgggc gcgcatgacc acctgcgcga    8520
gattgagctc cacgtgccgg gcgaagacgg cgtagtttcg caggcgctga agaggtagt    8580 tgagggtggt ggcggtgtgt tctgccacga agaagtacat aacccagcgt cgcaacgtgg    8640
attcgttgat aattgttgtg taggtactcc gccgccgagg gacctgagcg agtccgcatc    8700
gaccggatcg gaaaacctct cgagaaaggc gtctaaccag tcacagtcgc aaggtaggct    8760
gagcaccgtg gcgggcggca gcgggcggcg gtcgggggttg tttctggcgg aggtgctgct    8820
gatgatgtaa ttaaagtagg cggtcttgag acggcggatg gtcgacagaa gcaccatgtc    8880
cttgggtccg gcctgctgaa tgcgcaggcg gtcggccatg ccccaggctt cgttttgaca    8940
```

```
tcggcgcagg tctttgtagt agtcttgcat gagcctttct accggcactt cttcttctcc    9000
ttcctcttgt cctgcatctc ttgcatctat cgctgcggcg gcggcggagt ttggccgtag    9060
gtggcgccct cttcctccca tgcgtgtgac cccgaagccc ctcatcggct gaagcagggc    9120
taggtcggcg acaacgcgct cggctaatat ggcctgctgc acctgcgtga gggtagactg    9180
gaagtcatcc atgtccacaa agcggtggta tgcgcccgtg ttgatggtgt aagtgcagtt    9240
ggccataacg gaccagttaa cggtctggtg accggctgc gagagctcgg tgtacctgag     9300
acgcgagtaa gccctcgagt caaatacgta gtcgttgcaa gtccgcacca ggtactggta    9360
tcccaccaaa aagtgcggcg gcggctggcg gtagaggggc cagcgtaggg tggccggggc    9420 tccggggcg agatcttcca acataaggcg atgatatccg tagatgtacc tggacatcca     9480
ggtgatgccg gcggcggtgg tggaggcgcg cggaaagtcg cggacgcggt tccagatgtt    9540
gcgcagcggc aaaaagtgct ccatggtcgg gacgctctgg ccggtcaggc gcgcgcaatc    9600
gttgacgctc tagcgtgcaa aaggagagcc tgtaagcggg cactcttccg tggtctggtg    9660
gataaattcg caagggtatc atggcggacg accggggttc gagccccgta tccggccgtc    9720
cgccgtgatc catgcggtta ccgcccgcgt gtcgaaccca ggtgtgcgac gtcagacaac    9780
gggggagtgc tcctttggc ttccttccag gcgcggcggc tgctgcgcta gctttttgg      9840 ccactggccg cgcgcagcgt aagcggttag gctggaaagc gaaagcatta agtggctcgc    9900
tccctgtagc cggagggtta ttttccaagg gttgagtcgc ggaccccg gttcgagtct      9960 cggaccggcc ggactgcggc gaacgggggt ttgcctcccc gtcatgcaag accccgcttg   10020
caaattcctc cggaaacagg gacgagcccc ttttttgctt ttcccagatg catccggtgc   10080
tgcggcagat gcgccccct cctcagcagc ggcaagagca agagcagcgg cagacatgca    10140
gggcaccctc ccctcctcct accgcgtcag gaggggcgac atccgcggtt gacgcggcag   10200
cagatggtga ttacgaaccc ccgcggcgcc gggcccggca ctacctggac ttggaggagg   10260
gcgagggcct ggcgcggcta ggagcgccct ctcctgagcg gcacccaagg gtgcagctga   10320
agcgtgatac gcgtgaggcg tacgtgccgc ggcagaacct gtttcgcgac cgcgagggag   10380
aggagcccga ggagatgcgg gatcgaaagt tccacgcagg gcgcgagctg cggcatggcc   10440
tgaatcgcga gcggttgctg cgcgaggagg actttgagcc cgacgcgcga accgggatta   10500
gtcccgcgcg cgcacacgtg gcggccgccg acctggtaac cgcatacgag cagacgcgtga  10560 accaggagat taactttcaa aaaagcttta acaaccacgt gcgtacgctt gtggcgcgcg   10620
aggaggtggc tataggactg atgcatctgt gggactttgt aagcgcgctg gagcaaaacc   10680
caaatagcaa gccgctcatg gcgcagctgt tccttatagt gcagcacagc agggacaacg   10740
aggcattcag ggatgcgctg ctaaacatag tagagcccga gggccgctgg ctgctcgatt   10800
tgataaacat cctgcagagc atagtggtgc aggagcgcag cttgagcctg gctgacaagg   10860
tggccgccat caactattcc atgcttagcc tgggcaagtt ttacgcccgc aagatatacc   10920 ataccccta cgttcccata gacaaggagg taaagatcga ggggttctac atgcgcatgg     10980
cgctgaaggt gcttaccttg agcgacgacc tgggcgttta tcgcaacgag cgcatccaca   11040
aggccgtgag cgtgagccgg cggcgcgagc tcagcgaccg cgagctgatg cacagcctgc   11100
aaagggccct ggctggcacg ggcagcggcg atagagaggc cgagtcctac tttgacgcgg   11160
gcgctgacct cgcgctgggc ccaagccgac gcgcccggga ggcagctggg gccggacctg   11220
ggctggcggt ggcacccgcg cgcgctggca acgtcggcgg cgtggaggaa tatgacgagg   11280
acgatgagta cgagccagag gacggcgagt actaagcggt gatgtttctg atcagatgat   11340
```

```
gcaagacgca acggacccgg cggtgcgggc ggcgctgcag agccagccgt ccggccttaa    11400
ctccacggac gactggcgcc aggtcatgga ccgcatcatg tcgctgactg cgcgcaatcc    11460
tgacgcgttc cggcagcagc cgcaggccaa ccggctctcc gcaattctgg aagcggtggt    11520
cccggcgcgc gcaaacccca cgcacgagaa ggtgctggcg atcgtaaacg cgctggccga    11580
aaacagggcc atccggcccg acgaggccgg cctggtctac gacgcgctgc ttcagcgcgt    11640
ggctcgttac aacagcggca acgtgcagac caacctggac cggctggtgg gggatgtgcg    11700
cgaggccgtg gcgcagcgtg agcgcgcgca gcagcagggc aacctgggct ccatggttgc    11760
actaaacgcc ttcctgagta cacagcccgc caacgtgccg cggggacagg aggactacac    11820
caactttgtg agcgcactgc ggctaatggt gactgagaca ccgcaaagtg aggtgtacca    11880
gtctgggcca gactattttt tccagaccag tagacaaggc ctgcagaccg taaacctgag    11940
ccaggctttc aaaaacttgc aggggctgtg ggggtgcgg gctcccacag gcgaccgcgc    12000
gaccgtgtct agcttgctga cgcccaactc gcgcctgttg ctgctgctaa tagcgcsccctt    12060 cacggacagt ggcagcgtgt cccgggacac atacctaggt cacttgctga cactgtaccg    12120
cgaggccata ggtcaggcgc atgtggacga gcatactttc caggagatta caagtgtcag    12180
ccgcgcgctg gggcaggagg acacgggcag cctggaggca accctaaact acctgctgac    12240
caaccggcgg cagaagatcc cctcgttgca cagtttaaac agcgaggagg agcgcatttt    12300
gcgctacgtg cagcagagcg tgagccttaa cctgatgcgc gacggggtaa cgcccagcgt    12360
ggcgctggac atgaccgcgc gcaacatgga accgggcatg tatgcctcaa accggccgtt    12420
tatcaaccgc ctaatggact acttgcatcg cgcggccgcc gtgaaccccg agtatttcac    12480
caatgccatc ttgaacccgc actggctacc gccccctggt ttctacaccg ggggattcga    12540
ggtgcccgag ggtaacgatg gattcctctg ggacgacata gacgacagcg tgttttcccc    12600
gcaaccgcag accctgctag agttgcaaca gcgcgagcag gcagaggcgg cgctgcgaaa    12660
ggaaagcttc cgcaggccaa gcagcttgtc cgatctaggc gctgcggccc cgcggtcaga    12720
tgctagtagc ccatttccaa gcttgatagg gtctcttacc agcactcgca ccacccgccc    12780
gcgcctgctg ggcgaggagg agtacctaaa caactcgctg ctgcagccgc agcgcgaaaa    12840
aaacctgcct ccggcatttc ccaacaacgg gatagagagc ctagtggaca agatgagtag    12900
atggaagacg tacgcgcagg agcacaggga cgtgccaggc ccgcgcccgc ccacccgtcg    12960
tcaaaggcac gaccgtcagc ggggtctggt gtgggaggac gatgactcgg cagacgacag    13020
cagcgtcctg gatttgggag ggagtggcaa cccgtttgcg caccttcgcc ccaggctggg    13080
gagaatgttt taaaaaaaaa aaagcatgat gcaaataaaa aaactcacca aggccatggc    13140
accgagcgtt ggttttcttg tattcccctt agtatgcggc gcgcggcgat gtatgaggaa    13200
ggtcctcctc cctcctacga gagtgtggtg agcgcggcgc cagtggcggc ggcgctgggt    13260
tctcccttcg atgctcccct ggacccgccg tttgtgcctc cgcggtacct gcggcctacc    13320
ggggggagaa acagcatccg ttactctgag ttggcacccc tattcgacac cacccgtgtg    13380
tacctggtgg acaacaagtc aacggatgtg gcatccctga actaccagaa cgaccacagc    13440
aactttctga ccacggtcat tcaaaacaat gactacagcc cggggaggc aagcacacag    13500 accatcaatc ttgacgaccg gtcgcactgg ggcggcgacc tgaaaaccat cctgcatacc    13560
aacatgccaa atgtgaacga gttcatgttt accaataagt ttaagcgcgc ggtgatggtg    13620
tcgcgcttgc ctactaagga caatcaggtg gagctgaaat acgagtgggt ggagttcacg    13680
```

-continued

```
ctgcccgagg gcaactactc cgagaccatg accatagacc ttatgaacaa cgcgatcgtg    13740
gagcactact tgaaagtggg cagacagaac ggggttctgg aaagcgacat cggggtaaag    13800
tttgacaccc gcaacttcag actggggttt gaccccgtca ctggtcttgt catgcctggg    13860
gtatatacaa acgaagcctt ccatccagac atcattttgc tgccaggatg cggggtggac    13920
ttcacccaca gccgcctgag caacttgttg ggcatccgca agcggcaacc cttccaggag    13980
ggctttagga tcacctacga tgatctggag ggtggtaaca ttcccgcact gttggatgtg    14040
gacgcctacc aggcgagctt gaaagatgac accgaacagg gcggggtgg cgcaggcggc    14100 agcaacagca gtggcagcgg cgcggaagag aactccaacg cggcagccgc ggcaatgcag    14160
ccggtggagg acatgaacga tcatgccatt cgcggcgaca cctttgccac acgggctgag    14220
gagaagcgcg ctgaggccga agcagcggcc gaagctgccg cccccgctgc gcaacccgag    14280
gtcgagaagc ctcagaagaa accggtgatc aaaccccctga cagaggacag caagaaacgc    14340
agttacaacc taataagcaa tgacagcacc ttcacccagt accgcagctg gtaccttgca    14400
tacaactacg gcgaccctca gaccggaatc cgctcatgga ccctgctttg cactcctgac    14460
gtaacctgcg gctcggagca ggtctactgg tcgttgccag acatgatgca agaccccgtg    14520
accttccgct ccacgcgcca gatcagcaac tttccggtgg tgggcgccga gctgttgccc    14580
gtgcactcca agagcttcta caacgaccag gccgtctact cccaactcat ccgccagttt    14640
acctctctga cccacgtgtt caatcgcttt cccgagaacc agattttggc gcgcccgcca    14700
gcccccacca tcaccaccgt cagtgaaaac gttcctgctc tcacagatca cgggacgcta    14760
ccgctgcgca acagcatcgg aggagtccag cgagtgacca ttactgacgc cagacgccgc    14820
acctgcccct acgtttacaa ggccctgggc atagtctcgc cgcgcgtcct atcgagccgc    14880 acttttgag caagcatgtc catccttata tcgcccagca ataacacagg ctggggcctg    14940
cgcttcccaa gcaagatgtt tggcggggcc aagaagcgct ccgaccaaca cccagtgcgc    15000
gtgcgcgggc actaccgcgc gccctgggc gcgcacaaac gcggccgcac tgggcgcacc    15060
accgtcgatg acgccatcga cgcggtggtg gaggaggcgc gcaactacac gcccacgccg    15120
ccaccagtgt ccacagtgga cgcggccatt cagaccgtgg tgcgcggagc ccggcgctat    15180
gctaaaatga agagacggcg gaggcgcgta gcacgtcgcc accgccgccg acccggcact    15240
gccgcccaac gcgcggcggc ggccctgctt aaccgcgcac gtcgcaccgg ccgacgggcg    15300
gccatgcggg ccgctcgaag gctggccgcg ggtattgtca ctgtgccccc caggtccagg    15360
cgacgagcgg ccgccgcagc agccgcggcc attagtgcta tgactcaggg tcgcaggggc    15420
aacgtgtatt gggtgcgcga ctcggttagc ggcctgcgcg tgcccgtgcg cacccgcccc    15480
ccgcgcaact agattgcaag aaaaaactac ttagactcgt actgttgtat gtatccagcg    15540
gcggcggcgc gcaacgaagc tatgtccaag cgcaaaatca agaagagat gctccaggtc    15600 atcgcgccgg agatctatgg ccccccgaag aaggaagagc aggattacaa gccccgaaag    15660
ctaaagcggg tcaaaagaa aaagaaagat gatgatgatg aacttgacga cgaggtggaa    15720
ctgctgcacg ctaccgcgcc caggcgacgg gtacagtgga aggtcgacg cgtaaaacgt    15780 gttttgcgac ccggcaccac cgtagtcttt acgcccggtg agcgctccac ccgcacctac    15840
aagcgcgtgt atgatgaggt gtacggcgac gaggacctgc ttgagcaggc caacgagcgc    15900 ctcgggagt ttgcctacgg aaagcggcat aaggacatgc tggcgttgcc gctggacgag    15960
ggcaacccaa cacctagcct aaagcccgta acactgcagc aggtgctgcc cgcgcttgca    16020
ccgtccgaag aaaagcgcgg cctaaagcgc gagtctggtg acttggcacc caccgtgcag    16080
```

```
ctgatggtac caagcgcca gcgactggaa gatgtcttgg aaaaaatgac cgtggaacct   16140
gggctggagc ccgaggtccg cgtgcggcca atcaagcagg tggcgccggg actgggcgtg   16200
cagaccgtgg acgttcagat acccactacc agtagcacca gtattgccac cgccacagag   16260
ggcatggaga cacaaacgtc cccggttgcc tcagcggtgg cggatgccgc ggtgcaggcg   16320
gtcgctgcgg ccgcgtccaa gacctctacg gaggtgcaaa cggacccgtg gatgtttcgc   16380
gtttcagccc cccggcgccc gcgccgttcg aggaagtacg gcgccgccag cgcgctactg   16440
cccgaatatg ccctacatcc ttccattgcg cctacccccg gctatcgtgg ctacacctac   16500
cgccccagaa gacgagcaac tacccgacgc cgaaccacca ctggaacccg ccgccgccgt   16560
cgccgtcgcc agcccgtgct ggccccgatt ccgtgcgca gggtggctcg cgaaggaggc   16620
aggaccctgg tgctgccaac agcgcgctac cacccccagca tcgtttaaaa gccggtcttt   16680
gtggttcttg cagatatggc cctcacctgc cgcctccgtt tcccggtgcc gggattccga   16740
ggaagaatgc accgtaggag gggcatggcc ggccacggcc tgacgggcgg catgcgtcgt   16800
gcgcaccacc ggcggcggcg cgcgtcgcac cgtcgcatgc gcggcggtat cctgcccctc   16860
cttattccac tgatcgccgc ggcgattggc gccgtgcccg gaattgcatc cgtgccttg   16920
caggcgcaga gacactgatt aaaaacaagt tgcatgtgga aaatcaaaa taaaaagtct   16980
ggactctcac gctcgcttgg tcctgtaact attttgtaga atggaagaca tcaactttgc   17040
gtctctggcc ccgcgacacg gctcgcgccc gttcatggga aactggcaag atatcggcac   17100
cagcaatatg agcggtggcg ccttcagctg gggctcgctg tggagcggca ttaaaaattt   17160
cggttccacc gttaagaact atggcagcaa ggcctggaac agcagcacag gccagatgct   17220
gagggataag ttgaaagagc aaaatttcca acaaaaggtg gtagatggcc tggcctctgg   17280
cattagcggg gtggtggacc tggccaacca ggcagtgcaa aataagatta acagtaagct   17340
tgatccccgc cctcccgtag aggagcctcc accggccgtg gagacagtgt ctccagaggg   17400
gcgtggcgaa aagcgtccgc gccccgacag ggaagaaact ctggtgacgc aaatagacga   17460
gcctccctcg tacgaggagg cactaaagca aggcctgccc accacccgtc ccatcgcgcc   17520
catggctacc ggagtgctgg gccagcacac acccgtaacg ctggacctgc ctcccccgc   17580
cgacacccag cagaaacctg tgctgccagg cccgaccgcc gttgttgtaa cccgtcctag   17640
ccgcgcgtcc ctgcgccgcg ccgccagcgg tccgcgatcg ttgcggcccg tagccagtgg   17700
caactggcaa agcacactga acagcatcgt gggtctgggg gtgcaatccc tgaagcgccg   17760
acgatgcttc tgatagctaa cgtgtcgtat gtgtgtcatg tatgcgtcca tgtcgccgcc   17820
agaggagctg ctgagccgcc gcgcgcccgc tttccaagat ggctaccct tcgatgatgc   17880
cgcagtggtc ttacatgcac atctcgggcc aggacgcctc ggagtacctg agccccgggc   17940
tggtgcagtt tgcccgcgcc accgagacgt acttcagcct gaataacaag tttagaaacc   18000
ccacggtggc gcctacgcac gacgtgacca cagaccggtc ccagcgtttg acgctgcggt   18060
tcatccctgt ggaccgtgag gatactgcgt actcgtacaa ggcgcggttc accctagctg   18120
tgggtgataa ccgtgtgctg gacatggctt ccacgtactt tgacatccgc ggcgtgctgg   18180
acaggggccc tacttttaag ccctactctg gcactgccta caacgccctg gctcccaagg   18240
gtgccccaaa tccttgcgaa tgggatgaag ctgctactgc tcttgaaata aacctagaag   18300
aagaggacga tgcaacgaa gacgaagtag acgagcaagc tgagcagcaa aaaactcacg   18360
tatttgggca ggcgccttat tctggtataa atattacaaa ggagggtatt caaataggtg   18420
```

```
tcgaaggtca aacacctaaa tatgccgata aaacatttca acctgaacct caaataggag    18480
aatctcagtg gtacgaaaca gaaattaatc atgcagctgg gagagtccta aaaaagacta    18540
ccccaatgaa accatgttac ggttcatatg caaaacccac aaatgaaaat ggagggcaag    18600
gcattcttgt aaagcaacaa aatggaaagc tagaaagtca agtggaaatg caattttttct   18660 caactactga ggcagccgca ggcaatggtg ataacttgac tcctaaagtg gtattgtaca    18720
gtgaagatgt agatatagaa accccagaca ctcatatttc ttacatgccc actattaagg    18780
aaggtaactc acgagaacta atgggccaac aatctatgcc caacaggcct aattacattg    18840
cttttaggga caattttatt ggtctaatgt attacaacag cacgggtaat atgggtgttc    18900
tggcgggcca agcatcgcag ttgaatgctg ttgtagattt gcaagacaga aacacagagc    18960
tttcatacca gcttttgctt gattccattg gtgatagaac caggtacttt tctatgtgga    19020
atcaggctgt tgacagctat gatccagatg ttagaattat tgaaaatcat ggaactgaag    19080
atgaacttcc aaattactgc tttccactgg gaggtgtgat taatacagag actcttacca    19140
aggtaaaacc taaaacaggt caggaaaatg gatgggaaaa agatgctaca gaattttcag    19200
ataaaaatga aataagagtt ggaaataatt ttgccatgga aatcaatcta aatgccaacc    19260
tgtggagaaa tttcctgtac tccaacatag cgctgtattt gcccgacaag ctaaagtaca    19320
gtccttccaa cgtaaaaatt tctgataacc caaacaccta cgactacatg aacaagcgag    19380
tggtggctcc cgggctagtg gactgctaca ttaaccttgg agcacgctgg tcccttgact    19440
atatggacaa cgtcaaccca tttaaccacc accgcaatgc tggcctgcgc taccgctcaa    19500
tgttgctggg caatggtcgc tatgtgccct tccacatcca ggtgcctcag aagttctttg    19560
ccattaaaaa cctccttctc ctgccgggct catacaccta cgagtggaac ttcaggaagg    19620
atgttaacat ggttctgcag agctccctag gaaatgacct aagggttgac ggagccagca    19680
ttaagtttga tagcatttgc ctttacgcca ccttcttccc catggcccac aacaccgcct    19740
ccacgcttga ggccatgctt agaaacgaca ccaacgacca gtcctttaac gactatctct    19800
ccgccgccaa catgctctac cctatacccg ccaacgctac caacgtgccc atatccatcc    19860
cctcccgcaa ctgggcggct ttccgcggct gggccttcac gcgccttaag actaaggaaa    19920
ccccatcact gggctcgggc tacgaccctt attacaccta ctctggctct ataccctacc    19980
tagatggaac ctttttacctc aaccacacct ttaagaaggt ggccattacc tttgactctt    20040
ctgtcagctg gcctggcaat gaccgcctgc ttaccccccaa cgagtttgaa attaagcgct    20100
cagttgacgg ggaggggttac aacgttgccc agtgtaacat gaccaaagac tggttcctgg    20160
tacaaatgct agctaactat aacattggct accagggctt ctatatccca gagagctaca    20220
aggaccgcat gtactccttc tttagaaact tccagcccat gagccgtcag gtggtggatg    20280
atactaaata caaggactac caacaggtgg gcatcctaca ccaacacaac aactctggat    20340
ttgttggcta ccttgccccc accatgcgcg aaggacaggc ctaccctgct aacttcccct    20400
atccgcttat aggcaagacc gcagttgaca gcattaccca gaaaaagttt ctttgcgatc    20460 gcacccttg gcgcatccca ttctccagta actttatgtc catgggcgca ctcacagacc    20520
tgggccaaaa ccttctctac gccaactccg cccacgcgct agacatgact tttgaggtgg    20580
atcccatgga cgagcccacc cttctttatg ttttgtttga agtctttgac gtggtccgtg    20640
tgcaccagcc gcaccgcggc gtcatcgaaa ccgtgtacct gcgcacgccc ttctcggccg    20700
gcaacgccac aacataaaga agcaagcaac atcaacaaca gctgccgcca tgggctccag    20760
tgagcaggaa ctgaaagcca ttgtcaaaga tcttggttgt gggccatatt ttttgggcac    20820
```

```
ctatgacaag cgctttccag gctttgtttc tccacacaag ctcgcctgcg ccatagtcaa   20880 tacgccggt cgcgagactg ggggcgtaca ctggatggcc tttgcctgga acccgcactc   20940
aaaaacatgc tacctctttg agccctttgg cttttctgac cagcgactca agcaggttta   21000
ccagtttgag tacgagtcac tcctgcgccg tagcgccatt gcttcttccc ccgaccgctg   21060
tataacgctg gaaaagtcca cccaaagcgt acaggggccc aactcggccg cctgtggact   21120
attctgctgc atgtttctcc acgcctttgc caactggccc caaactccca tggatcacaa   21180
ccccaccatg aaccttatta ccggggtacc caactccatg ctcaacagtc cccaggtaca   21240
gcccaccctg cgtcgcaacc aggaacagct ctacagcttc ctggagcgcc actcgcccta   21300
cttccgcagc cacagtgcgc agattaggag cgccacttct ttttgtcact gaaaaacat   21360 gtaaaaataa tgtactagag cactttcaa taaaggcaaa tgcttttatt tgtacactct   21420
cgggtgatta tttacccca cccttgccgt ctgcgccgtt taaaaatcaa aggggttctg   21480
ccgcgcatcg ctatgcgcca ctggcaggga cacgttgcga tactggtgtt tagtgctcca   21540
cttaaactca ggcacaacca tccgcggcag ctcggtgaag ttttcactcc acaggctgcg   21600
caccatcacc aacgcgttta gcaggtcggg cgccgatatc ttgaagtcgc agttggggcc   21660
tccgccctgc gcgcgcgagt tgcgatacac agggttgcag cactggaaca ctatcagcgc   21720
cgggtggtgc acgctggcca gcacgctctt gtcggagatc agatccgcgt ccaggtcctc   21780
cgcgttgctc agggcgaacg gagtcaactt tggtagctgc cttcccaaaa agggcgcgtg   21840
cccaggcttt gagttgcact cgcaccgtag tggcatcaaa aggtgaccgt gcccggtctg   21900
ggcgttagga tacagcgcct gcataaaagc cttgatctgc ttaaaagcca cctgagcctt   21960
tgcgccttca gagaagaaca tgccgcaaga cttgccggaa aactgattgg ccggacaggc   22020
cgcgtcgtgc acgcagcacc ttgcgtcggt gttggagatc tgcaccacat tcggcccca   22080 ccggttcttc acgatcttgg ccttgctaga ctgctcctc agcgcgcgct gcccgttttc   22140
gctcgtcaca tccatttcaa tcacgtgctc cttatttatc ataatgcttc cgtgtagaca   22200
cttaagctcg ccttcgatct cagcgcagcg gtgcagccac aacgcgcagc ccgtgggctc   22260
gtgatgcttg taggtcacct ctgcaaacga ctgcaggtac gcctgcagga atcgcccat   22320 catcgtcaca aaggtcttgt tgctggtgaa ggtcagctgc aacccgcggt gctcctcgtt   22380
cagccaggtc ttgcatacgg ccgccagagc ttccacttgg tcaggcagta gtttgaagtt   22440
cgcctttaga tcgttatcca cgtggtactt gtccatcagc gcgcgcgcag cctccatgcc   22500
cttctcccac gcagacacga tcggcacact cagcgggttc atcaccgtaa tttcactttc   22560
cgcttcgctg ggctcttcct cttcctcttg cgtccgcata ccacgcgcca ctgggtcgtc   22620
ttcattcagc cgccgcactg tgcgcttacc tcctttgcca tgcttgatta gcaccggtgg   22680
gttgctgaaa cccaccattt gtagcgccac atcttctctt tcttcctcgc tgtccacgat   22740
tacctctggt gatggcgggc gctcgggctt gggagaaggg cgcttctttt tcttcttggg   22800
cgcaatggcc aaatccgccg ccgaggtcga tggccgcggg ctgggtgtgc gcggcaccag   22860
cgcgtcttgt gatgagtctt cctcgtcctc ggactcgata cgccgcctca tccgcttttt   22920
tgggggcgcc cggggaggcg gcggcgacgg ggacgggac gacacgtcct ccatggttgg   22980
gggacgtcgc gccgcaccgc gtccgcgctc ggggtggtt tcgcgctgct cctcttcccg   23040
actggccatt tccttctcct ataggcagaa aaagatcatg gagtcagtcg agaagaagga   23100
cagcctaacc gcccccctctg agttcgccac caccgcctcc accgatgccg ccaacgcgcc   23160
```

```
taccaccttc cccgtcgagg caccccccgct tgaggaggag gaagtgatta tcgagcagga    23220
cccaggtttt gtaagcgaag acgacgagga ccgctcagta ccaacagagg ataaaaagca    23280
agaccaggac aacgcagagg caaacgagga acaagtcggg cggggggacg aaaggcatgg    23340
cgactaccta gatgtgggag acgacgtgct gttgaagcat ctgcagcgcc agtgcgccat    23400
tatctgcgac gcgttgcaag agcgcagcga tgtgccccctc gccatagcgg atgtcagcct    23460
tgcctacgaa cgccacctat tctcaccgcg cgtaccccccc aaacgccaag aaaacggcac    23520
atgcgagccc aacccgcgcc tcaacttcta ccccgtattt gccgtgccag aggtgcttgc    23580
cacctatcac atctttttcc aaaactgcaa gatacccccta tcctgccgtg ccaaccgcag    23640
ccgagcggac aagcagctgg ccttgcggca gggcgctgtc atacctgata tcgcctcgct    23700
caacgaagtg ccaaaaatct ttgagggtct tggacgcgac gagaagcgcg cggcaaacgc    23760
tctgcaacag gaaaacagcg aaaatgaaag tcactctgga gtgttggtgg aactcgaggg    23820
tgacaacgcg cgcctagccg tactaaaacg cagcatcgag gtcacccact ttgcctaccc    23880
ggcacttaac ctaccccccca aggtcatgag cacagtcatg agtgagctga tcgtgcgccg    23940
tgcgcagccc ctggagaggg atgcaaattt gcaagaacaa acagaggagg gcctacccgc    24000
agttggcgac gagcagctag cgcgctggct tcaaacgcgc gagcctgccg acttggagga    24060
gcgacgcaaa ctaatgatgg ccgcagtgct cgttaccgtg gagcttgagt gcatgcagcg    24120
gttctttgct gacccggaga tgcagcgcaa gctagaggaa acattgcact acacctttcg    24180
acagggctac gtacgccagg cctgcaagat ctccaacgtg gagctctgca acctggtctc    24240
ctaccttgga attttgcacg aaaaccgcct tgggcaaaac gtgcttcatt ccacgctcaa    24300
gggcgaggcg cgccgcgact acgtccgcga ctgcgtttac ttatttctat gctacacctg    24360
gcagacggcc atgggcgttt ggcagcagtg cttggaggag tgcaacctca aggagctgca    24420
gaaactgcta aagcaaaact tgaaggacct atggacggcc ttcaacgagc gctccgtggc    24480
cgcgcacctg gcgacatca ttttcccccga acgcctgctt aaaaccctgc aacagggtct    24540
gccagacttc accagtcaaa gcatgttgca gaactttagg aactttatcc tagagcgctc    24600
aggaatcttg cccgccacct gctgtgcact tcctagcgac tttgtgccca ttaagtaccg    24660
cgaatgccct ccgccgcttt ggggccactg ctaccttctg cagctagcca actaccttgc    24720
ctaccactct gacataatgg aagacgtgag cggtgacggt ctactggagt gtcactgtcg    24780
ctgcaaccta tgcaccccgc accgctccct ggtttgcaat tcgcagctgc ttaacgaaag    24840
tcaaattatc ggtaccttg agctgcaggg tccctcgcct gacgaaaagt ccgcggctcc    24900
ggggttgaaa ctcactccgg ggctgtggac gtcggcttac cttcgcaaat ttgtacctga    24960
ggactaccac gcccacgaga ttaggttcta cgaagaccaa tcccgcccgc ctaatgcgga    25020
gcttaccgcc tgcgtcatta cccagggcca cattcttggc caattgcaag ccatcaacaa    25080
agcccgccaa gagtttctgc tacgaaaggg acgggggggtt tacttggacc cccagtccgg    25140
cgaggagctc aacccaatcc ccccgccgcc gcagccctat cagcagcagc gcgggcccct    25200
tgcttcccag gatggcaccc aaaaagaagc tgcagctgcc gccgccacccc acggacgagg    25260
aggaatactg ggacagtcag gcagaggagg ttttggacga ggaggaggag gacatgatgg    25320
aagactggga gagcctagac gaggaagctt ccgaggtcga agaggtgtca gacgaaacac    25380
cgtcacccctc ggtcgcattc ccctcgccgg cgccccagaa atcggcaacc ggttccagca    25440
tggctacaac ctccgctcct caggcgccgc cggcactgcc cgttcgccga cccaaccgta    25500
gatgggacac cactggaacc agggccggta agtccaagca gccgccgccg ttagcccaag    25560
```

```
agcaacaaca cgccaaggc taccgctcat ggcgcgggca caagaacgcc atagttgctt    25620
gcttgcaaga ctgtgggggc aacatctcct tcgcccgccg ctttcttctc taccatcacg    25680
gcgtggcctt cccccgtaac atcctgcatt actaccgtca tctctacagc ccatactgca    25740
ccggcggcag cggcagcaac agcagcggcc acacagaagc aaaggcgacc ggatagcaag    25800
actctgacaa gcccaagaa atccacagcg gcggcagcag caggaggagg agcgctgcgt    25860
ctggcgccca acgaacccgt atcgacccgc gagcttagaa acaggatttt tcccactctg    25920
tatgctatat ttcaacagag caggggccaa gaacaagagc tgaaaataaa aaacaggtct    25980
ctgcgatccc tcacccgcag ctgcctgtat cacaaaagcg aagatcagct tcggcgcacg    26040
ctggaagacg cggaggctct cttcagtaaa tactgcgcgc tgactcttaa ggactagttt    26100
cgcgcccttt ctcaaattta agcgcgaaaa ctacgtcatc tccagcggcc acacccggcg    26160
ccagcacctg ttgtcagcgc cattatgagc aaggaaattc ccacgcccta catgtggagt    26220
taccagccac aaatgggact tgcggctgga gctgcccaag actactcaac ccgaataaac    26280
tacatgagcg cgggacccca catgatatcc cgggtcaacg gaatacgcgc ccaccgaaac    26340
cgaattctcc tggaacaggc ggctattacc accacacctc gtaataacct taatccccgt    26400
agttggcccg ctgccctggt gtaccaggaa agtcccgctc ccaccactgt ggtacttccc    26460
agagacgccc aggccgaagt tcagatgact aactcagggg cgcagcttgc gggcggcttt    26520
cgtcacaggg tgcggtcgcc cgggcagggt ataactcacc tgacaatcag agggcgaggt    26580
attcagctca acgacgagtc ggtgagctcc tcgcttggtc tccgtccgga cgggacattt    26640
cagatcggcg gcgccggccg ctcttcattc acgcctcgtc aggcaatcct aactctgcag    26700
acctcgtcct ctgagccgcg ctctggaggc attggaactc tgcaatttat tgaggagttt    26760
gtgccatcgg tctactttaa ccccttctcg ggacctcccg gccactatcc ggatcaattt    26820
attcctaact ttgacgcggt aaaggactcg gcggacggct acgactgaat gttaagtgga    26880
gaggcagagc aactgcgcct gaaacacctg gtccactgtc gccgccacaa gtgctttgcc    26940
cgcgactccg gtgagttttg ctactttgaa ttgcccgagg atcatatcga gggcccggcg    27000
cacggcgtcc ggcttaccgc ccaggagag cttgcccgta gctgattcg ggagtttacc    27060 cagcgcccc tgctagttga gcgggacagg ggaccctgtg ttctcactgt gatttgcaac    27120
tgtcctaacc ctggattaca tcaagatcct ctagttaatg tcaggtcgcc taagtcgatt    27180
aactagagta cccggggatc ttattcccctt taactaataa aaaaaaataa taaagcatca    27240
cttacttaaa atcagttagc aaatttctgt ccagttatt cagcagcacc tccttgccct    27300
cctcccagct ctggtattgc agcttcctcc tggctgcaaa cttctccac aatctaaatg    27360 gaatgtcagt ttcctcctgt tcctgtccat ccgcacccac tatcttcatg ttgttgcaga    27420
tgaagcgcgc aagaccgtct gaagatacct tcaaccccgt gtatccatat gacacggaaa    27480
ccggtcctcc aactgtgcct tttcttactc ctcccttttgt atcccccaat gggtttcaag    27540
agagtccccc tggggtactc tctttgcgcc tatccgaacc tctagttacc tccaatggca    27600
tgcttgcgct caaatgggc aacggcctct ctctggacga ggccggcaac cttacctccc    27660
aaaatgtaac cactgtgagc ccacctctca aaaaaccaa gtcaaacata aacctggaaa    27720
tatctgcacc cctcacagtt acctcagaag ccctaactgt ggctgccgcc gcacctctaa    27780
tggtcgcggg caacacactc accatgcaat cacaggcccc gctaaccgtg cacgactcca    27840
aacttagcat tgccacccaa ggaccctca cagtgtcaga aggaaagcta gccctgcaaa    27900
```

```
catcaggccc cctcaccacc accgatagca gtacccttac tatcactgcc tcacccctc    27960
taactactgc cactggtagc ttgggcattg acttgaaaga gcccatttat acacaaaatg    28020
gaaaactagg actaaagtac ggggctcctt tgcatgtaac agacgaccta aacactttga    28080
ccgtagcaac tggtccaggt gtgactatta ataatacttc cttgcaaact aaagttactg    28140
gagccttggg ttttgattca caaggcaata tgcaacttaa tgtagcagga ggactaagga    28200
ttgattctca aaacagacgc cttatacttg atgttagtta ccgtttgat gctcaaaacc      28260
aactaaatct aagactagga cagggccctc tttttataaa ctcagcccac aacttggata    28320
ttaactacaa caaaggcctt tacttgttta cagcttcaaa caattccaaa agcttgagg     28380
ttaacctaag cactgccaag gggttgatgt ttgacgctac agccatagcc attaatgcag    28440
gagatgggct tgaatttggt tcacctaatg caccaaacac aaatccctc aaaacaaaaa      28500
ttggccatgg cctagaattt gattcaaaca aggctatggt tcctaaacta ggaactggcc    28560
ttagttttga cagcacaggt gccattacag taggaaacaa aaataatgat aagctaactt    28620
tgtggaccac accagctcca tctcctaact gtagactaaa tgcagagaaa gatgctaaac    28680
tcactttggt cttaacaaaa tgtggcagtc aaatacttgc tacagtttca gttttggctg    28740
ttaaaggcag tttggctcca atatctggaa cagttcaaag tgctcatctt attataagat    28800
ttgacgaaaa tggagtgcta ctaaacaatt ccttcctgga cccagaatat tggaacttta    28860
gaaatggaga tcttactgaa ggcacagcct atacaaacgc tgttggattt atgcctaacc    28920
tatcagctta ccaaaatctc acggtaaaa ctgccaaaag taacattgtc agtcaagttt      28980
acttaaacgg agacaaaact aaacctgtaa cactaaccat tacactaaac ggtacacagg    29040
aaacaggaga cacaactcca agtgcatact ctatgtcatt ttcatgggac tggtctggcc    29100
acaactacat taatgaaata tttgccacat cctcttacac ttttttcatac attgcccaag   29160
aataaagaat cgtttgtgtt atgtttcaac gtgttatttt ttcaattgca gaaaatttca    29220
agtcattttt cattcagtag tatagcccca ccaccacata gcttatacag atcaccgtac    29280
cttaatcaaa ctcacagaac cctagtattc aacctgccac ctccctccca acacacagag    29340
tacacagtcc tttctccccg gctggcctta aaaagcatca tatcatgggt aacagacata    29400
ttcttaggtg ttatattcca cacggtttcc tgtcgagcca aacgctcatc agtgatatta    29460
ataaactccc cggcagctc acttaagttc atgtcgctgt ccagctgctg agccacaggc     29520
tgctgtccaa cttgcggttg cttaacgggc ggcgaaggag aagtccacgc ctacatgggg    29580
gtagagtcat aatcgtgcat caggataggg cggtggtgct gcagcagcgc gcgaataaac    29640
tgctgccgcc gccgctccgt cctgcaggaa tacaacatgg cagtggtctc ctcagcgatg    29700
attcgcaccg cccgcagcat aaggcgcctt gtcctccggg cacagcagcg cccctgatc     29760
tcacttaaat cagcacagta actgcagcac agcaccacaa tattgttcaa aatcccacag    29820
tgcaaggcgc tgtatccaaa gctcatggcg gggaccacag aacccacgtg gccatcatac    29880
cacaagcgca ggtagattaa gtggcgaccc ctcataaaca cgctggacat aaacattacc    29940
tcttttggca tgttgtaatt caccacctcc cggtaccata taaacctctg attaaacatg    30000
gcgccatcca ccaccatcct aaaccagctg gccaaaacct gcccgccggc tatacactgc    30060
agggaaccgg gactggaaca atgacagtgg agagcccagg actcgtaacc atggatcatc    30120
atgctcgtca tgatatcaat gttggcacaa cacaggcaca cgtgcataca cttcctcagg    30180
attacaagct cctcccgcgt tagaaccata tcccagggaa caacccattc ctgaatcagc    30240
gtaaatccca cactgcaggg aagacctcgc acgtaactca cgttgtgcat tgtcaaagtg    30300
```

```
ttacattcgg gcagcagcgg atgatcctcc agtatggtag cgcgggtttc tgtctcaaaa    30360
ggaggtagac gatccctact gtacggagtg cgccgagaca accgagatcg tgttggtcgt    30420
agtgtcatgc caaatggaac gccggacgta gtcatatttc ctgaagcaaa accaggtgcg    30480
ggcgtgacaa acagatctgc gtctccggtc tcgccgctta gatcgctctg tgtagtagtt    30540
gtagtatatc cactctctca aagcatccag gcgcccctg gcttcgggtt ctatgtaaac      30600
tccttcatgc gccgctgccc tgataacatc caccaccgca gaataagcca cacccagcca    30660
acctacacat tcgttctgcg agtcacacac gggaggagcg ggaagagctg gaagaaccat    30720 gtttttttt ttattccaaa agattatcca aaacctcaaa atgaagatct attaagtgaa     30780
cgcgctcccc tccggtggcg tggtcaaact ctacagccaa agaacagata atggcatttg    30840
taagatgttg cacaatggct tccaaaaggc aaacggccct cacgtccaag tggacgtaaa    30900
ggctaaaccc ttcagggtga atctcctcta taaacattcc agcaccttca accatgccca    30960
aataattctc atctcgccac cttctcaata tatctctaag caaatcccga atattaagtc    31020
cggccattgt aaaaatctgc tccagagcgc cctccacctt cagcctcaag cagcgaatca    31080
tgattgcaaa aattcaggtt cctcacagac ctgtataaga ttcaaaagcg gaacattaac    31140
aaaaataccg cgatcccgta ggtcccttcg cagggccagc tgaacataat cgtgcaggtc    31200
tgcacggacc agcgcggcca cttccccgcc aggaaccatg acaaaagaac ccacactgat    31260
tatgacacgc atactcggag ctatgctaac cagcgtagcc ccgatgtaag cttgttgcat    31320
gggcggcgat ataaaatgca aggtgctgct caaaaaatca ggcaaagcct cgcgcaaaaa    31380
agaaagcaca tcgtagtcat gctcatgcag ataaaggcag gtaagctccg gaaccaccac    31440
agaaaaagac accattttc tctcaaacat gtctgcgggt ttctgcataa acacaaaata    31500
aaataacaaa aaaacattta aacattagaa gcctgtctta caacaggaaa aacaacccctt   31560 ataagcataa gacggactac ggccatgccg gcgtgaccgt aaaaaaactg gtcaccgtga    31620
ttaaaaagca ccaccgacag ctcctcggtc atgtccggag tcataatgta agactcggta    31680
aacacatcag gttgattcac atcggtcagt gctaaaaagc gaccgaaata gcccggggga    31740
atacataccc gcaggcgtag agacaacatt acagccccca taggaggtat aacaaaatta    31800
ataggagaga aaaacacata aacacctgaa aaaccctcct gcctaggcaa aatagcaccc    31860
tcccgctcca gaacaacata cagcgcttcc acagcggcag ccataacagt cagccttacc    31920
agtaaaaaag aaaacctatt aaaaaaacac cactcgacac ggcaccagct caatcagtca    31980
cagtgtaaaa aagggccaag tgcagagcga gtatatatag gactaaaaaa tgacgtaacg    32040
gttaaagtcc acaaaaaaca cccagaaaac cgcacgcgaa cctacgccca gaaacgaaag    32100
ccaaaaaacc cacaacttcc tcaaatcgtc acttccgttt tcccacgtta cgtcacttcc    32160
cattttaaga aaactacaat tcccaacaca tacaagttac tccgccctaa aacctacgtc    32220
acccgccccg ttcccacgcc ccgcgccacg tcacaaactc cacccctca ttatcatatt      32280 ggcttcaatc caaaataagg tatattattg atgat                               32315
```

<210> SEQ ID NO 4
<211> LENGTH: 9
<212> TYPE: PRT
<213> ORGANISM: Homo sapiens

<400> SEQUENCE: 4

Tyr Leu Ser Gly Ala Asn Leu Asn Leu
1               5

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Leu Ser Gly Ala Asp Leu Asn Leu
1               5

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 6 tctctccna                                                              9
```